United States Patent
Bourzat et al.

(10) Patent No.: US 6,632,814 B1
(45) Date of Patent: Oct. 14, 2003

(54) DIHYDRO-BENZO(1,4)OXAZINES

(75) Inventors: Jean-Dominique Bourzat, Vitry (FR); Alain Commercon, Vitry (FR); Bruno Jacques Christophe Filoche, Vitry (FR); Neil Victor Harris, Kent (GB); Thomas David Pallin, Kent (GB); Keith Alfred James Stuttle, Kent (GB)

(73) Assignees: Aventis Pharma Ltd., Kent (GB); Aventis Pharmaceuticals Recherche Developpment, Vitry (FR)

( * ) Notice: Subject to any disclaimer, the term of this patent is extended or adjusted under 35 U.S.C. 154(b) by 0 days.

(21) Appl. No.: 09/644,308

(22) Filed: Aug. 23, 2000

Related U.S. Application Data

(63) Continuation of application No. PCT/GB99/04430, filed on Dec. 23, 1999
(60) Provisional application No. 60/126,084, filed on Mar. 25, 1999.

(30) Foreign Application Priority Data

Dec. 23, 1998 (GB) .............................................. 98/28417

(51) Int. Cl.⁷ .................... C07D 241/38; C07D 265/36; A61K 31/495; A61K 31/535; A61P 11/06
(52) U.S. Cl. .................................... 514/230.5; 544/105
(58) Field of Search ........................ 544/105; 514/230.5

(56) References Cited

U.S. PATENT DOCUMENTS

| | | | |
|---|---|---|---|
| 5,334,598 A | 8/1994 | Bagley et al. | 514/303 |
| 5,688,913 A | 11/1997 | Arrhenius et al. | 530/330 |
| 5,977,125 A | 11/1999 | Hibi et al. | 514/277 |
| 6,083,961 A | 7/2000 | Oku et al. | 514/338 |

FOREIGN PATENT DOCUMENTS

| | | |
|---|---|---|
| EP | 0151539 | 8/1985 |
| EP | 0350846 | 1/1990 |
| EP | 0 376 870 | 7/1990 |
| EP | 407 137 A2 | 1/1991 |
| EP | 0509398 | 10/1992 |
| EP | 0 509 845 | 10/1992 |
| EP | 0 614 664 A1 | 9/1994 |
| EP | 0 842 945 A2 | 5/1998 |
| EP | 0 930 075 A1 | 7/1999 |
| EP | 1 025 857 A1 | 8/2000 |
| GB | 2 130 580 A | 6/1984 |
| JP | 58-8016 | 1/1983 |
| WO | WO 94/20473 | 9/1994 |
| WO | WO 95/09848 | 4/1995 |
| WO | WO 95/29177 | 11/1995 |
| WO | WO 96/13485 | 7/1996 |
| WO | WO 97/03094 | 1/1997 |
| WO | WO 97/34901 | 9/1997 |
| WO | WO 97/36862 | 10/1997 |
| WO | WO 99/23063 | 5/1999 |
| WO | WO 99/33789 | 7/1999 |
| WO | WO 99/54321 | 10/1999 |

OTHER PUBLICATIONS

Bombrun (WO 97/43287) (1997). Abstract.*
Kawakita et al. (JP 07242662). (1995) Abstract.*
Combs (EP 509845). (1992) Abstract.*
Moussavi et al. (Synth. Commun. (1991), 21(2), 271–8). Abstract.*
Sastry et al. (Indian J. Chem., Sect. B (1989), 28B (10), 882–4). Abstract.*
Kuroita et al, , Chemical and Pharmaceutical Bulletin 44(4):756–764(1996).

* cited by examiner

*Primary Examiner*—Bruck Kifle
(74) *Attorney, Agent, or Firm*—Ronald G. Ort

(57) ABSTRACT

The invention is directed to physiologically active compounds of formula (I):

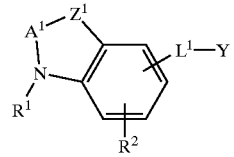

(I)

wherein $R^1$ represents $R^3-Z^3-$, $R^3-L^2-R^4-Z^3-$, $R^3-L^3-Ar^1-L^4-Z^3-$ or $R^3-L^3-Ar^1-L^2-R^4-Z^3-$;

$R^2$ represents hydrogen, halogen, lower alkyl or lower alkoxy;

$A^1$ represents a straight chain $C_{2-3}$alkylene linkage optionally substituted by one or more groups chosen from alkyl, aryl, arylalkyl, heteroaryl, heteroarylalkyl, imino, oxo, thioxo, or alkyl substituted by $-ZR^6$, $-NY^1Y^2$, $-CO_2R^6$ or $-C(=O)-NY^1Y^2$;

$L^1$ represents a direct bond; an alkenylene, alkylene, alkynylene, cycloalkenylene, cycloalkylene, heteroaryldiyl, heterocycloalkylene or arylene linkage each optionally substituted by (a) an acidic functional group, cyano, oxo, $-S(O)_mR^9$, $R^3$, $-C(=O)-R^3$, $-C(=O)-OR^3$, $-N(R^8)-C(=O)-R^9$, $-N(R^8)-C(=O)-OR^9$, $-N(R^8)-SO_2-R^9$, $-NY^4Y^5$ or $-[C(=O)-N(R^{10})-C(R^5)(R^{11})]_p-C(=O)-NY^4Y^5$, or by (b) alkyl substituted by an acidic functional group, or by $S(O)_mR^9$, $-C(=O)-NY^4Y^5$ or $-NY^4Y^5$; a $-[C(=O)-N(R^{10})-C(R^5)(R^{11})]_p-$ linkage; a $-Z^2-R^{12}-$ linkage; a $-C(=O)-CH_2-C(=O)-$ linkage; a $-R^{12}-Z^2-R^{12}-$ linkage; a $-C(R^4)(R^{13})-[C(=O)-N(R^{10})-C(R^5)(R^{11})]_p-$ linkage; or a $-L^5-L^6-L^7-$ linkage;

$Z^1$ is $NR^{17}$ or O;

Y is carboxy or an acid bioisostere;
and the corresponding N-oxides, and their prodrugs; and pharmaceutically acceptable salts and solvates of such compounds and their N-oxides and prodrugs.

Such compounds have valuable pharmaceutical properties, in particular the ability to regulate the interaction of VCAM-1 and fibronectin with the integrin VLA-4 (α4β1).

19 Claims, No Drawings

DIHYDRO-BENZO(1,4)OXAZINES

This application is a continuation of PCT/GB99/04430, filed Dec. 23, 1999, which claims priority from GB Application No. 9828417.7, filed Dec. 23, 1998, and U.S. Application No. 60/126,084, filed Mar. 25, 1999.

This invention is directed to aza-bicycles, their preparation, pharmaceutical compositions containing these compounds, and their pharmaceutical use in the treatment of disease states capable of being modulated by the inhibition of cell adhesion.

Cell adhesion is a process by which cells associate with each other, migrate towards a specific target or localise within the extra-cellular matrix. Many of the cell-cell and cell-extracellular matrix interactions are mediated by protein ligands (e.g. fibronectin, VCAM-1 and vitronectin) and their integrin receptors [e.g. α5β1 (VLA-5), α4β1 (VLA-4) and αVβ3]. Recent studies have shown these interactions to play an important part in many physiological (e.g. embryonic development and wound healing) and pathological conditions (e.g. tumour-cell invasion and metastasis, inflammation, atherosclerosis and autoimmune disease).

A wide variety of proteins serve as ligands for integrin receptors. In general, the proteins recognised by integrins fall into one of three classes: extracellular matrix proteins, plasma proteins and cell surface proteins. Extracellular matrix proteins such as collagen fibronectin, fibrinogen, laminin, thrombospondin and vitronectin bind to a number of integrins. Many of the adhesive proteins also circulate in plasma and bind to activated blood cells. Additional components in plasma that are ligands for integrins include fibrinogen and factor X. Cell bound complement C3bi and several transmembrane proteins, such as Ig-like cell adhesion molecule (ICAM-1,2,3) and vascular cell adhesion molecule (VCAM-1), which are members of the Ig superfamily, also serve as cell-surface ligands for some integrins.

Integrins are heterodimeric cell surface receptors consisting of two subunits called α and β. There are at least fifteen different α-subunits (α1-α9, α-L, α-M, α-X, α-IIb, α-V and α-E) and at least seven different β (β1-β7) subunits. The integrin family can be subdivided into classes based on the β subunits, which can be associated with one or more α-subunits. The most widely distributed integrins belong to the β1 class, also known as the very late antigens (VLA). The second class of integrins are leukocyte specific receptors and consist of one of three α-subunits (α-L, α-M or α-X) complexed with the β2 protein. The cytoadhesins α-IIbβ3 and α-Vβ3, constitute the third class of integrins.

The present invention principally relates to agents which modulate the interaction of the ligand VCAM-1 with its integrin receptor α4β1 (VLA-4), which is expressed on numerous hematopoietic cells and established cell lines, including hematopoietic precursors, peripheral and cytotoxic T lymphocytes, B lymphocytes, monocytes, thymocytes and eosinophils.

The integrin α4β1 mediates both cell-cell and cell-matrix interactions. Cells expressing α4β1 bind to the carboxyterminal cell binding domain (CS-1) of the extracellular matrix protein fibronectin, to the cytokine-inducible endothelial cell surface protein VCAM-1, and to each other to promote homotypic aggregation. The expression of VCAM-1 by endothelial cells is upregulated by proinflammatory cytokines such as INF-γ, TNF-α, IL-1β and IL-4.

Regulation of α4β1 mediated cell adhesion is important in numerous physiological processes, including T-cell proliferation, B-cell localisation to germinal centres, and adhesion of activated T-cells and eosinophils to endothelial cells. Evidence for the involvement of VLA-4/VCAM-1 interaction in various disease processes such as melanoma cell division in metastasis, T-cell infiltration of synovial membranes in rheumatoid arthritis, autoimmune diabetes, collitis and leukocyte penetration of the blood-brain barrier in experimental autoimmune encephalomyelitis, atherosclerosis, peripheral vascular disease, cardiovascular disease and multiple sclerosis, has been accumulated by investigating the role of the peptide CS-1 (the variable region of fibronectin to which α4β1 binds via the sequence Leu-Asp-Val) and antibodies specific for VLA-4 or VCAM-1 in various in vitro and in vivo experimental models of inflammation. For example, in a Streptococcal cell wall-induced experimental model of arthritis in rats, intravenous administration of CS-1 at the initiation of arthritis suppresses both acute and chronic inflammation (S. M. Wahl et al., J.Clin.Invest., 1994, 94, pages 655–662). In the oxazalone-sensitised model of inflammation (contact hypersensitivity response) in mice, intravenous administration of anti-α4 specific monoclonal antibodies significantly inhibited (50–60% reduction in the ear swelling response) the efferent response (P. L. Chisholm et al. J.Immunol., 1993, 23, pages 682–688). In a sheep model of allergic bronchoconstriction, HP1/2, an anti-α4 monoclonal antibody given intravenously or by aerosol, blocked the late response and the development of airway hyperresponsiveness (W. M. Abraham et al. J. Clin. Invest., 1994, 93 pages 776–787).

We have now found a novel group of aza-bicycles which have valuable pharmaceutical properties, in particular the ability to regulate the interaction of VCAM-1 and fibronectin with the integrin VLA-4 (α4β1).

Thus, in one aspect, the present invention is directed to aza-bicycles of general formula (I):

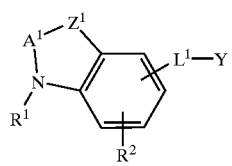

(I)

wherein:
R¹ represents a group selected from:
   (i) R³—Z³—
   (ii) R³—L²—R⁴—Z³—
   (iii) R³—L³—Ar¹—L⁴—Z³—
   (iv) R³—L³—Ar¹—L²—R⁴—Z³—

R² represents hydrogen, halogen, lower alkyl or lower alkoxy;

R³ is alkyl, alkenyl, alkynyl, aryl, arylalkyl, arylalkenyl, arylalkynyl, cycloalkyl, cycloalkylalkyl, cycloalkylalkenyl, cycloalkylalkynyl, cycloalkenyl, cycloalkenylalkyl, heteroaryl, heteroarylalkyl, heteroarylalkenyl, heteroarylalkynyl, heterocycloalkyl or heterocycloalkylalkyl;

R⁴ is an alkylene chain, an alkenylene chain, or an alkynylene chain;

R⁵ is hydrogen or lower alkyl;

R⁶ is hydrogen, alkyl, alkenyl, aryl, arylalkyl, cycloalkyl, cycloalkylalkyl, heteroaryl or heteroarylalkyl;

R⁷ is hydrogen or lower alkyl;

R⁸ is hydrogen, alkyl, aryl, arylalkyl, cycloalkyl, cycloalkylalkyl, heteroaryl, heteroarylalkyl, heterocycloalkyl or heterocycloalkylalkyl;

$R^9$ is alkyl, aryl, cycloalkyl, heteroaryl or heterocycloalkyl, or alkyl substituted by aryl, an acidic functional group, cycloalkyl, heteroaryl, heterocycloalkyl, —S(O)$_m$R$^3$, —C(=O)—NY$^4$Y$^5$ or —NY$^4$Y$^5$;

$R^{10}$ is hydrogen, $R^3$ or alkyl substituted with alkoxy, cycloalkyl, hydroxy, mercapto, alkylthio or —NY$^4$Y$^5$;

$R^{11}$ and $R^{13}$ are each independently selected from hydrogen or a group consisting amino acid side chains, an acidic functional group, $R^3$, —C(=O)—R$^3$, or —C(=O)—NY$^4$Y$^5$, or alkyl substituted by an acidic functional group or by $R^3$, —NY$^4$Y$^5$, —NH—C(=O)—R$^3$, —C(=O)—R$^4$—NH$_2$, —C(=O)—Ar$^1$—NH$_2$, —C(=O)—R$^4$—CO$_2$H, or —C(=O)—NY$^4$Y$^5$; or $R^{10}$ and $R^{11}$ or $R^{10}$ and $R^{13}$ together with the atoms to which they attached form a 3- to 6-membered heterocycloalkyl ring;

$R^{12}$ is C$_{1-6}$alkylene, optionally substituted by $R^3$;

$R^{14}$ is alkyl, aryl, arylalkyl, cycloalkyl, cycloalkylalkyl, heteroaryl, heteroarylalkyl, heterocycloalkyl or heterocycloalkylalkyl;

$R^{17}$ represents hydrogen, $R^9$, —C(=O)—R$^9$, —C(=O)—OR$^{14}$ or —SO$_2$R$^9$;

$A^1$ represents a straight chain C$_{2-3}$alkylene linkage optionally substituted by one or more groups chosen from alkyl, aryl, arylalkyl, heteroaryl, heteroarylalkyl, imino, oxo, thioxo, or alkyl substituted by —ZR$^6$, —NY$^1$Y$^2$, —CO$_2$R$^6$ or —C(=O)—NY$^1$Y$^2$;

Ar$^1$ is arylene or heteroaryldiyl;

L$^1$ represents:
  (i) a direct bond;
  (ii) an alkenylene, alkylene, alkynylene, cycloalkenylene, cycloalkylene, heteroaryldiyl, heterocycloalkylene or arylene linkage each optionally substituted by (a) an acidic functional group, cyano, oxo, —S(O)$_m$R$^9$, R$^3$, —C(=O)—R$^3$, —C(=O)—OR$^3$, —N(R$^8$)—C(=O)—R$^9$, —N(R$^8$)—C(=O)—OR$^9$, —N(R$^8$)—SO$_2$—R$^9$, —NY$^4$Y$^5$ or —[C(=O)—N(R$^{10}$)—C(R$^5$)(R$^{11}$)]$_p$—C(=O)—NY$^4$Y$^5$, or by (b) alkyl substituted by an acidic functional group, or by S(O)$_m$R$^9$, —C(=O)—NY$^4$Y$^5$ or —NY$^4$Y$^5$;
  (iii) a —[C(=O)—N(R$^{10}$)—C(R$^5$)(R$^{11}$)]$_p$— linkage;
  (iv) a —Z$^2$—R$^{12}$— linkage;
  (v) a —C(=O)—CH$_2$—C(=O)— linkage;
  (vi) a —R$^{12}$—Z$^2$—R$^{12}$— linkage;
  (vii) a —C(R$^5$)(R$^{13}$)—[C(=O)—N(R$^{10}$)—C(R$^5$)(R$^{11}$)]$_p$— linkage; or
  (viii) a —L$^5$—L$^6$—L$^7$— linkage;

L$^2$ represents a —NR$^5$—C(=Z)—NR$^5$—, —C(=Z)—NR$^5$—, —C(=O)—, —C(=Z)—O—, —NR$^5$—C(=Z)—, —Z—, —SO—, —SO$_2$—, —NR$^5$—, —SO$_2$—NR$^5$—, —NR$^5$—SO$_2$—, —NR$^5$—C(=O)—O—, —O—C(=O)—, or —O—C(=O)—NR$^5$— linkage;

L$^3$ represents a heteroaryldiyl, heterocycloalkylene, —NR$^5$—C(=Z)—NR$^5$—, —C(=Z)—NR$^5$—, —C(=Z)—O—, —NR$^5$—C(=Z)—, —Z—, —SO—, —SO$_2$—, NR$^5$—, —SO$_2$—NR$^5$—, —NR$^5$—SO$_2$—, —NR$^5$—C(=O)—O—, —O—C(=O)—, or —O—C(=O)—NR$^5$— linkage;

L$^4$ represents a direct bond, an alkylene, alkenylene or alkynylene chain;

L$^5$ and L$^7$ each independently represent a direct bond or an alkylene chain;

L$^6$ represents a cycloalkylene or heterocycloalkylene linkage;

Y is carboxy (or an acid bioisostere);

$Y^1$ and $Y^2$ are independently hydrogen, alkenyl, alkyl, aryl, arylalkyl, cycloalkyl, heteroaryl or heteroarylalkyl; or the group —NY$^1$Y$^2$ may form a cyclic amine;

$Y^4$ and $Y^5$ are independently hydrogen, alkenyl, alkyl, alkynyl, aryl, cycloalkenyl, cycloalkyl, heteroaryl, heterocycloalkyl, or alkyl substituted by alkoxy, aryl, cyano, cycloalkyl, heteroaryl, heterocycloalkyl, hydroxy, oxo, —NY$^1$Y$^2$, or one or more —CO$_2$R$^7$ or —C(=O)—NY$^1$Y$^2$ groups; or the group —NY$^4$Y$^5$ may form a 5- to 7-membered cyclic amine which (i) may be optionally substituted with one or more substituents selected from alkoxy, carboxamido, carboxy, hydroxy, oxo (or a 5-, 6- or 7-membered cyclic acetal derivative thereof), R$^9$; (ii) may also contain a further heteroatom selected from O, S, SO$_2$, or NY$^6$; and (iii) may also be fused to additional aryl, heteroaryl, heterocycloalkyl or cycloalkyl rings to form a bicyclic or tricyclic ring system;

$Y^6$ is hydrogen, alkyl, aryl, arylalkyl, —C(=O)—R$^{14}$, —C(=O)—OR$^{14}$ or —SO$_2$R$^{14}$;

Z represents an oxygen or sulphur atom;

$Z^1$ represents NR$^{17}$ or O;

$Z^2$ is O, S(O)$_n$, NR$^5$, SONR$^5$, C(=O)NR$^5$ or C(=O);

$Z^3$ represents a direct bond, C(=O), OC(=O), NR$^5$C(=O), or SO$_2$;

m is an integer 1 or 2;

n is zero or an integer 1 or 2; and p is zero or an integer 1 to 4;

but excluding compounds where an oxygen, nitrogen or sulphur atom is attached directly to a carbon carbon multiple bond of an alkenylene or alkynylene residue;

and the corresponding N-oxides, and their prodrugs; and pharmaceutically acceptable salts and solvates (e.g. hydrates) of such compounds and their N-oxides and prodrugs.

In the present specification, the term "compounds of the invention", and equivalent expressions, are meant to embrace compounds of general formula (I) as hereinbefore described, which expression includes the prodrugs, protected derivatives of compounds of formula (I) containing one or more acidic functional groups and/or amino-acid side chains, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986,21,p283 "Bioisosterism In Drug Design"; Yun, Hwahak Sekye, 1993,33,p576–579 "Application Of Bioisosterism To New Drug Design"; Zhao, Huaxue Tongbao, 1995,p34–38 "Bioisosteric Replacement And Development Of Lead Compounds In Drug Design";

Graham, Theochem, 1995,343,p105–109 "Theoretical Studies Applied To Drug Design:ab initio Electronic Distributions In Bioisosteres"). Examples of suitable acid bioisosteres include: —C(=O)—NHOH, —C(=O)—CH$_2$OH, —C(=O)—CH$_2$SH, —C(=O)—NH—CN, sulpho, phosphono, alkylsulphonylcarbamoyl, tetrazolyl, arylsulphonylcarbamoyl, heteroarylsulphonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acidic functional group" means a group with an acidic hydrogen within it. The "corresponding protected derivatives" are those where the acidic hydrogen atom has been replaced with a suitable protecting group. For suitable protecting groups see T. W. Greene and P. G. M. Wuts in "Protective Groups in Organic Chemistry" John Wiley and Sons, 1991. Exemplary acidic functional groups include carboxyl (and acid bioisosteres), hydroxy, mercapto and imidazole. Exemplary protected derivatives include esters of carboxy groups (i.e. —CO$_2$R$^{14}$), ethers of hydroxy groups (i.e. —OR$^{14}$), thioethers of mercapto groups (i.e. —SR$^{14}$), and N-benzyl derivatives of imidazoles.

"Acyl" means an H—CO— or alkyl—CO— group in which the alkyl group is as described herein.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenylene" means an aliphatic bivalent radical derived from a straight or branched alkenyl group, in which the alkenyl group is as described herein. Exemplary alkenylene radicals include vinylene and propylene.

"Alkoxy" means an alkyl-O— group in which the alkyl group is as described herein. Exemplary alkoxy groups include methoxy, ethoxy, n-propoxy, i-propoxy, n-butoxy and heptoxy.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched having about 1 to about 15 carbon atoms in the chain optionally substituted by alkoxy or by one or more halogen atoms. Particular alkyl groups have from 1 to about 6 carbon atoms. "Lower alkyl" as a group or part of a lower alkoxy, lower alkylthio, lower alkylsulphinyl or lower alkylsulphonyl group means unless otherwise specified, an aliphatic hydrocarbon group which may be straight or branched having about 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl.

"Alkylene" means an aliphatic bivalent radical derived from a straight or branched alkyl group, in which the alkyl group is as described herein. Exemplary alkylene radicals include methylene, ethylene and trimethylene.

"Alkylenedioxy" means an -O-alkyl-O— group in which the alkyl group is as defined above. Exemplary alkylenedioxy groups include methylenedioxy and ethylenedioxy.

"Alkylsulphinyl" means an alkyl-SO— group in which the alkyl group is as previously described. Preferred alkylsulphinyl groups are those in which the alkyl group is C$_{1-4}$alkyl.

"Alkylsulphonyl" means an alkyl-SO$_2$— group in which the alkyl group is as previously described. Preferred alkylsulphonyl groups are those in which the alkyl group is C$_{1-4}$alkyl.

"Alkylsulphonylcarbamoyl" means an alkyl-SO$_2$—NH—C(=O)— group in which the alkyl group is as previously described. Preferred alkylsulphonylcarbamoyl groups are those in which the alkyl group is C$_{1-4}$alkyl. "Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Exemplary alkynyl groups include ethynyl, propynyl, n-butynyl, i-butynyl, 3-methylbut-2-ynyl, and n-pentynyl.

"Alkynylene" means an aliphatic bivalent radical derived from a straight or branched alkynyl group, in which the alkynyl group is as described herein. Exemplary alkynylene radicals include ethynylene and propynylene.

"Amino acid side chains" means the substituent found on the carbon between the amino and carboxy groups in α-amino acids. For examples of "corresponding protected derivatives" of amino acid side chains, see T. W. Greene and P. G. M. Wuts in "Protective Groups in Organic Chemistry" John Wiley and Sons, 1991.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Aryl groups may be substituted with one or more aryl group substituents which may be the same or different, where "aryl group substituent" includes, for example, acyl, acylamino, alkoxy, alkoxycarbonyl, alkylenedioxy, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, heteroaroyl, heteroaryl, heteroarylalkyloxy, heteroaroylamino, heteroaryloxy, hydroxy, nitro, trifluoromethyl, Y$^1$Y$^2$N—, Y$^1$Y$^2$NCO—, Y$^1$Y$^2$NSO$_2$—, Y$^1$Y$^2$N—C$_{2-6}$alkylene-Z$^4$— {where Z$^4$ is O, NR$^5$ or S(O)$_n$}, alkylC(=O)—Y$^1$N—, alkylSO$_2$—Y$^1$N— or alkyl optionally substituted with aryl, heteroaryl, hydroxy, or Y$^1$Y$^2$N—.

"Arylalkenyl" means an aryl-alkenyl- group in which the aryl and alkenyl are as previously described. Preferred arylalkenyls contain a lower alkenyl moiety. Exemplary arylalkenyl groups include styryl and phenylallyl.

"Arylalkyl" means an aryl-alkyl- group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Arylalkynyl" means an aryl-alkynyl- group in which the aryl and alkynyl are as previously described. Exemplary arylalkynyl groups include phenylethynyl and 3-phenylbut-2-ynyl.

"Arylene" means an optionally substituted bivalent radical derived from an aryl group. Exemplary arylene groups include optionally substituted phenylene, naphthylene and indanylene. When $Ar^1$ is arylene this may particularly represent an optionally substituted phenylene. Suitable substituents include one or more "aryl group substituents" as defined above, particularly halogen, methyl or methoxy.

"Aryloxy" means an aryl-O— group in which the aryl group is as previously described. Exemplary aryloxy groups include optionally substituted phenoxy and naphthoxy.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulphinyl" means an aryl-SO— group in which the aryl group is as previously described.

"Arylsulphonyl" means an aryl-$SO_2$— group in which the aryl group is as previously described.

"Arylsulphonylcarbamoyl" means an aryl-$SO_2$—NH—C(=O)— group in which the aryl group is as previously described.

"Arylthio" means an aryl-S— group in which the aryl group is as previously described. Exemplary arylthio groups include phenylthio and naphthylthio.

"Azaheteroaryl" means an aromatic carbocyclic moiety of about 5 to about 10 ring members in which one of the ring members is nitrogen and the other ring members are chosen from carbon, oxygen, sulphur, or nitrogen. Examples of azaheteroaryl groups include pyridyl, pyrimidinyl, quinolinyl, isoquinolinyl, quinazolinyl, imidazolyl, and benzimidazolyl.

"Azaheteroaryldiyl" means an optionally substituted bivalent radical derived from a heteroaryl group.

"Cyclic amine" means a 3 to 8 membered monocyclic cycloalkyl ring system where one of the ring carbon atoms is replaced by nitrogen and which (i) may optionally contain an additional heteroatom selected from O, S or $NY^3$ (where $Y^3$ is hydrogen, alkyl, arylalkyl, and aryl) and (ii) may be fused to additional aryl or heteroaryl ring to form a bicyclic ring system. Exemplary cyclic amines include pyrrolidine, piperidine, morpholine, piperazine, indoline and pyrindoline.

"Cycloalkenyl" means a non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl or cycloheptenyl.

"Cycloalkenylalkyl" means a cycloalkenyl-alkyl- group in which the cycloalkenyl and alkyl moieties are as previously described. Exemplary cycloalkenylalkyl groups include cyclopentenylmethyl, cyclohexenylmethyl or cycloheptenylmethyl.

"Cycloalkenylene" means a bivalent radical derived from an unsaturated monocyclic hydrocarbon of about 3 to about 10 carbon atoms by removing a hydrogen atom from each of two different carbon atoms of the ring. Exemplary cycloalkenylene radicals include cyclopentenylene and cyclohexenylene.

"Cycloalkyl" means a saturated monocyclic or bicyclic ring system of about 3to about 10 carbon atoms optionally substituted by oxo. Exemplary monocyclic cycloalkyl rings include $C_{3-8}$cycloalkyl rings such as cyclopropyl, cyclopentyl, cyclohexyl and cycloheptyl.

"Cycloalkylalkenyl" means a cycloalkyl-alkenyl- group in which the cycloalkyl and alkenyl moieties are as previously described. Exemplary monocyclic cycloalkylalkenyl groups include cyclopentylvinylene and cyclohexylvinylene.

"Cycloalkylalkyl" means a cycloalkyl-alkyl- group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Cycloalkylalkynyl" means a cycloalkyl-alkynyl- group in which the cycloalkyl and alkynyl moieties are as previously described. Exemplary monocyclic cycloalkylalkynyl groups include cyclopropylethynyl, cyclopentylethynyl and cyclohexylethynyl.

"Cycloalkylene" means a bivalent radical derived from a saturated monocyclic hydrocarbon of about 3 to about 10 carbon atoms by removing a hydrogen atom from each of two different carbon atoms of the ring. Exemplary cycloalkenylene radicals include cyclopentylene and cyclohexylene.

"Halo" or "halogen" means fluoro, chloro, bromo, or iodo. Preferred are fluoro or chloro.

"Heteroaroyl" means a heteroaryl-C(=O)— group in which the heteroaryl group is as described herein. Exemplary groups include pyridylcarbonyl.

"Heteroaroylamino" means a heteroaroyl-NH— group in which the heteroaryl moiety are as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulphur (examples of such groups include benzimidazolyl, benzthiazolyl, furyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above); (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups). Optional substituents include one or more "aryl group substituents" as defined above.

"Heteroarylalkenyl" means a heteroaryl-alkenyl- group in which the heteroaryl and alkenyl moieties are as previously described. Preferred heteroarylalkenyl groups contain a lower alkenyl moiety. Exemplary heteroarylalkenyl groups include pyridylethenyl and pyridylallyl.

"Heteroarylalkyl" means a heteroaryl-alkyl- group in which the heteroaryl and alkyl moieties are as previously described. Preferred heteroarylalkyl groups contain a $C_{1-4}$alkyl moiety. Exemplary heteroarylalkyl groups include pyridylmethyl.

"Heteroarylalkyloxy" means an heteroarylalkyl-O— group in which the heteroarylalkyl group is as previously described. Exemplary heteroaryloxy groups include optionally substituted pyridylmethoxy.

"Heteroarylalkynyl" means a heteroaryl-alkynyl- group in which the heteroaryl and alkynyl moieties are as previously described. Exemplary heteroarylalkenyl groups include pyridylethynyl and 3-pyridylbut-2-ynyl.

"Heteroaryldiyl" means ambivalent radical derived from an aromatic monocyclic or multicyclic organic moiety of about 5 to about 10 ring members in which one or more of the ring members is/are element(s) other than carbon, for example nitrogen, oxygen or sulphur, and optionally substituted by one or more "aryl group substituents" as defined above. When $Ar^1$ is an optionally substituted heteroaryldiyl group this may particularly represent an optionally substituted "azaheteroaryldiyl" group.

"Heteroaryloxy" means an heteroaryl-O— group in which the heteroaryl group is as previously described. Exemplary heteroaryloxy groups include optionally substituted pyridyloxy.

"Heteroarylsulphonylcarbamoyl" means a heteroaryl-$SO_2$—NH—C(=O)— group in which the heteroaryl group is as previously described.

"Heterocycloalkyl" means: (i) a cycloalkyl group of about 3 to 7 ring members which contains one or more heteroatoms selected from O, S or $NY^3$ and which may optionally be substituted by oxo; (ii) an optionally substituted partially saturated multicyclic heterocarbocyclic moiety in which an aryl (or heteroaryl ring) and a heterocycloalkyl group are fused together to form a cyclic structure (examples of such groups include chromanyl, dihydrobenzofuranyl, indolinyl and pyrindolinyl groups).

"Heterocycloalkylalkyl" means a heterocycloalkyl-alkyl-group in which the heterocycloalkyl and alkyl moieties are as previously described.

"Heterocycloalkylene" means a bivalent radical derived from a saturated monocyclic hydrocarbon of about 5 to about 7 atoms, which contains one or more heteroatoms selected from O, S or $NY^3$ and is optionally substituted by oxo, by removing a hydrogen atom from each of two different carbon atoms of the ring, or when $NY^3$ is NH by removing a hydrogen atom from one carbon atom of the ring and a hydrogen atom from the NH, or when the ring contains two $NY^3$ heteroatoms and $NY^3$ is NH by removing a hydrogen atom from both nitrogen atoms. When $L^1$ is a heterocycloalkylene group this may particularly represent a bivalent radical derived pyrrolidine, especially 3,4-pyrrolidinediyl.

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

Suitable esters of compounds of formula (I) containing a hydroxy group, are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulphamates and quinates.

Suitable esters of compounds of formula (I) containing a carboxy group, are for example those described by F. J. Leinweber, Drug Metab. Res., 1987, 18 page 379.

Suitable esters of compounds of formula (I) containing both a carboxy group and a hydroxy group within the moiety —$L^1$—Y, include lactones, formed by loss of water between said carboxy and hydroxy groups. Examples of lactones include caprolactones and butyrolactones.

An especially useful class of esters of compounds of formula (I) containing a hydroxy group, may be formed from acid moieties selected from those described by Bundgaard et. al., J. Med. Chem., 1989, 32, page 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Where the compound of the invention contains a carboxy group, or a sufficiently acidic bioisostere, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, tetramethylammonium hydroxide, and the like.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

$R^1$ may particularly represent a group $R^3$—$Z^3$— in which $Z^3$ is as defined above, especially C(=O), and $R^3$ is as defined above, especially (i) optionally substituted aryl, such as optionally substituted phenyl [preferred optional substituents include aryloxy, cyano, halo (e.g. chloro or fluoro), lower alkoxy (e.g. methoxy), lower alkyl (e.g. methyl), nitro and perfluoroloweralkyl (e.g. trifluoromethyl)], (ii) optionally substituted heteroaryl, such as isoquinolinyl, isoxazolyl, pyrazolopyrimidinyl, pyridyl, pyrimidinyl, quinolinyl, thiazolyl and triazolyl, each optionally substituted by one or more aryl group substituents as described hereinbefore [preferred optional substituents include alkyl-C(=O)—, aryl, cyano, halo, (e.g. chloro or fluoro), lower alkoxy (e.g. methoxy), lower alkyl (e.g. methyl), lower alkylsulphonyl, lower alkylthio, nitro and perfluoroloweralkyl (e.g. trifluoromethyl)] or (iii) optionally substituted arylalkyl in which the aryl group is optionally substituted by one, or preferably two aryl group substituents (preferred optional substituents include halo, hydroxy and methoxy). $R^1$ may particularly represent a group $R^3$—C(=O)— in which $R^3$ is a substituted aryl selected from 2-chlorophenyl, 5-chloro-2-cyanophenyl, 2-chloro-6-methylphenyl, 2,6-dichlorophenyl, 2,6-difluorophenyl, 4-fluoro-2-trifluoromethyl, 2-methyl-4-nitrophenyl, 2-methyl-5-nitrophenyl, 2-nitrophenyl, 3-nitrophenyl, 2-phenoxyphenyl or an optionally substituted heteroaryl selected from quinolin-4-yl, isoquinolin-2-yl, 2,4-yridin-3-yl, 2,6-dimethyl-4-trifluoromethylpyridin-3-yl, 4-trifluoromethylpyridin3-yl, 2-phenyl-4-methyl-1,2,3-triazol-5-yl, 3,5-dimethylisoxazol-4-yl, 2,7-dimethylpyrazolo-[1,5-a]pyrimidin-6-yl, 2-isopropyl-4-methylthiazol-5-yl, 4-trifluoromethylpyrimidin-5-yl, 4-hydroxybenzyl, 3-chloro- 4-hydroxybenzyl, 3-fluoro-4-hydroxybenzyl, and 4-hydroxy-3-methoxybenzyl.

$R^1$ may also particularly represent a group $R^3$—$L^3$—$Ar^1$—$L^4$—$Z^3$— in which $Z^3$ is as defined above, especially C(=O); $L^4$ represents a straight or branched $C_{1-6}$alkylene chain, more particularly a straight $C_{1-4}$alkylene chain such as methylene or ethylene, preferably methylene; $Ar^1$ is an optionally substituted phenylene, such as optionally substituted m- or p-phenylene, preferably optionally substituted p-phenylene, more preferably a 3-substituted p-phenylene, in which the substituent is ortho to the $R^3$—$L^3$— group, (preferred optional substituents include halo, $C_{1-4}$alkyl, $C_{1-4}$alkoxy, $C_{1-4}$alkylthio, $C_{1-4}$alkylsulphinyl and $C_{1-4}$alkylsulphonyl, especially chloro, methyl, ethyl, methoxy, methylthio, methylsulphinyl and methylsulphonyl), or $Ar^1$ is an optionally substituted heteroaryldiyl, such as optionally substituted azaheteroaryldiyl, (e.g. optionally substituted pyridinediyl, preferably a p-pyridinediyl), where the optional substituents include $C_{1-4}$alkyl and $C_{1-4}$alkoxy, especially methyl and methoxy, more preferably a pyridine-2,5-diyl, in which the $R^3$—$L^3$— group is adjacent to the pyridyl nitrogen atom, and which is substituted in the 4- or 6-position with a methyl or methoxy group; $L^3$ represents a —NH—C(=O)—NH— linkage; and $R^3$ is as defined above, particularly an optionally substituted aryl group (such as optionally substituted phenyl) or an optionally substituted heteroaryl (such as optionally substituted pyridyl), and is preferably 2- or 3-methyl(or methoxy)phenyl, more preferably 2-methylphenyl, or 3-methyl-2-pyridyl.

$R^1$ may also particularly represent a group $R^3$—$L^3$—$Ar^1$—$L^4$—$Z^3$— in which: $Z^3$ is as defined above, especially C(=O); $L^4$ represents a straight or branched $C_{1-6}$alkylene chain, more particularly a straight $C_{1-4}$alkylene chain such as methylene or ethylene, preferably methylene; $Ar^1$ is an 8 to 10 membered bicyclic system

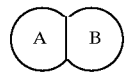

in which (i) ring is

is a 5 or 6 membered optionally substituted heterocycle, preferably a 5 membered heteroaryl ring, (ii) ring

is a 5 or 6 membered optionally substituted heterocycle or an optionally substituted benzene ring, preferably a benzene ring, (iii) each ring is optionally substituted by one or more "aryl group substituents" as defined above, (iv) the two rings are joined together by a carbon-carbon linkage or a carbon-nitrogen linkage, and

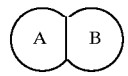

is preferably optionally substituted benzoxazolyl or optionally substituted benzimidazolyl, each [more particularly ring

]

optionally substituted by one or more "aryl group substituents" as defined above [examples of particular aryl group substituents include lower alkyl (e.g. methyl), lower alkoxy (e.g. methoxy), amino, halogen, hydroxy, lower alkylthio, lower alkylsulphinyl, lower alkylsulphonyl, nitro or trifluoromethyl]; $L^3$ represents $NR^5$, especially NH; and $R^3$ is as defined above, particularly optionally substituted aryl, such as a 2-substituted phenyl, [examples of particular aryl group substituents include lower alkyl (e.g. methyl), lower alkoxy (e.g. methoxy), halo (e.g. fluoro or chloro) and $Y^1Y^2N$— (e.g. dimethylamino)], and is preferably 2-methylphenyl.

$R^1$ may also particularly represent a group $R^3$—$L^3$—$Ar^1$—$L^4$—$Z^3$— in which: $Z^3$ is as defined above, especially C(=O); $L^4$ represents a straight or branched $C_{1-6}$alkylene chain, more particularly a straight $C_{1-4}$alkylene chain such as methylene or ethylene, preferably methylene; $Ar^1$ is an optionally substituted phenylene, such as optionally substituted m- or p-phenylene, preferably optionally substituted p-phenylene, more preferably a 3-substituted p-phenylene, in which the substituent is ortho to the $R^3$—$L^3$— group, (preferred optional substituents include chloro, $C_{1-4}$alkyl, $C_{1-4}$alkoxy, $C_{1-4}$alkylthio, $C_{1-4}$alkylsulphinyl and $C_{1-4}$alkylsulphonyl, especially chloro, methyl, ethyl, methoxy, methylthio, methylsulphinyl and methylsulphonyl), or $Ar^1$ is an optionally substituted heteroaryldiyl, such as optionally substituted azaheteroaryldiyl, (e.g. optionally substituted pyridinediyl, preferably a p-pyridinediyl), where the optional substituents include $C_{1-4}$alkyl and $C_{1-4}$alkoxy, especially methyl and methoxy, more preferably a pyridine-2,5-diyl, in which the $R^3$—$L^3$— group is adjacent to the pyridyl nitrogen atom, and which is substituted in the 4- or 6-position with a methyl or methoxy group; $L^3$ represents —C(=O)—NH— and $R^3$ is heterocycloalkyl, more particularly a bicyclic amine containing 9–10 atoms, especially indolinyl.

$R^2$ may particularly represent hydrogen.

$R^2$ may also particularly represent lower alkyl, (e.g. methyl).

$R^2$ may also particularly represent lower alkoxy (e.g. methoxy).

$A^1$ may particularly represent a straight chain $C_{2-3}$alkylene linkage, e.g. ethylene and trimethylene, especially ethylene.

$Z^1$ may particularly represent O.

$Z^1$ may also particularly represent $NR^{17}$ where $R^{17}$ is (i) hydrogen, (ii) —C(=O)—$R^9$ in which $R^9$ is as defined above, particularly an optionally substituted aryl group (such as optionally substituted phenyl), $C_{1-4}$alkyl (e.g. methyl), $C_{1-4}$alkyl substituted by an acidic group (e.g. —$CH_2CH_2CO_2H$) or $C_{2-4}$alkyl substituted by —$NY^4Y^5$ in which $Y^4$ and $Y^5$ are as defined above (e.g. —$CH_2CH_2NMe_2$) or (iii) —C(=O)—$OR^{14}$ in which $R^{14}$ is as defined above, particularly alkyl (e.g. tertiary-butyl).

$L^1$ may particularly represent an optionally substituted alkylene linkage, especially optionally substituted ethylene or propylene, preferably optionally substituted ethylene. Preferred optional substituents include lower alkyl, aryl, heteroaryl, —N($R^8$)—C(=O)—$R^9$, —N($R^8$)—C(=O)—$OR^9$, —N($R^8$)—$SO_2$—$R^9$, —$NY^4Y^5$ and —[C(=O)—N($R^{10}$)—C($R^5$)($R^{11}$)]$_p$—C(=O)—$NY^4Y^5$ or alkyl substituted by carboxy (or an acid bioisostere), —ZH, —$ZR^{14}$, —C(=O)—$NY^4Y^5$ or $NY^4Y^5$. In one preferred embodiment $L^1$ is a group

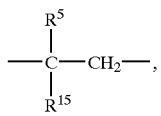

[where $R^5$ is hydrogen or lower alkyl (e.g. methyl) and $R^{15}$ represents hydrogen or lower alkyl, or where $R^5$ is hydrogen and $R^{15}$ represents aryl, heteroaryl, —N($R^8$)—C(=O)—$R^9$, —N($R^8$)—C(=O)—$OR^9$, —N($R^8$)—$SO_2$—$R^9$, —$NY^4Y^5$ or —[C(=O)—N($R^{10}$)—C($R^5$)($R^{11}$)]$_p$—C(=O)—$NY^4Y^5$, or is alkyl substituted by carboxy (or an acid bioisostere), —ZH, —$ZR^{14}$, —C(=O)—$NY^4Y^5$ or —$NY^4Y^5$], and more preferably a group

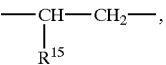

particularly

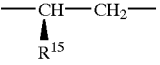

[where $R^{15}$ represents hydrogen, lower alkyl, aryl, heteroaryl, —N($R^8$)—C(=O)—$R^9$, —N($R^8$)—C(=O)—$OR^9$, —N($R^8$)—$SO_2$—$R^9$ or —$NY^4Y^5$ or alkyl substituted by carboxy, —OH, —$OR^{14}$ or —C(=O)—$NY^4Y^5$]. In another preferred embodiment $L^1$ is a group

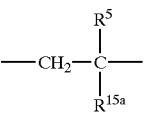

where $R^5$ is hydrogen or lower alkyl (e.g. methyl) and $R^{15a}$ represents lower alkyl, or where $R^5$ is hydrogen and $R^{15a}$ represents aryl, heteroaryl, —N($R^8$)—C(=O)—$R^9$, —N($R^8$)—C(=O)—$OR^9$, —N($R^8$)—$SO_2$—$R^9$, —$NY^4Y^5$ or —[C(=O)—N($R^{10}$)—C($R^5$)($R^{11}$)]$_p$—C(=O)—$NY^4Y^5$, or alkyl substituted by carboxy (or an acid bioisostere), —ZH, —$ZR^{14}$, —C(=O)—$NY^4Y^5$ or —$NY^4Y^5$], and is more preferably a group

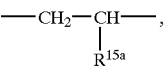

particularly

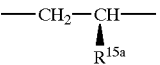

[where $R^{15a}$ represents —N($R^8$)—C(=O)—$R^9$, or —N($R^8$)—$SO_2$—$R^9$].

$L^1$ may also particularly represent an unsubstituted alkenylene linkage, especially vinylene.

$L^1$ may also particularly represent a —$Z^2$—$R^{12}$ linkage, such as —O—$CH_2$—, —O—$CH_2$—$CH_2$—, —S(O)$_n$—$CH_2$—, S(O)$_n$—$CH_2$—$CH_2$—, —NH—$CH_2$—, or —NH—$CH_2$—$CH_2$—.

$L^1$ may also particularly represent a —$L^5$—$L^6$—$L^7$— linkage, in which (i) $L^5$ and $L^7$ are both a direct bond and $L^6$ is optionally substituted heterocycloalkylene, such as pyrrolidindiyl, especially 3,4-pyrrolidindiyl, or cycloalkylene, such as cyclopentyl, (ii) $L^5$ is alkylene, such as methylene, $L^6$ is cycloalkylene, such as cyclopentyl, and $L^7$ is a direct bond, or (iii) $L^5$ is a direct bond, $L^6$ is cycloalkylene, such as cyclopentyl, and $L^7$ is alkylene, such as methylene.

Y may particularly represent carboxy.

It is to be understood that this invention covers all appropriate combinations of the particular and preferred groupings referred to herein.

A particular group of compounds of the invention are compounds of formula (Ix):

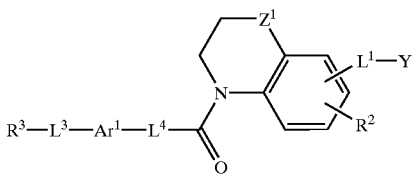

(Ix)

in which $R^2$, $R^3$, $Ar^1$, $L^1$, $L^3$, $L^4$ and Y are as hereinbefore defined and $Z^1$ represents $NR^{17}$ (where $R^{17}$ is as hereinbefore defined) and their prodrugs and pharmaceutically acceptable salts, and solvates (e.g. hydrates) of compounds of formula (Ix) and their prodrugs.

Another particular group of compounds of the invention are compounds of formula (Ia):

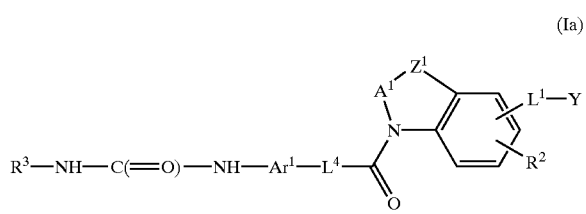

(Ia)

in which $R^2$, $R^3$, $A^1$, $Ar^1$, $L^1$, $L^4$, Y and $Z^1$ are as hereinbefore defined, and the corresponding N-oxides, and their prodrugs; and pharmaceutically acceptable salts and solvates (e.g. hydrates) of such compounds and their N-oxides and prodrugs.

Compounds of formula (Ia) in which $R^3$ represents an optionally substituted aryl group, particularly an optionally substituted phenyl group, such as a 2-substituted phenyl, especially 2-methylphenyl, are preferred.

Compounds of formula (Ia) in which $R^3$ represents an optionally substituted heteroaryl group, particularly an optionally substituted pyridyl, such as optionally substituted 2-pyridyl, especially 3-methyl-2-pyridyl, are also preferred.

Compounds of formula (Ia) in which $Ar^1$ represents an optionally substituted phenylene, especially optionally substituted m- or p-phenylene, more especially optionally substituted p-phenylene, are preferred. Compounds of formula (Ia) in which $Ar^1$ represents 3-substituted p-phenylene, in which the substituent is ortho to the $R^3$—NH—C(=O)—NH— group, are particularly preferred. Preferred optional substituents include halo, $C_{1-4}$alkyl, $C_{1-4}$alkoxy, $C_{1-4}$alkylthio, $C_{1-4}$alkylsulphinyl and $C_{1-4}$alkylsulphonyl, especially chloro, methyl, ethyl, methoxy, methylthio, methylsulphinyl and methylsulphonyl.

Compounds of formula (Ia) in which $Ar^1$ is an optionally substituted heteroaryldiyl, such as optionally substituted pyridinediyl, particularly a p-pyridinediyl, more particularly a pyridine-2,5-diyl, in which the $R^3$—NH—C(=O)—NH— group is adjacent to the pyridyl nitrogen atom, and which is substituted in the 4- or 6-position, are also preferred. Preferred optional substituents include $C_{1-4}$alkyl and $C_{1-4}$alkoxy, especially methyl and methoxy.

Compounds of formula (Ia) in which $L^4$ represents a straight or branched $C_{1-6}$alkylene chain, more particularly a straight $C_{1-4}$alkylene chain such as methylene or ethylene, especially methylene, are preferred.

Compounds of formula (Ia) in which $A^1$ represents ethylene are preferred.

Compounds of formula (Ia) in which $Z^1$ represents O are preferred.

Compounds of formula (Ia) in which $Z^1$ represents NH are also preferred.

Compounds of formula (Ia) in which $Z^1$ represents N—C (=O)—$R^9$ in which $R^9$ is (i) optionally substituted aryl, such as optionally substituted phenyl, (ii) $C_{1-4}$alkyl (e.g. methyl), $C_{1-4}$alkyl substituted by an acidic group (e.g. —$CH_2CH_2CO_2H$) or $C_{2-4}$alkyl substituted by —$NY^4Y^5$ in which $Y^4$ and $Y^5$ are as defined above (e.g. —$CH_2CH_2NMe_2$) are also preferred.

Compounds of formula (Ia) in which $Z^1$ represents N—C (=O)—$OR^{14}$ in which $R^{14}$ is alkyl (e.g. tertiary-butyl) are also preferred.

Compounds of formula (Ia) in which $R^2$ represents hydrogen are preferred.

Compounds of formula (Ia) in which $L^1$ represents an optionally substituted alkylene linkage, particularly optionally substituted ethylene or optionally substituted propylene, especially ethylene optionally substituted with lower alkyl, aryl, heteroaryl, —$N(R^8)$—C(=O)—$R^9$, —$N(R^8)$—C (=O)—$OR^9$, —$N(R^8)$—$SO_2$—$R^9$, —$NY^4Y^5$ or —[C (=O)—$N(R^{10})$—$C(R^5)(R^{11})]_p$—C(=O)—$NY^4Y^5$, or alkyl substituted by carboxy (or an acid bioisostere), —ZH, —$ZR^{14}$, —C(=O)—$NY^4Y^5$ or —$NY^4Y^5$, are preferred. In one preferred embodiment $L^1$ is a group

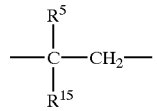

[where $R^5$ is hydrogen or lower alkyl (e.g. methyl) and $R^{15}$ represents hydrogen or lower alkyl, or where $R^5$ is hydrogen and $R^{15}$ represents aryl, heteroaryl, —$N(R^8)$—C(=O)—$R^9$, —$N(R^8)$—C(=O)—$OR^9$, —$N(R^8)$—$SO_2$—$R^9$, —$NY^4Y^5$ or —[C(=O)—$N(R^{10})$—$C(R^5)(R^{11})]_p$—C(=O)—$NY^4Y^5$, or alkyl substituted by carboxy (or an acid bioisostere), —ZH, —$ZR^{14}$, —C(=O)—$NY^4Y^5$ or —$NY^4Y^5$], and is more preferably a group

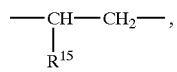

particularly

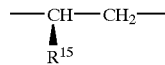

[where $R^{15}$ represents hydrogen, lower alkyl, aryl, heteroaryl, —$N(R^8)$—C(=O)—$R^9$, —$N(R^8)$—C(=O)—$OR^9$, —$N(R^8)$—$SO_2$—$R^9$ or —$NY^4Y^5$ or alkyl substituted by carboxy, —OH, —$OR^{14}$ or —C(=O)—$NY^4Y^5$]. In another preferred embodiment $L^1$ is a group

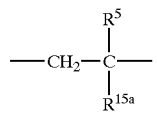

[where $R^5$ is hydrogen or lower alkyl (e.g. methyl) and $R^{15a}$ represents lower alkyl, or where $R^5$ is hydrogen and $R^{15a}$ represents aryl, heteroaryl, —$N(R^8)$—C(=O)—$R^9$, —$N(R^8)$—C(=O)—$OR^9$, —$N(R^8)$—$SO_2$—$R^9$, —$NY^4Y^5$ or —[C(=O)—$N(R^{10})$—$C(R^5)(R^{11})]_p$—C(=O)—$NY^4Y^5$, or alkyl substituted by carboxy (or an acid bioisostere), —ZH, —$ZR^{14}$, —C(=O)—$NY^4Y^5$ or —$NY^4Y^5$], and is more preferably a group

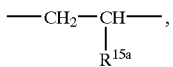

particularly

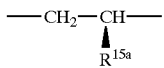

[where $R^{15a}$ represents —N($R^8$)—C(=O)—$R^9$, or —N($R^8$)—SO$_2$—$R^9$].

Compounds of formula (Ia) in which Y represents carboxy are preferred.

A preferred group of compounds of the invention are compounds of formula (Ia) in which: $R^2$ is hydrogen; $R^3$ is a 2-substituted phenyl [especially 2-methyl(or methoxy) phenyl]; $A^1$ is ethylene; $Ar^1$ is optionally substituted m- or p-phenylene (especially 3-chloro-p-phenylene, 3-methyl-p-phenylene, 3-ethyl-p-phenylene, 3-methoxy-p-phenylene, 3-methylthio-p-phenylene, 3-methylsulphinyl-p-phenylene and 3-methylsulphonyl-p-phenylene) or optionally substituted p-pyridinediyl [especially 4(or 6)-methyl(or methoxy)-p-pyridine-2,5-diyl]; $L^1$ is a

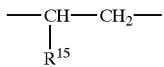

group particularly a

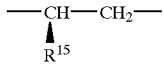

group, where $R^{15}$ represents hydrogen, lower alkyl, aryl, heteroaryl, —N($R^8$)—C(=O)—$R^9$, —N($R^8$)—C(=O)—O$R^9$, —N($R^8$)—S$_2$—$R^9$ or —N$Y^4Y^5$, or alkyl substituted by carboxy (or an acid bioisostere), —OH, —O$R^{14}$, —C(=O)—N$Y^4Y^5$; $L^4$ represents a straight or branched $C_{1-6}$alkylene chain, especially methylene; Y represents carboxy; and $Z^1$ represents O, NH, N—C(=O)$R^9$ [especially N—C(=O)-Ph, N—C(=O)—CH$_3$, N—C(=O)—CH$_2$CH$_2$CO$_2$H and N—C(=O)—CH$_2$CH$_2$NMe$_2$] or N—C(=O)—O$R^{14}$ [especially N—C(=O)—OCMe$_3$]; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ia) in which: $R^2$ is hydrogen; $R^3$ is a 2-substituted phenyl [especially 2-methyl(or methoxy) phenyl]; $A^1$ is ethylene; $Ar^1$ is optionally substituted m- or p-phenylene (especially 3-chloro-p-phenylene, 3-methyl-p-phenylene, 3-methoxy-p-phenylene, 3-methylthio-p-phenylene, 3-methylsulphinyl-p-phenylene and 3-methylsulphonyl-p-phenylene) or optionally substituted p-pyridinediyl [especially 4(or 6)-methyl(or methoxy)-p-pyridine-2,5-diyl]; $L^1$ is a

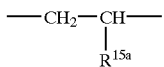

group, particularly

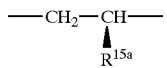

[where $R^{15a}$ represents —N($R^8$)—C(=O)—$R^9$, or —N($R^8$)—SO$_2$—$R^9$]; $L^4$ represents a straight or branched $C_{1-6}$alkylene chain, especially methylene; Y represents carboxy; and $Z^1$ represents O, NH, N—C(=O)$R^9$ [especially N—C(=O)-Ph, N—C(=O)—CH$_3$, N—C(=O)—CH$_2$CH$_2$CO$_2$H and N—C(=O)—CH$_2$CH$_2$NMe$_2$] or N—C(=O)—O$R^{14}$ [especially N—C(=O)—OCMe$_3$]; and the corresponding N-oxides, and their prodrugs; and pharmaceutically acceptable salts and solvates (e.g. hydrates) of such compounds and their N-oxides and prodrugs.

Another particular group of compounds of the invention are compounds of formula (Ib):

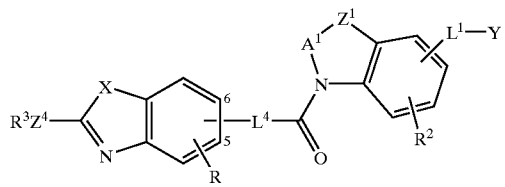

(Ib)

in which $R^2$, $R^3$, $A^1$, $L^2$, Y and $Z^1$ are as hereinbefore defined, X is N$R^5$ or O, $Z^4$ represents a direct bond, N$R^5$, O or S(O)$_n$ (where $R^5$ and n are as hereinbefore defined), and R is hydrogen or an aryl group substituent, and the corresponding N-oxides, and their prodrugs; and pharmaceutically acceptable salts and solvates (e.g. hydrates) of such compounds and their N-oxides and prodrugs.

Compounds of formula (Ib) in which $R^3$ represents optionally substituted aryl, especially 2-substituted phenyl, are preferred. Preferred optional substituents include lower alkyl (e.g. methyl), lower alkoxy (e.g. methoxy), halo (e.g. fluoro or chloro) and $Y^1Y^2$N— (e.g. dimethylamino). $R^3$ especially represents ortho-tolyl.

Compounds of formula (Ib) in which $Z^4$ represents NH are preferred.

Compounds of formula (Ib) in which R represents hydrogen, halo (e.g. chloro), lower alkyl (e.g. methyl or ethyl) or lower alkoxy (e.g. methoxy) are preferred.

Compounds of formula (Ib) in which $L^4$ represents a straight or branched $C_{1-6}$alkylene chain, especially a straight or branched $C_{1-4}$alkylene chain, more especially methylene, are preferred.

Compounds of formula (Ib) in which $A^1$ represents ethylene are preferred.

Compounds of formula (Ib) in which $Z^1$ represents O are preferred.

Compounds of formula (Ib) in which $Z^1$ represents NH are also preferred.

Compounds of formula (Ib) in which $Z^1$ represents N—C(=O)—$R^9$ in which $R^9$ is (i) optionally substituted aryl, such as optionally substituted phenyl, (ii) $C_{1-4}$alkyl (e.g. methyl), $C_{1-4}$alkyl substituted by an acidic group (e.g. —CH$_2$CH$_2$CO$_2$H) or $C_{2-4}$alkyl substituted by —N$Y^4Y^5$ in which $Y^4$ and $Y^5$ are as defined above (e.g. —CH$_2$CH$_2$NMe$_2$) are also preferred.

Compounds of formula (Ib) in which $Z^1$ represents N—C(=O)—O$R^{14}$ in which $R^{14}$ is alkyl (e.g. tertiary-butyl) are also preferred.

Compounds of formula (Ib) in which $R^2$ represents hydrogen are preferred.

Compounds of formula (Ib) in which $L^1$ represents an optionally substituted alkylene linkage, particularly optionally substituted ethylene or optionally substituted propylene, especially ethylene optionally substituted with lower alkyl, aryl, heteroaryl, —N($R^8$)—C(=O)—$R^9$, —N($R^8$)—C(=O)—O$R^9$, —N($R^8$)—$SO_2$—$R^9$, —N$Y^4Y^5$ or —[C(=O)—N($R^{10}$)—C($R^5$)($R^{11}$)]$_p$—C(=C)—N$Y^4Y^5$, or alkyl substituted by carboxy (or an acid bioisostere), —ZH, —Z$R^{14}$, —C(=O)—N$Y^4Y^5$ or —N$Y^4Y^5$, are preferred. In one preferred embodiment $L^1$ is a group

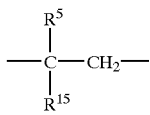

[where $R^5$ is hydrogen or lower alkyl (e.g. methyl) and $R^{15}$ represents hydrogen or lower alkyl, or where $R^5$ is hydrogen and $R^{15}$ represents aryl, heteroaryl, —N($R^8$)—C(=O)—$R^9$, —N($R^8$)—C(=O)—O$R^9$, —N($R^8$)—$SO_2$—$R^9$, —N$Y^4Y^5$ or —[C(=O)—N($R^{10}$)—C($R^5$)($R^{11}$)]$_p$—C(=O)—N$Y^4Y^5$, or alkyl substituted by carboxy (or an acid bioisostere), —ZH, —Z$R^{14}$, —C(=O)—N$Y^4Y^5$ or —N$Y^4Y^5$], and is more preferably a group

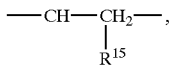

particularly

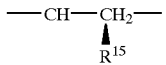

[where $R^{15}$ represents hydrogen, lower alkyl, aryl, heteroaryl, —N($R^8$)—C(=O)—$R^9$, —N($R^8$)—C(=O)—O$R^9$, —N($R^8$)—$SO_2$—$R^9$ or —N$Y^4Y^5$ or alkyl substituted by carboxy, —OH, —O$R^{14}$ or —C(=O)—N$Y^4Y^5$]. In another preferred embodiment $L^1$ is a group

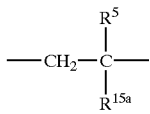

[where $R^5$ is hydrogen or lower alkyl (e.g. methyl) and $R^{15a}$ represents lower alkyl, or where $R^5$ is hydrogen and $R^{15a}$ represents aryl, heteroaryl, —N($R^8$)—C(=O)—$R^9$, —N($R^8$)—C(=O)—O$R^9$, —N($R^8$)—$SO_2$—$R^9$, —N$Y^4Y^5$ or —[C(=O)—N($R^{10}$)—C($R^5$)($R^{11}$)]$_p$—C(=O)—N$Y^4Y^5$, or alkyl substituted by carboxy (or an acid bioisostere), —ZH, —Z$R^{14}$, —C(=O)—N$Y^4Y^5$ or —N$Y^4Y^5$], and is more preferably a group

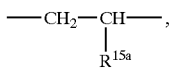

particularly

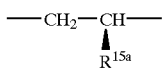

[where $R^{15a}$ represents —N($R^8$)—C(=O)—$R^9$, or —N($R^8$)—$SO_2$—$R^9$].

Compounds of formula (Ib) in which Y represents carboxy are preferred.

The group

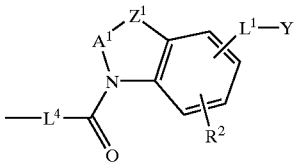

may preferably be attached at the ring 6 position or the ring 5 or 6 position when X is N$R^5$ and $R^5$ is lower alkyl.

A preferred group of compounds of the invention are compounds of formula (Ib) in which: R is hydrogen, chloro, methyl, ethyl or methoxy; $R^2$ is hydrogen; $R^3$ is optionally substituted aryl (especially ortho-tolyl); $A^1$ is ethylene; $L^1$ is a

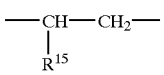

group particularly a

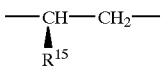

group, where $R^{15}$ represents hydrogen, lower alkyl, aryl, heteroaryl, —N($R^8$)—C(=O)—$R^9$, —N($R^8$)—C(=O)—O$R^9$, —N($R^8$)—$SO_2$—$R^9$ or —N$Y^4Y^5$, or alkyl substituted by carboxy (or an acid bioisostere), —OH, —Z$R^{14}$, —C(=O)—N$Y^4Y^5$ or —N$Y^4Y^5$; $L^4$ is a straight or branched $C_{1-4}$alkylene chain, especially methylene; X is O; Y is carboxy; $Z^1$ is O, NH, N—C(=O)$R^9$ [especially N—C(=O)-Ph, N—C(=O)—$CH_3$, N—C(=O)—$CH_2CH_2CO_2H$ and N—C(=O)—$CH_2CH_2NMe_2$) or N—C(=O)—O$R^{14}$ [especially N—C(=O)—O$CMe_3$]; $Z^4$ is NH; and the group

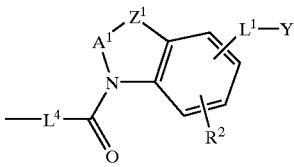

is attached at the ring 6 position; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ib) in which: R is hydrogen, chloro, methyl, ethyl or methoxy; $R^2$ is hydrogen; $R^3$ is optionally substituted aryl (especially ortho-tolyl); $A^1$ is ethylene; $L^1$ is a

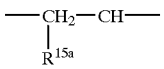

group, particularly

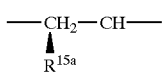

[where $R^{15a}$ represents —N($R^8$)—C(=O)—$R^9$, or —N($R^8$)—SO$_2$—$R^9$]; $L^4$ is a straight or branched $C_{1-4}$alkylene chain, especially methylene; X is O; Y is carboxy; $Z^1$ is O, NH, N—C(=O)$R^9$ [especially N—C(=O)-Ph, N—C(=O)—CH$_3$, N—C(=O)—CH$_2$CH$_2$CO$_2$H and N—C(=O)—CH$_2$CH$_2$NMe$_2$] or N—C(=O)—OR$^{14}$ [especially N—C(=O)—OCMe$_3$]; $Z^4$ is NH; and the group

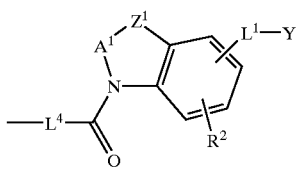

is attached at the ring 6 position; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ib) in which: $R^2$ is hydrogen; $R^3$ is optionally substituted aryl (especially ortho-tolyl); $A^1$ is ethylene; $L^1$ is a

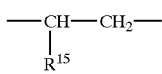

group particularly a

group, where $R^{15}$ represents hydrogen, lower alkyl, aryl, heteroaryl, —N($R^8$)—C(=O)—$R^9$, —N($R^8$)—C(=O)—OR$^9$, —N($R^8$)—SO$_2$—$R^9$ or —NY$^4$Y$^5$, or alkyl substituted by carboxy (or an acid bioisostere), —OH, —OR$^{14}$, —C(=O)—NY$^4$Y$^5$ or —NY$^4$Y$^5$; $L^4$ is a straight or branched $C_{1-4}$alkylene chain, (especially methylene); X is NR$^5$ (especially NH); Y is carboxy; $Z^1$ is O, NH, N—C(=O)$R^9$ [especially N—C(=O)-Ph, N—C(=O)—CH$_3$, N—C(=O)—CH$_2$CH$_2$CO$_2$H and N—C(=O)—CH$_2$CH$_2$NMe$_2$] or N—C(=O)—OR$^{14}$ [especially N—C(=O)—OCMe$_3$]; $Z^4$ is NH; and the group

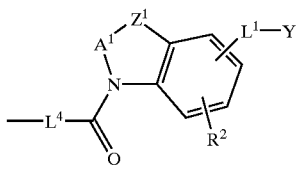

is attached at the ring 5 or 6 position; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ib) in which: $R^2$ is hydrogen; $R^3$ is optionally substituted aryl (especially ortho-tolyl); $A^1$ is ethylene; $L^1$ is a

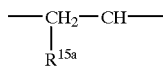

group, particularly

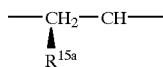

[where $R^{15a}$ represents —N($R^8$)—C(=O)—$R^9$, or —N($R^8$)—SO$_2$—$R^9$]; $L^4$ is a straight or branched $C_{1-4}$alkylene chain, especially methylene); X is NR$^5$ (especially NH); Y is carboxy; $Z^1$ represents O, NH, N—C(=O)$R^9$ [especially N—C(=O)-Ph, N—C(=O)CH$_3$, N—C(=O)—CH$_2$CH$_2$CO$_2$H and N—C(=O)—CH$_2$CH$_2$NMe$_2$] or N—C(=O)—OR$^{14}$ [especially N—C(=O)—OCMe$_3$]; $Z^4$ is NH; and the group

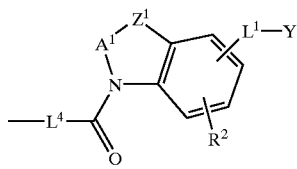

is attached at the ring 5 or 6 position; and the corresponding N-oxides, and their prodrugs; and pharmaceutically acceptable salts and solvates (e.g. hydrates) of such compounds and their N-oxides and prodrugs.

Another particular group of compounds of the invention are compounds of formula (Ic):

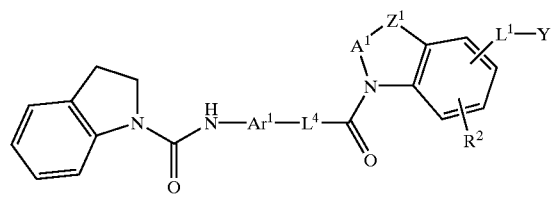

(Ic)

in which Ar$^1$, $L^4$, $A^1$, $R^2$, $L^1$, Y and $Z^1$ are as hereinbefore defined, and the corresponding N-oxides, and their prodrugs; and pharmaceutically acceptable salts and solvates (e.g. hydrates) of such compounds and their N-oxides and prodrugs.

Compounds of formula (Ic) in which Ar$^1$ represents an optionally substituted phenylene, especially optionally substituted m- or p-phenylene, more especially optionally substituted p-phenylene, are preferred. Compounds of formula (Ic) in which Ar$^1$ represents 3-substituted p-phenylene, in which the substituent is ortho to the

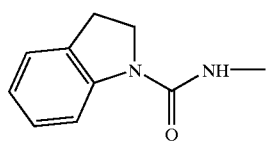

group, are particularly preferred. Preferred optional substituents include halo, $C_{1-4}$alkyl, $C_{1-4}$alkoxy, $C_{1-4}$alkylthio, $C_{1-4}$alkylsulphinyl and $C_{1-4}$alkylsulphonyl, especially chloro, methyl, ethyl, methoxy, methylthio, methylsulphinyl and methylsulphonyl.

Compounds of formula (Ic) in which $Ar^1$ is an optionally substituted heteroaryldiyl, such as optionally substituted pyridinediyl, particularly a p-pyridinediyl, more particularly a pyridine-2,5-diyl, in which the

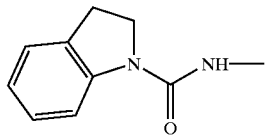

group is adjacent to the pyridyl nitrogen atom, and which is substituted in the 4- or 6-position, are also preferred. Preferred optional substituents include $C_{1-4}$alkyl and $C_{1-4}$alkoxy, especially methyl and methoxy.

Compounds of formula (Ic) in which $L^4$ represents a straight or branched $C_{1-6}$alkylene chain, especially a straight or branched $C_{1-4}$alkylene chain, more especially methylene, are preferred.

Compounds of formula (Ic) in which $A^1$ represents ethylene are preferred.

Compounds of formula (Ic) in which $Z^1$ represents O are preferred.

Compounds of formula (Ic) in which $Z^1$ represents NH are also preferred.

Compounds of formula (Ic) in which $Z^1$ represents N—C(=O)—$R^9$ in which $R^9$ is (i) optionally substituted aryl, such as optionally substituted phenyl, (ii) $C_{1-4}$alkyl (e.g. methyl), $C_{1-4}$alkyl substituted by an acidic group (e.g. —$CH_2CH_2CO_2H$) or $C_{2-4}$alkyl substituted by —$NY^4Y^5$ in which $Y^4$ and $Y^5$ are as defined above (e.g. —$CH_2CH_2NMe_2$) are also preferred.

Compounds of formula (Ic) in which $Z^1$ represents N—C(=O)—$OR^{14}$ in which $R^{14}$ is alkyl (e.g. tertiary-butyl) are also preferred.

Compounds of formula (Ic) in which $R^2$ represents hydrogen are preferred.

Compounds of formula (Ic) in which $L^1$ represents an optionally substituted alkylene linkage, particularly optionally substituted ethylene or optionally substituted propylene, especially ethylene optionally substituted with lower alkyl, aryl, heteroaryl, —N($R^8$)—C(=O)—$R^9$, —N($R^8$)—C(=O)—$OR^9$, —N($R^8$)—$SO_2$—$R^9$, —$NY^4Y^5$ or —[C(=O)—N($R^{10}$)—C($R^5$)($R^{11}$)]$_p$—C(=O)—$NY^4Y^5$, or alkyl substituted by carboxy (or an acid bioisostere), —ZH, —$ZR^{14}$, —C(=O)—$NY^4Y^5$ or —$NY^4Y^5$, are preferred. In one preferred embodiment $L^1$ is a group

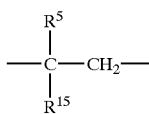

[where $R^5$ is hydrogen or lower alkyl (e.g. methyl) and $R^{15}$ represents hydrogen or lower alkyl, or where $R^5$ is hydrogen and $R^{15}$ represents aryl, heteroaryl, —N($R^8$)—C(=O)—$R^9$, —N($R^8$)—C(=O)—$OR^9$, —N($R^8$)—$SO_2$—$R^9$, —$NY^4Y^5$ or —[C(=O)—N($R^{10}$)—C($R^5$)($R^{11}$)]$_p$—C(=O)—$NY^4Y^5$, or alkyl substituted by carboxy (or an acid bioisostere), —ZH, —$ZR^{14}$, —C(=O)—$NY^4Y^5$ or —$NY^4Y^5$], and is more preferably a group

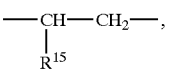

particularly

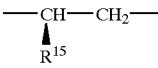

[where $R^{15}$ represents hydrogen, lower alkyl, aryl, heteroaryl, —N($R^8$)—C(=O)$R^9$, —N($R^8$)—C(=O)—$OR^9$, —N($R^8$)—$SO_2$—$R^9$ or —$NY^4Y^5$ or alkyl substituted by carboxy, —OH, —$OR^{14}$ or —C(=O)—$NY^4Y^5$]. In another preferred embodiment $L^1$ is a group

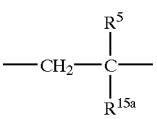

[where $R^5$ is hydrogen or lower alkyl (e.g. methyl) and $R^{15a}$ represents lower alkyl (e.g. methyl), or where $R^5$ is hydrogen and $R^{15a}$ represents aryl, heteroaryl, —N($R^8$)—C(=O)—$R^9$, —N($R^8$)—C(=O)—$OR^9$, —N($R^8$)—$SO_2$—$R^9$, —$NY^4Y^5$ or —[C(=O)—N($R^{10}$)—C($R^5$)($R^{11}$)]$_p$—C(=O)—$NY^4Y^5$ or alkyl substituted by carboxy (or an acid bioisostere), —ZH, —$ZR^{14}$, —C(=O)—$NY^4Y^5$ or —$NY^4Y^5$], and is more preferably a group

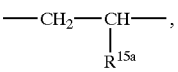

particularly

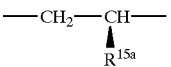

where $R^{15a}$ represents —N($R^8$)—C(=O)—$R^9$, or —N($R^8$)—$SO_2$—$R^9$].

Compounds of formula (Ic) in which Y represents carboxy are preferred.

A preferred group of compounds of the invention are compounds of formula (Ic) in which: $R^2$ is hydrogen; $A^1$ is ethylene; $Ar^1$ is optionally substituted m- or p-phenylene (especially 3-chloro-p-phenylene, 3-methyl-p-phenylene, 3-methoxy-p-phenylene, 3-methylthio-p-phenylene, 3-methylsulphinyl-p-phenylene and 3-methylsulphonyl-p-phenylene) or optionally substituted p-pyridinediyl [especially 4(or 6)-methyl(or methoxy)-p-pyridine-2,5-diyl]; $L^1$ is a

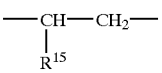

group particularly a

group, where $R^{15}$ represents hydrogen, methyl, aryl, heteroaryl, —N($R^8$)—C(=O)—$R^9$, —N($R^8$)—C(=O)—

OR$^9$, —N(R$^8$)—SO$_2$—R$^9$ or —NY$^4$Y$^5$, or alkyl substituted by carboxy, —OH, —OR$^{14}$ or —C(=O)—NY$^4$Y$^5$]; L$^4$ is a straight or branched C$_{1-4}$alkylene chain, (especially methylene); Y is carboxy; and Z$^1$ is O, NH, N—C(=O)R$^9$ [especially N—C(=O)-Ph, N—C(=O)—CH$_3$, N—C(=O)—CH$_2$CH$_2$CO$_2$H and N—C(=O)—CH$_2$CH$_2$NMe$_2$] or N—C(=O)—OR$^{14}$ [especially N—C(=O)—OCMe$_3$]; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ic) in which: R$^2$ is hydrogen; A$^1$ is ethylene; Ar$^1$ is optionally substituted m- or p-phenylene (especially 3-chloro-p-phenylene, 3-methyl-p-phenylene, 3-methoxy-p-phenylene, 3-methylthio-p-phenylene, 3-methylsulphinyl-p-phenylene and 3-methylsulphonyl-p-phenylene) or optionally substituted p-pyridinediyl [especially 4(or 6)-methyl(or methoxy)-p-pyridine-2,5-diyl]; L$^1$ is a

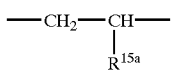

group, particularly

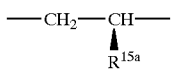

[where R$^{15a}$ represents —N(R$^8$)—C(=O)—R$^9$, or —N(R$^8$)—SO$_2$—R$^9$]; L$^4$ is a straight or branched C$_{1-4}$alkylene chain, (especially methylene); Y is carboxy; and Z$^1$ is O, NH, N—C(=O)R$^9$ [especially N—C(=O)-Ph, N—C(=O)—CH$_3$, N—C(=O)—CH$_2$CH$_2$CO$_2$H and N—C(=O)—CH$_2$CH$_2$NMe$_2$] or N—C(=O)—OR$^{14}$ [especially N—C(=O)—OCMe$_3$]; and the corresponding N-oxides, and their prodrugs; and pharmaceutically acceptable salts and solvates (e.g. hydrates) of such compounds and their N-oxides and prodrugs.

Another particular group of compounds of the invention are compounds of formula (Id):

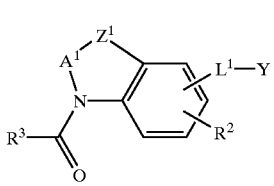

(Id)

in which R$^3$, A$^1$, R$^2$, L$^1$, Y and Z$^1$ are as hereinbefore defined, and the corresponding N-oxides, and their prodrugs; and pharmaceutically acceptable salts and solvates (e.g. hydrates) of such compounds and their N-oxides and prodrugs.

Compounds of formula (Id) in which R$^3$ represents optionally substituted aryl, especially optionally substituted phenyl, are preferred. Preferred optional substituents include aryloxy, cyano, halo (e.g. chloro or fluoro), lower alkoxy (e.g. methoxy), lower alkyl (e.g. methyl), nitro and perfluoroloweralkyl (e.g. trifluoromethyl). R$^3$ especially represents 2-chlorophenyl, 5-chloro-2-cyanophenyl, 2-chloro-6-methylphenyl, 2,6-dichlorophenyl, 2,6-difluorophenyl, 4-fluoro-2-trifluoromethyl, 2-methyl-4-nitrophenyl, 2-methyl-5-nitrophenyl, 2-nitrophenyl, 3-nitrophenyl and 2-phenoxyphenyl.

Compounds of formula (Id) in which R$^3$ represents optionally substituted heteroaryl, especially isoquinolinyl, isoxazolyl, pyrazolopyrimidinyl, pyridyl, pyrimidinyl, quinolinyl, thiazolyl and triazolyl, each optionally substituted by one or more aryl group substituents, are preferred. Preferred optional substituents include alkyl-C(=O)—, aryl, cyano, halo, (e.g. chloro or fluoro), lower alkoxy (e.g. methoxy), lower alkyl (e.g. methyl), lower alkylsulphonyl, lower alkylthio, nitro and perfluoroloweralkyl (e.g. trifluoromethyl). R$^3$ especially represents quinolin-4-yl, isoquinolin-2-yl, 2,4-pyridin-3-yl, 2,6-dimethyl-4-trifluoromethylpyridin-3-yl, 4-trifluoromethylpyridin3-yl, 2-phenyl-4-methyl-1,2,3-triazol-5-yl, 3,5-dimethylisoxazol-4-yl, 2,7-dimethylpyrazolo[1,5-a]pyrimidin-6-yl, 2-isopropyl-4-methylthiazol-5-yl and 4-trifluoromethylpyrimidin-5-yl.

Compounds of formula (Id) in which R$^3$ represents arylalkyl in which the aryl is optionally substituted by one or more aryl group substituents (particular optional substituents include halo, hydroxy and methoxy) are also preferred. R$^3$ especially represents optionally substituted benzyl, particularly 4-hydroxybenzyl, 3-chloro-4-hydroxybenzyl, 3-fluoro-4-hydroxybenzyl and 4-hydroxy-3-methoxybenzyl.

Compounds of formula (Id) in which A$^1$ represents ethylene are also preferred.

Compounds of formula (Id) in which Z$^1$ represents O are preferred.

Compounds of formula (Id) in which Z$^1$ represents NH are also preferred.

Compounds of formula (Id) in which Z$^1$ represents N—C(=O)—R$^9$ in which R$^9$ is (i) optionally substituted aryl, such as optionally substituted phenyl, (ii) C$_{1-4}$alkyl (e.g. methyl), C$_{1-4}$alkyl substituted by an acidic group (e.g. —CH$_2$CH$_2$CO$_2$H) or C$_{2-4}$alkyl substituted by —NY$^4$Y$^5$ in which Y$^4$ and Y$^5$ are as defined above (e.g. —CH$_2$CH$_2$NMe$_2$) are also preferred.

Compounds of formula (Id) in which Z$^1$ represents N—C(=O)—OR$^{14}$ in which R$^{14}$ is alkyl (e.g. tertiary-butyl) are also preferred.

Compounds of formula (Id) in which R$^2$ represents hydrogen are preferred.

Compounds of formula (Id) in which L$^1$ represents an optionally substituted alkylene linkage, particularly optionally substituted ethylene or optionally substituted propylene, especially ethylene optionally substituted with lower alkyl (e.g. methyl), aryl, heteroaryl, —N(R$^8$)—C(=O)—R$^9$, —N(R$^8$)—C(=O)—OR$^9$, —N(R$^8$)—SO$_2$—R$^9$, —NY$^4$Y$^5$ or —[C(=O)—N(R$^{10}$)—C(R$^5$)(R$^{11}$)]$_p$—C(=O)—NY$^4$Y$^5$, or alkyl substituted by carboxy (or an acid bioisostere), —ZH, —ZR$^{14}$, —C(=O)—NY$^4$Y$^5$ or —NY$^4$Y$^5$, are preferred. In one preferred embodiment L$^1$ is a group

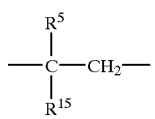

[where R$^5$ is hydrogen or lower alkyl (e.g. methyl) and R$^{15}$ represents hydrogen or lower alkyl, or where R$^5$ is hydrogen and R$^{15}$ represents aryl, heteroaryl, —N(R$^8$)—C(=O)—R$^9$, —N(R$^8$)—C(=O)—OR$^9$, —N(R$^8$)—SO$_2$—R$^9$, —NY$^4$Y$^5$ or —[C(=O)—N(R$^{10}$)—C(R$^5$)(R$^{11}$)]$_p$—C(=O)—NY$^4$Y$^5$, or alkyl substituted by carboxy (or an acid bioisostere), —ZH, —ZR$^{14}$, —C(=O)—NY$^4$Y$^5$ or —NY$^4$Y$^5$], and is more preferably a group

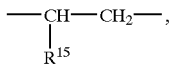

particularly

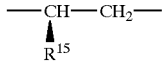

[where $R^{15}$ represents hydrogen, lower alkyl, aryl, heteroaryl, —N($R^8$)—C(=O)—$R^9$, —N($R^8$)—C(=O)—O$R^9$, —N($R^8$)—SO$_2$—$R^9$ or —N$Y^4Y^5$, or alkyl substituted by carboxy, —OH, —O$R^{14}$ or —C(=O)—N$Y^4Y^5$]. In another preferred embodiment $L^1$ is a group

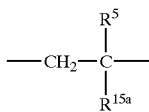

[where $R^5$ is hydrogen or lower alkyl (e.g. methyl) and $R^{15a}$ represents lower alkyl, or, where $R^5$ is hydrogen and $R^{15a}$ represents aryl, heteroaryl, —N($R^8$)—C(=O)—$R^9$, —N($R^8$)—C(=O)—O$R^9$, —N($R^8$)—SO$_2$—$R^9$, —N$Y^4Y^5$ or —[C(=O)—N($R^{10}$)—C($R^5$)($R^{11}$)]$_p$—C(=O)—N$Y^4Y^5$, or alkyl substituted by carboxy (or an acid bioisostere), —ZH, —Z$R^{14}$, —C(=O)—N$Y^4Y^5$ or —N$Y^4Y^5$], and is more preferably a group

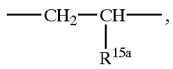

particularly

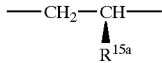

[where $R^{15a}$ represents —N($R^8$)—C(=O)—$R^9$, or —N($R^8$)—SO$_2$—$R^9$].

Compounds of formula (Id) in which Y represents carboxy are preferred.

A preferred group of compounds of the invention are compounds of formula (Id) in which: $R^2$ is hydrogen; $R^3$ is optionally substituted phenyl (especially 2-chlorophenyl, 5-chloro-2-cyanophenyl, 2-chloro-6-methylphenyl, 2,6-dichlorophenyl, 2,6-difluorophenyl, 4-fluoro-2-trifluoromethyl, 2-methyl-4-nitrophenyl, 2-methyl-5-nitrophenyl, 2-nitrophenyl, 3-nitrophenyl and 2-phenoxyphenyl), optionally substituted heteroaryl (especially quinolin-4-yl, isoquinolin-2-yl, 2,4-pyridin-3-yl, 2,6dimethyl-4-trifluoromethylpyridin-3-yl, 4-trifluoromethylpyridin3-yl, 2-phenyl-4-methyl-1,2,3-triazol-5-yl, 3,5-dimethylisoxazol-4-yl, 2,7-dimethylpyrazolo-[1,5a]pyrimidin-6-yl, 2-isopropyl-4-methylthiazol-5-yl and 4-trifluoromethylpyrimidin-5-yl) or optionally substituted benzyl (especially 4-hydroxybenzyl, 3-chloro-4-hydroxybenzyl, 3-fluoro-4-hydroxybenzyl and 4-hydroxy-3-methoxybenzyl); $A^1$ is ethylene; $L^1$ is a

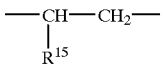

group particularly a

group, where $R^{15}$ represents hydrogen, methyl, aryl, heteroaryl, —N($R^8$)—C(=O)—$R^9$, —N($R^8$)—C(=O)—O$R^9$, —N($R^8$)—SO$_2$—$R^9$ or —N$Y^4Y^5$, or alkyl substituted by carboxy, —OH, —O$R^{14}$ or —C(=O)—N$Y^4Y^5$]; Y is carboxy; and $Z^1$ represents O, NH, N—C(=O)$R^9$ [especially N—C(=O)-Ph, N—C(=O)—CH$_3$, N—C(=O)—CH$_2$CH$_2$CO$_2$H and N—C(=O)—CH$_2$CH$_2$NMe$_2$] or N—C(=O)—O$R^{14}$ [especially N—C(=O)—OCMe$_3$]; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Id) in which: $R^2$ is hydrogen; $R^3$ is optionally substituted phenyl (especially 2-chlorophenyl, 5-chloro-2-cyanophenyl, 2-chloro-6-methylphenyl, 2,6-dichlorophenyl, 2,6-difluorophenyl, 4-fluoro-2-trifluoromethyl, 2-methyl-4-nitrophenyl, 2-methyl-5-nitrophenyl, 2-nitrophenyl, 3-nitrophenyl and 2-phenoxyphenyl), optionally substituted heteroaryl (especially quinolin-4-yl, isoquinolin-2-yl, 2,4-pyridin-3-yl, 2,6-dimethyl-4-trifluoromethylpyridin-3-yl, 4-trifluoromethylpyridin3-yl, 2-phenyl-4-methyl-1,2,3-triazol-5-yl, 3,5-dimethylisoxazol-4-yl, 2,7-dimethylpyrazolo-[1,5-a]pyrimidin-6-yl, 2-isopropyl-4-methylthiazol-5-yl and 4-trifluoromethylpyrimidin-5-yl) or optionally substituted benzyl (especially 4-hydroxybenzyl, 3-chloro-4-hydroxybenzyl, 3-fluoro-4-hydroxybenzyl and 4-hydroxy-3-methoxybenzyl); $A^1$ is ethylene; $L^1$ is a

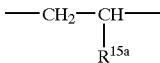

group, particularly

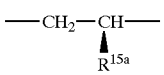

[where $R^{15a}$ represents —N($R^8$)—C(=O)—$R^9$, or —N($R^8$)—SO$_2$—$R^9$]; Y is carboxy; and $Z^1$ represents O, NH, N—C(=O)$R^9$ [especially N—C(=O)-Ph, N—C(=O)—CH$_3$, N—C(=O)—CH$_2$CH$_2$CO$_2$H and N—C(=O)—CH$_2$CH$_2$NMe$_2$] or N—C(=O)—O$R^{14}$ [especially N—C(=O)—OCMe$_3$]; and the corresponding N-oxides, and their prodrugs; and pharmaceutically acceptable salts and solvates (e.g. hydrates) of such compounds and their N-oxides and prodrugs.

Compounds of formula (Ia), (Ib), (Ic) and (Id) in which $R^{15}$ represents hydrogen are preferred.

Compounds of formula (Ia), (Ib), (Ic) and (Id) in which $R^{15}$ represents lower alkyl (e.g. methyl, ethyl, propyl, butyl) are also preferred.

Compounds of formula (Ia), (Ib), (Ic) and (Id) in which $R^{15}$ represents aryl (e.g. optionally substituted phenyl) are also preferred.

Compounds of formula (Ia), (Ib), (Ic) and (Id) in which $R^{15}$ represents —N($R^8$)—C(=O)—$R^9$, especially where $R^8$ is hydrogen or lower alkyl (e.g. methyl) and $R^9$ is lower alkyl (e.g. methyl), aryl (e.g. optionally substituted phenyl), heteroaryl (e.g. pyridyl, isoxazolyl, triazolyl, pyrimidinyl, thiazolyl, or pyrazolopyrimidinyl each optionally substituted by one or more aryl group substituents), alkyl substituted by alkoxy (e.g. —$CH_2$—O—$CH_2$—$CH_2$—$OCH_3$), alkyl substituted by carboxy (e.g. —$CH_2$—$CH_2$—$CO_2H$ and —$CH_2$—$CH_2$—$CH_2$—$CO_2H$) or alkyl substituted by —$NY^4Y^5$ (e.g. aminomethyl and morpholin-1-ylmethyl), are preferred.

Compounds of formula (Ia), (Ib), (Ic) and (Id) in which $R^{15}$ represents —N($R^8$)—C(=O)—$OR^9$, especially where $R^8$ is hydrogen or lower alkyl (e.g. methyl) and $R^9$ is lower alkyl (e.g. ethyl) or alkyl substituted by aryl (e.g. benzyl), are also preferred.

Compounds of formula(Ia), (Ib), (Ic) and (Id) in which $R^{15}$ represents —N($R^8$)—$SO_2$—$R^9$, especially where $R^8$ is hydrogen or lower alkyl (e.g. methyl) and $R^9$ is lower alkyl (e.g. methyl), aryl [e.g. optionally substituted phenyl or optionally substituted naphthyl (especially dimethylaminonaphth-1-yl)], heteroaryl (e.g. optionally substituted pyridyl or optionally substituted imidazolyl), are also preferred.

Compounds of formula (Ia), (Ib), (Ic) and (Id) in which $R^{15}$ represents —$NY^4Y^5$, especially where $Y^4$ and $Y^5$ represent hydrogen are also preferred.

Compounds of formula (Ia), (Ib), (Ic) and (Id) in which $R^{15}$ represents —$NY^4Y^5$, especially where $Y^4$ is hydrogen and $Y^5$ is or lower alkyl (e.g. propyl), or alkyl substituted by aryl (e.g. —$CH_2$-Ph or —$CH_2$—$CH_2$-Ph), are also preferred.

Compounds of formula (Ia), (Ib), (Ic) and (Id) in which $R^{15}$ represents —$NY^4Y^5$, especially where $Y^4$ and $Y^5$ represent alkyl substituted by aryl (e.g. —$CH_2$-Ph or —CH($CH_3$)-Ph), are also preferred.

Compounds of formula (Ia), (Ib), (Ic) and (Id) in which $R^{15}$ represents alkyl substituted by carboxy (or an acid bioisostere), especially lower alkyl substituted by carboxy (e.g. carboxymethyl), are also preferred.

Compounds of formula (Ia), (Ib), (Ic) and (Id) in which $R^{15}$ represents alkyl substituted by —OH, especially lower alkyl substituted by —OH (e.g. hydroxymethyl), are also preferred.

Compounds of formula (Ia), (Ib), (Ic) and (Id) in which $R^{15}$ represents alkyl substituted by —$OR^3$, especially lower alkyl substituted by —$OR^3$ (e.g. methoxymethyl), are also preferred.

Compounds of formula(Ia), (Ib), (Ic) and (Id) in which $R^{15}$ represents alkyl substituted by —C(=O)—$NY^4Y^5$, especially lower alkyl substituted by —C(=O)—$NY^4Y^5$ (e.g.

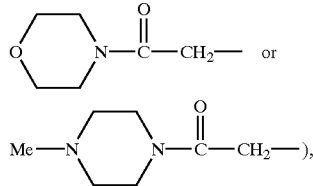

are also preferred.

Particularly preferred compounds of formula (Ia), (Ib), (Ic) and (Id) are those in which $R^{15}$ is —H, —$NH_2$, —$NHCH_2CH_2CH_3$,

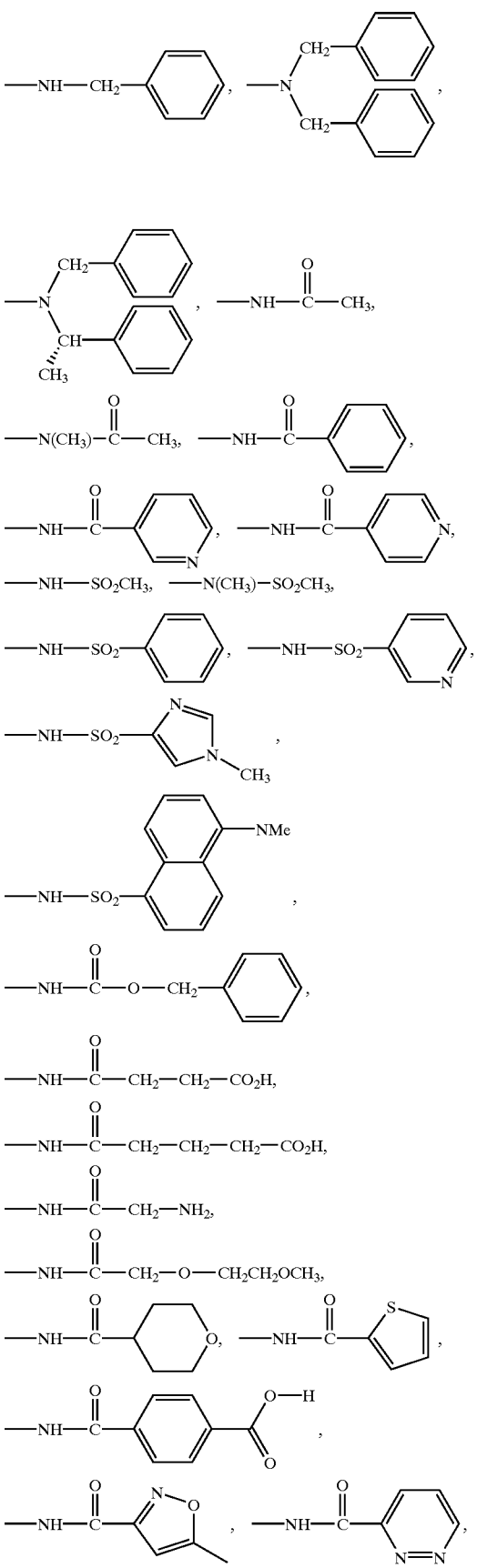

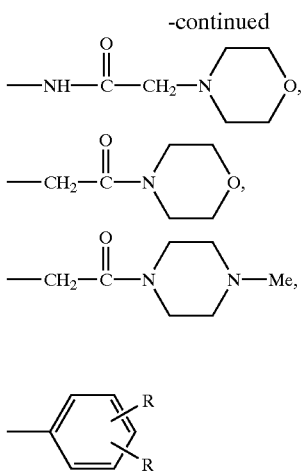

(in which R is hydrogen or an aryl group substituent), —CH$_3$, —CH$_2$CH$_3$, —CH$_2$CH$_2$CH$_3$, —CH$_2$CH$_2$CH$_2$CH$_3$, —CH(CH$_3$)$_2$, —CH$_2$—CH(CH$_3$)$_2$, —CH$_2$—OH, —CH$_2$—CO$_2$H or —CH$_2$—OMe.

Compounds of formula (Ia), (Ib), (Ic) and (Id) in which $R^{15a}$ represents —N($R^8$)—C(=O)—$R^9$, especially where $R^8$ is hydrogen or lower alkyl (e.g. methyl) and $R^9$ is lower alkyl (e.g. methyl), aryl (e.g. optionally substituted phenyl), heteroaryl (e.g. pyridyl, isoxazolyl, triazolyl, pyrimidinyl, thiazolyl, or pyrazolopyrimidinyl each optionally substituted by one or more aryl group substituents), alkyl substituted by alkoxy (e.g. —CH$_2$—O—CH$_2$—CH$_2$—OCH$_3$), alkyl substituted by carboxy (e.g. —CH$_2$—CH$_2$—CO$_2$H and —CH$_2$—CH$_2$—CH$_2$—CO$_2$H) or alkyl substituted by —NY$^4$Y$^5$ (e.g. aminomethyl and morpholin-1-ylmethyl), are preferred.

Compounds of formula (Ia), (Ib), (Ic) and (Id) in which $R^{15a}$ represents —N($R^8$)—C(=O)—$R^9$ where $R^9$ is substituted phenyl selected from 2-chlorophenyl, 5-chloro-2-cyanophenyl, 2-chloro-6-methylphenyl, 2,6-dichlorophenyl, 2,6-difluorophenyl, 4-fluoro-2-trifluoromethyl, 2-methyl-4-nitrophenyl, 2-methyl-5-nitrophenyl, 2-nitrophenyl, 3-nitrophenyl or 2-phenoxyphenyl are particularly preferred.

Compounds of formula (Ia), (Ib), (Ic) and (Id) in which $R^{15a}$ represents —N($R^8$)—C(=O)—$R^9$ where $R^9$ is an optionally substituted heteroaryl selected from quinolin-4-yl, isoquinolin-2-yl, 2,4-pyridin-3-yl, 2,6-dimethyl-4-trifluoromethylpyridin-3-yl, 4-trifluoromethylpyridin3-yl, 2-phenyl-4-methyl-1,2,3-triazol-5-yl, 3,5-dimethylisoxazol-4-yl, 2,7-dimethylpyrazolo-[1,5-a]pyrimidin-6-yl, 2-isopropyl-4-methylthiazol-5-yl and 4-trifluoromethylpyrimidin-5-yl are also particularly preferred.

Particular compounds of the invention are selected from the compounds formed by joining the acyl carbon atom (C*) of one of the fragments (A1 to A34) shown in Table 1 to the nitrogen atom (N*) of one of the aza-bicyclic fragments (B1 to B6) shown in Table 2, and joining the carbon atom (C*) of the phenyl ring in one of the aza-bicyclic fragments (B1 to B6) shown in Table 2 to the carbon atom (C*) of one of the acidic fragments (C1 to C59) depicted in Table 3.

TABLE 1

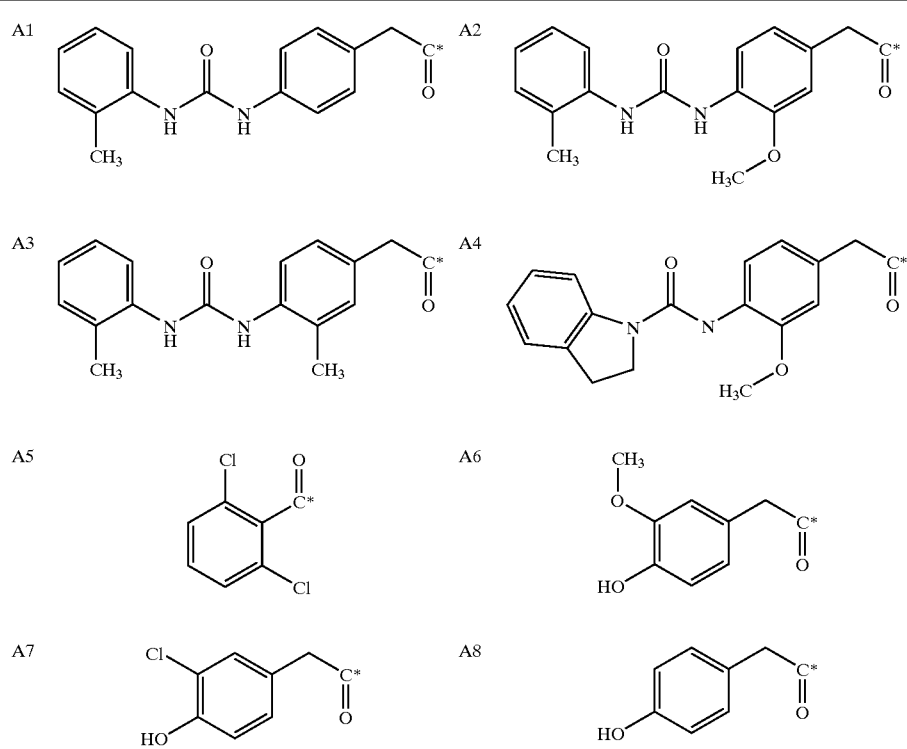

TABLE 1-continued
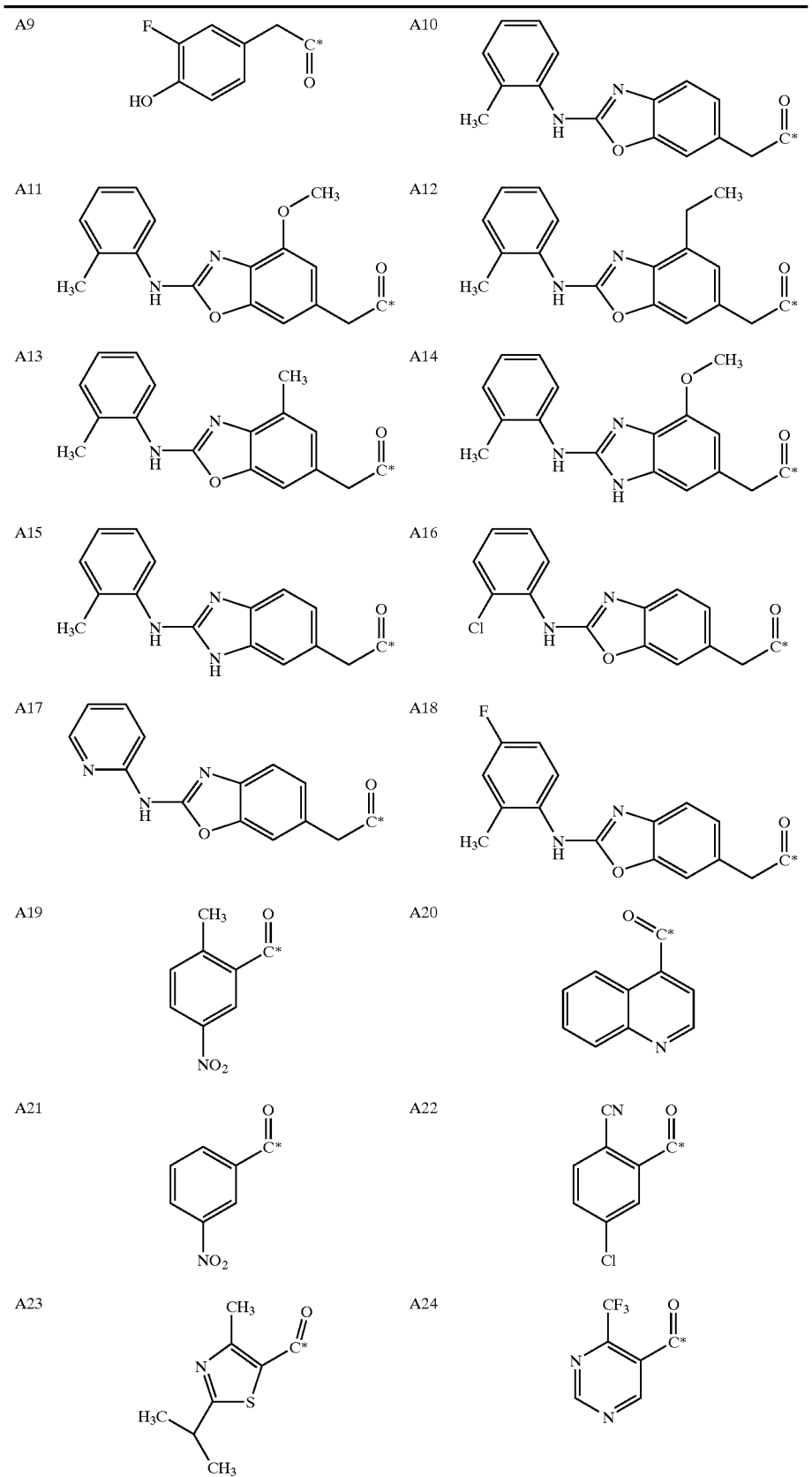

TABLE 1-continued
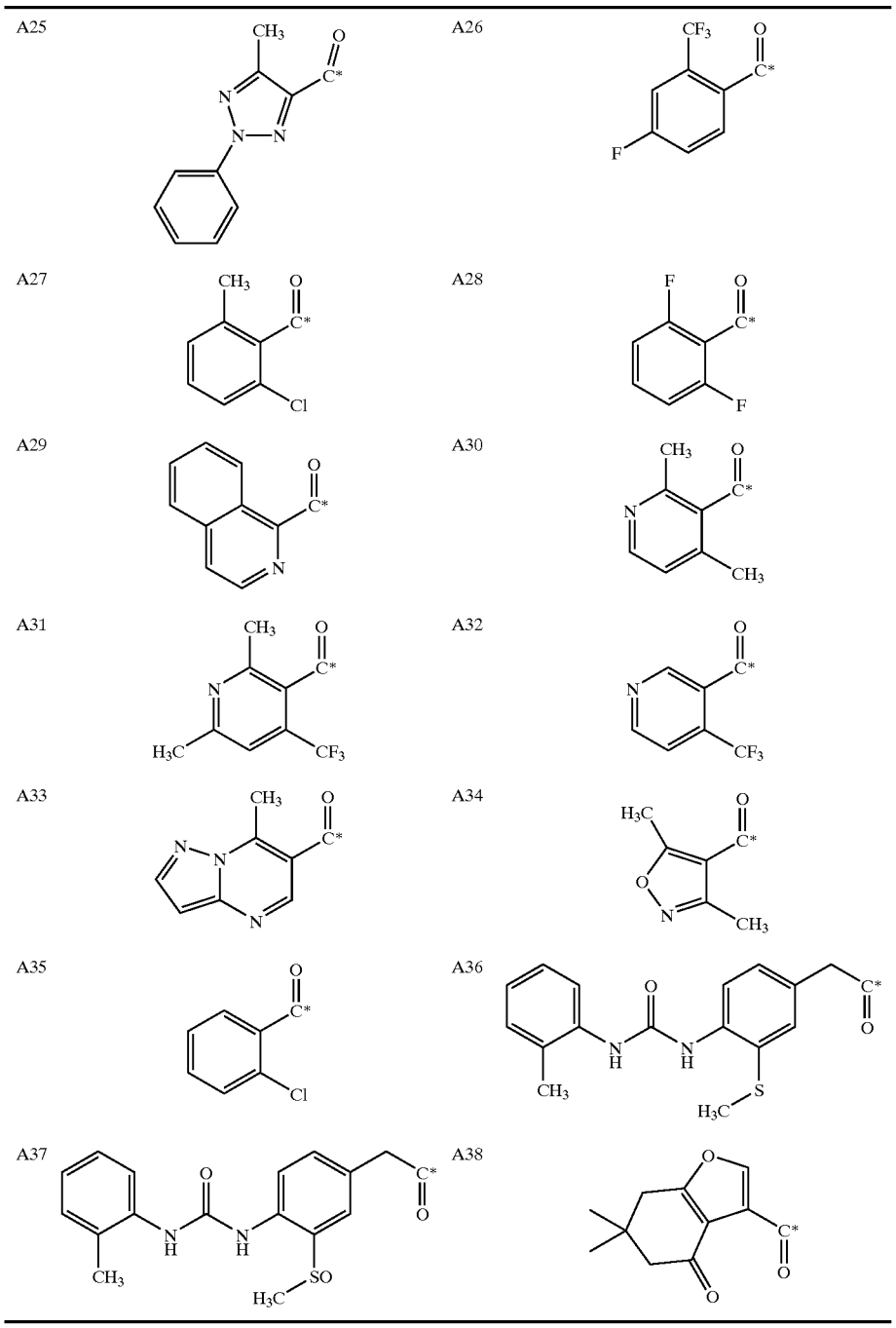

TABLE 2
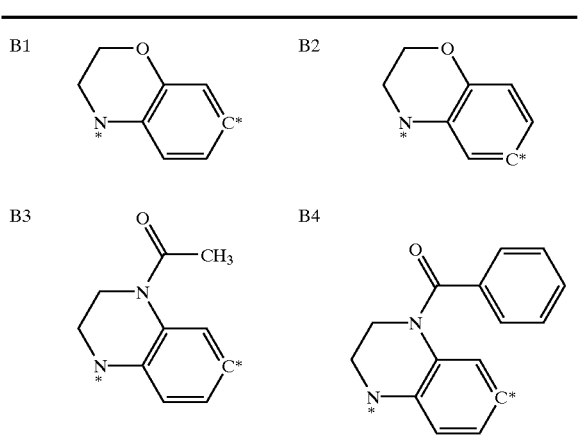
TABLE 2-continued
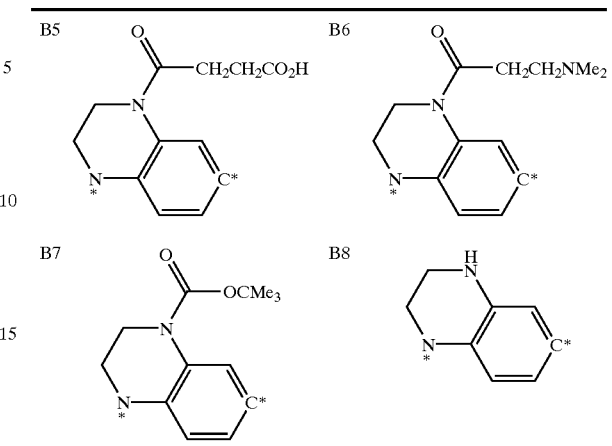
TABLE 3
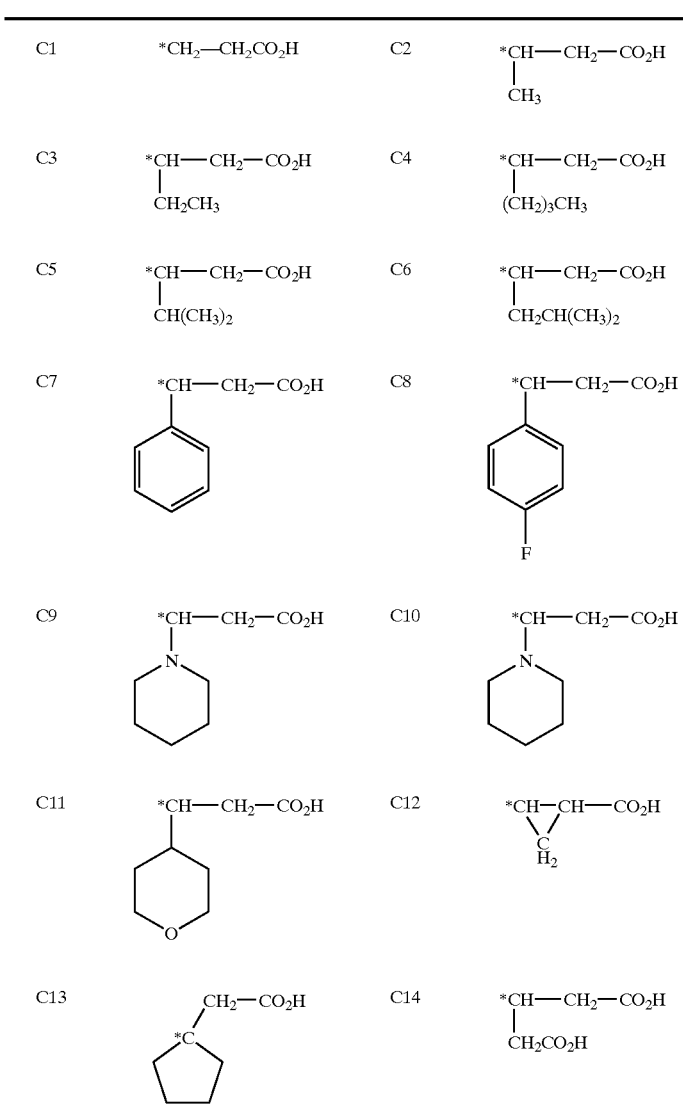

TABLE 3-continued

| | | | |
|---|---|---|---|
| C15 | *CH—CH$_2$—CO$_2$H, H$_2$C—C(=O)—N(pyrrolidine) | C16 | *CH—CH$_2$—CO$_2$H, H$_2$C—C(=O)—N(morpholine) |
| C17 | *CH—CH$_2$—CO$_2$H, H$_2$C—C(=O)—N(piperidine) | C18 | *CH—CH$_2$—CH$_2$—CO$_2$H, OMe |
| C19 | *CH—CH$_2$—CH$_2$—CO$_2$H, OCHMe$_2$ | C20 | *CH$_2$—CH(NH$_2$)—CO$_2$H |
| C21 | *CH$_2$—CH(CO$_2$H)—NH—C(=O)—(2-Me-6-Cl-phenyl) | C22 | *CH$_2$—CH(CO$_2$H)—NH—C(=O)—(2,6-diCl-phenyl) |
| C23 | *CH$_2$—CH(CO$_2$H)—NH—C(=O)—(2-F-6-CF$_3$-phenyl) | C24 | *CH$_2$—CH(CO$_2$H)—NH—C(=O)—(2,6-diMe-phenyl) |
| C25 | *CH$_2$—CH(CO$_2$H)—NH—C(=O)—(2-OMe-phenyl) | C26 | *CH$_2$—CH(CO$_2$H)—NH—C(=O)—(2-Cl-5-OH-phenyl) |
| C27 | *CH$_2$—CH(CO$_2$H)—NH—C(=O)—(2,6-diF-phenyl) | C28 | *CH$_2$—CH(CO$_2$H)—NH—C(=O)—(2-Cl-3-Me-phenyl) |

TABLE 3-continued
| | | | |
|---|---|---|---|
| C29 | 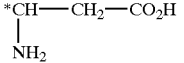 | C30 | 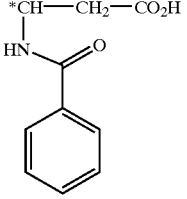 |
| C31 | 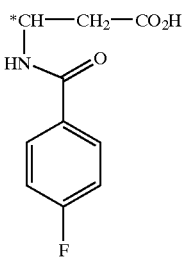 | C32 | 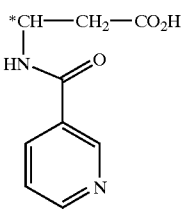 |
| C33 | 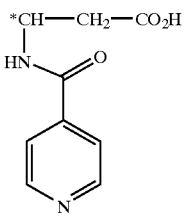 | C34 | 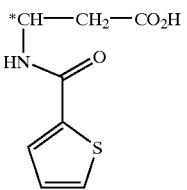 |
| C35 | 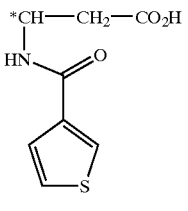 | C36 | 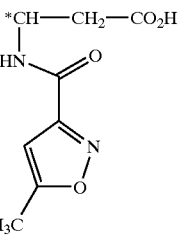 |
| C37 | 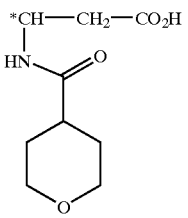 | C38 | 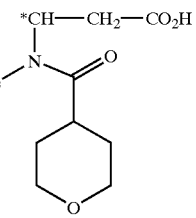 |
| C39 | 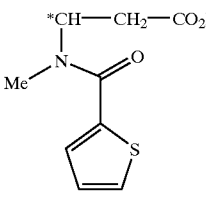 | C40 | 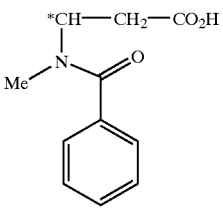 |
| C41 | 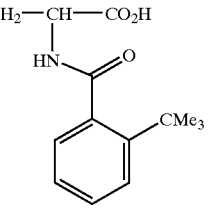 | C42 | 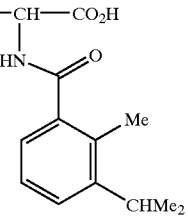 |

TABLE 3-continued
| | | | |
|---|---|---|---|
| C43 | 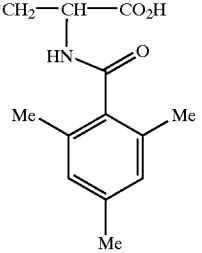 | C44 | 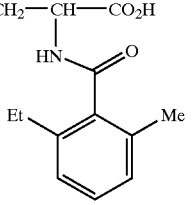 |
| C45 | 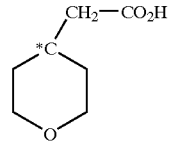 | C46 | 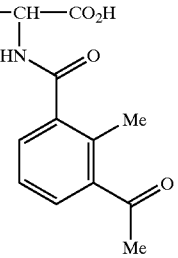 |
| C47 | 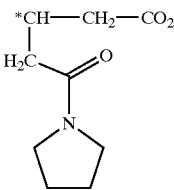 | C48 | 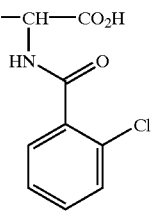 |
| C49 | 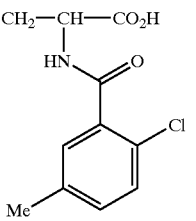 | C50 | 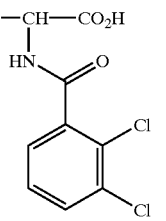 |
| C51 | 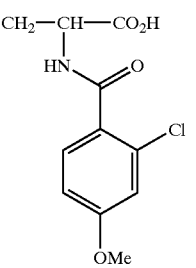 | C52 | 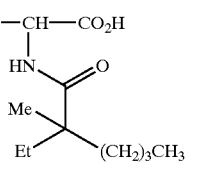 |
| C53 | 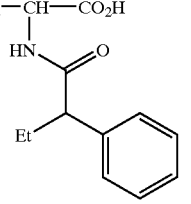 | C54 | 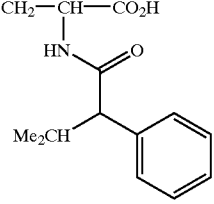 |

TABLE 3-continued
| | | | | |
|---|---|---|---|---|
| C55 | 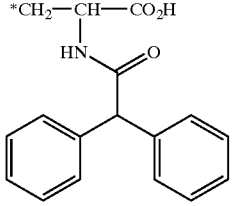 | C56 | 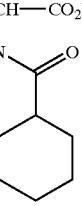 | |
| C57 | 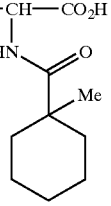 | C58 | 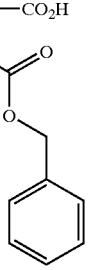 | |
| C59 | *CH$_2$—CH$_2$—CH$_2$—CO$_2$H | C60 | *CH=CH—CO$_2$H | |
| C61 | 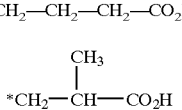 | C62 | 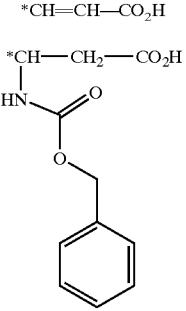 | |
| C63 | 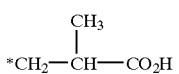 | C64 | 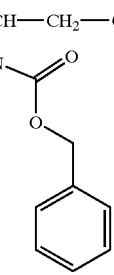 | |
| C65 | 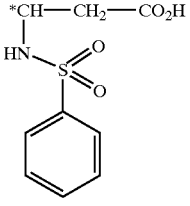 | C66 | 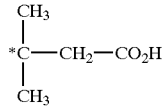 | |
| C67 | 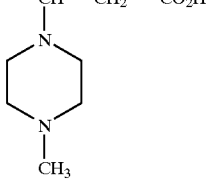 | C68 | 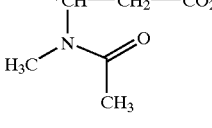 | |

Particular compounds of the invention are:

A1-B1-C1;
A1-B1-C2;
A1-B1-C3;
A1-B1-C4;
A1-B1-C5;
A1-B1-C6;
A1-B1-C7;
A1-B1-C8;
A1-B1-C9;
A1-B1-C10;
A1-B1-C11;
A1-B1-C12;
A1-B1-C13;
A1-B1-C14;
A1-B1-C15;
A1-B1-C16;
A1-B1-C17;
A1-B1-C18;
A1-B1-C19;
A1-B1-C20;
A1-B1-C21;
A1-B1-C22;
A1-B1-C23;
A1-B1-C24;
A1-B1-C25;
A1-B1-C26;
A1-B1-C27;
A1-B1-C28;
A1-B1-C29;
A1-B1-C30;
A1-B1-C31;
A1-B1-C32;
A1-B1-C33;
A1-B1-C34;
A1-B1-C35;
A1-B1-C36;
A1-B1-C37;
A1-B1-C38;
A1-B1-C39;
A1-B1-C40;
A1-B1-C41;
A1-B1-C42;
A1-B1-C43;
A1-B1-C44;
A1-B1-C45;
A1-B1-C46;
A1-B1-C47;
A1-B1-C48;
A1-B1-C49;
A1-B1-C50;
A1-B1-C51;
A1-B1-C52;
A1-B1-C53;
A1-B1-C54;
A1-B1-C55;
A1-B1-C56;
A1-B1-C57;
A1-B1-C58;
A1-B1-C59;
A1-B1-C60;
A1-B1-C61;
A1-B1-C62;
A1-B1-C63;
A1-B1-C64;
A1-B1-C65;
A1-B1-C66;
A1-B1-C67;
A1-B1-C68;
A2-B1-C1;
A2-B1-C2;
A2-B1-C3;
A2-B1-C4;
A2-B1-C5;
A2-B1-C6;
A2-B1-C7;
A2-B1-C8;
A2-B1-C9;
A2-B1-C10;
A2-B1-C11;
A2-B1-C12;
A2-B1-C13;
A2-B1-C14;
A2-B1-C15;
A2-B1-C16;
A2-B1-C17;
A2-B1-C18;
A2-B1-C19;
A2-B1-C20;
A2-B1-C21;
A2-B1-C22;
A2-B1-C23;
A2-B1-C24;
A2-B1-C25;
A2-B1-C26;
A2-B1-C27;
A2-B1-C28;
A2-B1-C29;
A2-B1-C30;
A2-B1-C31;
A2-B1-C32;
A2-B1-C33;
A2-B1-C34;
A2-B1-C35;
A2-B1-C36;
A2-B1-C37;
A2-B1-C38;
A2-B1-C39;
A2-B1-C40;
A2-B1-C41;
A2-B1-C42;
A2-B1-C43;
A2-B1-C44;
A2-B1-C45;
A2-B1-C46;
A2-B1-C47;
A2-B1-C48;
A2-B1-C49;
A2-B1-C50;
A2-B1-C51;
A2-B1-C52;
A2-B1-C53;
A2-B1-C54;
A2-B1-C55;
A2-B1-C56;
A2-B1-C57;
A2-B1-C58;
A2-B1-C59;
A2-B1-C60;
A2-B1-C61;
A2-B1-C62;
A2-B1-C63;
A2-B1-C64;
A2-B1-C65;
A2-B1-C66;
A2-B1-C67;
A2-B1-C68;
A3-B1-C1;
A3-B1-C2;
A3-B1-C3;
A3-B1-C4;
A3-B1-C5;
A3-B1-C6;
A3-B1-C7;
A3-B1-C8;
A3-B1-C9;
A3-B1-C10;
A3-B1-C11;
A3-B1-C12;
A3-B1-C13;
A3-B1-C14;
A3-B1-C15;
A3-B1-C16;
A3-B1-C17;
A3-B1-C18;
A3-B1-C19;
A3-B1-C20;

A3-B1-C21;
A3-B1-C22;
A3-B1-C23;
A3-B1-C24;
A3-B1-C25;
A3-B1-C26;
A3-B1-C27;
A3-B1-C28;
A3-B1-C29;
A3-B1-C30;
A3-B1-C31;
A3-B1-C32;
A3-B1-C33;
A3-B1-C34;
A3-B1-C35;
A3-B1-C36;
A3-B1-C37;
A3-B1-C38;
A3-B1-C39;
A3-B1-C40;
A3-B1-C41;
A3-B1-C42;
A3-B1-C43;
A3-B1-C44;
A3-B1-C45;
A3-B1-C46;
A3-B1-C47;
A3-B1-C48;
A3-B1-C49;
A3-B1-C50;
A3-B1-C51;
A3-B1-C52;
A3-B1-C53;
A3-B1-C54;
A3-B1-C55;
A3-B1-C56;
A3-B1-C57;
A3-B1-C58;
A3-B1-C59;
A3-B1-C60;
A3-B1-C61;
A3-B1-C62;
A3-B1-C63;
A3-B1-C64;
A3-B1-C65;
A3-B1-C66;
A3-B1-C67;
A3-B1-C68;
A4-B1-C1;
A4-B1-C2;
A4-B1-C3;
A4-B1-C4;
A4-B1-C5;
A4-B1-C6;
A4-B1-C7;
A4-B1-C8;
A4-B1-C9;
A4-B1-C10;
A4-B1-C11;
A4-B1-C12;
A4-B1-C13;
A4-B1-C14;
A4-B1-C15;
A4-B1-C16;
A4-B1-C17;
A4-B1-C18;
A4-B1-C19;
A4-B1-C20;
A4-B1-C21;
A4-B1-C22;
A4-B1-C23;
A4-B1-C24;
A4-B1-C25;
A4-B1-C26;
A4-B1-C27;
A4-B1-C28;
A4-B1-C29;
A4-B1-C30;
A4-B1-C31;
A4-B1-C32;
A4-B1-C33;
A4-B1-C34;
A4-B1-C35;
A4-B1-C36;
A4-B1-C37;
A4-B1-C38;
A4-B1-C39;
A4-B1-C40;
A4-B1-C41;
A4-B1-C42;
A4-B1-C43;
A4-B1-C44;
A4-B1-C45;
A4-B1-C46;
A4-B1-C47;
A4-B1-C48;
A4-B1-C49;
A4-B1-C50;
A4-B1-C51;
A4-B1-C52;
A4-B1-C53;
A4-B1-C54;
A4-B1-C55;
A4-B1-C56;
A4-B1-C57;
A4-B1-C58;
A4-B1-C59;
A4-B1-C60;
A4-B1-C61;
A4-B1-C62;
A4-B1-C63;
A4-B1-C64;
A4-B1-C65;
A4-B1-C66;
A4-B1-C67;
A4-B1-C68;
A5-B1-C1;
A5-B1-C2;
A5-B1-C3;
A5-B1-C4;
A5-B1-C5;
A5-B1-C6;
A5-B1-C7;
A5-B1-C8;
A5-B1-C9;
A5-B1-C10;
A5-B1-C11;
A5-B1-C12;
A5-B1-C13;
A5-B1-C14;
A5-B1-C15;
A5-B1-C16;
A5-B1-C17;
A5-B1-C18;
A5-B1-C19;
A5-B1-C20;
A5-B1-C21;
A5-B1-C22;
A5-B1-C23;
A5-B1-C24;
A5-B1-C25;
A5-B1-C26;
A5-B1-C27;
A5-B1-C28;
A5-B1-C29;
A5-B1-C30;
A5-B1-C31;
A5-B1-C32;
A5-B1-C33;
A5-B1-C34;
A5-B1-C35;
A5-B1-C36;
A5-B1-C37;
A5-B1-C38;
A5-B1-C39;
A5-B1-C40;
A5-B1-C41;
A5-B1-C42;

-continued

A5-B1-C43;
A5-B1-C44;
A5-B1-C45;
A5-B1-C46;
A5-B1-C47;
A5-B1-C48;
A5-B1-C49;
A5-B1-C50;
A5-B1-C51;
A5-B1-C52;
A5-B1-C53;
A5-B1-C54;
A5-B1-C55;
A5-B1-C56;
A5-B1-C57;
A5-B1-C58;
A5-B1-C59;
A5-B1-C60;
A5-B1-C61;
A5-B1-C62;
A5-B1-C63;
A5-B1-C64;
A5-B1-C65;
A5-B1-C66;
A5-B1-C67;
A5-B1-C68;
A6-B1-C1;
A6-B1-C2;
A6-B1-C3;
A6-B1-C4;
A6-B1-C5;
A6-B1-C6;
A6-B1-C7;
A6-B1-C8;
A6-B1-C9;
A6-B1-C10;
A6-B1-C11;
A6-B1-C12;
A6-B1-C13;
A6-B1-C14;
A6-B1-C15;
A6-B1-C16;
A6-B1-C17;
A6-B1-C18;
A6-B1-C19;
A6-B1-C20;
A6-B1-C21;
A6-B1-C22;
A6-B1-C23;
A6-B1-C24;
A6-B1-C25;
A6-B1-C26;
A6-B1-C27;
A6-B1-C28;
A6-B1-C29;
A6-B1-C30;
A6-B1-C31;
A6-B1-C32;
A6-B1-C33;
A6-B1-C34;
A6-B1-C35;
A6-B1-C36;
A6-B1-C37;
A6-B1-C38;
A6-B1-C39;
A6-B1-C40;
A6-B1-C41;
A6-B1-C42;
A6-B1-C43;
A6-B1-C44;
A6-B1-C45;
A6-B1-C46;
A6-B1-C47;
A6-B1-C48;
A6-B1-C49;
A6-B1-C50;
A6-B1-C51;
A6-B1-C52;
A6-B1-C53;

-continued

A6-B1-C54;
A6-B1-C55;
A6-B1-C56;
A6-B1-C57;
A6-B1-C58;
A6-B1-C59;
A6-B1-C60;
A6-B1-C61;
A6-B1-C62;
A6-B1-C63;
A6-B1-C64;
A6-B1-C65;
A6-B1-C66;
A6-B1-C67;
A6-B1-C68;
A7-B1-C1;
A7-B1-C2;
A7-B1-C3;
A7-B1-C4;
A7-B1-C5;
A7-B1-C6;
A7-B1-C7;
A7-B1-C8;
A7-B1-C9;
A7-B1-C10;
A7-B1-C11;
A7-B1-C12;
A7-B1-C13;
A7-B1-C14;
A7-B1-C15;
A7-B1-C16;
A7-B1-C17;
A7-B1-C18;
A7-B1-C19;
A7-B1-C20;
A7-B1-C21;
A7-B1-C22;
A7-B1-C23;
A7-B1-C24;
A7-B1-C25;
A7-B1-C26;
A7-B1-C27;
A7-B1-C28;
A7-B1-C29;
A7-B1-C30;
A7-B1-C31;
A7-B1-C32;
A7-B1-C33;
A7-B1-C34;
A7-B1-C35;
A7-B1-C36;
A7-B1-C37;
A7-B1-C38;
A7-B1-C39;
A7-B1-C40;
A7-B1-C41;
A7-B1-C42;
A7-B1-C43;
A7-B1-C44;
A7-B1-C45;
A7-B1-C46;
A7-B1-C47;
A7-B1-C48;
A7-B1-C49;
A7-B1-C50;
A7-B1-C51;
A7-B1-C52;
A7-B1-C53;
A7-B1-C54;
A7-B1-C55;
A7-B1-C56;
A7-B1-C57;
A7-B1-C58;
A7-B1-C59;
A7-B1-C60;
A7-B1-C61;
A7-B1-C62;
A7-B1-C63;
A7-B1-C64;

-continued

A7-B1-C65;
A7-B1-C66;
A7-B1-C67;
A7-B1-C68;
A8-B1-C1;
A8-B1-C2;
A8-B1-C3;
A8-B1-C4;
A8-B1-C5;
A8-B1-C6;
A8-B1-C7;
A8-B1-C8;
A8-B1-C9;
A8-B1-C10;
A8-B1-C11;
A8-B1-C12;
A8-B1-C13;
A8-B1-C14;
A8-B1-C15;
A8-B1-C16;
A8-B1-C17;
A8-B1-C18;
A8-B1-C19;
A8-B1-C20;
A8-B1-C21;
A8-B1-C22;
A8-B1-C23;
A8-B1-C24;
A8-B1-C25;
A8-B1-C26;
A8-B1-C27;
A8-B1-C28;
A8-B1-C29;
A8-B1-C30;
A8-B1-C31;
A8-B1-C32;
A8-B1-C33;
A8-B1-C34;
A8-B1-C35;
A8-B1-C36;
A8-B1-C37;
A8-B1-C38;
A8-B1-C39;
A8-B1-C40;
A8-B1-C41;
A8-B1-C42;
A8-B1-C43;
A8-B1-C44;
A8-B1-C45;
A8-B1-C46;
A8-B1-C47;
A8-B1-C48;
A8-B1-C49;
A8-B1-C50;
A8-B1-C51;
A8-B1-C52;
A8-B1-C53;
A8-B1-C54;
A8-B1-C55;
A8-B1-C56;
A8-B1-C57;
A8-B1-C58;
A8-B1-C59;
A8-B1-C60;
A8-B1-C61;
A8-B1-C62;
A8-B1-C63;
A8-B1-C64;
A8-B1-C65;
A8-B1-C66;
A8-B1-C67;
A8-B1-C68;
A9-B1-C1;
A9-B1-C2;
A9-B1-C3;
A9-B1-C4;
A9-B1-C5;
A9-B1-C6;
A9-B1-C7;

-continued

A9-B1-C8;
A9-B1-C9;
A9-B1-C10;
A9-B1-C11;
A9-B1-C12;
A9-B1-C13;
A9-B1-C14;
A9-B1-C15;
A9-B1-C16;
A9-B1-C17;
A9-B1-C18;
A9-B1-C19;
A9-B1-C20;
A9-B1-C21;
A9-B1-C22;
A9-B1-C23;
A9-B1-C24;
A9-B1-C25;
A9-B1-C26;
A9-B1-C27;
A9-B1-C28;
A9-B1-C29;
A9-B1-C30;
A9-B1-C31;
A9-B1-C32;
A9-B1-C33;
A9-B1-C34;
A9-B1-C35;
A9-B1-C36;
A9-B1-C37;
A9-B1-C38;
A9-B1-C39;
A9-B1-C40;
A9-B1-C41;
A9-B1-C42;
A9-B1-C43;
A9-B1-C44;
A9-B1-C45;
A9-B1-C46;
A9-B1-C47;
A9-B1-C48;
A9-B1-C49;
A9-B1-C50;
A9-B1-C51;
A9-B1-C52;
A9-B1-C53;
A9-B1-C54;
A9-B1-C55;
A9-B1-C56;
A9-B1-C57;
A9-B1-C58;
A9-B1-C59;
A9-B1-C60;
A9-B1-C61;
A9-B1-C62;
A9-B1-C63;
A9-B1-C64;
A9-B1-C65;
A9-B1-C66;
A9-B1-C67;
A9-B1-C68;
A10-B1-C1;
A10-B1-C2;
A10-B1-C3;
A10-B1-C4;
A10-B1-C5;
A10-B1-C6;
A10-B1-C7;
A10-B1-C8;
A10-B1-C9;
A10-B1-C10;
A10-B1-C11;
A10-B1-C12;
A10-B1-C13;
A10-B1-C14;
A10-B1-C15;
A10-B1-C16;
A10-B1-C17;
A10-B1-C18;

-continued

A10-B1-C19;
A10-B1-C20;
A10-B1-C21;
A10-B1-C22;
A10-B1-C23;
A10-B1-C24;
A10-B1-C25;
A10-B1-C26;
A10-B1-C27;
A10-B1-C28;
A10-B1-C29;
A10-B1-C30;
A10-B1-C31;
A10-B1-C32;
A10-B1-C33;
A10-B1-C34;
A10-B1-C35;
A10-B1-C36;
A10-B1-C37;
A10-B1-C38;
A10-B1-C39;
A10-B1-C40;
A10-B1-C41;
A10-B1-C42;
A10-B1-C43;
A10-B1-C44;
A10-B1-C45;
A10-B1-C46;
A10-B1-C47;
A10-B1-C48;
A10-B1-C49;
A10-B1-C50;
A10-B1-C51;
A10-B1-C52;
A10-B1-C53;
A10-B1-C54;
A10-B1-C55;
A10-B1-C56;
A10-B1-C57;
A10-B1-C58;
A10-B1-C59;
A10-B1-C60;
A10-B1-C61;
A10-B1-C62;
A10-B1-C63;
A10-B1-C64;
A10-B1-C65;
A10-B1-C66;
A10-B1-C67;
A10-B1-C68;
A11-B1-C1;
A11-B1-C2;
A11-B1-C3;
A11-B1-C4;
A11-B1-C5;
A11-B1-C6;
A11-B1-C7;
A11-B1-C8;
A11-B1-C9;
A11-B1-C10;
A11-B1-C11;
A11-B1-C12;
A11-B1-C13;
A11-B1-C14;
A11-B1-C15;
A11-B1-C16;
A11-B1-C17;
A11-B1-C18;
A11-B1-C19;
A11-B1-C20;
A11-B1-C21;
A11-B1-C22;
A11-B1-C23;
A11-B1-C24;
A11-B1-C25;
A11-B1-C26;
A11-B1-C27;
A11-B1-C28;
A11-B1-C29;

-continued

A11-B1-C30;
A11-B1-C31;
A11-B1-C32;
A11-B1-C33;
A11-B1-C34;
A11-B1-C35;
A11-B1-C36;
A11-B1-C37;
A11-B1-C38;
A11-B1-C39;
A11-B1-C40;
A11-B1-C41;
A11-B1-C42;
A11-B1-C43;
A11-B1-C44;
A11-B1-C45;
A11-B1-C46;
A11-B1-C47;
A11-B1-C48;
A11-B1-C49;
A11-B1-C50;
A11-B1-C51;
A11-B1-C52;
A11-B1-C53;
A11-B1-C54;
A11-B1-C55;
A11-B1-C56;
A11-B1-C57;
A11-B1-C58;
A11-B1-C59;
A11-B1-C60;
A11-B1-C61;
A11-B1-C62;
A11-B1-C63;
A11-B1-C64;
A11-B1-C65;
A11-B1-C66;
A11-B1-C67;
A11-B1-C68;
A12-B1-C1;
A12-B1-C2;
A12-B1-C3;
A12-B1-C4;
A12-B1-C5;
A12-B1-C6;
A12-B1-C7;
A12-B1-C8;
A12-B1-C9;
A12-B1-C10;
A12-B1-C11;
A12-B1-C12;
A12-B1-C13;
A12-B1-C14;
A12-B1-C15;
A12-B1-C16;
A12-B1-C17;
A12-B1-C18;
A12-B1-C19;
A12-B1-C20;
A12-B1-C21;
A12-B1-C22;
A12-B1-C23;
A12-B1-C24;
A12-B1-C25;
A12-B1-C26;
A12-B1-C27;
A12-B1-C28;
A12-B1-C29;
A12-B1-C30;
A12-B1-C31;
A12-B1-C32;
A12-B1-C33;
A12-B1-C34;
A12-B1-C35;
A12-B1-C36;
A12-B1-C37;
A12-B1-C38;
A12-B1-C39;
A12-B1-C40;

-continued

A12-B1-C41;
A12-B1-C42;
A12-B1-C43;
A12-B1-C44;
A12-B1-C45;
A12-B1-C46;
A12-B1-C47;
A12-B1-C48;
A12-B1-C49;
A12-B1-C50;
A12-B1-C51;
A12-B1-C52;
A12-B1-C53;
A12-B1-C54;
A12-B1-C55;
A12-B1-C56;
A12-B1-C57;
A12-B1-C58;
A12-B1-C59;
A12-B1-C60;
A12-B1-C61;
A12-B1-C62;
A12-B1-C63;
A12-B1-C64;
A12-B1-C65;
A12-B1-C66;
A12-B1-C67;
A12-B1-C68;
A13-B1-C1;
A13-B1-C2;
A13-B1-C3;
A13-B1-C4;
A13-B1-C5;
A13-B1-C6;
A13-B1-C7;
A13-B1-C8;
A13-B1-C9;
A13-B1-C10;
A13-B1-C11;
A13-B1-C12;
A13-B1-C13;
A13-B1-C14;
A13-B1-C15;
A13-B1-C16;
A13-B1-C17;
A13-B1-C18;
A13-B1-C19;
A13-B1-C20;
A13-B1-C21;
A13-B1-C22;
A13-B1-C23;
A13-B1-C24;
A13-B1-C25;
A13-B1-C26;
A13-B1-C27;
A13-B1-C28;
A13-B1-C29;
A13-B1-C30;
A13-B1-C31;
A13-B1-C32;
A13-B1-C33;
A13-B1-C34;
A13-B1-C35;
A13-B1-C36;
A13-B1-C37;
A13-B1-C38;
A13-B1-C39;
A13-B1-C40;
A13-B1-C41;
A13-B1-C42;
A13-B1-C43;
A13-B1-C44;
A13-B1-C45;
A13-B1-C46;
A13-B1-C47;
A13-B1-C48;
A13-B1-C49;
A13-B1-C50;
A13-B1-C51;

-continued

A13-B1-C52;
A13-B1-C53;
A13-B1-C54;
A13-B1-C55;
A13-B1-C56;
A13-B1-C57;
A13-B1-C58;
A13-B1-C59;
A13-B1-C60;
A13-B1-C61;
A13-B1-C62;
A13-B1-C63;
A13-B1-C64;
A13-B1-C65;
A13-B1-C66;
A13-B1-C67;
A13-B1-C68;
A14-B1-C1;
A14-B1-C2;
A14-B1-C3;
A14-B1-C4;
A14-B1-C5;
A14-B1-C6;
A14-B1-C7;
A14-B1-C8;
A14-B1-C9;
A14-B1-C10;
A14-B1-C11;
A14-B1-C12;
A14-B1-C13;
A14-B1-C14;
A14-B1-C15;
A14-B1-C16;
A14-B1-C17;
A14-B1-C18;
A14-B1-C19;
A14-B1-C20;
A14-B1-C21;
A14-B1-C22;
A14-B1-C23;
A14-B1-C24;
A14-B1-C25;
A14-B1-C26;
A14-B1-C27;
A14-B1-C28;
A14-B1-C29;
A14-B1-C30;
A14-B1-C31;
A14-B1-C32;
A14-B1-C33;
A14-B1-C34;
A14-B1-C35;
A14-B1-C36;
A14-B1-C37;
A14-B1-C38;
A14-B1-C39;
A14-B1-C40;
A14-B1-C41;
A14-B1-C42;
A14-B1-C43;
A14-B1-C44;
A14-B1-C45;
A14-B1-C46;
A14-B1-C47;
A14-B1-C48;
A14-B1-C49;
A14-B1-C50;
A14-B1-C51;
A14-B1-C52;
A14-B1-C53;
A14-B1-C54;
A14-B1-C55;
A14-B1-C56;
A14-B1-C57;
A14-B1-C58;
A14-B1-C59;
A14-B1-C60;
A14-B1-C61;
A14-B1-C62;

-continued

A14-B1-C63;
A14-B1-C64;
A14-B1-C65;
A14-B1-C66;
A14-B1-C67;
A14-B1-C68;
A15-B1-C1;
A15-B1-C2;
A15-B1-C3;
A15-B1-C4;
A15-B1-C5;
A15-B1-C6;
A15-B1-C7;
A15-B1-C8;
A15-B1-C9;
A15-B1-C10;
A15-B1-C11;
A15-B1-C12;
A15-B1-C13;
A15-B1-C14;
A15-B1-C15;
A15-B1-C16;
A15-B1-C17;
A15-B1-C18;
A15-B1-C19;
A15-B1-C20;
A15-B1-C21;
A15-B1-C22;
A15-B1-C23;
A15-B1-C24;
A15-B1-C25;
A15-B1-C26;
A15-B1-C27;
A15-B1-C28;
A15-B1-C29;
A15-B1-C30;
A15-B1-C31;
A15-B1-C32;
A15-B1-C33;
A15-B1-C34;
A15-B1-C35;
A15-B1-C36;
A15-B1-C37;
A15-B1-C38;
A15-B1-C39;
A15-B1-C40;
A15-B1-C41;
A15-B1-C42;
A15-B1-C43;
A15-B1-C44;
A15-B1-C45;
A15-B1-C46;
A15-B1-C47;
A15-B1-C48;
A15-B1-C49;
A15-B1-C50;
A15-B1-C51;
A15-B1-C52;
A15-B1-C53;
A15-B1-C54;
A15-B1-C55;
A15-B1-C56;
A15-B1-C57;
A15-B1-C58;
A15-B1-C59;
A15-B1-C60;
A15-B1-C61;
A15-B1-C62;
A15-B1-C63;
A15-B1-C64;
A15-B1-C65;
A15-B1-C66;
A15-B1-C67;
A15-B1-C68;
A16-B1-C1;
A16-B1-C2;
A16-B1-C3;
A16-B1-C4;
A16-B1-C5;

-continued

A16-B1-C6;
A16-B1-C7;
A16-B1-C8;
A16-B1-C9;
A16-B1-C10;
A16-B1-C11;
A16-B1-C12;
A16-B1-C13;
A16-B1-C14;
A16-B1-C15;
A16-B1-C16;
A16-B1-C17;
A16-B1-C18;
A16-B1-C19;
A16-B1-C20;
A16-B1-C21;
A16-B1-C22;
A16-B1-C23;
A16-B1-C24;
A16-B1-C25;
A16-B1-C26;
A16-B1-C27;
A16-B1-C28;
A16-B1-C29;
A16-B1-C30;
A16-B1-C31;
A16-B1-C32;
A16-B1-C33;
A16-B1-C34;
A16-B1-C35;
A16-B1-C36;
A16-B1-C37;
A16-B1-C38;
A16-B1-C39;
A16-B1-C40;
A16-B1-C41;
A16-B1-C42;
A16-B1-C43;
A16-B1-C44;
A16-B1-C45;
A16-B1-C46;
A16-B1-C47;
A16-B1-C48;
A16-B1-C49;
A16-B1-C50;
A16-B1-C51;
A16-B1-C52;
A16-B1-C53;
A16-B1-C54;
A16-B1-C55;
A16-B1-C56;
A16-B1-C57;
A16-B1-C58;
A16-B1-C59;
A16-B1-C60;
A16-B1-C61;
A16-B1-C62;
A16-B1-C63;
A16-B1-C64;
A16-B1-C65;
A16-B1-C66;
A16-B1-C67;
A16-B1-C68;
A17-B1-C1;
A17-B1-C2;
A17-B1-C3;
A17-B1-C4;
A17-B1-C5;
A17-B1-C6;
A17-B1-C7;
A17-B1-C8;
A17-B1-C9;
A17-B1-C10;
A17-B1-C11;
A17-B1-C12;
A17-B1-C13;
A17-B1-C14;
A17-B1-C15;
A17-B1-C16;

-continued

A17-B1-C17;
A17-B1-C18;
A17-B1-C19;
A17-B1-C20;
A17-B1-C21;
A17-B1-C22;
A17-B1-C23;
A17-B1-C24;
A17-B1-C25;
A17-B1-C26;
A17-B1-C27;
A17-B1-C28;
A17-B1-C29;
A17-B1-C30;
A17-B1-C31;
A17-B1-C32;
A17-B1-C33;
A17-B1-C34;
A17-B1-C35;
A17-B1-C36;
A17-B1-C37;
A17-B1-C38;
A17-B1-C39;
A17-B1-C40;
A17-B1-C41;
A17-B1-C42;
A17-B1-C43;
A17-B1-C44;
A17-B1-C45;
A17-B1-C46;
A17-B1-C47;
A17-B1-C48;
A17-B1-C49;
A17-B1-C50;
A17-B1-C51;
A17-B1-C52;
A17-B1-C53;
A17-B1-C54;
A17-B1-C55;
A17-B1-C56;
A17-B1-C57;
A17-B1-C58;
A17-B1-C59;
A17-B1-C60;
A17-B1-C61;
A17-B1-C62;
A17-B1-C63;
A17-B1-C64;
A17-B1-C65;
A17-B1-C66;
A17-B1-C67;
A17-B1-C68;
A18-B1-C1;
A18-B1-C2;
A18-B1-C3;
A18-B1-C4;
A18-B1-C5;
A18-B1-C6;
A18-B1-C7;
A18-B1-C8;
A18-B1-C9;
A18-B1-C10;
A18-B1-C11;
A18-B1-C12;
A18-B1-C13;
A18-B1-C14;
A18-B1-C15;
A18-B1-C16;
A18-B1-C17;
A18-B1-C18;
A18-B1-C19;
A18-B1-C20;
A18-B1-C21;
A18-B1-C22;
A18-B1-C23;
A18-B1-C24;
A18-B1-C25;
A18-B1-C26;
A18-B1-C27;

-continued

A18-B1-C28;
A18-B1-C29;
A18-B1-C30;
A18-B1-C31;
A18-B1-C32;
A18-B1-C33;
A18-B1-C34;
A18-B1-C35;
A18-B1-C36;
A18-B1-C37;
A18-B1-C38;
A18-B1-C39;
A18-B1-C40;
A18-B1-C41;
A18-B1-C42;
A18-B1-C43;
A18-B1-C44;
A18-B1-C45;
A18-B1-C46;
A18-B1-C47;
A18-B1-C48;
A18-B1-C49;
A18-B1-C50;
A18-B1-C51;
A18-B1-C52;
A18-B1-C53;
A18-B1-C54;
A18-B1-C55;
A18-B1-C56;
A18-B1-C57;
A18-B1-C58;
A18-B1-C59;
A18-B1-C60;
A18-B1-C61;
A18-B1-C62;
A18-B1-C63;
A18-B1-C64;
A18-B1-C65;
A18-B1-C66;
A18-B1-C67;
A18-B1-C68;
A19-B1-C1;
A19-B1-C2;
A19-B1-C3;
A19-B1-C4;
A19-B1-C5;
A19-B1-C6;
A19-B1-C7;
A19-B1-C8;
A19-B1-C9;
A19-B1-C10;
A19-B1-C11;
A19-B1-C12;
A19-B1-C13;
A19-B1-C14;
A19-B1-C15;
A19-B1-C16;
A19-B1-C17;
A19-B1-C18;
A19-B1-C19;
A19-B1-C20;
A19-B1-C21;
A19-B1-C22;
A19-B1-C23;
A19-B1-C24;
A19-B1-C25;
A19-B1-C26;
A19-B1-C27;
A19-B1-C28;
A19-B1-C29;
A19-B1-C30;
A19-B1-C31;
A19-B1-C32;
A19-B1-C33;
A19-B1-C34;
A19-B1-C35;
A19-B1-C36;
A19-B1-C37;
A19-B1-C38;

-continued

A19-B1-C39;
A19-B1-C40;
A19-B1-C41;
A19-B1-C42;
A19-B1-C43;
A19-B1-C44;
A19-B1-C45;
A19-B1-C46;
A19-B1-C47;
A19-B1-C48;
A19-B1-C49;
A19-B1-C50;
A19-B1-C51;
A19-B1-C52;
A19-B1-C53;
A19-B1-C54;
A19-B1-C55;
A19-B1-C56;
A19-B1-C57;
A19-B1-C58;
A19-B1-C59;
A19-B1-C60;
A19-B1-C61;
A19-B1-C62;
A19-B1-C63;
A19-B1-C64;
A19-B1-C65;
A19-B1-C66;
A19-B1-C67;
A19-B1-C68;
A20-B1-C1;
A20-B1-C2;
A20-B1-C3;
A20-B1-C4;
A20-B1-C5;
A20-B1-C6;
A20-B1-C7;
A20-B1-C8;
A20-B1-C9;
A20-B1-C10;
A20-B1-C11;
A20-B1-C12;
A20-B1-C13;
A20-B1-C14;
A20-B1-C15;
A20-B1-C16;
A20-B1-C17;
A20-B1-C18;
A20-B1-C19;
A20-B1-C20;
A20-B1-C21;
A20-B1-C22;
A20-B1-C23;
A20-B1-C24;
A20-B1-C25;
A20-B1-C26;
A20-B1-C27;
A20-B1-C28;
A20-B1-C29;
A20-B1-C30;
A20-B1-C31;
A20-B1-C32;
A20-B1-C33;
A20-B1-C34;
A20-B1-C35;
A20-B1-C36;
A20-B1-C37;
A20-B1-C38;
A20-B1-C39;
A20-B1-C40;
A20-B1-C41;
A20-B1-C42;
A20-B1-C43;
A20-B1-C44;
A20-B1-C45;
A20-B1-C46;
A20-B1-C47;
A20-B1-C48;
A20-B1-C49;

-continued

A20-B1-C50;
A20-B1-C51;
A20-B1-C52;
A20-B1-C53;
A20-B1-C54;
A20-B1-C55;
A20-B1-C56;
A20-B1-C57;
A20-B1-C58;
A20-B1-C59;
A20-B1-C60;
A20-B1-C61;
A20-B1-C62;
A20-B1-C63;
A20-B1-C64;
A20-B1-C65;
A20-B1-C66;
A20-B1-C67;
A20-B1-C68;
A21-B1-C1;
A21-B1-C2;
A21-B1-C3;
A21-B1-C4;
A21-B1-C5;
A21-B1-C6;
A21-B1-C7;
A21-B1-C8;
A21-B1-C9;
A21-B1-C10;
A21-B1-C11;
A21-B1-C12;
A21-B1-C13;
A21-B1-C14;
A21-B1-C15;
A21-B1-C16;
A21-B1-C17;
A21-B1-C18;
A21-B1-C19;
A21-B1-C20;
A21-B1-C21;
A21-B1-C22;
A21-B1-C23;
A21-B1-C24;
A21-B1-C25;
A21-B1-C26;
A21-B1-C27;
A21-B1-C28;
A21-B1-C29;
A21-B1-C30;
A21-B1-C31;
A21-B1-C32;
A21-B1-C33;
A21-B1-C34;
A21-B1-C35;
A21-B1-C36;
A21-B1-C37;
A21-B1-C38;
A21-B1-C39;
A21-B1-C40;
A21-B1-C41;
A21-B1-C42;
A21-B1-C43;
A21-B1-C44;
A21-B1-C45;
A21-B1-C46;
A21-B1-C47;
A21-B1-C48;
A21-B1-C49;
A21-B1-C50;
A21-B1-C51;
A21-B1-C52;
A21-B1-C53;
A21-B1-C54;
A21-B1-C55;
A21-B1-C56;
A21-B1-C57;
A21-B1-C58;
A21-B1-C59;
A21-B1-C60;

A21-B1-C61;
A21-B1-C62;
A21-B1-C63;
A21-B1-C64;
A21-B1-C65;
A21-B1-C66;
A21-B1-C67;
A21-B1-C68;
A22-B1-C1;
A22-B1-C2;
A22-B1-C3;
A22-B1-C4;
A22-B1-C5;
A22-B1-C6;
A22-B1-C7;
A22-B1-C8;
A22-B1-C9;
A22-B1-C10;
A22-B1-C11;
A22-B1-C12;
A22-B1-C13;
A22-B1-C14;
A22-B1-C15;
A22-B1-C16;
A22-B1-C17;
A22-B1-C18;
A22-B1-C19;
A22-B1-C20;
A22-B1-C21;
A22-B1-C22;
A22-B1-C23;
A22-B1-C24;
A22-B1-C25;
A22-B1-C26;
A22-B1-C27;
A22-B1-C28;
A22-B1-C29;
A22-B1-C30;
A22-B1-C31;
A22-B1-C32;
A22-B1-C33;
A22-B1-C34;
A22-B1-C35;
A22-B1-C36;
A22-B1-C37;
A22-B1-C38;
A22-B1-C39;
A22-B1-C40;
A22-B1-C41;
A22-B1-C42;
A22-B1-C43;
A22-B1-C44;
A22-B1-C45;
A22-B1-C46;
A22-B1-C47;
A22-B1-C48;
A22-B1-C49;
A22-B1-C50;
A22-B1-C51;
A22-B1-C52;
A22-B1-C53;
A22-B1-C54;
A22-B1-C55;
A22-B1-C56;
A22-B1-C57;
A22-B1-C58;
A22-B1-C59;
A22-B1-C60;
A22-B1-C61;
A22-B1-C62;
A22-B1-C63;
A22-B1-C64;
A22-B1-C65;
A22-B1-C66;
A22-B1-C67;
A22-B1-C68;
A23-B1-C1;
A23-B1-C2;
A23-B1-C3;
A23-B1-C4;
A23-B1-C5;
A23-B1-C6;
A23-B1-C7;
A23-B1-C8;
A23-B1-C9;
A23-B1-C10;
A23-B1-C11;
A23-B1-C12;
A23-B1-C13;
A23-B1-C14;
A23-B1-C15;
A23-B1-C16;
A23-B1-C17;
A23-B1-C18;
A23-B1-C19;
A23-B1-C20;
A23-B1-C21;
A23-B1-C22;
A23-B1-C23;
A23-B1-C24;
A23-B1-C25;
A23-B1-C26;
A23-B1-C27;
A23-B1-C28;
A23-B1-C29;
A23-B1-C30;
A23-B1-C31;
A23-B1-C32;
A23-B1-C33;
A23-B1-C34;
A23-B1-C35;
A23-B1-C36;
A23-B1-C37;
A23-B1-C38;
A23-B1-C39;
A23-B1-C40;
A23-B1-C41;
A23-B1-C42;
A23-B1-C43;
A23-B1-C44;
A23-B1-C45;
A23-B1-C46;
A23-B1-C47;
A23-B1-C48;
A23-B1-C49;
A23-B1-C50;
A23-B1-C51;
A23-B1-C52;
A23-B1-C53;
A23-B1-C54;
A23-B1-C55;
A23-B1-C56;
A23-B1-C57;
A23-B1-C58;
A23-B1-C59;
A23-B1-C60;
A23-B1-C61;
A23-B1-C62;
A23-B1-C63;
A23-B1-C64;
A23-B1-C65;
A23-B1-C66;
A23-B1-C67;
A23-B1-C68;
A24-B1-C1;
A24-B1-C2;
A24-B1-C3;
A24-B1-C4;
A24-B1-C5;
A24-B1-C6;
A24-B1-C7;
A24-B1-C8;
A24-B1-C9;
A24-B1-C10;
A24-B1-C11;
A24-B1-C12;
A24-B1-C13;
A24-B1-C14;

-continued

A24-B1-C15;
A24-B1-C16;
A24-B1-C17;
A24-B1-C18;
A24-B1-C19;
A24-B1-C20;
A24-B1-C21;
A24-B1-C22;
A24-B1-C23;
A24-B1-C24;
A24-B1-C25;
A24-B1-C26;
A24-B1-C27;
A24-B1-C28;
A24-B1-C29;
A24-B1-C30;
A24-B1-C31;
A24-B1-C32;
A24-B1-C33;
A24-B1-C34;
A24-B1-C35;
A24-B1-C36;
A24-B1-C37;
A24-B1-C38;
A24-B1-C39;
A24-B1-C40;
A24-B1-C41;
A24-B1-C42;
A24-B1-C43;
A24-B1-C44;
A24-B1-C45;
A24-B1-C46;
A24-B1-C47;
A24-B1-C48;
A24-B1-C49;
A24-B1-C50;
A24-B1-C51;
A24-B1-C52;
A24-B1-C53;
A24-B1-C54;
A24-B1-C55;
A24-B1-C56;
A24-B1-C57;
A24-B1-C58;
A24-B1-C59;
A24-B1-C60;
A24-B1-C61;
A24-B1-C62;
A24-B1-C63;
A24-B1-C64;
A24-B1-C65;
A24-B1-C66;
A24-B1-C67;
A24-B1-C68;
A25-B1-C1;
A25-B1-C2;
A25-B1-C3;
A25-B1-C4;
A25-B1-C5;
A25-B1-C6;
A25-B1-C7;
A25-B1-C8;
A25-B1-C9;
A25-B1-C10;
A25-B1-C11;
A25-B1-C12;
A25-B1-C13;
A25-B1-C14;
A25-B1-C15;
A25-B1-C16;
A25-B1-C17;
A25-B1-C18;
A25-B1-C19;
A25-B1-C20;
A25-B1-C21;
A25-B1-C22;
A25-B1-C23;
A25-B1-C24;
A25-B1-C25;

-continued

A25-B1-C26;
A25-B1-C27;
A25-B1-C28;
A25-B1-C29;
A25-B1-C30;
A25-B1-C31;
A25-B1-C32;
A25-B1-C33;
A25-B1-C34;
A25-B1-C35;
A25-B1-C36;
A25-B1-C37;
A25-B1-C38;
A25-B1-C39;
A25-B1-C40;
A25-B1-C41;
A25-B1-C42;
A25-B1-C43;
A25-B1-C44;
A25-B1-C45;
A25-B1-C46;
A25-B1-C47;
A25-B1-C48;
A25-B1-C49;
A25-B1-C50;
A25-B1-C51;
A25-B1-C52;
A25-B1-C53;
A25-B1-C54;
A25-B1-C55;
A25-B1-C56;
A25-B1-C57;
A25-B1-C58;
A25-B1-C59;
A25-B1-C60;
A25-B1-C61;
A25-B1-C62;
A25-B1-C63;
A25-B1-C64;
A25-B1-C65;
A25-B1-C66;
A25-B1-C67;
A25-B1-C68;
A26-B1-C1;
A26-B1-C2;
A26-B1-C3;
A26-B1-C4;
A26-B1-C5;
A26-B1-C6;
A26-B1-C7;
A26-B1-C8;
A26-B1-C9;
A26-B1-C10;
A26-B1-C11;
A26-B1-C12;
A26-B1-C13;
A26-B1-C14;
A26-B1-C15;
A26-B1-C16;
A26-B1-C17;
A26-B1-C18;
A26-B1-C19;
A26-B1-C20;
A26-B1-C21;
A26-B1-C22;
A26-B1-C23;
A26-B1-C24;
A26-B1-C25;
A26-B1-C26;
A26-B1-C27;
A26-B1-C28;
A26-B1-C29;
A26-B1-C30;
A26-B1-C31;
A26-B1-C32;
A26-B1-C33;
A26-B1-C34;
A26-B1-C35;
A26-B1-C36;

-continued

A26-B1-C37;
A26-B1-C38;
A26-B1-C39;
A26-B1-C40;
A26-B1-C41;
A26-B1-C42;
A26-B1-C43;
A26-B1-C44;
A26-B1-C45;
A26-B1-C46;
A26-B1-C47;
A26-B1-C48;
A26-B1-C49;
A26-B1-C50;
A26-B1-C51;
A26-B1-C52;
A26-B1-C53;
A26-B1-C54;
A26-B1-C55;
A26-B1-C56;
A26-B1-C57;
A26-B1-C58;
A26-B1-C59;
A26-B1-C60;
A26-B1-C61;
A26-B1-C62;
A26-B1-C63;
A26-B1-C64;
A26-B1-C65;
A26-B1-C66;
A26-B1-C67;
A26-B1-C68;
A27-B1-C1;
A27-B1-C2;
A27-B1-C3;
A27-B1-C4;
A27-B1-C5;
A27-B1-C6;
A27-B1-C7;
A27-B1-C8;
A27-B1-C9;
A27-B1-C10;
A27-B1-C11;
A27-B1-C12;
A27-B1-C13;
A27-B1-C14;
A27-B1-C15;
A27-B1-C16;
A27-B1-C17;
A27-B1-C18;
A27-B1-C19;
A27-B1-C20;
A27-B1-C21;
A27-B1-C22;
A27-B1-C23;
A27-B1-C24;
A27-B1-C25;
A27-B1-C26;
A27-B1-C27;
A27-B1-C28;
A27-B1-C29;
A27-B1-C30;
A27-B1-C31;
A27-B1-C32;
A27-B1-C33;
A27-B1-C34;
A27-B1-C35;
A27-B1-C36;
A27-B1-C37;
A27-B1-C38;
A27-B1-C39;
A27-B1-C40;
A27-B1-C41;
A27-B1-C42;
A27-B1-C43;
A27-B1-C44;
A27-B1-C45;
A27-B1-C46;
A27-B1-C47;

-continued

A27-B1-C48;
A27-B1-C49;
A27-B1-C50;
A27-B1-C51;
A27-B1-C52;
A27-B1-C53;
A27-B1-C54;
A27-B1-C55;
A27-B1-C56;
A27-B1-C57;
A27-B1-C58;
A27-B1-C59;
A27-B1-C60;
A27-B1-C61;
A27-B1-C62;
A27-B1-C63;
A27-B1-C64;
A27-B1-C65;
A27-B1-C66;
A27-B1-C67;
A27-B1-C68;
A28-B1-C1;
A28-B1-C2;
A28-B1-C3;
A28-B1-C4;
A28-B1-C5;
A28-B1-C6;
A28-B1-C7;
A28-B1-C8;
A28-B1-C9;
A28-B1-C10;
A28-B1-C11;
A28-B1-C12;
A28-B1-C13;
A28-B1-C14;
A28-B1-C15;
A28-B1-C16;
A28-B1-C17;
A28-B1-C18;
A28-B1-C19;
A28-B1-C20;
A28-B1-C21;
A28-B1-C22;
A28-B1-C23;
A28-B1-C24;
A28-B1-C25;
A28-B1-C26;
A28-B1-C27;
A28-B1-C28;
A28-B1-C29;
A28-B1-C30;
A28-B1-C31;
A28-B1-C32;
A28-B1-C33;
A28-B1-C34;
A28-B1-C35;
A28-B1-C36;
A28-B1-C37;
A28-B1-C38;
A28-B1-C39;
A28-B1-C40;
A28-B1-C41;
A28-B1-C42;
A28-B1-C43;
A28-B1-C44;
A28-B1-C45;
A28-B1-C46;
A28-B1-C47;
A28-B1-C48;
A28-B1-C49;
A28-B1-C50;
A28-B1-C51;
A28-B1-C52;
A28-B1-C53;
A28-B1-C54;
A28-B1-C55;
A28-B1-C56;
A28-B1-C57;
A28-B1-C58;

A28-B1-C59;
A28-B1-C60;
A28-B1-C61;
A28-B1-C62;
A28-B1-C63;
A28-B1-C64;
A28-B1-C65;
A28-B1-C66;
A28-B1-C67;
A28-B1-C68;
A29-B1-C1;
A29-B1-C2;
A29-B1-C3;
A29-B1-C4;
A29-B1-C5;
A29-B1-C6;
A29-B1-C7;
A29-B1-C8;
A29-B1-C9;
A29-B1-C10;
A29-B1-C11;
A29-B1-C12;
A29-B1-C13;
A29-B1-C14;
A29-B1-C15;
A29-B1-C16;
A29-B1-C17;
A29-B1-C18;
A29-B1-C19;
A29-B1-C20;
A29-B1-C21;
A29-B1-C22;
A29-B1-C23;
A29-B1-C24;
A29-B1-C25;
A29-B1-C26;
A29-B1-C27;
A29-B1-C28;
A29-B1-C29;
A29-B1-C30;
A29-B1-C31;
A29-B1-C32;
A29-B1-C33;
A29-B1-C34;
A29-B1-C35;
A29-B1-C36;
A29-B1-C37;
A29-B1-C38;
A29-B1-C39;
A29-B1-C40;
A29-B1-C41;
A29-B1-C42;
A29-B1-C43;
A29-B1-C44;
A29-B1-C45;
A29-B1-C46;
A29-B1-C47;
A29-B1-C48;
A29-B1-C49;
A29-B1-C50;
A29-B1-C51;
A29-B1-C52;
A29-B1-C53;
A29-B1-C54;
A29-B1-C55;
A29-B1-C56;
A29-B1-C57;
A29-B1-C58;
A29-B1-C59;
A29-B1-C60;
A29-B1-C61;
A29-B1-C62;
A29-B1-C63;
A29-B1-C64;
A29-B1-C65;
A29-B1-C66;
A29-B1-C67;
A29-B1-C68;
A30-B1-C1;
A30-B1-C2;
A30-B1-C3;
A30-B1-C4;
A30-B1-C5;
A30-B1-C6;
A30-B1-C7;
A30-B1-C8;
A30-B1-C9;
A30-B1-C10;
A30-B1-C11;
A30-B1-C12;
A30-B1-C13;
A30-B1-C14;
A30-B1-C15;
A30-B1-C16;
A30-B1-C17;
A30-B1-C18;
A30-B1-C19;
A30-B1-C20;
A30-B1-C21;
A30-B1-C22;
A30-B1-C23;
A30-B1-C24;
A30-B1-C25;
A30-B1-C26;
A30-B1-C27;
A30-B1-C28;
A30-B1-C29;
A30-B1-C30;
A30-B1-C31;
A30-B1-C32;
A30-B1-C33;
A30-B1-C34;
A30-B1-C35;
A30-B1-C36;
A30-B1-C37;
A30-B1-C38;
A30-B1-C39;
A30-B1-C40;
A30-B1-C41;
A30-B1-C42;
A30-B1-C43;
A30-B1-C44;
A30-B1-C45;
A30-B1-C46;
A30-B1-C47;
A30-B1-C48;
A30-B1-C49;
A30-B1-C50;
A30-B1-C51;
A30-B1-C52;
A30-B1-C53;
A30-B1-C54;
A30-B1-C55;
A30-B1-C56;
A30-B1-C57;
A30-B1-C58;
A30-B1-C59;
A30-B1-C60;
A30-B1-C61;
A30-B1-C62;
A30-B1-C63;
A30-B1-C64;
A30-B1-C65;
A30-B1-C66;
A30-B1-C67;
A30-B1-C68;
A31-B1-C1;
A31-B1-C2;
A31-B1-C3;
A31-B1-C4;
A31-B1-C5;
A31-B1-C6;
A31-B1-C7;
A31-B1-C8;
A31-B1-C9;
A31-B1-C10;
A31-B1-C11;
A31-B1-C12;

-continued

A31-B1-C13;
A31-B1-C14;
A31-B1-C15;
A31-B1-C16;
A31-B1-C17;
A31-B1-C18;
A31-B1-C19;
A31-B1-C20;
A31-B1-C21;
A31-B1-C22;
A31-B1-C23;
A31-B1-C24;
A31-B1-C25;
A31-B1-C26;
A31-B1-C27;
A31-B1-C28;
A31-B1-C29;
A31-B1-C30;
A31-B1-C31;
A31-B1-C32;
A31-B1-C33;
A31-B1-C34;
A31-B1-C35;
A31-B1-C36;
A31-B1-C37;
A31-B1-C38;
A31-B1-C39;
A31-B1-C40;
A31-B1-C41;
A31-B1-C42;
A31-B1-C43;
A31-B1-C44;
A31-B1-C45;
A31-B1-C46;
A31-B1-C47;
A31-B1-C48;
A31-B1-C49;
A31-B1-C50;
A31-B1-C51;
A31-B1-C52;
A31-B1-C53;
A31-B1-C54;
A31-B1-C55;
A31-B1-C56;
A31-B1-C57;
A31-B1-C58;
A31-B1-C59;
A31-B1-C60;
A31-B1-C61;
A31-B1-C62;
A31-B1-C63;
A31-B1-C64;
A31-B1-C65;
A31-B1-C66;
A31-B1-C67;
A31-B1-C68;
A32-B1-C1;
A32-B1-C2;
A32-B1-C3;
A32-B1-C4;
A32-B1-C5;
A32-B1-C6;
A32-B1-C7;
A32-B1-C8;
A32-B1-C9;
A32-B1-C10;
A32-B1-C11;
A32-B1-C12;
A32-B1-C13;
A32-B1-C14;
A32-B1-C15;
A32-B1-C16;
A32-B1-C17;
A32-B1-C18;
A32-B1-C19;
A32-B1-C20;
A32-B1-C21;
A32-B1-C22;
A32-B1-C23;

-continued

A32-B1-C24;
A32-B1-C25;
A32-B1-C26;
A32-B1-C27;
A32-B1-C28;
A32-B1-C29;
A32-B1-C30;
A32-B1-C31;
A32-B1-C32;
A32-B1-C33;
A32-B1-C34;
A32-B1-C35;
A32-B1-C36;
A32-B1-C37;
A32-B1-C38;
A32-B1-C39;
A32-B1-C40;
A32-B1-C41;
A32-B1-C42;
A32-B1-C43;
A32-B1-C44;
A32-B1-C45;
A32-B1-C46;
A32-B1-C47;
A32-B1-C48;
A32-B1-C49;
A32-B1-C50;
A32-B1-C51;
A32-B1-C52;
A32-B1-C53;
A32-B1-C54;
A32-B1-C55;
A32-B1-C56;
A32-B1-C57;
A32-B1-C58;
A32-B1-C59;
A32-B1-C60;
A32-B1-C61;
A32-B1-C62;
A32-B1-C63;
A32-B1-C64;
A32-B1-C65;
A32-B1-C66;
A32-B1-C67;
A32-B1-C68;
A33-B1-C1;
A33-B1-C2;
A33-B1-C3;
A33-B1-C4;
A33-B1-C5;
A33-B1-C6;
A33-B1-C7;
A33-B1-C8;
A33-B1-C9;
A33-B1-C10;
A33-B1-C11;
A33-B1-C12;
A33-B1-C13;
A33-B1-C14;
A33-B1-C15;
A33-B1-C16;
A33-B1-C17;
A33-B1-C18;
A33-B1-C19;
A33-B1-C20;
A33-B1-C21;
A33-B1-C22;
A33-B1-C23;
A33-B1-C24;
A33-B1-C25;
A33-B1-C26;
A33-B1-C27;
A33-B1-C28;
A33-B1-C29;
A33-B1-C30;
A33-B1-C31;
A33-B1-C32;
A33-B1-C33;
A33-B1-C34;

-continued

A33-B1-C35;
A33-B1-C36;
A33-B1-C37;
A33-B1-C38;
A33-B1-C39;
A33-B1-C40;
A33-B1-C41;
A33-B1-C42;
A33-B1-C43;
A33-B1-C44;
A33-B1-C45;
A33-B1-C46;
A33-B1-C47;
A33-B1-C48;
A33-B1-C49;
A33-B1-C50;
A33-B1-C51;
A33-B1-C52;
A33-B1-C53;
A33-B1-C54;
A33-B1-C55;
A33-B1-C56;
A33-B1-C57;
A33-B1-C58;
A33-B1-C59;
A33-B1-C60;
A33-B1-C61;
A33-B1-C62;
A33-B1-C63;
A33-B1-C64;
A33-B1-C65;
A33-B1-C66;
A33-B1-C67;
A33-B1-C68;
A34-B1-C1;
A34-B1-C2;
A34-B1-C3;
A34-B1-C4;
A34-B1-C5;
A34-B1-C6;
A34-B1-C7;
A34-B1-C8;
A34-B1-C9;
A34-B1-C10;
A34-B1-C11;
A34-B1-C12;
A34-B1-C13;
A34-B1-C14;
A34-B1-C15;
A34-B1-C16;
A34-B1-C17;
A34-B1-C18;
A34-B1-C19;
A34-B1-C20;
A34-B1-C21;
A34-B1-C22;
A34-B1-C23;
A34-B1-C24;
A34-B1-C25;
A34-B1-C26;
A34-B1-C27;
A34-B1-C28;
A34-B1-C29;
A34-B1-C30;
A34-B1-C31;
A34-B1-C32;
A34-B1-C33;
A34-B1-C34;
A34-B1-C35;
A34-B1-C36;
A34-B1-C37;
A34-B1-C38;
A34-B1-C39;
A34-B1-C40;
A34-B1-C41;
A34-B1-C42;
A34-B1-C43;
A34-B1-C44;
A34-B1-C45;

-continued

A34-B1-C46;
A34-B1-C47;
A34-B1-C48;
A34-B1-C49;
A34-B1-C50;
A34-B1-C51;
A34-B1-C52;
A34-B1-C53;
A34-B1-C54;
A34-B1-C55;
A34-B1-C56;
A34-B1-C57;
A34-B1-C58;
A34-B1-C59;
A34-B1-C60;
A34-B1-C61;
A34-B1-C62;
A34-B1-C63;
A34-B1-C64;
A34-B1-C65;
A34-B1-C66;
A34-B1-C67;
A34-B1-C68;
A35-B1-C1;
A35-B1-C2;
A35-B1-C3;
A35-B1-C4;
A35-B1-C5;
A35-B1-C6;
A35-B1-C7;
A35-B1-C8;
A35-B1-C9;
A35-B1-C10;
A35-B1-C11;
A35-B1-C12;
A35-B1-C13;
A35-B1-C14;
A35-B1-C15;
A35-B1-C16;
A35-B1-C17;
A35-B1-C18;
A35-B1-C19;
A35-B1-C20;
A35-B1-C21;
A35-B1-C22;
A35-B1-C23;
A35-B1-C24;
A35-B1-C25;
A35-B1-C26;
A35-B1-C27;
A35-B1-C28;
A35-B1-C29;
A35-B1-C30;
A35-B1-C31;
A35-B1-C32;
A35-B1-C33;
A35-B1-C34;
A35-B1-C35;
A35-B1-C36;
A35-B1-C37;
A35-B1-C38;
A35-B1-C39;
A35-B1-C40;
A35-B1-C41;
A35-B1-C42;
A35-B1-C43;
A35-B1-C44;
A35-B1-C45;
A35-B1-C46;
A35-B1-C47;
A35-B1-C48;
A35-B1-C49;
A35-B1-C50;
A35-B1-C51;
A35-B1-C52;
A35-B1-C53;
A35-B1-C54;
A35-B1-C55;
A35-B1-C56;

-continued

A35-B1-C57;
A35-B1-C58;
A35-B1-C59;
A35-B1-C60;
A35-B1-C61;
A35-B1-C62;
A35-B1-C63;
A35-B1-C64;
A35-B1-C65;
A35-B1-C66;
A35-B1-C67;
A35-B1-C68;
A36-B1-C1;
A36-B1-C2;
A36-B1-C3;
A36-B1-C4;
A36-B1-C5;
A36-B1-C6;
A36-B1-C7;
A36-B1-C8;
A36-B1-C9;
A36-B1-C10;
A36-B1-C11;
A36-B1-C12;
A36-B1-C13;
A36-B1-C14;
A36-B1-C15;
A36-B1-C16;
A36-B1-C17;
A36-B1-C18;
A36-B1-C19;
A36-B1-C20;
A36-B1-C21;
A36-B1-C22;
A36-B1-C23;
A36-B1-C24;
A36-B1-C25;
A36-B1-C26;
A36-B1-C27;
A36-B1-C28;
A36-B1-C29;
A36-B1-C30;
A36-B1-C31;
A36-B1-C32;
A36-B1-C33;
A36-B1-C34;
A36-B1-C35;
A36-B1-C36;
A36-B1-C37;
A36-B1-C38;
A36-B1-C39;
A36-B1-C40;
A36-B1-C41;
A36-B1-C42;
A36-B1-C43;
A36-B1-C44;
A36-B1-C45;
A36-B1-C46;
A36-B1-C47;
A36-B1-C48;
A36-B1-C49;
A36-B1-C50;
A36-B1-C51;
A36-B1-C52;
A36-B1-C53;
A36-B1-C54;
A36-B1-C55;
A36-B1-C56;
A36-B1-C57;
A36-B1-C58;
A36-B1-C59;
A36-B1-C60;
A36-B1-C61;
A36-B1-C62;
A36-B1-C63;
A36-B1-C64;
A36-B1-C65;
A36-B1-C66;
A36-B1-C67;

-continued

A36-B1-C68;
A37-B1-C1;
A37-B1-C2;
A37-B1-C3;
A37-B1-C4;
A37-B1-C5;
A37-B1-C6;
A37-B1-C7;
A37-B1-C8;
A37-B1-C9;
A37-B1-C10;
A37-B1-C11;
A37-B1-C12;
A37-B1-C13;
A37-B1-C14;
A37-B1-C15;
A37-B1-C16;
A37-B1-C17;
A37-B1-C18;
A37-B1-C19;
A37-B1-C20;
A37-B1-C21;
A37-B1-C22;
A37-B1-C23;
A37-B1-C24;
A37-B1-C25;
A37-B1-C26;
A37-B1-C27;
A37-B1-C28;
A37-B1-C29;
A37-B1-C30;
A37-B1-C31;
A37-B1-C32;
A37-B1-C33;
A37-B1-C34;
A37-B1-C35;
A37-B1-C36;
A37-B1-C37;
A37-B1-C38;
A37-B1-C39;
A37-B1-C40;
A37-B1-C41;
A37-B1-C42;
A37-B1-C43;
A37-B1-C44;
A37-B1-C45;
A37-B1-C46;
A37-B1-C47;
A37-B1-C48;
A37-B1-C49;
A37-B1-C50;
A37-B1-C51;
A37-B1-C52;
A37-B1-C53;
A37-B1-C54;
A37-B1-C55;
A37-B1-C56;
A37-B1-C57;
A37-B1-C58;
A37-B1-C59;
A37-B1-C60;
A37-B1-C61;
A37-B1-C62;
A37-B1-C63;
A37-B1-C64;
A37-B1-C65;
A37-B1-C66;
A37-B1-C67;
A37-B1-C68;
A38-B1-C1;
A38-B1-C2;
A38-B1-C3;
A38-B1-C4;
A38-B1-C5;
A38-B1-C6;
A38-B1-C7;
A38-B1-C8;
A38-B1-C9;
A38-B1-C10;

A38-B1-C11;
A38-B1-C12;
A38-B1-C13;
A38-B1-C14;
A38-B1-C15;
A38-B1-C16;
A38-B1-C17;
A38-B1-C18;
A38-B1-C19;
A38-B1-C20;
A38-B1-C21;
A38-B1-C22;
A38-B1-C23;
A38-B1-C24;
A38-B1-C25;
A38-B1-C26;
A38-B1-C27;
A38-B1-C28;
A38-B1-C29;
A38-B1-C30;
A38-B1-C31;
A38-B1-C32;
A38-B1-C33;
A38-B1-C34;
A38-B1-C35;
A38-B1-C36;
A38-B1-C37;
A38-B1-C38;
A38-B1-C39;
A38-B1-C40;
A38-B1-C41;
A38-B1-C42;
A38-B1-C43;
A38-B1-C44;
A38-B1-C45;
A38-B1-C46;
A38-B1-C47;
A38-B1-C48;
A38-B1-C49;
A38-B1-C50;
A38-B1-C51;
A38-B1-C52;
A38-B1-C53;
A38-B1-C54;
A38-B1-C55;
A38-B1-C56;
A38-B1-C57;
A38-B1-C58;
A38-B1-C59;
A38-B1-C60;
A38-B1-C61;
A38-B1-C62;
A38-B1-C63;
A38-B1-C64;
A38-B1-C65;
A38-B1-C66;
A38-B1-C67;
A38-B1-C68;
A1-B2-C1;
A1-B2-C2;
A1-B2-C3;
A1-B2-C4;
A1-B2-C5;
A1-B2-C6;
A1-B2-C7;
A1-B2-C8;
A1-B2-C9;
A1-B2-C10;
A1-B2-C11;
A1-B2-C12;
A1-B2-C13;
A1-B2-C14;
A1-B2-C15;
A1-B2-C16;
A1-B2-C17;
A1-B2-C18;
A1-B2-C19;
A1-B2-C20;
A1-B2-C21;
A1-B2-C22;
A1-B2-C23;
A1-B2-C24;
A1-B2-C25;
A1-B2-C26;
A1-B2-C27;
A1-B2-C28;
A1-B2-C29;
A1-B2-C30;
A1-B2-C31;
A1-B2-C32;
A1-B2-C33;
A1-B2-C34;
A1-B2-C35;
A1-B2-C36;
A1-B2-C37;
A1-B2-C38;
A1-B2-C39;
A1-B2-C40;
A1-B2-C41;
A1-B2-C42;
A1-B2-C43;
A1-B2-C44;
A1-B2-C45;
A1-B2-C46;
A1-B2-C47;
A1-B2-C48;
A1-B2-C49;
A1-B2-C50;
A1-B2-C51;
A1-B2-C52;
A1-B2-C53;
A1-B2-C54;
A1-B2-C55;
A1-B2-C56;
A1-B2-C57;
A1-B2-C58;
A1-B2-C59;
A1-B2-C60;
A1-B2-C61;
A1-B2-C62;
A1-B2-C63;
A1-B2-C64;
A1-B2-C65;
A1-B2-C66;
A1-B2-C67;
A1-B2-C68;
A2-B2-C1;
A2-B2-C2;
A2-B2-C3;
A2-B2-C4;
A2-B2-C5;
A2-B2-C6;
A2-B2-C7;
A2-B2-C8;
A2-B2-C9;
A2-B2-C10;
A2-B2-C11;
A2-B2-C12;
A2-B2-C13;
A2-B2-C14;
A2-B2-C15;
A2-B2-C16;
A2-B2-C17;
A2-B2-C18;
A2-B2-C19;
A2-B2-C20;
A2-B2-C21;
A2-B2-C22;
A2-B2-C23;
A2-B2-C24;
A2-B2-C25;
A2-B2-C26;
A2-B2-C27;
A2-B2-C28;
A2-B2-C29;
A2-B2-C30;
A2-B2-C31;
A2-B2-C32;

A2-B2-C33;
A2-B2-C34;
A2-B2-C35;
A2-B2-C36;
A2-B2-C37;
A2-B2-C38;
A2-B2-C39;
A2-B2-C40;
A2-B2-C41;
A2-B2-C42;
A2-B2-C43;
A2-B2-C44;
A2-B2-C45;
A2-B2-C46;
A2-B2-C47;
A2-B2-C48;
A2-B2-C49;
A2-B2-C50;
A2-B2-C51;
A2-B2-C52;
A2-B2-C53;
A2-B2-C54;
A2-B2-C55;
A2-B2-C56;
A2-B2-C57;
A2-B2-C58;
A2-B2-C59;
A2-B2-C60;
A2-B2-C61;
A2-B2-C62;
A2-B2-C63;
A2-B2-C64;
A2-B2-C65;
A2-B2-C66;
A2-B2-C67;
A2-B2-C68;
A3-B2-C1;
A3-B2-C2;
A3-B2-C3;
A3-B2-C4;
A3-B2-C5;
A3-B2-C6;
A3-B2-C7;
A3-B2-C8;
A3-B2-C9;
A3-B2-C10;
A3-B2-C11;
A3-B2-C12;
A3-B2-C13;
A3-B2-C14;
A3-B2-C15;
A3-B2-C16;
A3-B2-C17;
A3-B2-C18;
A3-B2-C19;
A3-B2-C20;
A3-B2-C21;
A3-B2-C22;
A3-B2-C23;
A3-B2-C24;
A3-B2-C25;
A3-B2-C26;
A3-B2-C27;
A3-B2-C28;
A3-B2-C29;
A3-B2-C30;
A3-B2-C31;
A3-B2-C32;
A3-B2-C33;
A3-B2-C34;
A3-B2-C35;
A3-B2-C36;
A3-B2-C37;
A3-B2-C38;
A3-B2-C39;
A3-B2-C40;
A3-B2-C41;
A3-B2-C42;
A3-B2-C43;
A3-B2-C44;
A3-B2-C45;
A3-B2-C46;
A3-B2-C47;
A3-B2-C48;
A3-B2-C49;
A3-B2-C50;
A3-B2-C51;
A3-B2-C52;
A3-B2-C53;
A3-B2-C54;
A3-B2-C55;
A3-B2-C56;
A3-B2-C57;
A3-B2-C58;
A3-B2-C59;
A3-B2-C60;
A3-B2-C61;
A3-B2-C62;
A3-B2-C63;
A3-B2-C64;
A3-B2-C65;
A3-B2-C66;
A3-B2-C67;
A3-B2-C68;
A4-B2-C1;
A4-B2-C2;
A4-B2-C3;
A4-B2-C4;
A4-B2-C5;
A4-B2-C6;
A4-B2-C7;
A4-B2-C8;
A4-B2-C9;
A4-B2-C10;
A4-B2-C11;
A4-B2-C12;
A4-B2-C13;
A4-B2-C14;
A4-B2-C15;
A4-B2-C16;
A4-B2-C17;
A4-B2-C18;
A4-B2-C19;
A4-B2-C20;
A4-B2-C21;
A4-B2-C22;
A4-B2-C23;
A4-B2-C24;
A4-B2-C25;
A4-B2-C26;
A4-B2-C27;
A4-B2-C28;
A4-B2-C29;
A4-B2-C30;
A4-B2-C31;
A4-B2-C32;
A4-B2-C33;
A4-B2-C34;
A4-B2-C35;
A4-B2-C36;
A4-B2-C37;
A4-B2-C38;
A4-B2-C39;
A4-B2-C40;
A4-B2-C41;
A4-B2-C42;
A4-B2-C43;
A4-B2-C44;
A4-B2-C45;
A4-B2-C46;
A4-B2-C47;
A4-B2-C48;
A4-B2-C49;
A4-B2-C50;
A4-B2-C51;
A4-B2-C52;
A4-B2-C53;
A4-B2-C54;

-continued

A4-B2-C55;
A4-B2-C56;
A4-B2-C57;
A4-B2-C58;
A4-B2-C59;
A4-B2-C60;
A4-B2-C61;
A4-B2-C62;
A4-B2-C63;
A4-B2-C64;
A4-B2-C65;
A4-B2-C66;
A4-B2-C67;
A4-B2-C68;
A5-B2-C1;
A5-B2-C2;
A5-B2-C3;
A5-B2-C4;
A5-B2-C5;
A5-B2-C6;
A5-B2-C7;
A5-B2-C8;
A5-B2-C9;
A5-B2-C10;
A5-B2-C11;
A5-B2-C12;
A5-B2-C13;
A5-B2-C14;
A5-B2-C15;
A5-B2-C16;
A5-B2-C17;
A5-B2-C18;
A5-B2-C19;
A5-B2-C20;
A5-B2-C21;
A5-B2-C22;
A5-B2-C23;
A5-B2-C24;
A5-B2-C25;
A5-B2-C26;
A5-B2-C27;
A5-B2-C28;
A5-B2-C29;
A5-B2-C30;
A5-B2-C31;
A5-B2-C32;
A5-B2-C33;
A5-B2-C34;
A5-B2-C35;
A5-B2-C36;
A5-B2-C37;
A5-B2-C38;
A5-B2-C39;
A5-B2-C40;
A5-B2-C41;
A5-B2-C42;
A5-B2-C43;
A5-B2-C44;
A5-B2-C45;
A5-B2-C46;
A5-B2-C47;
A5-B2-C48;
A5-B2-C49;
A5-B2-C50;
A5-B2-C51;
A5-B2-C52;
A5-B2-C53;
A5-B2-C54;
A5-B2-C55;
A5-B2-C56;
A5-B2-C57;
A5-B2-C58;
A5-B2-C59;
A5-B2-C60;
A5-B2-C61;
A5-B2-C62;
A5-B2-C63;
A5-B2-C64;
A5-B2-C65;

-continued

A5-B2-C66;
A5-B2-C67;
A5-B2-C68;
A6-B2-C1;
A6-B2-C2;
A6-B2-C3;
A6-B2-C4;
A6-B2-C5;
A6-B2-C6;
A6-B2-C7;
A6-B2-C8;
A6-B2-C9;
A6-B2-C10;
A6-B2-C11;
A6-B2-C12;
A6-B2-C13;
A6-B2-C14;
A6-B2-C15;
A6-B2-C16;
A6-B2-C17;
A6-B2-C18;
A6-B2-C19;
A6-B2-C20;
A6-B2-C21;
A6-B2-C22;
A6-B2-C23;
A6-B2-C24;
A6-B2-C25;
A6-B2-C26;
A6-B2-C27;
A6-B2-C28;
A6-B2-C29;
A6-B2-C30;
A6-B2-C31;
A6-B2-C32;
A6-B2-C33;
A6-B2-C34;
A6-B2-C35;
A6-B2-C36;
A6-B2-C37;
A6-B2-C38;
A6-B2-C39;
A6-B2-C40;
A6-B2-C41;
A6-B2-C42;
A6-B2-C43;
A6-B2-C44;
A6-B2-C45;
A6-B2-C46;
A6-B2-C47;
A6-B2-C48;
A6-B2-C49;
A6-B2-C50;
A6-B2-C51;
A6-B2-C52;
A6-B2-C53;
A6-B2-C54;
A6-B2-C55;
A6-B2-C56;
A6-B2-C57;
A6-B2-C58;
A6-B2-C59;
A6-B2-C60;
A6-B2-C61;
A6-B2-C62;
A6-B2-C63;
A6-B2-C64;
A6-B2-C65;
A6-B2-C66;
A6-B2-C67;
A6-B2-C68;
A7-B2-C1;
A7-B2-C2;
A7-B2-C3;
A7-B2-C4;
A7-B2-C5;
A7-B2-C6;
A7-B2-C7;
A7-B2-C8;

-continued

A7-B2-C9;
A7-B2-C10;
A7-B2-C11;
A7-B2-C12;
A7-B2-C13;
A7-B2-C14;
A7-B2-C15;
A7-B2-C16;
A7-B2-C17;
A7-B2-C18;
A7-B2-C19;
A7-B2-C20;
A7-B2-C21;
A7-B2-C22;
A7-B2-C23;
A7-B2-C24;
A7-B2-C25;
A7-B2-C26;
A7-B2-C27;
A7-B2-C28;
A7-B2-C29;
A7-B2-C30;
A7-B2-C31;
A7-B2-C32;
A7-B2-C33;
A7-B2-C34;
A7-B2-C35;
A7-B2-C36;
A7-B2-C37;
A7-B2-C38;
A7-B2-C39;
A7-B2-C40;
A7-B2-C41;
A7-B2-C42;
A7-B2-C43;
A7-B2-C44;
A7-B2-C45;
A7-B2-C46;
A7-B2-C47;
A7-B2-C48;
A7-B2-C49;
A7-B2-C50;
A7-B2-C51;
A7-B2-C52;
A7-B2-C53;
A7-B2-C54;
A7-B2-C55;
A7-B2-C56;
A7-B2-C57;
A7-B2-C58;
A7-B2-C59;
A7-B2-C60;
A7-B2-C61;
A7-B2-C62;
A7-B2-C63;
A7-B2-C64;
A7-B2-C65;
A7-B2-C66;
A7-B2-C67;
A7-B2-C68;
A8-B2-C1;
A8-B2-C2;
A8-B2-C3;
A8-B2-C4;
A8-B2-C5;
A8-B2-C6;
A8-B2-C7;
A8-B2-C8;
A8-B2-C9;
A8-B2-C10;
A8-B2-C11;
A8-B2-C12;
A8-B2-C13;
A8-B2-C14;
A8-B2-C15;
A8-B2-C16;
A8-B2-C17;
A8-B2-C18;
A8-B2-C19;

-continued

A8-B2-C20;
A8-B2-C21;
A8-B2-C22;
A8-B2-C23;
A8-B2-C24;
A8-B2-C25;
A8-B2-C26;
A8-B2-C27;
A8-B2-C28;
A8-B2-C29;
A8-B2-C30;
A8-B2-C31;
A8-B2-C32;
A8-B2-C33;
A8-B2-C34;
A8-B2-C35;
A8-B2-C36;
A8-B2-C37;
A8-B2-C38;
A8-B2-C39;
A8-B2-C40;
A8-B2-C41;
A8-B2-C42;
A8-B2-C43;
A8-B2-C44;
A8-B2-C45;
A8-B2-C46;
A8-B2-C47;
A8-B2-C48;
A8-B2-C49;
A8-B2-C50;
A8-B2-C51;
A8-B2-C52;
A8-B2-C53;
A8-B2-C54;
A8-B2-C55;
A8-B2-C56;
A8-B2-C57;
A8-B2-C58;
A8-B2-C59;
A8-B2-C60;
A8-B2-C61;
A8-B2-C62;
A8-B2-C63;
A8-B2-C64;
A8-B2-C65;
A8-B2-C66;
A8-B2-C67;
A8-B2-C68;
A9-B2-C1;
A9-B2-C2;
A9-B2-C3;
A9-B2-C4;
A9-B2-C5;
A9-B2-C6;
A9-B2-C7;
A9-B2-C8;
A9-B2-C9;
A9-B2-C10;
A9-B2-C11;
A9-B2-C12;
A9-B2-C13;
A9-B2-C14;
A9-B2-C15;
A9-B2-C16;
A9-B2-C17;
A9-B2-C18;
A9-B2-C19;
A9-B2-C20;
A9-B2-C21;
A9-B2-C22;
A9-B2-C23;
A9-B2-C24;
A9-B2-C25;
A9-B2-C26;
A9-B2-C27;
A9-B2-C28;
A9-B2-C29;
A9-B2-C30;

A9-B2-C31;
A9-B2-C32;
A9-B2-C33;
A9-B2-C34;
A9-B2-C35;
A9-B2-C36;
A9-B2-C37;
A9-B2-C38;
A9-B2-C39;
A9-B2-C40;
A9-B2-C41;
A9-B2-C42;
A9-B2-C43;
A9-B2-C44;
A9-B2-C45;
A9-B2-C46;
A9-B2-C47;
A9-B2-C48;
A9-B2-C49;
A9-B2-C50;
A9-B2-C51;
A9-B2-C52;
A9-B2-C53;
A9-B2-C54;
A9-B2-C55;
A9-B2-C56;
A9-B2-C57;
A9-B2-C58;
A9-B2-C59;
A9-B2-C60;
A9-B2-C61;
A9-B2-C62;
A9-B2-C63;
A9-B2-C64;
A9-B2-C65;
A9-B2-C66;
A9-B2-C67;
A9-B2-C68;
A10-B2-C1;
A10-B2-C2;
A10-B2-C3;
A10-B2-C4;
A10-B2-C5;
A10-B2-C6;
A10-B2-C7;
A10-B2-C8;
A10-B2-C9;
A10-B2-C10;
A10-B2-C11;
A10-B2-C12;
A10-B2-C13;
A10-B2-C14;
A10-B2-C15;
A10-B2-C16;
A10-B2-C17;
A10-B2-C18;
A10-B2-C19;
A10-B2-C20;
A10-B2-C21;
A10-B2-C22;
A10-B2-C23;
A10-B2-C24;
A10-B2-C25;
A10-B2-C26;
A10-B2-C27;
A10-B2-C28;
A10-B2-C29;
A10-B2-C30;
A10-B2-C31;
A10-B2-C32;
A10-B2-C33;
A10-B2-C34;
A10-B2-C35;
A10-B2-C36;
A10-B2-C37;
A10-B2-C38;
A10-B2-C39;
A10-B2-C40;
A10-B2-C41;
A10-B2-C42;
A10-B2-C43;
A10-B2-C44;
A10-B2-C45;
A10-B2-C46;
A10-B2-C47;
A10-B2-C48;
A10-B2-C49;
A10-B2-C50;
A10-B2-C51;
A10-B2-C52;
A10-B2-C53;
A10-B2-C54;
A10-B2-C55;
A10-B2-C56;
A10-B2-C57;
A10-B2-C58;
A10-B2-C59;
A10-B2-C60;
A10-B2-C61;
A10-B2-C62;
A10-B2-C63;
A10-B2-C64;
A10-B2-C65;
A10-B2-C66;
A10-B2-C67;
A10-B2-C68;
A11-B2-C1;
A11-B2-C2;
A11-B2-C3;
A11-B2-C4;
A11-B2-C5;
A11-B2-C6;
A11-B2-C7;
A11-B2-C8;
A11-B2-C9;
A11-B2-C10;
A11-B2-C11;
A11-B2-C12;
A11-B2-C13;
A11-B2-C14;
A11-B2-C15;
A11-B2-C16;
A11-B2-C17;
A11-B2-C18;
A11-B2-C19;
A11-B2-C20;
A11-B2-C21;
A11-B2-C22;
A11-B2-C23;
A11-B2-C24;
A11-B2-C25;
A11-B2-C26;
A11-B2-C27;
A11-B2-C28;
A11-B2-C29;
A11-B2-C30;
A11-B2-C31;
A11-B2-C32;
A11-B2-C33;
A11-B2-C34;
A11-B2-C35;
A11-B2-C36;
A11-B2-C37;
A11-B2-C38;
A11-B2-C39;
A11-B2-C40;
A11-B2-C41;
A11-B2-C42;
A11-B2-C43;
A11-B2-C44;
A11-B2-C45;
A11-B2-C46;
A11-B2-C47;
A11-B2-C48;
A11-B2-C49;
A11-B2-C50;
A11-B2-C51;
A11-B2-C52;

A11-B2-C53;
A11-B2-C54;
A11-B2-C55;
A11-B2-C56;
A11-B2-C57;
A11-B2-C58;
A11-B2-C59;
A11-B2-C60;
A11-B2-C61;
A11-B2-C62;
A11-B2-C63;
A11-B2-C64;
A11-B2-C65;
A11-B2-C66;
A11-B2-C67;
A11-B2-C68;
A12-B2-C1;
A12-B2-C2;
A12-B2-C3;
A12-B2-C4;
A12-B2-C5;
A12-B2-C6;
A12-B2-C7;
A12-B2-C8;
A12-B2-C9;
A12-B2-C10;
A12-B2-C11;
A12-B2-C12;
A12-B2-C13;
A12-B2-C14;
A12-B2-C15;
A12-B2-C16;
A12-B2-C17;
A12-B2-C18;
A12-B2-C19;
A12-B2-C20;
A12-B2-C21;
A12-B2-C22;
A12-B2-C23;
A12-B2-C24;
A12-B2-C25;
A12-B2-C26;
A12-B2-C27;
A12-B2-C28;
A12-B2-C29;
A12-B2-C30;
A12-B2-C31;
A12-B2-C32;
A12-B2-C33;
A12-B2-C34;
A12-B2-C35;
A12-B2-C36;
A12-B2-C37;
A12-B2-C38;
A12-B2-C39;
A12-B2-C40;
A12-B2-C41;
A12-B2-C42;
A12-B2-C43;
A12-B2-C44;
A12-B2-C45;
A12-B2-C46;
A12-B2-C47;
A12-B2-C48;
A12-B2-C49;
A12-B2-C50;
A12-B2-C51;
A12-B2-C52;
A12-B2-C53;
A12-B2-C54;
A12-B2-C55;
A12-B2-C56;
A12-B2-C57;
A12-B2-C58;
A12-B2-C59;
A12-B2-C60;
A12-B2-C61;
A12-B2-C62;
A12-B2-C63;
A12-B2-C64;
A12-B2-C65;
A12-B2-C66;
A12-B2-C67;
A12-B2-C68;
A13-B2-C1;
A13-B2-C2;
A13-B2-C3;
A13-B2-C4;
A13-B2-C5;
A13-B2-C6;
A13-B2-C7;
A13-B2-C8;
A13-B2-C9;
A13-B2-C10;
A13-B2-C11;
A13-B2-C12;
A13-B2-C13;
A13-B2-C14;
A13-B2-C15;
A13-B2-C16;
A13-B2-C17;
A13-B2-C18;
A13-B2-C19;
A13-B2-C20;
A13-B2-C21;
A13-B2-C22;
A13-B2-C23;
A13-B2-C24;
A13-B2-C25;
A13-B2-C26;
A13-B2-C27;
A13-B2-C28;
A13-B2-C29;
A13-B2-C30;
A13-B2-C31;
A13-B2-C32;
A13-B2-C33;
A13-B2-C34;
A13-B2-C35;
A13-B2-C36;
A13-B2-C37;
A13-B2-C38;
A13-B2-C39;
A13-B2-C40;
A13-B2-C41;
A13-B2-C42;
A13-B2-C43;
A13-B2-C44;
A13-B2-C45;
A13-B2-C46;
A13-B2-C47;
A13-B2-C48;
A13-B2-C49;
A13-B2-C50;
A13-B2-C51;
A13-B2-C52;
A13-B2-C53;
A13-B2-C54;
A13-B2-C55;
A13-B2-C56;
A13-B2-C57;
A13-B2-C58;
A13-B2-C59;
A13-B2-C60;
A13-B2-C61;
A13-B2-C62;
A13-B2-C63;
A13-B2-C64;
A13-B2-C65;
A13-B2-C66;
A13-B2-C67;
A13-B2-C68;
A14-B2-C1;
A14-B2-C2;
A14-B2-C3;
A14-B2-C4;
A14-B2-C5;
A14-B2-C6;

-continued

A14-B2-C7;
A14-B2-C8;
A14-B2-C9;
A14-B2-C10;
A14-B2-C11;
A14-B2-C12;
A14-B2-C13;
A14-B2-C14;
A14-B2-C15;
A14-B2-C16;
A14-B2-C17;
A14-B2-C18;
A14-B2-C19;
A14-B2-C20;
A14-B2-C21;
A14-B2-C22;
A14-B2-C23;
A14-B2-C24;
A14-B2-C25;
A14-B2-C26;
A14-B2-C27;
A14-B2-C28;
A14-B2-C29;
A14-B2-C30;
A14-B2-C31;
A14-B2-C32;
A14-B2-C33;
A14-B2-C34;
A14-B2-C35;
A14-B2-C36;
A14-B2-C37;
A14-B2-C38;
A14-B2-C39;
A14-B2-C40;
A14-B2-C41;
A14-B2-C42;
A14-B2-C43;
A14-B2-C44;
A14-B2-C45;
A14-B2-C46;
A14-B2-C47;
A14-B2-C48;
A14-B2-C49;
A14-B2-C50;
A14-B2-C51;
A14-B2-C52;
A14-B2-C53;
A14-B2-C54;
A14-B2-C55;
A14-B2-C56;
A14-B2-C57;
A14-B2-C58;
A14-B2-C59;
A14-B2-C60;
A14-B2-C61;
A14-B2-C62;
A14-B2-C63;
A14-B2-C64;
A14-B2-C65;
A14-B2-C66;
A14-B2-C67;
A14-B2-C68;
A15-B2-C1;
A15-B2-C2;
A15-B2-C3;
A15-B2-C4;
A15-B2-C5;
A15-B2-C6;
A15-B2-C7;
A15-B2-C8;
A15-B2-C9;
A15-B2-C10;
A15-B2-C11;
A15-B2-C12;
A15-B2-C13;
A15-B2-C14;
A15-B2-C15;
A15-B2-C16;
A15-B2-C17;
A15-B2-C18;
A15-B2-C19;
A15-B2-C20;
A15-B2-C21;
A15-B2-C22;
A15-B2-C23;
A15-B2-C24;
A15-B2-C25;
A15-B2-C26;
A15-B2-C27;
A15-B2-C28;
A15-B2-C29;
A15-B2-C30;
A15-B2-C31;
A15-B2-C32;
A15-B2-C33;
A15-B2-C34;
A15-B2-C35;
A15-B2-C36;
A15-B2-C37;
A15-B2-C38;
A15-B2-C39;
A15-B2-C40;
A15-B2-C41;
A15-B2-C42;
A15-B2-C43;
A15-B2-C44;
A15-B2-C45;
A15-B2-C46;
A15-B2-C47;
A15-B2-C48;
A15-B2-C49;
A15-B2-C50;
A15-B2-C51;
A15-B2-C52;
A15-B2-C53;
A15-B2-C54;
A15-B2-C55;
A15-B2-C56;
A15-B2-C57;
A15-B2-C58;
A15-B2-C59;
A15-B2-C60;
A15-B2-C61;
A15-B2-C62;
A15-B2-C63;
A15-B2-C64;
A15-B2-C65;
A15-B2-C66;
A15-B2-C67;
A15-B2-C68;
A16-B2-C1;
A16-B2-C2;
A16-B2-C3;
A16-B2-C4;
A16-B2-C5;
A16-B2-C6;
A16-B2-C7;
A16-B2-C8;
A16-B2-C9;
A16-B2-C10;
A16-B2-C11;
A16-B2-C12;
A16-B2-C13;
A16-B2-C14;
A16-B2-C15;
A16-B2-C16;
A16-B2-C17;
A16-B2-C18;
A16-B2-C19;
A16-B2-C20;
A16-B2-C21;
A16-B2-C22;
A16-B2-C23;
A16-B2-C24;
A16-B2-C25;
A16-B2-C26;
A16-B2-C27;
A16-B2-C28;

A16-B2-C29;
A16-B2-C30;
A16-B2-C31;
A16-B2-C32;
A16-B2-C33;
A16-B2-C34;
A16-B2-C35;
A16-B2-C36;
A16-B2-C37;
A16-B2-C38;
A16-B2-C39;
A16-B2-C40;
A16-B2-C41;
A16-B2-C42;
A16-B2-C43;
A16-B2-C44;
A16-B2-C45;
A16-B2-C46;
A16-B2-C47;
A16-B2-C48;
A16-B2-C49;
A16-B2-C50;
A16-B2-C51;
A16-B2-C52;
A16-B2-C53;
A16-B2-C54;
A16-B2-C55;
A16-B2-C56;
A16-B2-C57;
A16-B2-C58;
A16-B2-C59;
A16-B2-C60;
A16-B2-C61;
A16-B2-C62;
A16-B2-C63;
A16-B2-C64;
A16-B2-C65;
A16-B2-C66;
A16-B2-C67;
A16-B2-C68;
A17-B2-C1;
A17-B2-C2;
A17-B2-C3;
A17-B2-C4;
A17-B2-C5;
A17-B2-C6;
A17-B2-C7;
A17-B2-C8;
A17-B2-C9;
A17-B2-C10;
A17-B2-C11;
A17-B2-C12;
A17-B2-C13;
A17-B2-C14;
A17-B2-C15;
A17-B2-C16;
A17-B2-C17;
A17-B2-C18;
A17-B2-C19;
A17-B2-C20;
A17-B2-C21;
A17-B2-C22;
A17-B2-C23;
A17-B2-C24;
A17-B2-C25;
A17-B2-C26;
A17-B2-C27;
A17-B2-C28;
A17-B2-C29;
A17-B2-C30;
A17-B2-C31;
A17-B2-C32;
A17-B2-C33;
A17-B2-C34;
A17-B2-C35;
A17-B2-C36;
A17-B2-C37;
A17-B2-C38;
A17-B2-C39;
A17-B2-C40;
A17-B2-C41;
A17-B2-C42;
A17-B2-C43;
A17-B2-C44;
A17-B2-C45;
A17-B2-C46;
A17-B2-C47;
A17-B2-C48;
A17-B2-C49;
A17-B2-C50;
A17-B2-C51;
A17-B2-C52;
A17-B2-C53;
A17-B2-C54;
A17-B2-C55;
A17-B2-C56;
A17-B2-C57;
A17-B2-C58;
A17-B2-C59;
A17-B2-C60;
A17-B2-C61;
A17-B2-C62;
A17-B2-C63;
A17-B2-C64;
A17-B2-C65;
A17-B2-C66;
A17-B2-C67;
A17-B2-C68;
A18-B2-C1;
A18-B2-C2;
A18-B2-C3;
A18-B2-C4;
A18-B2-C5;
A18-B2-C6;
A18-B2-C7;
A18-B2-C8;
A18-B2-C9;
A18-B2-C10;
A18-B2-C11;
A18-B2-C12;
A18-B2-C13;
A18-B2-C14;
A18-B2-C15;
A18-B2-C16;
A18-B2-C17;
A18-B2-C18;
A18-B2-C19;
A18-B2-C20;
A18-B2-C21;
A18-B2-C22;
A18-B2-C23;
A18-B2-C24;
A18-B2-C25;
A18-B2-C26;
A18-B2-C27;
A18-B2-C28;
A18-B2-C29;
A18-B2-C30;
A18-B2-C31;
A18-B2-C32;
A18-B2-C33;
A18-B2-C34;
A18-B2-C35;
A18-B2-C36;
A18-B2-C37;
A18-B2-C38;
A18-B2-C39;
A18-B2-C40;
A18-B2-C41;
A18-B2-C42;
A18-B2-C43;
A18-B2-C44;
A18-B2-C45;
A18-B2-C46;
A18-B2-C47;
A18-B2-C48;
A18-B2-C49;
A18-B2-C50;

-continued

A18-B2-C51;
A18-B2-C52;
A18-B2-C53;
A18-B2-C54;
A18-B2-C55;
A18-B2-C56;
A18-B2-C57;
A18-B2-C58;
A18-B2-C59;
A18-B2-C60;
A18-B2-C61;
A18-B2-C62;
A18-B2-C63;
A18-B2-C64;
A18-B2-C65;
A18-B2-C66;
A18-B2-C67;
A18-B2-C68;
A19-B2-C1;
A19-B2-C2;
A19-B2-C3;
A19-B2-C4;
A19-B2-C5;
A19-B2-C6;
A19-B2-C7;
A19-B2-C8;
A19-B2-C9;
A19-B2-C10;
A19-B2-C11;
A19-B2-C12;
A19-B2-C13;
A19-B2-C14;
A19-B2-C15;
A19-B2-C16;
A19-B2-C17;
A19-B2-C18;
A19-B2-C19;
A19-B2-C20;
A19-B2-C21;
A19-B2-C22;
A19-B2-C23;
A19-B2-C24;
A19-B2-C25;
A19-B2-C26;
A19-B2-C27;
A19-B2-C28;
A19-B2-C29;
A19-B2-C30;
A19-B2-C31;
A19-B2-C32;
A19-B2-C33;
A19-B2-C34;
A19-B2-C35;
A19-B2-C36;
A19-B2-C37;
A19-B2-C38;
A19-B2-C39;
A19-B2-C40;
A19-B2-C41;
A19-B2-C42;
A19-B2-C43;
A19-B2-C44;
A19-B2-C45;
A19-B2-C46;
A19-B2-C47;
A19-B2-C48;
A19-B2-C49;
A19-B2-C50;
A19-B2-C51;
A19-B2-C52;
A19-B2-C53;
A19-B2-C54;
A19-B2-C55;
A19-B2-C56;
A19-B2-C57;
A19-B2-C58;
A19-B2-C59;
A19-B2-C60;
A19-B2-C61;

-continued

A19-B2-C62;
A19-B2-C63;
A19-B2-C64;
A19-B2-C65;
A19-B2-C66;
A19-B2-C67;
A19-B2-C68;
A20-B2-C1;
A20-B2-C2;
A20-B2-C3;
A20-B2-C4;
A20-B2-C5;
A20-B2-C6;
A20-B2-C7;
A20-B2-C8;
A20-B2-C9;
A20-B2-C10;
A20-B2-C11;
A20-B2-C12;
A20-B2-C13;
A20-B2-C14;
A20-B2-C15;
A20-B2-C16;
A20-B2-C17;
A20-B2-C18;
A20-B2-C19;
A20-B2-C20;
A20-B2-C21;
A20-B2-C22;
A20-B2-C23;
A20-B2-C24;
A20-B2-C25;
A20-B2-C26;
A20-B2-C27;
A20-B2-C28;
A20-B2-C29;
A20-B2-C30;
A20-B2-C31;
A20-B2-C32;
A20-B2-C33;
A20-B2-C34;
A20-B2-C35;
A20-B2-C36;
A20-B2-C37;
A20-B2-C38;
A20-B2-C39;
A20-B2-C40;
A20-B2-C41;
A20-B2-C42;
A20-B2-C43;
A20-B2-C44;
A20-B2-C45;
A20-B2-C46;
A20-B2-C47;
A20-B2-C48;
A20-B2-C49;
A20-B2-C50;
A20-B2-C51;
A20-B2-C52;
A20-B2-C53;
A20-B2-C54;
A20-B2-C55;
A20-B2-C56;
A20-B2-C57;
A20-B2-C58;
A20-B2-C59;
A20-B2-C60;
A20-B2-C61;
A20-B2-C62;
A20-B2-C63;
A20-B2-C64;
A20-B2-C65;
A20-B2-C66;
A20-B2-C67;
A20-B2-C68;
A21-B2-C1;
A21-B2-C2;
A21-B2-C3;
A21-B2-C4;

A21-B2-C5;
A21-B2-C6;
A21-B2-C7;
A21-B2-C8;
A21-B2-C9;
A21-B2-C10;
A21-B2-C11;
A21-B2-C12;
A21-B2-C13;
A21-B2-C14;
A21-B2-C15;
A21-B2-C16;
A21-B2-C17;
A21-B2-C18;
A21-B2-C19;
A21-B2-C20;
A21-B2-C21;
A21-B2-C22;
A21-B2-C23;
A21-B2-C24;
A21-B2-C25;
A21-B2-C26;
A21-B2-C27;
A21-B2-C28;
A21-B2-C29;
A21-B2-C30;
A21-B2-C31;
A21-B2-C32;
A21-B2-C33;
A21-B2-C34;
A21-B2-C35;
A21-B2-C36;
A21-B2-C37;
A21-B2-C38;
A21-B2-C39;
A21-B2-C40;
A21-B2-C41;
A21-B2-C42;
A21-B2-C43;
A21-B2-C44;
A21-B2-C45;
A21-B2-C46;
A21-B2-C47;
A21-B2-C48;
A21-B2-C49;
A21-B2-C50;
A21-B2-C51;
A21-B2-C52;
A21-B2-C53;
A21-B2-C54;
A21-B2-C55;
A21-B2-C56;
A21-B2-C57;
A21-B2-C58;
A21-B2-C59;
A21-B2-C60;
A21-B2-C61;
A21-B2-C62;
A21-B2-C63;
A21-B2-C64;
A21-B2-C65;
A21-B2-C66;
A21-B2-C67;
A21-B2-C68;
A22-B2-C1;
A22-B2-C2;
A22-B2-C3;
A22-B2-C4;
A22-B2-C5;
A22-B2-C6;
A22-B2-C7;
A22-B2-C8;
A22-B2-C9;
A22-B2-C10;
A22-B2-C11;
A22-B2-C12;
A22-B2-C13;
A22-B2-C14;
A22-B2-C15;
A22-B2-C16;
A22-B2-C17;
A22-B2-C18;
A22-B2-C19;
A22-B2-C20;
A22-B2-C21;
A22-B2-C22;
A22-B2-C23;
A22-B2-C24;
A22-B2-C25;
A22-B2-C26;
A22-B2-C27;
A22-B2-C28;
A22-B2-C29;
A22-B2-C30;
A22-B2-C31;
A22-B2-C32;
A22-B2-C33;
A22-B2-C34;
A22-B2-C35;
A22-B2-C36;
A22-B2-C37;
A22-B2-C38;
A22-B2-C39;
A22-B2-C40;
A22-B2-C41;
A22-B2-C42;
A22-B2-C43;
A22-B2-C44;
A22-B2-C45;
A22-B2-C46;
A22-B2-C47;
A22-B2-C48;
A22-B2-C49;
A22-B2-C50;
A22-B2-C51;
A22-B2-C52;
A22-B2-C53;
A22-B2-C54;
A22-B2-C55;
A22-B2-C56;
A22-B2-C57;
A22-B2-C58;
A22-B2-C59;
A22-B2-C60;
A22-B2-C61;
A22-B2-C62;
A22-B2-C63;
A22-B2-C64;
A22-B2-C65;
A22-B2-C66;
A22-B2-C67;
A22-B2-C68;
A23-B2-C1;
A23-B2-C2;
A23-B2-C3;
A23-B2-C4;
A23-B2-C5;
A23-B2-C6;
A23-B2-C7;
A23-B2-C8;
A23-B2-C9;
A23-B2-C10;
A23-B2-C11;
A23-B2-C12;
A23-B2-C13;
A23-B2-C14;
A23-B2-C15;
A23-B2-C16;
A23-B2-C17;
A23-B2-C18;
A23-B2-C19;
A23-B2-C20;
A23-B2-C21;
A23-B2-C22;
A23-B2-C23;
A23-B2-C24;
A23-B2-C25;
A23-B2-C26;

-continued

A23-B2-C27;
A23-B2-C28;
A23-B2-C29;
A23-B2-C30;
A23-B2-C31;
A23-B2-C32;
A23-B2-C33;
A23-B2-C34;
A23-B2-C35;
A23-B2-C36;
A23-B2-C37;
A23-B2-C38;
A23-B2-C39;
A23-B2-C40;
A23-B2-C41;
A23-B2-C42;
A23-B2-C43;
A23-B2-C44;
A23-B2-C45;
A23-B2-C46;
A23-B2-C47;
A23-B2-C48;
A23-B2-C49;
A23-B2-C50;
A23-B2-C51;
A23-B2-C52;
A23-B2-C53;
A23-B2-C54;
A23-B2-C55;
A23-B2-C56;
A23-B2-C57;
A23-B2-C58;
A23-B2-C59;
A23-B2-C60;
A23-B2-C61;
A23-B2-C62;
A23-B2-C63;
A23-B2-C64;
A23-B2-C65;
A23-B2-C66;
A23-B2-C67;
A23-B2-C68;
A24-B2-C1;
A24-B2-C2;
A24-B2-C3;
A24-B2-C4;
A24-B2-C5;
A24-B2-C6;
A24-B2-C7;
A24-B2-C8;
A24-B2-C9;
A24-B2-C10;
A24-B2-C11;
A24-B2-C12;
A24-B2-C13;
A24-B2-C14;
A24-B2-C15;
A24-B2-C16;
A24-B2-C17;
A24-B2-C18;
A24-B2-C19;
A24-B2-C20;
A24-B2-C21;
A24-B2-C22;
A24-B2-C23;
A24-B2-C24;
A24-B2-C25;
A24-B2-C26;
A24-B2-C27;
A24-B2-C28;
A24-B2-C29;
A24-B2-C30;
A24-B2-C31;
A24-B2-C32;
A24-B2-C33;
A24-B2-C34;
A24-B2-C35;
A24-B2-C36;
A24-B2-C37;

-continued

A24-B2-C38;
A24-B2-C39;
A24-B2-C40;
A24-B2-C41;
A24-B2-C42;
A24-B2-C43;
A24-B2-C44;
A24-B2-C45;
A24-B2-C46;
A24-B2-C47;
A24-B2-C48;
A24-B2-C49;
A24-B2-C50;
A24-B2-C51;
A24-B2-C52;
A24-B2-C53;
A24-B2-C54;
A24-B2-C55;
A24-B2-C56;
A24-B2-C57;
A24-B2-C58;
A24-B2-C59;
A24-B2-C60;
A24-B2-C61;
A24-B2-C62;
A24-B2-C63;
A24-B2-C64;
A24-B2-C65;
A24-B2-C66;
A24-B2-C67;
A24-B2-C68;
A25-B2-C1;
A25-B2-C2;
A25-B2-C3;
A25-B2-C4;
A25-B2-C5;
A25-B2-C6;
A25-B2-C7;
A25-B2-C8;
A25-B2-C9;
A25-B2-C10;
A25-B2-C11;
A25-B2-C12;
A25-B2-C13;
A25-B2-C14;
A25-B2-C15;
A25-B2-C16;
A25-B2-C17;
A25-B2-C18;
A25-B2-C19;
A25-B2-C20;
A25-B2-C21;
A25-B2-C22;
A25-B2-C23;
A25-B2-C24;
A25-B2-C25;
A25-B2-C26;
A25-B2-C27;
A25-B2-C28;
A25-B2-C29;
A25-B2-C30;
A25-B2-C31;
A25-B2-C32;
A25-B2-C33;
A25-B2-C34;
A25-B2-C35;
A25-B2-C36;
A25-B2-C37;
A25-B2-C38;
A25-B2-C39;
A25-B2-C40;
A25-B2-C41;
A25-B2-C42;
A25-B2-C43;
A25-B2-C44;
A25-B2-C45;
A25-B2-C46;
A25-B2-C47;
A25-B2-C48;

-continued

A25-B2-C49;
A25-B2-C50;
A25-B2-C51;
A25-B2-C52;
A25-B2-C53;
A25-B2-C54;
A25-B2-C55;
A25-B2-C56;
A25-B2-C57;
A25-B2-C58;
A25-B2-C59;
A25-B2-C60;
A25-B2-C61;
A25-B2-C62;
A25-B2-C63;
A25-B2-C64;
A25-B2-C65;
A25-B2-C66;
A25-B2-C67;
A25-B2-C68;
A26-B2-C1;
A26-B2-C2;
A26-B2-C3;
A26-B2-C4;
A26-B2-C5;
A26-B2-C6;
A26-B2-C7;
A26-B2-C8;
A26-B2-C9;
A26-B2-C10;
A26-B2-C11;
A26-B2-C12;
A26-B2-C13;
A26-B2-C14;
A26-B2-C15;
A26-B2-C16;
A26-B2-C17;
A26-B2-C18;
A26-B2-C19;
A26-B2-C20;
A26-B2-C21;
A26-B2-C22;
A26-B2-C23;
A26-B2-C24;
A26-B2-C25;
A26-B2-C26;
A26-B2-C27;
A26-B2-C28;
A26-B2-C29;
A26-B2-C30;
A26-B2-C31;
A26-B2-C32;
A26-B2-C33;
A26-B2-C34;
A26-B2-C35;
A26-B2-C36;
A26-B2-C37;
A26-B2-C38;
A26-B2-C39;
A26-B2-C40;
A26-B2-C41;
A26-B2-C42;
A26-B2-C43;
A26-B2-C44;
A26-B2-C45;
A26-B2-C46;
A26-B2-C47;
A26-B2-C48;
A26-B2-C49;
A26-B2-C50;
A26-B2-C51;
A26-B2-C52;
A26-B2-C53;
A26-B2-C54;
A26-B2-C55;
A26-B2-C56;
A26-B2-C57;
A26-B2-C58;
A26-B2-C59;

-continued

A26-B2-C60;
A26-B2-C61;
A26-B2-C62;
A26-B2-C63;
A26-B2-C64;
A26-B2-C65;
A26-B2-C66;
A26-B2-C67;
A26-B2-C68;
A27-B2-C1;
A27-B2-C2;
A27-B2-C3;
A27-B2-C4;
A27-B2-C5;
A27-B2-C6;
A27-B2-C7;
A27-B2-C8;
A27-B2-C9;
A27-B2-C10;
A27-B2-C11;
A27-B2-C12;
A27-B2-C13;
A27-B2-C14;
A27-B2-C15;
A27-B2-C16;
A27-B2-C17;
A27-B2-C18;
A27-B2-C19;
A27-B2-C20;
A27-B2-C21;
A27-B2-C22;
A27-B2-C23;
A27-B2-C24;
A27-B2-C25;
A27-B2-C26;
A27-B2-C27;
A27-B2-C28;
A27-B2-C29;
A27-B2-C30;
A27-B2-C31;
A27-B2-C32;
A27-B2-C33;
A27-B2-C34;
A27-B2-C35;
A27-B2-C36;
A27-B2-C37;
A27-B2-C38;
A27-B2-C39;
A27-B2-C40;
A27-B2-C41;
A27-B2-C42;
A27-B2-C43;
A27-B2-C44;
A27-B2-C45;
A27-B2-C46;
A27-B2-C47;
A27-B2-C48;
A27-B2-C49;
A27-B2-C50;
A27-B2-C51;
A27-B2-C52;
A27-B2-C53;
A27-B2-C54;
A27-B2-C55;
A27-B2-C56;
A27-B2-C57;
A27-B2-C58;
A27-B2-C59;
A27-B2-C60;
A27-B2-C61;
A27-B2-C62;
A27-B2-C63;
A27-B2-C64;
A27-B2-C65;
A27-B2-C66;
A27-B2-C67;
A27-B2-C68;
A28-B2-C1;
A28-B2-C2;

A28-B2-C3;
A28-B2-C4;
A28-B2-C5;
A28-B2-C6;
A28-B2-C7;
A28-B2-C8;
A28-B2-C9;
A28-B2-C10;
A28-B2-C11;
A28-B2-C12;
A28-B2-C13;
A28-B2-C14;
A28-B2-C15;
A28-B2-C16;
A28-B2-C17;
A28-B2-C18;
A28-B2-C19;
A28-B2-C20;
A28-B2-C21;
A28-B2-C22;
A28-B2-C23;
A28-B2-C24;
A28-B2-C25;
A28-B2-C26;
A28-B2-C27;
A28-B2-C28;
A28-B2-C29;
A28-B2-C30;
A28-B2-C31;
A28-B2-C32;
A28-B2-C33;
A28-B2-C34;
A28-B2-C35;
A28-B2-C36;
A28-B2-C37;
A28-B2-C38;
A28-B2-C39;
A28-B2-C40;
A28-B2-C41;
A28-B2-C42;
A28-B2-C43;
A28-B2-C44;
A28-B2-C45;
A28-B2-C46;
A28-B2-C47;
A28-B2-C48;
A28-B2-C49;
A28-B2-C50;
A28-B2-C51;
A28-B2-C52;
A28-B2-C53;
A28-B2-C54;
A28-B2-C55;
A28-B2-C56;
A28-B2-C57;
A28-B2-C58;
A28-B2-C59;
A28-B2-C60;
A28-B2-C61;
A28-B2-C62;
A28-B2-C63;
A28-B2-C64;
A28-B2-C65;
A28-B2-C66;
A28-B2-C67;
A28-B2-C68;
A29-B2-C1;
A29-B2-C2;
A29-B2-C3;
A29-B2-C4;
A29-B2-C5;
A29-B2-C6;
A29-B2-C7;
A29-B2-C8;
A29-B2-C9;
A29-B2-C10;
A29-B2-C11;
A29-B2-C12;
A29-B2-C13;
A29-B2-C14;
A29-B2-C15;
A29-B2-C16;
A29-B2-C17;
A29-B2-C18;
A29-B2-C19;
A29-B2-C20;
A29-B2-C21;
A29-B2-C22;
A29-B2-C23;
A29-B2-C24;
A29-B2-C25;
A29-B2-C26;
A29-B2-C27;
A29-B2-C28;
A29-B2-C29;
A29-B2-C30;
A29-B2-C31;
A29-B2-C32;
A29-B2-C33;
A29-B2-C34;
A29-B2-C35;
A29-B2-C36;
A29-B2-C37;
A29-B2-C38;
A29-B2-C39;
A29-B2-C40;
A29-B2-C41;
A29-B2-C42;
A29-B2-C43;
A29-B2-C44;
A29-B2-C45;
A29-B2-C46;
A29-B2-C47;
A29-B2-C48;
A29-B2-C49;
A29-B2-C50;
A29-B2-C51;
A29-B2-C52;
A29-B2-C53;
A29-B2-C54;
A29-B2-C55;
A29-B2-C56;
A29-B2-C57;
A29-B2-C58;
A29-B2-C59;
A29-B2-C60;
A29-B2-C61;
A29-B2-C62;
A29-B2-C63;
A29-B2-C64;
A29-B2-C65;
A29-B2-C66;
A29-B2-C67;
A29-B2-C68;
A30-B2-C1;
A30-B2-C2;
A30-B2-C3;
A30-B2-C4;
A30-B2-C5;
A30-B2-C6;
A30-B2-C7;
A30-B2-C8;
A30-B2-C9;
A30-B2-C10;
A30-B2-C11;
A30-B2-C12;
A30-B2-C13;
A30-B2-C14;
A30-B2-C15;
A30-B2-C16;
A30-B2-C17;
A30-B2-C18;
A30-B2-C19;
A30-B2-C20;
A30-B2-C21;
A30-B2-C22;
A30-B2-C23;
A30-B2-C24;

A30-B2-C25;
A30-B2-C26;
A30-B2-C27;
A30-B2-C28;
A30-B2-C29;
A30-B2-C30;
A30-B2-C31;
A30-B2-C32;
A30-B2-C33;
A30-B2-C34;
A30-B2-C35;
A30-B2-C36;
A30-B2-C37;
A30-B2-C38;
A30-B2-C39;
A30-B2-C40;
A30-B2-C41;
A30-B2-C42;
A30-B2-C43;
A30-B2-C44;
A30-B2-C45;
A30-B2-C46;
A30-B2-C47;
A30-B2-C48;
A30-B2-C49;
A30-B2-C50;
A30-B2-C51;
A30-B2-C52;
A30-B2-C53;
A30-B2-C54;
A30-B2-C55;
A30-B2-C56;
A30-B2-C57;
A30-B2-C58;
A30-B2-C59;
A30-B2-C60;
A30-B2-C61;
A30-B2-C62;
A30-B2-C63;
A30-B2-C64;
A30-B2-C65;
A30-B2-C66;
A30-B2-C67;
A30-B2-C68;
A31-B2-C1;
A31-B2-C2;
A31-B2-C3;
A31-B2-C4;
A31-B2-C5;
A31-B2-C6;
A31-B2-C7;
A31-B2-C8;
A31-B2-C9;
A31-B2-C10;
A31-B2-C11;
A31-B2-C12;
A31-B2-C13;
A31-B2-C14;
A31-B2-C15;
A31-B2-C16;
A31-B2-C17;
A31-B2-C18;
A31-B2-C19;
A31-B2-C20;
A31-B2-C21;
A31-B2-C22;
A31-B2-C23;
A31-B2-C24;
A31-B2-C25;
A31-B2-C26;
A31-B2-C27;
A31-B2-C28;
A31-B2-C29;
A31-B2-C30;
A31-B2-C31;
A31-B2-C32;
A31-B2-C33;
A31-B2-C34;
A31-B2-C35;
A31-B2-C36;
A31-B2-C37;
A31-B2-C38;
A31-B2-C39;
A31-B2-C40;
A31-B2-C41;
A31-B2-C42;
A31-B2-C43;
A31-B2-C44;
A31-B2-C45;
A31-B2-C46;
A31-B2-C47;
A31-B2-C48;
A31-B2-C49;
A31-B2-C50;
A31-B2-C51;
A31-B2-C52;
A31-B2-C53;
A31-B2-C54;
A31-B2-C55;
A31-B2-C56;
A31-B2-C57;
A31-B2-C58;
A31-B2-C59;
A31-B2-C60;
A31-B2-C61;
A31-B2-C62;
A31-B2-C63;
A31-B2-C64;
A31-B2-C65;
A31-B2-C66;
A31-B2-C67;
A31-B2-C68;
A32-B2-C1;
A32-B2-C2;
A32-B2-C3;
A32-B2-C4;
A32-B2-C5;
A32-B2-C6;
A32-B2-C7;
A32-B2-C8;
A32-B2-C9;
A32-B2-C10;
A32-B2-C11;
A32-B2-C12;
A32-B2-C13;
A32-B2-C14;
A32-B2-C15;
A32-B2-C16;
A32-B2-C17;
A32-B2-C18;
A32-B2-C19;
A32-B2-C20;
A32-B2-C21;
A32-B2-C22;
A32-B2-C23;
A32-B2-C24;
A32-B2-C25;
A32-B2-C26;
A32-B2-C27;
A32-B2-C28;
A32-B2-C29;
A32-B2-C30;
A32-B2-C31;
A32-B2-C32;
A32-B2-C33;
A32-B2-C34;
A32-B2-C35;
A32-B2-C36;
A32-B2-C37;
A32-B2-C38;
A32-B2-C39;
A32-B2-C40;
A32-B2-C41;
A32-B2-C42;
A32-B2-C43;
A32-B2-C44;
A32-B2-C45;
A32-B2-C46;

A32-B2-C47;
A32-B2-C48;
A32-B2-C49;
A32-B2-C50;
A32-B2-C51;
A32-B2-C52;
A32-B2-C53;
A32-B2-C54;
A32-B2-C55;
A32-B2-C56;
A32-B2-C57;
A32-B2-C58;
A32-B2-C59;
A32-B2-C60;
A32-B2-C61;
A32-B2-C62;
A32-B2-C63;
A32-B2-C64;
A32-B2-C65;
A32-B2-C66;
A32-B2-C67;
A32-B2-C68;
A33-B2-C1;
A33-B2-C2;
A33-B2-C3;
A33-B2-C4;
A33-B2-C5;
A33-B2-C6;
A33-B2-C7;
A33-B2-C8;
A33-B2-C9;
A33-B2-C10;
A33-B2-C11;
A33-B2-C12;
A33-B2-C13;
A33-B2-C14;
A33-B2-C15;
A33-B2-C16;
A33-B2-C17;
A33-B2-C18;
A33-B2-C19;
A33-B2-C20;
A33-B2-C21;
A33-B2-C22;
A33-B2-C23;
A33-B2-C24;
A33-B2-C25;
A33-B2-C26;
A33-B2-C27;
A33-B2-C28;
A33-B2-C29;
A33-B2-C30;
A33-B2-C31;
A33-B2-C32;
A33-B2-C33;
A33-B2-C34;
A33-B2-C35;
A33-B2-C36;
A33-B2-C37;
A33-B2-C38;
A33-B2-C39;
A33-B2-C40;
A33-B2-C41;
A33-B2-C42;
A33-B2-C43;
A33-B2-C44;
A33-B2-C45;
A33-B2-C46;
A33-B2-C47;
A33-B2-C48;
A33-B2-C49;
A33-B2-C50;
A33-B2-C51;
A33-B2-C52;
A33-B2-C53;
A33-B2-C54;
A33-B2-C55;
A33-B2-C56;
A33-B2-C57;
A33-B2-C58;
A33-B2-C59;
A33-B2-C60;
A33-B2-C61;
A33-B2-C62;
A33-B2-C63;
A33-B2-C64;
A33-B2-C65;
A33-B2-C66;
A33-B2-C67;
A33-B2-C68;
A34-B2-C1;
A34-B2-C2;
A34-B2-C3;
A34-B2-C4;
A34-B2-C5;
A34-B2-C6;
A34-B2-C7;
A34-B2-C8;
A34-B2-C9;
A34-B2-C10;
A34-B2-C11;
A34-B2-C12;
A34-B2-C13;
A34-B2-C14;
A34-B2-C15;
A34-B2-C16;
A34-B2-C17;
A34-B2-C18;
A34-B2-C19;
A34-B2-C20;
A34-B2-C21;
A34-B2-C22;
A34-B2-C23;
A34-B2-C24;
A34-B2-C25;
A34-B2-C26;
A34-B2-C27;
A34-B2-C28;
A34-B2-C29;
A34-B2-C30;
A34-B2-C31;
A34-B2-C32;
A34-B2-C33;
A34-B2-C34;
A34-B2-C35;
A34-B2-C36;
A34-B2-C37;
A34-B2-C38;
A34-B2-C39;
A34-B2-C40;
A34-B2-C41;
A34-B2-C42;
A34-B2-C43;
A34-B2-C44;
A34-B2-C45;
A34-B2-C46;
A34-B2-C47;
A34-B2-C48;
A34-B2-C49;
A34-B2-C50;
A34-B2-C51;
A34-B2-C52;
A34-B2-C53;
A34-B2-C54;
A34-B2-C55;
A34-B2-C56;
A34-B2-C57;
A34-B2-C58;
A34-B2-C59;
A34-B2-C60;
A34-B2-C61;
A34-B2-C62;
A34-B2-C63;
A34-B2-C64;
A34-B2-C65;
A34-B2-C66;
A34-B2-C67;
A34-B2-C68;

A35-B2-C1;
A35-B2-C2;
A35-B2-C3;
A35-B2-C4;
A35-B2-C5;
A35-B2-C6;
A35-B2-C7;
A35-B2-C8;
A35-B2-C9;
A35-B2-C10;
A35-B2-C11;
A35-B2-C12;
A35-B2-C13;
A35-B2-C14;
A35-B2-C15;
A35-B2-C16;
A35-B2-C17;
A35-B2-C18;
A35-B2-C19;
A35-B2-C20;
A35-B2-C21;
A35-B2-C22;
A35-B2-C23;
A35-B2-C24;
A35-B2-C25;
A35-B2-C26;
A35-B2-C27;
A35-B2-C28;
A35-B2-C29;
A35-B2-C30;
A35-B2-C31;
A35-B2-C32;
A35-B2-C33;
A35-B2-C34;
A35-B2-C35;
A35-B2-C36;
A35-B2-C37;
A35-B2-C38;
A35-B2-C39;
A35-B2-C40;
A35-B2-C41;
A35-B2-C42;
A35-B2-C43;
A35-B2-C44;
A35-B2-C45;
A35-B2-C46;
A35-B2-C47;
A35-B2-C48;
A35-B2-C49;
A35-B2-C50;
A35-B2-C51;
A35-B2-C52;
A35-B2-C53;
A35-B2-C54;
A35-B2-C55;
A35-B2-C56;
A35-B2-C57;
A35-B2-C58;
A35-B2-C59;
A35-B2-C60;
A35-B2-C61;
A35-B2-C62;
A35-B2-C63;
A35-B2-C64;
A35-B2-C65;
A35-B2-C66;
A35-B2-C67;
A35-B2-C68;
A36-B2-C1;
A36-B2-C2;
A36-B2-C3;
A36-B2-C4;
A36-B2-C5;
A36-B2-C6;
A36-B2-C7;
A36-B2-C8;
A36-B2-C9;
A36-B2-C10;
A36-B2-C11;
A36-B2-C12;
A36-B2-C13;
A36-B2-C14;
A36-B2-C15;
A36-B2-C16;
A36-B2-C17;
A36-B2-C18;
A36-B2-C19;
A36-B2-C20;
A36-B2-C21;
A36-B2-C22;
A36-B2-C23;
A36-B2-C24;
A36-B2-C25;
A36-B2-C26;
A36-B2-C27;
A36-B2-C28;
A36-B2-C29;
A36-B2-C30;
A36-B2-C31;
A36-B2-C32;
A36-B2-C33;
A36-B2-C34;
A36-B2-C35;
A36-B2-C36;
A36-B2-C37;
A36-B2-C38;
A36-B2-C39;
A36-B2-C40;
A36-B2-C41;
A36-B2-C42;
A36-B2-C43;
A36-B2-C44;
A36-B2-C45;
A36-B2-C46;
A36-B2-C47;
A36-B2-C48;
A36-B2-C49;
A36-B2-C50;
A36-B2-C51;
A36-B2-C52;
A36-B2-C53;
A36-B2-C54;
A36-B2-C55;
A36-B2-C56;
A36-B2-C57;
A36-B2-C58;
A36-B2-C59;
A36-B2-C60;
A36-B2-C61;
A36-B2-C62;
A36-B2-C63;
A36-B2-C64;
A36-B2-C65;
A36-B2-C66;
A36-B2-C67;
A36-B2-C68;
A37-B2-C1;
A37-B2-C2;
A37-B2-C3;
A37-B2-C4;
A37-B2-C5;
A37-B2-C6;
A37-B2-C7;
A37-B2-C8;
A37-B2-C9;
A37-B2-C10;
A37-B2-C11;
A37-B2-C12;
A37-B2-C13;
A37-B2-C14;
A37-B2-C15;
A37-B2-C16;
A37-B2-C17;
A37-B2-C18;
A37-B2-C19;
A37-B2-C20;
A37-B2-C21;
A37-B2-C22;

A37-B2-C23;
A37-B2-C24;
A37-B2-C25;
A37-B2-C26;
A37-B2-C27;
A37-B2-C28;
A37-B2-C29;
A37-B2-C30;
A37-B2-C31;
A37-B2-C32;
A37-B2-C33;
A37-B2-C34;
A37-B2-C35;
A37-B2-C36;
A37-B2-C37;
A37-B2-C38;
A37-B2-C39;
A37-B2-C40;
A37-B2-C41;
A37-B2-C42;
A37-B2-C43;
A37-B2-C44;
A37-B2-C45;
A37-B2-C46;
A37-B2-C47;
A37-B2-C48;
A37-B2-C49;
A37-B2-C50;
A37-B2-C51;
A37-B2-C52;
A37-B2-C53;
A37-B2-C54;
A37-B2-C55;
A37-B2-C56;
A37-B2-C57;
A37-B2-C58;
A37-B2-C59;
A37-B2-C60;
A37-B2-C61;
A37-B2-C62;
A37-B2-C63;
A37-B2-C64;
A37-B2-C65;
A37-B2-C66;
A37-B2-C67;
A37-B2-C68;
A38-B2-C1;
A38-B2-C2;
A38-B2-C3;
A38-B2-C4;
A38-B2-C5;
A38-B2-C6;
A38-B2-C7;
A38-B2-C8;
A38-B2-C9;
A38-B2-C10;
A38-B2-C11;
A38-B2-C12;
A38-B2-C13;
A38-B2-C14;
A38-B2-C15;
A38-B2-C16;
A38-B2-C17;
A38-B2-C18;
A38-B2-C19;
A38-B2-C20;
A38-B2-C21;
A38-B2-C22;
A38-B2-C23;
A38-B2-C24;
A38-B2-C25;
A38-B2-C26;
A38-B2-C27;
A38-B2-C28;
A38-B2-C29;
A38-B2-C30;
A38-B2-C31;
A38-B2-C32;
A38-B2-C33;
A38-B2-C34;
A38-B2-C35;
A38-B2-C36;
A38-B2-C37;
A38-B2-C38;
A38-B2-C39;
A38-B2-C40;
A38-B2-C41;
A38-B2-C42;
A38-B2-C43;
A38-B2-C44;
A38-B2-C45;
A38-B2-C46;
A38-B2-C47;
A38-B2-C48;
A38-B2-C49;
A38-B2-C50;
A38-B2-C51;
A38-B2-C52;
A38-B2-C53;
A38-B2-C54;
A38-B2-C55;
A38-B2-C56;
A38-B2-C57;
A38-B2-C58;
A38-B2-C59;
A38-B2-C60;
A38-B2-C61;
A38-B2-C62;
A38-B2-C63;
A38-B2-C64;
A38-B2-C65;
A38-B2-C66;
A38-B2-C67;
A38-B2-C68;
A1-B3-C1;
A1-B3-C2;
A1-B3-C3;
A1-B3-C4;
A1-B3-C5;
A1-B3-C6;
A1-B3-C7;
A1-B3-C8;
A1-B3-C9;
A1-B3-C10;
A1-B3-C11;
A1-B3-C12;
A1-B3-C13;
A1-B3-C14;
A1-B3-C15;
A1-B3-C16;
A1-B3-C17;
A1-B3-C18;
A1-B3-C19;
A1-B3-C20;
A1-B3-C21;
A1-B3-C22;
A1-B3-C23;
A1-B3-C24;
A1-B3-C25;
A1-B3-C26;
A1-B3-C27;
A1-B3-C28;
A1-B3-C29;
A1-B3-C30;
A1-B3-C31;
A1-B3-C32;
A1-B3-C33;
A1-B3-C34;
A1-B3-C35;
A1-B3-C36;
A1-B3-C37;
A1-B3-C38;
A1-B3-C39;
A1-B3-C40;
A1-B3-C41;
A1-B3-C42;
A1-B3-C43;
A1-B3-C44;

-continued

A1-B3-C45;
A1-B3-C46;
A1-B3-C47;
A1-B3-C48;
A1-B3-C49;
A1-B3-C50;
A1-B3-C51;
A1-B3-C52;
A1-B3-C53;
A1-B3-C54;
A1-B3-C55;
A1-B3-C56;
A1-B3-C57;
A1-B3-C58;
A1-B3-C59;
A1-B3-C60;
A1-B3-C61;
A1-B3-C62;
A1-B3-C63;
A1-B3-C64;
A1-B3-C65;
A1-B3-C66;
A1-B3-C67;
A1-B3-C68;
A2-B3-C1;
A2-B3-C2;
A2-B3-C3;
A2-B3-C4;
A2-B3-C5;
A2-B3-C6;
A2-B3-C7;
A2-B3-C8;
A2-B3-C9;
A2-B3-C10;
A2-B3-C11;
A2-B3-C12;
A2-B3-C13;
A2-B3-C14;
A2-B3-C15;
A2-B3-C16;
A2-B3-C17;
A2-B3-C18;
A2-B3-C19;
A2-B3-C20;
A2-B3-C21;
A2-B3-C22;
A2-B3-C23;
A2-B3-C24;
A2-B3-C25;
A2-B3-C26;
A2-B3-C27;
A2-B3-C28;
A2-B3-C29;
A2-B3-C30;
A2-B3-C31;
A2-B3-C32;
A2-B3-C33;
A2-B3-C34;
A2-B3-C35;
A2-B3-C36;
A2-B3-C37;
A2-B3-C38;
A2-B3-C39;
A2-B3-C40;
A2-B3-C41;
A2-B3-C42;
A2-B3-C43;
A2-B3-C44;
A2-B3-C45;
A2-B3-C46;
A2-B3-C47;
A2-B3-C48;
A2-B3-C49;
A2-B3-C50;
A2-B3-C51;
A2-B3-C52;
A2-B3-C53;
A2-B3-C54;
A2-B3-C55;

-continued

A2-B3-C56;
A2-B3-C57;
A2-B3-C58;
A2-B3-C59;
A2-B3-C60;
A2-B3-C61;
A2-B3-C62;
A2-B3-C63;
A2-B3-C64;
A2-B3-C65;
A2-B3-C66;
A2-B3-C67;
A2-B3-C68;
A3-B3-C1;
A3-B3-C2;
A3-B3-C3;
A3-B3-C4;
A3-B3-C5;
A3-B3-C6;
A3-B3-C7;
A3-B3-C8;
A3-B3-C9;
A3-B3-C10;
A3-B3-C11;
A3-B3-C12;
A3-B3-C13;
A3-B3-C14;
A3-B3-C15;
A3-B3-C16;
A3-B3-C17;
A3-B3-C18;
A3-B3-C19;
A3-B3-C20;
A3-B3-C21;
A3-B3-C22;
A3-B3-C23;
A3-B3-C24;
A3-B3-C25;
A3-B3-C26;
A3-B3-C27;
A3-B3-C28;
A3-B3-C29;
A3-B3-C30;
A3-B3-C31;
A3-B3-C32;
A3-B3-C33;
A3-B3-C34;
A3-B3-C35;
A3-B3-C36;
A3-B3-C37;
A3-B3-C38;
A3-B3-C39;
A3-B3-C40;
A3-B3-C41;
A3-B3-C42;
A3-B3-C43;
A3-B3-C44;
A3-B3-C45;
A3-B3-C46;
A3-B3-C47;
A3-B3-C48;
A3-B3-C49;
A3-B3-C50;
A3-B3-C51;
A3-B3-C52;
A3-B3-C53;
A3-B3-C54;
A3-B3-C55;
A3-B3-C56;
A3-B3-C57;
A3-B3-C58;
A3-B3-C59;
A3-B3-C60;
A3-B3-C61;
A3-B3-C62;
A3-B3-C63;
A3-B3-C64;
A3-B3-C65;
A3-B3-C66;

A3-B3-C67;
A3-B3-C68;
A4-B3-C1;
A4-B3-C2;
A4-B3-C3;
A4-B3-C4;
A4-B3-C5;
A4-B3-C6;
A4-B3-C7;
A4-B3-C8;
A4-B3-C9;
A4-B3-C10;
A4-B3-C11;
A4-B3-C12;
A4-B3-C13;
A4-B3-C14;
A4-B3-C15;
A4-B3-C16;
A4-B3-C17;
A4-B3-C18;
A4-B3-C19;
A4-B3-C20;
A4-B3-C21;
A4-B3-C22;
A4-B3-C23;
A4-B3-C24;
A4-B3-C25;
A4-B3-C26;
A4-B3-C27;
A4-B3-C28;
A4-B3-C29;
A4-B3-C30;
A4-B3-C31;
A4-B3-C32;
A4-B3-C33;
A4-B3-C34;
A4-B3-C35;
A4-B3-C36;
A4-B3-C37;
A4-B3-C38;
A4-B3-C39;
A4-B3-C40;
A4-B3-C41;
A4-B3-C42;
A4-B3-C43;
A4-B3-C44;
A4-B3-C45;
A4-B3-C46;
A4-B3-C47;
A4-B3-C48;
A4-B3-C49;
A4-B3-C50;
A4-B3-C51;
A4-B3-C52;
A4-B3-C53;
A4-B3-C54;
A4-B3-C55;
A4-B3-C56;
A4-B3-C57;
A4-B3-C58;
A4-B3-C59;
A4-B3-C60;
A4-B3-C61;
A4-B3-C62;
A4-B3-C63;
A4-B3-C64;
A4-B3-C65;
A4-B3-C66;
A4-B3-C67;
A4-B3-C68;
A5-B3-C1;
A5-B3-C2;
A5-B3-C3;
A5-B3-C4;
A5-B3-C5;
A5-B3-C6;
A5-B3-C7;
A5-B3-C8;
A5-B3-C9;
A5-B3-C10;
A5-B3-C11;
A5-B3-C12;
A5-B3-C13;
A5-B3-C14;
A5-B3-C15;
A5-B3-C16;
A5-B3-C17;
A5-B3-C18;
A5-B3-C19;
A5-B3-C20;
A5-B3-C21;
A5-B3-C22;
A5-B3-C23;
A5-B3-C24;
A5-B3-C25;
A5-B3-C26;
A5-B3-C27;
A5-B3-C28;
A5-B3-C29;
A5-B3-C30;
A5-B3-C31;
A5-B3-C32;
A5-B3-C33;
A5-B3-C34;
A5-B3-C35;
A5-B3-C36;
A5-B3-C37;
A5-B3-C38;
A5-B3-C39;
A5-B3-C40;
A5-B3-C41;
A5-B3-C42;
A5-B3-C43;
A5-B3-C44;
A5-B3-C45;
A5-B3-C46;
A5-B3-C47;
A5-B3-C48;
A5-B3-C49;
A5-B3-C50;
A5-B3-C51;
A5-B3-C52;
A5-B3-C53;
A5-B3-C54;
A5-B3-C55;
A5-B3-C56;
A5-B3-C57;
A5-B3-C58;
A5-B3-C59;
A5-B3-C60;
A5-B3-C61;
A5-B3-C62;
A5-B3-C63;
A5-B3-C64;
A5-B3-C65;
A5-B3-C66;
A5-B3-C67;
A5-B3-C68;
A6-B3-C1;
A6-B3-C2;
A6-B3-C3;
A6-B3-C4;
A6-B3-C5;
A6-B3-C6;
A6-B3-C7;
A6-B3-C8;
A6-B3-C9;
A6-B3-C10;
A6-B3-C11;
A6-B3-C12;
A6-B3-C13;
A6-B3-C14;
A6-B3-C15;
A6-B3-C16;
A6-B3-C17;
A6-B3-C18;
A6-B3-C19;
A6-B3-C20;

A6-B3-C21;
A6-B3-C22;
A6-B3-C23;
A6-B3-C24;
A6-B3-C25;
A6-B3-C26;
A6-B3-C27;
A6-B3-C28;
A6-B3-C29;
A6-B3-C30;
A6-B3-C31;
A6-B3-C32;
A6-B3-C33;
A6-B3-C34;
A6-B3-C35;
A6-B3-C36;
A6-B3-C37;
A6-B3-C38;
A6-B3-C39;
A6-B3-C40;
A6-B3-C41;
A6-B3-C42;
A6-B3-C43;
A6-B3-C44;
A6-B3-C45;
A6-B3-C46;
A6-B3-C47;
A6-B3-C48;
A6-B3-C49;
A6-B3-C50;
A6-B3-C51;
A6-B3-C52;
A6-B3-C53;
A6-B3-C54;
A6-B3-C55;
A6-B3-C56;
A6-B3-C57;
A6-B3-C58;
A6-B3-C59;
A6-B3-C60;
A6-B3-C61;
A6-B3-C62;
A6-B3-C63;
A6-B3-C64;
A6-B3-C65;
A6-B3-C66;
A6-B3-C67;
A6-B3-C68;
A7-B3-C1;
A7-B3-C2;
A7-B3-C3;
A7-B3-C4;
A7-B3-C5;
A7-B3-C6;
A7-B3-C7;
A7-B3-C8;
A7-B3-C9;
A7-B3-C10;
A7-B3-C11;
A7-B3-C12;
A7-B3-C13;
A7-B3-C14;
A7-B3-C15;
A7-B3-C16;
A7-B3-C17;
A7-B3-C18;
A7-B3-C19;
A7-B3-C20;
A7-B3-C21;
A7-B3-C22;
A7-B3-C23;
A7-B3-C24;
A7-B3-C25;
A7-B3-C26;
A7-B3-C27;
A7-B3-C28;
A7-B3-C29;
A7-B3-C30;
A7-B3-C31;
A7-B3-C32;
A7-B3-C33;
A7-B3-C34;
A7-B3-C35;
A7-B3-C36;
A7-B3-C37;
A7-B3-C38;
A7-B3-C39;
A7-B3-C40;
A7-B3-C41;
A7-B3-C42;
A7-B3-C43;
A7-B3-C44;
A7-B3-C45;
A7-B3-C46;
A7-B3-C47;
A7-B3-C48;
A7-B3-C49;
A7-B3-C50;
A7-B3-C51;
A7-B3-C52;
A7-B3-C53;
A7-B3-C54;
A7-B3-C55;
A7-B3-C56;
A7-B3-C57;
A7-B3-C58;
A7-B3-C59;
A7-B3-C60;
A7-B3-C61;
A7-B3-C62;
A7-B3-C63;
A7-B3-C64;
A7-B3-C65;
A7-B3-C66;
A7-B3-C67;
A7-B3-C68;
A8-B3-C1;
A8-B3-C2;
A8-B3-C3;
A8-B3-C4;
A8-B3-C5;
A8-B3-C6;
A8-B3-C7;
A8-B3-C8;
A8-B3-C9;
A8-B3-C10;
A8-B3-C11;
A8-B3-C12;
A8-B3-C13;
A8-B3-C14;
A8-B3-C15;
A8-B3-C16;
A8-B3-C17;
A8-B3-C18;
A8-B3-C19;
A8-B3-C20;
A8-B3-C21;
A8-B3-C22;
A8-B3-C23;
A8-B3-C24;
A8-B3-C25;
A8-B3-C26;
A8-B3-C27;
A8-B3-C28;
A8-B3-C29;
A8-B3-C30;
A8-B3-C31;
A8-B3-C32;
A8-B3-C33;
A8-B3-C34;
A8-B3-C35;
A8-B3-C36;
A8-B3-C37;
A8-B3-C38;
A8-B3-C39;
A8-B3-C40;
A8-B3-C41;
A8-B3-C42;

-continued

A8-B3-C43;
A8-B3-C44;
A8-B3-C45;
A8-B3-C46;
A8-B3-C47;
A8-B3-C48;
A8-B3-C49;
A8-B3-C50;
A8-B3-C51;
A8-B3-C52;
A8-B3-C53;
A8-B3-C54;
A8-B3-C55;
A8-B3-C56;
A8-B3-C57;
A8-B3-C58;
A8-B3-C59;
A8-B3-C60;
A8-B3-C61;
A8-B3-C62;
A8-B3-C63;
A8-B3-C64;
A8-B3-C65;
A8-B3-C66;
A8-B3-C67;
A8-B3-C68;
A9-B3-C1;
A9-B3-C2;
A9-B3-C3;
A9-B3-C4;
A9-B3-C5;
A9-B3-C6;
A9-B3-C7;
A9-B3-C8;
A9-B3-C9;
A9-B3-C10;
A9-B3-C11;
A9-B3-C12;
A9-B3-C13;
A9-B3-C14;
A9-B3-C15;
A9-B3-C16;
A9-B3-C17;
A9-B3-C18;
A9-B3-C19;
A9-B3-C20;
A9-B3-C21;
A9-B3-C22;
A9-B3-C23;
A9-B3-C24;
A9-B3-C25;
A9-B3-C26;
A9-B3-C27;
A9-B3-C28;
A9-B3-C29;
A9-B3-C30;
A9-B3-C31;
A9-B3-C32;
A9-B3-C33;
A9-B3-C34;
A9-B3-C35;
A9-B3-C36;
A9-B3-C37;
A9-B3-C38;
A9-B3-C39;
A9-B3-C40;
A9-B3-C41;
A9-B3-C42;
A9-B3-C43;
A9-B3-C44;
A9-B3-C45;
A9-B3-C46;
A9-B3-C47;
A9-B3-C48;
A9-B3-C49;
A9-B3-C50;
A9-B3-C51;
A9-B3-C52;
A9-B3-C53;
A9-B3-C54;
A9-B3-C55;
A9-B3-C56;
A9-B3-C57;
A9-B3-C58;
A9-B3-C59;
A9-B3-C60;
A9-B3-C61;
A9-B3-C62;
A9-B3-C63;
A9-B3-C64;
A9-B3-C65;
A9-B3-C66;
A9-B3-C67;
A9-B3-C68;
A10-B3-C1;
A10-B3-C2;
A10-B3-C3;
A10-B3-C4;
A10-B3-C5;
A10-B3-C6;
A10-B3-C7;
A10-B3-C8;
A10-B3-C9;
A10-B3-C10;
A10-B3-C11;
A10-B3-C12;
A10-B3-C13;
A10-B3-C14;
A10-B3-C15;
A10-B3-C16;
A10-B3-C17;
A10-B3-C18;
A10-B3-C19;
A10-B3-C20;
A10-B3-C21;
A10-B3-C22;
A10-B3-C23;
A10-B3-C24;
A10-B3-C25;
A10-B3-C26;
A10-B3-C27;
A10-B3-C28;
A10-B3-C29;
A10-B3-C30;
A10-B3-C31;
A10-B3-C32;
A10-B3-C33;
A10-B3-C34;
A10-B3-C35;
A10-B3-C36;
A10-B3-C37;
A10-B3-C38;
A10-B3-C39;
A10-B3-C40;
A10-B3-C41;
A10-B3-C42;
A10-B3-C43;
A10-B3-C44;
A10-B3-C45;
A10-B3-C46;
A10-B3-C47;
A10-B3-C48;
A10-B3-C49;
A10-B3-C50;
A10-B3-C51;
A10-B3-C52;
A10-B3-C53;
A10-B3-C54;
A10-B3-C55;
A10-B3-C56;
A10-B3-C57;
A10-B3-C58;
A10-B3-C59;
A10-B3-C60;
A10-B3-C61;
A10-B3-C62;
A10-B3-C63;
A10-B3-C64;

A10-B3-C65;
A10-B3-C66;
A10-B3-C67;
A10-B3-C68;
A11-B3-C1;
A11-B3-C2;
A11-B3-C3;
A11-B3-C4;
A11-B3-C5;
A11-B3-C6;
A11-B3-C7;
A11-B3-C8;
A11-B3-C9;
A11-B3-C10;
A11-B3-C11;
A11-B3-C12;
A11-B3-C13;
A11-B3-C14;
A11-B3-C15;
A11-B3-C16;
A11-B3-C17;
A11-B3-C18;
A11-B3-C19;
A11-B3-C20;
A11-B3-C21;
A11-B3-C22;
A11-B3-C23;
A11-B3-C24;
A11-B3-C25;
A11-B3-C26;
A11-B3-C27;
A11-B3-C28;
A11-B3-C29;
A11-B3-C30;
A11-B3-C31;
A11-B3-C32;
A11-B3-C33;
A11-B3-C34;
A11-B3-C35;
A11-B3-C36;
A11-B3-C37;
A11-B3-C38;
A11-B3-C39;
A11-B3-C40;
A11-B3-C41;
A11-B3-C42;
A11-B3-C43;
A11-B3-C44;
A11-B3-C45;
A11-B3-C46;
A11-B3-C47;
A11-B3-C48;
A11-B3-C49;
A11-B3-C50;
A11-B3-C51;
A11-B3-C52;
A11-B3-C53;
A11-B3-C54;
A11-B3-C55;
A11-B3-C56;
A11-B3-C57;
A11-B3-C58;
A11-B3-C59;
A11-B3-C60;
A11-B3-C61;
A11-B3-C62;
A11-B3-C63;
A11-B3-C64;
A11-B3-C65;
A11-B3-C66;
A11-B3-C67;
A11-B3-C68;
A12-B3-C1;
A12-B3-C2;
A12-B3-C3;
A12-B3-C4;
A12-B3-C5;
A12-B3-C6;
A12-B3-C7;
A12-B3-C8;
A12-B3-C9;
A12-B3-C10;
A12-B3-C11;
A12-B3-C12;
A12-B3-C13;
A12-B3-C14;
A12-B3-C15;
A12-B3-C16;
A12-B3-C17;
A12-B3-C18;
A12-B3-C19;
A12-B3-C20;
A12-B3-C21;
A12-B3-C22;
A12-B3-C23;
A12-B3-C24;
A12-B3-C25;
A12-B3-C26;
A12-B3-C27;
A12-B3-C28;
A12-B3-C29;
A12-B3-C30;
A12-B3-C31;
A12-B3-C32;
A12-B3-C33;
A12-B3-C34;
A12-B3-C35;
A12-B3-C36;
A12-B3-C37;
A12-B3-C38;
A12-B3-C39;
A12-B3-C40;
A12-B3-C41;
A12-B3-C42;
A12-B3-C43;
A12-B3-C44;
A12-B3-C45;
A12-B3-C46;
A12-B3-C47;
A12-B3-C48;
A12-B3-C49;
A12-B3-C50;
A12-B3-C51;
A12-B3-C52;
A12-B3-C53;
A12-B3-C54;
A12-B3-C55;
A12-B3-C56;
A12-B3-C57;
A12-B3-C58;
A12-B3-C59;
A12-B3-C60;
A12-B3-C61;
A12-B3-C62;
A12-B3-C63;
A12-B3-C64;
A12-B3-C65;
A12-B3-C66;
A12-B3-C67;
A12-B3-C68;
A13-B3-C1;
A13-B3-C2;
A13-B3-C3;
A13-B3-C4;
A13-B3-C5;
A13-B3-C6;
A13-B3-C7;
A13-B3-C8;
A13-B3-C9;
A13-B3-C10;
A13-B3-C11;
A13-B3-C12;
A13-B3-C13;
A13-B3-C14;
A13-B3-C15;
A13-B3-C16;
A13-B3-C17;
A13-B3-C18;

A13-B3-C19;
A13-B3-C20;
A13-B3-C21;
A13-B3-C22;
A13-B3-C23;
A13-B3-C24;
A13-B3-C25;
A13-B3-C26;
A13-B3-C27;
A13-B3-C28;
A13-B3-C29;
A13-B3-C30;
A13-B3-C31;
A13-B3-C32;
A13-B3-C33;
A13-B3-C34;
A13-B3-C35;
A13-B3-C36;
A13-B3-C37;
A13-B3-C38;
A13-B3-C39;
A13-B3-C40;
A13-B3-C41;
A13-B3-C42;
A13-B3-C43;
A13-B3-C44;
A13-B3-C45;
A13-B3-C46;
A13-B3-C47;
A13-B3-C48;
A13-B3-C49;
A13-B3-C50;
A13-B3-C51;
A13-B3-C52;
A13-B3-C53;
A13-B3-C54;
A13-B3-C55;
A13-B3-C56;
A13-B3-C57;
A13-B3-C58;
A13-B3-C59;
A13-B3-C60;
A13-B3-C61;
A13-B3-C62;
A13-B3-C63;
A13-B3-C64;
A13-B3-C65;
A13-B3-C66;
A13-B3-C67;
A13-B3-C68;
A14-B3-C1;
A14-B3-C2;
A14-B3-C3;
A14-B3-C4;
A14-B3-C5;
A14-B3-C6;
A14-B3-C7;
A14-B3-C8;
A14-B3-C9;
A14-B3-C10;
A14-B3-C11;
A14-B3-C12;
A14-B3-C13;
A14-B3-C14;
A14-B3-C15;
A14-B3-C16;
A14-B3-C17;
A14-B3-C18;
A14-B3-C19;
A14-B3-C20;
A14-B3-C21;
A14-B3-C22;
A14-B3-C23;
A14-B3-C24;
A14-B3-C25;
A14-B3-C26;
A14-B3-C27;
A14-B3-C28;
A14-B3-C29;
A14-B3-C30;
A14-B3-C31;
A14-B3-C32;
A14-B3-C33;
A14-B3-C34;
A14-B3-C35;
A14-B3-C36;
A14-B3-C37;
A14-B3-C38;
A14-B3-C39;
A14-B3-C40;
A14-B3-C41;
A14-B3-C42;
A14-B3-C43;
A14-B3-C44;
A14-B3-C45;
A14-B3-C46;
A14-B3-C47;
A14-B3-C48;
A14-B3-C49;
A14-B3-C50;
A14-B3-C51;
A14-B3-C52;
A14-B3-C53;
A14-B3-C54;
A14-B3-C55;
A14-B3-C56;
A14-B3-C57;
A14-B3-C58;
A14-B3-C59;
A14-B3-C60;
A14-B3-C61;
A14-B3-C62;
A14-B3-C63;
A14-B3-C64;
A14-B3-C65;
A14-B3-C66;
A14-B3-C67;
A14-B3-C68;
A15-B3-C1;
A15-B3-C2;
A15-B3-C3;
A15-B3-C4;
A15-B3-C5;
A15-B3-C6;
A15-B3-C7;
A15-B3-C8;
A15-B3-C9;
A15-B3-C10;
A15-B3-C11;
A15-B3-C12;
A15-B3-C13;
A15-B3-C14;
A15-B3-C15;
A15-B3-C16;
A15-B3-C17;
A15-B3-C18;
A15-B3-C19;
A15-B3-C20;
A15-B3-C21;
A15-B3-C22;
A15-B3-C23;
A15-B3-C24;
A15-B3-C25;
A15-B3-C26;
A15-B3-C27;
A15-B3-C28;
A15-B3-C29;
A15-B3-C30;
A15-B3-C31;
A15-B3-C32;
A15-B3-C33;
A15-B3-C34;
A15-B3-C35;
A15-B3-C36;
A15-B3-C37;
A15-B3-C38;
A15-B3-C39;
A15-B3-C40;

-continued

A15-B3-C41;
A15-B3-C42;
A15-B3-C43;
A15-B3-C44;
A15-B3-C45;
A15-B3-C46;
A15-B3-C47;
A15-B3-C48;
A15-B3-C49;
A15-B3-C50;
A15-B3-C51;
A15-B3-C52;
A15-B3-C53;
A15-B3-C54;
A15-B3-C55;
A15-B3-C56;
A15-B3-C57;
A15-B3-C58;
A15-B3-C59;
A15-B3-C60;
A15-B3-C61;
A15-B3-C62;
A15-B3-C63;
A15-B3-C64;
A15-B3-C65;
A15-B3-C66;
A15-B3-C67;
A15-B3-C68;
A16-B3-C1;
A16-B3-C2;
A16-B3-C3;
A16-B3-C4;
A16-B3-C5;
A16-B3-C6;
A16-B3-C7;
A16-B3-C8;
A16-B3-C9;
A16-B3-C10;
A16-B3-C11;
A16-B3-C12;
A16-B3-C13;
A16-B3-C14;
A16-B3-C15;
A16-B3-C16;
A16-B3-C17;
A16-B3-C18;
A16-B3-C19;
A16-B3-C20;
A16-B3-C21;
A16-B3-C22;
A16-B3-C23;
A16-B3-C24;
A16-B3-C25;
A16-B3-C26;
A16-B3-C27;
A16-B3-C28;
A16-B3-C29;
A16-B3-C30;
A16-B3-C31;
A16-B3-C32;
A16-B3-C33;
A16-B3-C34;
A16-B3-C35;
A16-B3-C36;
A16-B3-C37;
A16-B3-C38;
A16-B3-C39;
A16-B3-C40;
A16-B3-C41;
A16-B3-C42;
A16-B3-C43;
A16-B3-C44;
A16-B3-C45;
A16-B3-C46;
A16-B3-C47;
A16-B3-C48;
A16-B3-C49;
A16-B3-C50;
A16-B3-C51;

-continued

A16-B3-C52;
A16-B3-C53;
A16-B3-C54;
A16-B3-C55;
A16-B3-C56;
A16-B3-C57;
A16-B3-C58;
A16-B3-C59;
A16-B3-C60;
A16-B3-C61;
A16-B3-C62;
A16-B3-C63;
A16-B3-C64;
A16-B3-C65;
A16-B3-C66;
A16-B3-C67;
A16-B3-C68;
A17-B3-C1;
A17-B3-C2;
A17-B3-C3;
A17-B3-C4;
A17-B3-C5;
A17-B3-C6;
A17-B3-C7;
A17-B3-C8;
A17-B3-C9;
A17-B3-C10;
A17-B3-C11;
A17-B3-C12;
A17-B3-C13;
A17-B3-C14;
A17-B3-C15;
A17-B3-C16;
A17-B3-C17;
A17-B3-C18;
A17-B3-C19;
A17-B3-C20;
A17-B3-C21;
A17-B3-C22;
A17-B3-C23;
A17-B3-C24;
A17-B3-C25;
A17-B3-C26;
A17-B3-C27;
A17-B3-C28;
A17-B3-C29;
A17-B3-C30;
A17-B3-C31;
A17-B3-C32;
A17-B3-C33;
A17-B3-C34;
A17-B3-C35;
A17-B3-C36;
A17-B3-C37;
A17-B3-C38;
A17-B3-C39;
A17-B3-C40;
A17-B3-C41;
A17-B3-C42;
A17-B3-C43;
A17-B3-C44;
A17-B3-C45;
A17-B3-C46;
A17-B3-C47;
A17-B3-C48;
A17-B3-C49;
A17-B3-C50;
A17-B3-C51;
A17-B3-C52;
A17-B3-C53;
A17-B3-C54;
A17-B3-C55;
A17-B3-C56;
A17-B3-C57;
A17-B3-C58;
A17-B3-C59;
A17-B3-C60;
A17-B3-C61;
A17-B3-C62;

-continued

A17-B3-C63;
A17-B3-C64;
A17-B3-C65;
A17-B3-C66;
A17-B3-C67;
A17-B3-C68;
A18-B3-C1;
A18-B3-C2;
A18-B3-C3;
A18-B3-C4;
A18-B3-C5;
A18-B3-C6;
A18-B3-C7;
A18-B3-C8;
A18-B3-C9;
A18-B3-C10;
A18-B3-C11;
A18-B3-C12;
A18-B3-C13;
A18-B3-C14;
A18-B3-C15;
A18-B3-C16;
A18-B3-C17;
A18-B3-C18;
A18-B3-C19;
A18-B3-C20;
A18-B3-C21;
A18-B3-C22;
A18-B3-C23;
A18-B3-C24;
A18-B3-C25;
A18-B3-C26;
A18-B3-C27;
A18-B3-C28;
A18-B3-C29;
A18-B3-C30;
A18-B3-C31;
A18-B3-C32;
A18-B3-C33;
A18-B3-C34;
A18-B3-C35;
A18-B3-C36;
A18-B3-C37;
A18-B3-C38;
A18-B3-C39;
A18-B3-C40;
A18-B3-C41;
A18-B3-C42;
A18-B3-C43;
A18-B3-C44;
A18-B3-C45;
A18-B3-C46;
A18-B3-C47;
A18-B3-C48;
A18-B3-C49;
A18-B3-C50;
A18-B3-C51;
A18-B3-C52;
A18-B3-C53;
A18-B3-C54;
A18-B3-C55;
A18-B3-C56;
A18-B3-C57;
A18-B3-C58;
A18-B3-C59;
A18-B3-C60;
A18-B3-C61;
A18-B3-C62;
A18-B3-C63;
A18-B3-C64;
A18-B3-C65;
A18-B3-C66;
A18-B3-C67;
A18-B3-C68;
A19-B3-C1;
A19-B3-C2;
A19-B3-C3;
A19-B3-C4;
A19-B3-C5;

-continued

A19-B3-C6;
A19-B3-C7;
A19-B3-C8;
A19-B3-C9;
A19-B3-C10;
A19-B3-C11;
A19-B3-C12;
A19-B3-C13;
A19-B3-C14;
A19-B3-C15;
A19-B3-C16;
A19-B3-C17;
A19-B3-C18;
A19-B3-C19;
A19-B3-C20;
A19-B3-C21;
A19-B3-C22;
A19-B3-C23;
A19-B3-C24;
A19-B3-C25;
A19-B3-C26;
A19-B3-C27;
A19-B3-C28;
A19-B3-C29;
A19-B3-C30;
A19-B3-C31;
A19-B3-C32;
A19-B3-C33;
A19-B3-C34;
A19-B3-C35;
A19-B3-C36;
A19-B3-C37;
A19-B3-C38;
A19-B3-C39;
A19-B3-C40;
A19-B3-C41;
A19-B3-C42;
A19-B3-C43;
A19-B3-C44;
A19-B3-C45;
A19-B3-C46;
A19-B3-C47;
A19-B3-C48;
A19-B3-C49;
A19-B3-C50;
A19-B3-C51;
A19-B3-C52;
A19-B3-C53;
A19-B3-C54;
A19-B3-C55;
A19-B3-C56;
A19-B3-C57;
A19-B3-C58;
A19-B3-C59;
A19-B3-C60;
A19-B3-C61;
A19-B3-C62;
A19-B3-C63;
A19-B3-C64;
A19-B3-C65;
A19-B3-C66;
A19-B3-C67;
A19-B3-C68;
A20-B3-C1;
A20-B3-C2;
A20-B3-C3;
A20-B3-C4;
A20-B3-C5;
A20-B3-C6;
A20-B3-C7;
A20-B3-C8;
A20-B3-C9;
A20-B3-C10;
A20-B3-C11;
A20-B3-C12;
A20-B3-C13;
A20-B3-C14;
A20-B3-C15;
A20-B3-C16;

A20-B3-C17;
A20-B3-C18;
A20-B3-C19;
A20-B3-C20;
A20-B3-C21;
A20-B3-C22;
A20-B3-C23;
A20-B3-C24;
A20-B3-C25;
A20-B3-C26;
A20-B3-C27;
A20-B3-C28;
A20-B3-C29;
A20-B3-C30;
A20-B3-C31;
A20-B3-C32;
A20-B3-C33;
A20-B3-C34;
A20-B3-C35;
A20-B3-C36;
A20-B3-C37;
A20-B3-C38;
A20-B3-C39;
A20-B3-C40;
A20-B3-C41;
A20-B3-C42;
A20-B3-C43;
A20-B3-C44;
A20-B3-C45;
A20-B3-C46;
A20-B3-C47;
A20-B3-C48;
A20-B3-C49;
A20-B3-C50;
A20-B3-C51;
A20-B3-C52;
A20-B3-C53;
A20-B3-C54;
A20-B3-C55;
A20-B3-C56;
A20-B3-C57;
A20-B3-C58;
A20-B3-C59;
A20-B3-C60;
A20-B3-C61;
A20-B3-C62;
A20-B3-C63;
A20-B3-C64;
A20-B3-C65;
A20-B3-C66;
A20-B3-C67;
A20-B3-C68;
A21-B3-C1;
A21-B3-C2;
A21-B3-C3;
A21-B3-C4;
A21-B3-C5;
A21-B3-C6;
A21-B3-C7;
A21-B3-C8;
A21-B3-C9;
A21-B3-C10;
A21-B3-C11;
A21-B3-C12;
A21-B3-C13;
A21-B3-C14;
A21-B3-C15;
A21-B3-C16;
A21-B3-C17;
A21-B3-C18;
A21-B3-C19;
A21-B3-C20;
A21-B3-C21;
A21-B3-C22;
A21-B3-C23;
A21-B3-C24;
A21-B3-C25;
A21-B3-C26;
A21-B3-C27;
A21-B3-C28;
A21-B3-C29;
A21-B3-C30;
A21-B3-C31;
A21-B3-C32;
A21-B3-C33;
A21-B3-C34;
A21-B3-C35;
A21-B3-C36;
A21-B3-C37;
A21-B3-C38;
A21-B3-C39;
A21-B3-C40;
A21-B3-C41;
A21-B3-C42;
A21-B3-C43;
A21-B3-C44;
A21-B3-C45;
A21-B3-C46;
A21-B3-C47;
A21-B3-C48;
A21-B3-C49;
A21-B3-C50;
A21-B3-C51;
A21-B3-C52;
A21-B3-C53;
A21-B3-C54;
A21-B3-C55;
A21-B3-C56;
A21-B3-C57;
A21-B3-C58;
A21-B3-C59;
A21-B3-C60;
A21-B3-C61;
A21-B3-C62;
A21-B3-C63;
A21-B3-C64;
A21-B3-C65;
A21-B3-C66;
A21-B3-C67;
A21-B3-C68;
A22-B3-C1;
A22-B3-C2;
A22-B3-C3;
A22-B3-C4;
A22-B3-C5;
A22-B3-C6;
A22-B3-C7;
A22-B3-C8;
A22-B3-C9;
A22-B3-C10;
A22-B3-C11;
A22-B3-C12;
A22-B3-C13;
A22-B3-C14;
A22-B3-C15;
A22-B3-C16;
A22-B3-C17;
A22-B3-C18;
A22-B3-C19;
A22-B3-C20;
A22-B3-C21;
A22-B3-C22;
A22-B3-C23;
A22-B3-C24;
A22-B3-C25;
A22-B3-C26;
A22-B3-C27;
A22-B3-C28;
A22-B3-C29;
A22-B3-C30;
A22-B3-C31;
A22-B3-C32;
A22-B3-C33;
A22-B3-C34;
A22-B3-C35;
A22-B3-C36;
A22-B3-C37;
A22-B3-C38;

A22-B3-C39;
A22-B3-C40;
A22-B3-C41;
A22-B3-C42;
A22-B3-C43;
A22-B3-C44;
A22-B3-C45;
A22-B3-C46;
A22-B3-C47;
A22-B3-C48;
A22-B3-C49;
A22-B3-C50;
A22-B3-C51;
A22-B3-C52;
A22-B3-C53;
A22-B3-C54;
A22-B3-C55;
A22-B3-C56;
A22-B3-C57;
A22-B3-C58;
A22-B3-C59;
A22-B3-C60;
A22-B3-C61;
A22-B3-C62;
A22-B3-C63;
A22-B3-C64;
A22-B3-C65;
A22-B3-C66;
A22-B3-C67;
A22-B3-C68;
A23-B3-C1;
A23-B3-C2;
A23-B3-C3;
A23-B3-C4;
A23-B3-C5;
A23-B3-C6;
A23-B3-C7;
A23-B3-C8;
A23-B3-C9;
A23-B3-C10;
A23-B3-C11;
A23-B3-C12;
A23-B3-C13;
A23-B3-C14;
A23-B3-C15;
A23-B3-C16;
A23-B3-C17;
A23-B3-C18;
A23-B3-C19;
A23-B3-C20;
A23-B3-C21;
A23-B3-C22;
A23-B3-C23;
A23-B3-C24;
A23-B3-C25;
A23-B3-C26;
A23-B3-C27;
A23-B3-C28;
A23-B3-C29;
A23-B3-C30;
A23-B3-C31;
A23-B3-C32;
A23-B3-C33;
A23-B3-C34;
A23-B3-C35;
A23-B3-C36;
A23-B3-C37;
A23-B3-C38;
A23-B3-C39;
A23-B3-C40;
A23-B3-C41;
A23-B3-C42;
A23-B3-C43;
A23-B3-C44;
A23-B3-C45;
A23-B3-C46;
A23-B3-C47;
A23-B3-C48;
A23-B3-C49;
A23-B3-C50;
A23-B3-C51;
A23-B3-C52;
A23-B3-C53;
A23-B3-C54;
A23-B3-C55;
A23-B3-C56;
A23-B3-C57;
A23-B3-C58;
A23-B3-C59;
A23-B3-C60;
A23-B3-C61;
A23-B3-C62;
A23-B3-C63;
A23-B3-C64;
A23-B3-C65;
A23-B3-C66;
A23-B3-C67;
A23-B3-C68;
A24-B3-C1;
A24-B3-C2;
A24-B3-C3;
A24-B3-C4;
A24-B3-C5;
A24-B3-C6;
A24-B3-C7;
A24-B3-C8;
A24-B3-C9;
A24-B3-C10;
A24-B3-C11;
A24-B3-C12;
A24-B3-C13;
A24-B3-C14;
A24-B3-C15;
A24-B3-C16;
A24-B3-C17;
A24-B3-C18;
A24-B3-C19;
A24-B3-C20;
A24-B3-C21;
A24-B3-C22;
A24-B3-C23;
A24-B3-C24;
A24-B3-C25;
A24-B3-C26;
A24-B3-C27;
A24-B3-C28;
A24-B3-C29;
A24-B3-C30;
A24-B3-C31;
A24-B3-C32;
A24-B3-C33;
A24-B3-C34;
A24-B3-C35;
A24-B3-C36;
A24-B3-C37;
A24-B3-C38;
A24-B3-C39;
A24-B3-C40;
A24-B3-C41;
A24-B3-C42;
A24-B3-C43;
A24-B3-C44;
A24-B3-C45;
A24-B3-C46;
A24-B3-C47;
A24-B3-C48;
A24-B3-C49;
A24-B3-C50;
A24-B3-C51;
A24-B3-C52;
A24-B3-C53;
A24-B3-C54;
A24-B3-C55;
A24-B3-C56;
A24-B3-C57;
A24-B3-C58;
A24-B3-C59;
A24-B3-C60;

-continued

A24-B3-C61;
A24-B3-C62;
A24-B3-C63;
A24-B3-C64;
A24-B3-C65;
A24-B3-C66;
A24-B3-C67;
A24-B3-C68;
A25-B3-C1;
A25-B3-C2;
A25-B3-C3;
A25-B3-C4;
A25-B3-C5;
A25-B3-C6;
A25-B3-C7;
A25-B3-C8;
A25-B3-C9;
A25-B3-C10;
A25-B3-C11;
A25-B3-C12;
A25-B3-C13;
A25-B3-C14;
A25-B3-C15;
A25-B3-C16;
A25-B3-C17;
A25-B3-C18;
A25-B3-C19;
A25-B3-C20;
A25-B3-C21;
A25-B3-C22;
A25-B3-C23;
A25-B3-C24;
A25-B3-C25;
A25-B3-C26;
A25-B3-C27;
A25-B3-C28;
A25-B3-C29;
A25-B3-C30;
A25-B3-C31;
A25-B3-C32;
A25-B3-C33;
A25-B3-C34;
A25-B3-C35;
A25-B3-C36;
A25-B3-C37;
A25-B3-C38;
A25-B3-C39;
A25-B3-C40;
A25-B3-C41;
A25-B3-C42;
A25-B3-C43;
A25-B3-C44;
A25-B3-C45;
A25-B3-C46;
A25-B3-C47;
A25-B3-C48;
A25-B3-C49;
A25-B3-C50;
A25-B3-C51;
A25-B3-C52;
A25-B3-C53;
A25-B3-C54;
A25-B3-C55;
A25-B3-C56;
A25-B3-C57;
A25-B3-C58;
A25-B3-C59;
A25-B3-C60;
A25-B3-C61;
A25-B3-C62;
A25-B3-C63;
A25-B3-C64;
A25-B3-C65;
A25-B3-C66;
A25-B3-C67;
A25-B3-C68;
A26-B3-C1;
A26-B3-C2;
A26-B3-C3;

-continued

A26-B3-C4;
A26-B3-C5;
A26-B3-C6;
A26-B3-C7;
A26-B3-C8;
A26-B3-C9;
A26-B3-C10;
A26-B3-C11;
A26-B3-C12;
A26-B3-C13;
A26-B3-C14;
A26-B3-C15;
A26-B3-C16;
A26-B3-C17;
A26-B3-C18;
A26-B3-C19;
A26-B3-C20;
A26-B3-C21;
A26-B3-C22;
A26-B3-C23;
A26-B3-C24;
A26-B3-C25;
A26-B3-C26;
A26-B3-C27;
A26-B3-C28;
A26-B3-C29;
A26-B3-C30;
A26-B3-C31;
A26-B3-C32;
A26-B3-C33;
A26-B3-C34;
A26-B3-C35;
A26-B3-C36;
A26-B3-C37;
A26-B3-C38;
A26-B3-C39;
A26-B3-C40;
A26-B3-C41;
A26-B3-C42;
A26-B3-C43;
A26-B3-C44;
A26-B3-C45;
A26-B3-C46;
A26-B3-C47;
A26-B3-C48;
A26-B3-C49;
A26-B3-C50;
A26-B3-C51;
A26-B3-C52;
A26-B3-C53;
A26-B3-C54;
A26-B3-C55;
A26-B3-C56;
A26-B3-C57;
A26-B3-C58;
A26-B3-C59;
A26-B3-C60;
A26-B3-C61;
A26-B3-C62;
A26-B3-C63;
A26-B3-C64;
A26-B3-C65;
A26-B3-C66;
A26-B3-C67;
A26-B3-C68;
A27-B3-C1;
A27-B3-C2;
A27-B3-C3;
A27-B3-C4;
A27-B3-C5;
A27-B3-C6;
A27-B3-C7;
A27-B3-C8;
A27-B3-C9;
A27-B3-C10;
A27-B3-C11;
A27-B3-C12;
A27-B3-C13;
A27-B3-C14;

A27-B3-C15;
A27-B3-C16;
A27-B3-C17;
A27-B3-C18;
A27-B3-C19;
A27-B3-C20;
A27-B3-C21;
A27-B3-C22;
A27-B3-C23;
A27-B3-C24;
A27-B3-C25;
A27-B3-C26;
A27-B3-C27;
A27-B3-C28;
A27-B3-C29;
A27-B3-C30;
A27-B3-C31;
A27-B3-C32;
A27-B3-C33;
A27-B3-C34;
A27-B3-C35;
A27-B3-C36;
A27-B3-C37;
A27-B3-C38;
A27-B3-C39;
A27-B3-C40;
A27-B3-C41;
A27-B3-C42;
A27-B3-C43;
A27-B3-C44;
A27-B3-C45;
A27-B3-C46;
A27-B3-C47;
A27-B3-C48;
A27-B3-C49;
A27-B3-C50;
A27-B3-C51;
A27-B3-C52;
A27-B3-C53;
A27-B3-C54;
A27-B3-C55;
A27-B3-C56;
A27-B3-C57;
A27-B3-C58;
A27-B3-C59;
A27-B3-C60;
A27-B3-C61;
A27-B3-C62;
A27-B3-C63;
A27-B3-C64;
A27-B3-C65;
A27-B3-C66;
A27-B3-C67;
A27-B3-C68;
A28-B3-C1;
A28-B3-C2;
A28-B3-C3;
A28-B3-C4;
A28-B3-C5;
A28-B3-C6;
A28-B3-C7;
A28-B3-C8;
A28-B3-C9;
A28-B3-C10;
A28-B3-C11;
A28-B3-C12;
A28-B3-C13;
A28-B3-C14;
A28-B3-C15;
A28-B3-C16;
A28-B3-C17;
A28-B3-C18;
A28-B3-C19;
A28-B3-C20;
A28-B3-C21;
A28-B3-C22;
A28-B3-C23;
A28-B3-C24;
A28-B3-C25;
A28-B3-C26;
A28-B3-C27;
A28-B3-C28;
A28-B3-C29;
A28-B3-C30;
A28-B3-C31;
A28-B3-C32;
A28-B3-C33;
A28-B3-C34;
A28-B3-C35;
A28-B3-C36;
A28-B3-C37;
A28-B3-C38;
A28-B3-C39;
A28-B3-C40;
A28-B3-C41;
A28-B3-C42;
A28-B3-C43;
A28-B3-C44;
A28-B3-C45;
A28-B3-C46;
A28-B3-C47;
A28-B3-C48;
A28-B3-C49;
A28-B3-C50;
A28-B3-C51;
A28-B3-C52;
A28-B3-C53;
A28-B3-C54;
A28-B3-C55;
A28-B3-C56;
A28-B3-C57;
A28-B3-C58;
A28-B3-C59;
A28-B3-C60;
A28-B3-C61;
A28-B3-C62;
A28-B3-C63;
A28-B3-C64;
A28-B3-C65;
A28-B3-C66;
A28-B3-C67;
A28-B3-C68;
A29-B3-C1;
A29-B3-C2;
A29-B3-C3;
A29-B3-C4;
A29-B3-C5;
A29-B3-C6;
A29-B3-C7;
A29-B3-C8;
A29-B3-C9;
A29-B3-C10;
A29-B3-C11;
A29-B3-C12;
A29-B3-C13;
A29-B3-C14;
A29-B3-C15;
A29-B3-C16;
A29-B3-C17;
A29-B3-C18;
A29-B3-C19;
A29-B3-C20;
A29-B3-C21;
A29-B3-C22;
A29-B3-C23;
A29-B3-C24;
A29-B3-C25;
A29-B3-C26;
A29-B3-C27;
A29-B3-C28;
A29-B3-C29;
A29-B3-C30;
A29-B3-C31;
A29-B3-C32;
A29-B3-C33;
A29-B3-C34;
A29-B3-C35;
A29-B3-C36;

-continued

A29-B3-C37;
A29-B3-C38;
A29-B3-C39;
A29-B3-C40;
A29-B3-C41;
A29-B3-C42;
A29-B3-C43;
A29-B3-C44;
A29-B3-C45;
A29-B3-C46;
A29-B3-C47;
A29-B3-C48;
A29-B3-C49;
A29-B3-C50;
A29-B3-C51;
A29-B3-C52;
A29-B3-C53;
A29-B3-C54;
A29-B3-C55;
A29-B3-C56;
A29-B3-C57;
A29-B3-C58;
A29-B3-C59;
A29-B3-C60;
A29-B3-C61;
A29-B3-C62;
A29-B3-C63;
A29-B3-C64;
A29-B3-C65;
A29-B3-C66;
A29-B3-C67;
A29-B3-C68;
A30-B3-C1;
A30-B3-C2;
A30-B3-C3;
A30-B3-C4;
A30-B3-C5;
A30-B3-C6;
A30-B3-C7;
A30-B3-C8;
A30-B3-C9;
A30-B3-C10;
A30-B3-C11;
A30-B3-C12;
A30-B3-C13;
A30-B3-C14;
A30-B3-C15;
A30-B3-C16;
A30-B3-C17;
A30-B3-C18;
A30-B3-C19;
A30-B3-C20;
A30-B3-C21;
A30-B3-C22;
A30-B3-C23;
A30-B3-C24;
A30-B3-C25;
A30-B3-C26;
A30-B3-C27;
A30-B3-C28;
A30-B3-C29;
A30-B3-C30;
A30-B3-C31;
A30-B3-C32;
A30-B3-C33;
A30-B3-C34;
A30-B3-C35;
A30-B3-C36;
A30-B3-C37;
A30-B3-C38;
A30-B3-C39;
A30-B3-C40;
A30-B3-C41;
A30-B3-C42;
A30-B3-C43;
A30-B3-C44;
A30-B3-C45;
A30-B3-C46;
A30-B3-C47;

-continued

A30-B3-C48;
A30-B3-C49;
A30-B3-C50;
A30-B3-C51;
A30-B3-C52;
A30-B3-C53;
A30-B3-C54;
A30-B3-C55;
A30-B3-C56;
A30-B3-C57;
A30-B3-C58;
A30-B3-C59;
A30-B3-C60;
A30-B3-C61;
A30-B3-C62;
A30-B3-C63;
A30-B3-C64;
A30-B3-C65;
A30-B3-C66;
A30-B3-C67;
A30-B3-C68;
A31-B3-C1;
A31-B3-C2;
A31-B3-C3;
A31-B3-C4;
A31-B3-C5;
A31-B3-C6;
A31-B3-C7;
A31-B3-C8;
A31-B3-C9;
A31-B3-C10;
A31-B3-C11;
A31-B3-C12;
A31-B3-C13;
A31-B3-C14;
A31-B3-C15;
A31-B3-C16;
A31-B3-C17;
A31-B3-C18;
A31-B3-C19;
A31-B3-C20;
A31-B3-C21;
A31-B3-C22;
A31-B3-C23;
A31-B3-C24;
A31-B3-C25;
A31-B3-C26;
A31-B3-C27;
A31-B3-C28;
A31-B3-C29;
A31-B3-C30;
A31-B3-C31;
A31-B3-C32;
A31-B3-C33;
A31-B3-C34;
A31-B3-C35;
A31-B3-C36;
A31-B3-C37;
A31-B3-C38;
A31-B3-C39;
A31-B3-C40;
A31-B3-C41;
A31-B3-C42;
A31-B3-C43;
A31-B3-C44;
A31-B3-C45;
A31-B3-C46;
A31-B3-C47;
A31-B3-C48;
A31-B3-C49;
A31-B3-C50;
A31-B3-C51;
A31-B3-C52;
A31-B3-C53;
A31-B3-C54;
A31-B3-C55;
A31-B3-C56;
A31-B3-C57;
A31-B3-C58;

-continued

A31-B3-C59;
A31-B3-C60;
A31-B3-C61;
A31-B3-C62;
A31-B3-C63;
A31-B3-C64;
A31-B3-C65;
A31-B3-C66;
A31-B3-C67;
A31-B3-C68;
A32-B3-C1;
A32-B3-C2;
A32-B3-C3;
A32-B3-C4;
A32-B3-C5;
A32-B3-C6;
A32-B3-C7;
A32-B3-C8;
A32-B3-C9;
A32-B3-C10;
A32-B3-C11;
A32-B3-C12;
A32-B3-C13;
A32-B3-C14;
A32-B3-C15;
A32-B3-C16;
A32-B3-C17;
A32-B3-C18;
A32-B3-C19;
A32-B3-C20;
A32-B3-C21;
A32-B3-C22;
A32-B3-C23;
A32-B3-C24;
A32-B3-C25;
A32-B3-C26;
A32-B3-C27;
A32-B3-C28;
A32-B3-C29;
A32-B3-C30;
A32-B3-C31;
A32-B3-C32;
A32-B3-C33;
A32-B3-C34;
A32-B3-C35;
A32-B3-C36;
A32-B3-C37;
A32-B3-C38;
A32-B3-C39;
A32-B3-C40;
A32-B3-C41;
A32-B3-C42;
A32-B3-C43;
A32-B3-C44;
A32-B3-C45;
A32-B3-C46;
A32-B3-C47;
A32-B3-C48;
A32-B3-C49;
A32-B3-C50;
A32-B3-C51;
A32-B3-C52;
A32-B3-C53;
A32-B3-C54;
A32-B3-C55;
A32-B3-C56;
A32-B3-C57;
A32-B3-C58;
A32-B3-C59;
A32-B3-C60;
A32-B3-C61;
A32-B3-C62;
A32-B3-C63;
A32-B3-C64;
A32-B3-C65;
A32-B3-C66;
A32-B3-C67;
A32-B3-C68;
A33-B3-C1;

-continued

A33-B3-C2;
A33-B3-C3;
A33-B3-C4;
A33-B3-C5;
A33-B3-C6;
A33-B3-C7;
A33-B3-C8;
A33-B3-C9;
A33-B3-C10;
A33-B3-C11;
A33-B3-C12;
A33-B3-C13;
A33-B3-C14;
A33-B3-C15;
A33-B3-C16;
A33-B3-C17;
A33-B3-C18;
A33-B3-C19;
A33-B3-C20;
A33-B3-C21;
A33-B3-C22;
A33-B3-C23;
A33-B3-C24;
A33-B3-C25;
A33-B3-C26;
A33-B3-C27;
A33-B3-C28;
A33-B3-C29;
A33-B3-C30;
A33-B3-C31;
A33-B3-C32;
A33-B3-C33;
A33-B3-C34;
A33-B3-C35;
A33-B3-C36;
A33-B3-C37;
A33-B3-C38;
A33-B3-C39;
A33-B3-C40;
A33-B3-C41;
A33-B3-C42;
A33-B3-C43;
A33-B3-C44;
A33-B3-C45;
A33-B3-C46;
A33-B3-C47;
A33-B3-C48;
A33-B3-C49;
A33-B3-C50;
A33-B3-C51;
A33-B3-C52;
A33-B3-C53;
A33-B3-C54;
A33-B3-C55;
A33-B3-C56;
A33-B3-C57;
A33-B3-C58;
A33-B3-C59;
A33-B3-C60;
A33-B3-C61;
A33-B3-C62;
A33-B3-C63;
A33-B3-C64;
A33-B3-C65;
A33-B3-C66;
A33-B3-C67;
A33-B3-C68;
A34-B3-C1;
A34-B3-C2;
A34-B3-C3;
A34-B3-C4;
A34-B3-C5;
A34-B3-C6;
A34-B3-C7;
A34-B3-C8;
A34-B3-C9;
A34-B3-C10;
A34-B3-C11;
A34-B3-C12;

-continued

A34-B3-C13;
A34-B3-C14;
A34-B3-C15;
A34-B3-C16;
A34-B3-C17;
A34-B3-C18;
A34-B3-C19;
A34-B3-C20;
A34-B3-C21;
A34-B3-C22;
A34-B3-C23;
A34-B3-C24;
A34-B3-C25;
A34-B3-C26;
A34-B3-C27;
A34-B3-C28;
A34-B3-C29;
A34-B3-C30;
A34-B3-C31;
A34-B3-C32;
A34-B3-C33;
A34-B3-C34;
A34-B3-C35;
A34-B3-C36;
A34-B3-C37;
A34-B3-C38;
A34-B3-C39;
A34-B3-C40;
A34-B3-C41;
A34-B3-C42;
A34-B3-C43;
A34-B3-C44;
A34-B3-C45;
A34-B3-C46;
A34-B3-C47;
A34-B3-C48;
A34-B3-C49;
A34-B3-C50;
A34-B3-C51;
A34-B3-C52;
A34-B3-C53;
A34-B3-C54;
A34-B3-C55;
A34-B3-C56;
A34-B3-C57;
A34-B3-C58;
A34-B3-C59;
A34-B3-C60;
A34-B3-C61;
A34-B3-C62;
A34-B3-C63;
A34-B3-C64;
A34-B3-C65;
A34-B3-C66;
A34-B3-C67;
A34-B3-C68;
A35-B3-C1;
A35-B3-C2;
A35-B3-C3;
A35-B3-C4;
A35-B3-C5;
A35-B3-C6;
A35-B3-C7;
A35-B3-C8;
A35-B3-C9;
A35-B3-C10;
A35-B3-C11;
A35-B3-C12;
A35-B3-C13;
A35-B3-C14;
A35-B3-C15;
A35-B3-C16;
A35-B3-C17;
A35-B3-C18;
A35-B3-C19;
A35-B3-C20;
A35-B3-C21;
A35-B3-C22;
A35-B3-C23;

-continued

A35-B3-C24;
A35-B3-C25;
A35-B3-C26;
A35-B3-C27;
A35-B3-C28;
A35-B3-C29;
A35-B3-C30;
A35-B3-C31;
A35-B3-C32;
A35-B3-C33;
A35-B3-C34;
A35-B3-C35;
A35-B3-C36;
A35-B3-C37;
A35-B3-C38;
A35-B3-C39;
A35-B3-C40;
A35-B3-C41;
A35-B3-C42;
A35-B3-C43;
A35-B3-C44;
A35-B3-C45;
A35-B3-C46;
A35-B3-C47;
A35-B3-C48;
A35-B3-C49;
A35-B3-C50;
A35-B3-C51;
A35-B3-C52;
A35-B3-C53;
A35-B3-C54;
A35-B3-C55;
A35-B3-C56;
A35-B3-C57;
A35-B3-C58;
A35-B3-C59;
A35-B3-C60;
A35-B3-C61;
A35-B3-C62;
A35-B3-C63;
A35-B3-C64;
A35-B3-C65;
A35-B3-C66;
A35-B3-C67;
A35-B3-C68;
A36-B3-C1;
A36-B3-C2;
A36-B3-C3;
A36-B3-C4;
A36-B3-C5;
A36-B3-C6;
A36-B3-C7;
A36-B3-C8;
A36-B3-C9;
A36-B3-C10;
A36-B3-C11;
A36-B3-C12;
A36-B3-C13;
A36-B3-C14;
A36-B3-C15;
A36-B3-C16;
A36-B3-C17;
A36-B3-C18;
A36-B3-C19;
A36-B3-C20;
A36-B3-C21;
A36-B3-C22;
A36-B3-C23;
A36-B3-C24;
A36-B3-C25;
A36-B3-C26;
A36-B3-C27;
A36-B3-C28;
A36-B3-C29;
A36-B3-C30;
A36-B3-C31;
A36-B3-C32;
A36-B3-C33;
A36-B3-C34;

-continued

A36-B3-C35;
A36-B3-C36;
A36-B3-C37;
A36-B3-C38;
A36-B3-C39;
A36-B3-C40;
A36-B3-C41;
A36-B3-C42;
A36-B3-C43;
A36-B3-C44;
A36-B3-C45;
A36-B3-C46;
A36-B3-C47;
A36-B3-C48;
A36-B3-C49;
A36-B3-C50;
A36-B3-C51;
A36-B3-C52;
A36-B3-C53;
A36-B3-C54;
A36-B3-C55;
A36-B3-C56;
A36-B3-C57;
A36-B3-C58;
A36-B3-C59;
A36-B3-C60;
A36-B3-C61;
A36-B3-C62;
A36-B3-C63;
A36-B3-C64;
A36-B3-C65;
A36-B3-C66;
A36-B3-C67;
A36-B3-C68;
A37-B3-C1;
A37-B3-C2;
A37-B3-C3;
A37-B3-C4;
A37-B3-C5;
A37-B3-C6;
A37-B3-C7;
A37-B3-C8;
A37-B3-C9;
A37-B3-C10;
A37-B3-C11;
A37-B3-C12;
A37-B3-C13;
A37-B3-C14;
A37-B3-C15;
A37-B3-C16;
A37-B3-C17;
A37-B3-C18;
A37-B3-C19;
A37-B3-C20;
A37-B3-C21;
A37-B3-C22;
A37-B3-C23;
A37-B3-C24;
A37-B3-C25;
A37-B3-C26;
A37-B3-C27;
A37-B3-C28;
A37-B3-C29;
A37-B3-C30;
A37-B3-C31;
A37-B3-C32;
A37-B3-C33;
A37-B3-C34;
A37-B3-C35;
A37-B3-C36;
A37-B3-C37;
A37-B3-C38;
A37-B3-C39;
A37-B3-C40;
A37-B3-C41;
A37-B3-C42;
A37-B3-C43;
A37-B3-C44;
A37-B3-C45;

-continued

A37-B3-C46;
A37-B3-C47;
A37-B3-C48;
A37-B3-C49;
A37-B3-C50;
A37-B3-C51;
A37-B3-C52;
A37-B3-C53;
A37-B3-C54;
A37-B3-C55;
A37-B3-C56;
A37-B3-C57;
A37-B3-C58;
A37-B3-C59;
A37-B3-C60;
A37-B3-C61;
A37-B3-C62;
A37-B3-C63;
A37-B3-C64;
A37-B3-C65;
A37-B3-C66;
A37-B3-C67;
A37-B3-C68;
A38-B3-C1;
A38-B3-C2;
A38-B3-C3;
A38-B3-C4;
A38-B3-C5;
A38-B3-C6;
A38-B3-C7;
A38-B3-C8;
A38-B3-C9;
A38-B3-C10;
A38-B3-C11;
A38-B3-C12;
A38-B3-C13;
A38-B3-C14;
A38-B3-C15;
A38-B3-C16;
A38-B3-C17;
A38-B3-C18;
A38-B3-C19;
A38-B3-C20;
A38-B3-C21;
A38-B3-C22;
A38-B3-C23;
A38-B3-C24;
A38-B3-C25;
A38-B3-C26;
A38-B3-C27;
A38-B3-C28;
A38-B3-C29;
A38-B3-C30;
A38-B3-C31;
A38-B3-C32;
A38-B3-C33;
A38-B3-C34;
A38-B3-C35;
A38-B3-C36;
A38-B3-C37;
A38-B3-C38;
A38-B3-C39;
A38-B3-C40;
A38-B3-C41;
A38-B3-C42;
A38-B3-C43;
A38-B3-C44;
A38-B3-C45;
A38-B3-C46;
A38-B3-C47;
A38-B3-C48;
A38-B3-C49;
A38-B3-C50;
A38-B3-C51;
A38-B3-C52;
A38-B3-C53;
A38-B3-C54;
A38-B3-C55;
A38-B3-C56;

A38-B3-C57;
A38-B3-C58;
A38-B3-C59;
A38-B3-C60;
A38-B3-C61;
A38-B3-C62;
A38-B3-C63;
A38-B3-C64;
A38-B3-C65;
A38-B3-C66;
A38-B3-C67;
A38-B3-C68;
A1-B4-C1;
A1-B4-C2;
A1-B4-C3;
A1-B4-C4;
A1-B4-C5;
A1-B4-C6;
A1-B4-C7;
A1-B4-C8;
A1-B4-C9;
A1-B4-C10;
A1-B4-C11;
A1-B4-C12;
A1-B4-C13;
A1-B4-C14;
A1-B4-C15;
A1-B4-C16;
A1-B4-C17;
A1-B4-C18;
A1-B4-C19;
A1-B4-C20;
A1-B4-C21;
A1-B4-C22;
A1-B4-C23;
A1-B4-C24;
A1-B4-C25;
A1-B4-C26;
A1-B4-C27;
A1-B4-C28;
A1-B4-C29;
A1-B4-C30;
A1-B4-C31;
A1-B4-C32;
A1-B4-C33;
A1-B4-C34;
A1-B4-C35;
A1-B4-C36;
A1-B4-C37;
A1-B4-C38;
A1-B4-C39;
A1-B4-C40;
A1-B4-C41;
A1-B4-C42;
A1-B4-C43;
A1-B4-C44;
A1-B4-C45;
A1-B4-C46;
A1-B4-C47;
A1-B4-C48;
A1-B4-C49;
A1-B4-C50;
A1-B4-C51;
A1-B4-C52;
A1-B4-C53;
A1-B4-C54;
A1-B4-C55;
A1-B4-C56;
A1-B4-C57;
A1-B4-C58;
A1-B4-C59;
A1-B4-C60;
A1-B4-C61;
A1-B4-C62;
A1-B4-C63;
A1-B4-C64;
A1-B4-C65;
A1-B4-C66;
A1-B4-C67;
A1-B4-C68;
A2-B4-C1;
A2-B4-C2;
A2-B4-C3;
A2-B4-C4;
A2-B4-C5;
A2-B4-C6;
A2-B4-C7;
A2-B4-C8;
A2-B4-C9;
A2-B4-C10;
A2-B4-C11;
A2-B4-C12;
A2-B4-C13;
A2-B4-C14;
A2-B4-C15;
A2-B4-C16;
A2-B4-C17;
A2-B4-C18;
A2-B4-C19;
A2-B4-C20;
A2-B4-C21;
A2-B4-C22;
A2-B4-C23;
A2-B4-C24;
A2-B4-C25;
A2-B4-C26;
A2-B4-C27;
A2-B4-C28;
A2-B4-C29;
A2-B4-C30;
A2-B4-C31;
A2-B4-C32;
A2-B4-C33;
A2-B4-C34;
A2-B4-C35;
A2-B4-C36;
A2-B4-C37;
A2-B4-C38;
A2-B4-C39;
A2-B4-C40;
A2-B4-C41;
A2-B4-C42;
A2-B4-C43;
A2-B4-C44;
A2-B4-C45;
A2-B4-C46;
A2-B4-C47;
A2-B4-C48;
A2-B4-C49;
A2-B4-C50;
A2-B4-C51;
A2-B4-C52;
A2-B4-C53;
A2-B4-C54;
A2-B4-C55;
A2-B4-C56;
A2-B4-C57;
A2-B4-C58;
A2-B4-C59;
A2-B4-C60;
A2-B4-C61;
A2-B4-C62;
A2-B4-C63;
A2-B4-C64;
A2-B4-C65;
A2-B4-C66;
A2-B4-C67;
A2-B4-C68;
A3-B4-C1;
A3-B4-C2;
A3-B4-C3;
A3-B4-C4;
A3-B4-C5;
A3-B4-C6;
A3-B4-C7;
A3-B4-C8;
A3-B4-C9;
A3-B4-C10;

-continued

A3-B4-C11;
A3-B4-C12;
A3-B4-C13;
A3-B4-C14;
A3-B4-C15;
A3-B4-C16;
A3-B4-C17;
A3-B4-C18;
A3-B4-C19;
A3-B4-C20;
A3-B4-C21;
A3-B4-C22;
A3-B4-C23;
A3-B4-C24;
A3-B4-C25;
A3-B4-C26;
A3-B4-C27;
A3-B4-C28;
A3-B4-C29;
A3-B4-C30;
A3-B4-C31;
A3-B4-C32;
A3-B4-C33;
A3-B4-C34;
A3-B4-C35;
A3-B4-C36;
A3-B4-C37;
A3-B4-C38;
A3-B4-C39;
A3-B4-C40;
A3-B4-C41;
A3-B4-C42;
A3-B4-C43;
A3-B4-C44;
A3-B4-C45;
A3-B4-C46;
A3-B4-C47;
A3-B4-C48;
A3-B4-C49;
A3-B4-C50;
A3-B4-C51;
A3-B4-C52;
A3-B4-C53;
A3-B4-C54;
A3-B4-C55;
A3-B4-C56;
A3-B4-C57;
A3-B4-C58;
A3-B4-C59;
A3-B4-C60;
A3-B4-C61;
A3-B4-C62;
A3-B4-C63;
A3-B4-C64;
A3-B4-C65;
A3-B4-C66;
A3-B4-C67;
A3-B4-C68;
A4-B4-C1;
A4-B4-C2;
A4-B4-C3;
A4-B4-C4;
A4-B4-C5;
A4-B4-C6;
A4-B4-C7;
A4-B4-C8;
A4-B4-C9;
A4-B4-C10;
A4-B4-C11;
A4-B4-C12;
A4-B4-C13;
A4-B4-C14;
A4-B4-C15;
A4-B4-C16;
A4-B4-C17;
A4-B4-C18;
A4-B4-C19;
A4-B4-C20;
A4-B4-C21;

-continued

A4-B4-C22;
A4-B4-C23;
A4-B4-C24;
A4-B4-C25;
A4-B4-C26;
A4-B4-C27;
A4-B4-C28;
A4-B4-C29;
A4-B4-C30;
A4-B4-C31;
A4-B4-C32;
A4-B4-C33;
A4-B4-C34;
A4-B4-C35;
A4-B4-C36;
A4-B4-C37;
A4-B4-C38;
A4-B4-C39;
A4-B4-C40;
A4-B4-C41;
A4-B4-C42;
A4-B4-C43;
A4-B4-C44;
A4-B4-C45;
A4-B4-C46;
A4-B4-C47;
A4-B4-C48;
A4-B4-C49;
A4-B4-C50;
A4-B4-C51;
A4-B4-C52;
A4-B4-C53;
A4-B4-C54;
A4-B4-C55;
A4-B4-C56;
A4-B4-C57;
A4-B4-C58;
A4-B4-C59;
A4-B4-C60;
A4-B4-C61;
A4-B4-C62;
A4-B4-C63;
A4-B4-C64;
A4-B4-C65;
A4-B4-C66;
A4-B4-C67;
A4-B4-C68;
A5-B4-C1;
A5-B4-C2;
A5-B4-C3;
A5-B4-C4;
A5-B4-C5;
A5-B4-C6;
A5-B4-C7;
A5-B4-C8;
A5-B4-C9;
A5-B4-C10;
A5-B4-C11;
A5-B4-C12;
A5-B4-C13;
A5-B4-C14;
A5-B4-C15;
A5-B4-C16;
A5-B4-C17;
A5-B4-C18;
A5-B4-C19;
A5-B4-C20;
A5-B4-C21;
A5-B4-C22;
A5-B4-C23;
A5-B4-C24;
A5-B4-C25;
A5-B4-C26;
A5-B4-C27;
A5-B4-C28;
A5-B4-C29;
A5-B4-C30;
A5-B4-C31;
A5-B4-C32;

-continued

A5-B4-C33;
A5-B4-C34;
A5-B4-C35;
A5-B4-C36;
A5-B4-C37;
A5-B4-C38;
A5-B4-C39;
A5-B4-C40;
A5-B4-C41;
A5-B4-C42;
A5-B4-C43;
A5-B4-C44;
A5-B4-C45;
A5-B4-C46;
A5-B4-C47;
A5-B4-C48;
A5-B4-C49;
A5-B4-C50;
A5-B4-C51;
A5-B4-C52;
A5-B4-C53;
A5-B4-C54;
A5-B4-C55;
A5-B4-C56;
A5-B4-C57;
A5-B4-C58;
A5-B4-C59;
A5-B4-C60;
A5-B4-C61;
A5-B4-C62;
A5-B4-C63;
A5-B4-C64;
A5-B4-C65;
A5-B4-C66;
A5-B4-C67;
A5-B4-C68;
A6-B4-C1;
A6-B4-C2;
A6-B4-C3;
A6-B4-C4;
A6-B4-C5;
A6-B4-C6;
A6-B4-C7;
A6-B4-C8;
A6-B4-C9;
A6-B4-C10;
A6-B4-C11;
A6-B4-C12;
A6-B4-C13;
A6-B4-C14;
A6-B4-C15;
A6-B4-C16;
A6-B4-C17;
A6-B4-C18;
A6-B4-C19;
A6-B4-C20;
A6-B4-C21;
A6-B4-C22;
A6-B4-C23;
A6-B4-C24;
A6-B4-C25;
A6-B4-C26;
A6-B4-C27;
A6-B4-C28;
A6-B4-C29;
A6-B4-C30;
A6-B4-C31;
A6-B4-C32;
A6-B4-C33;
A6-B4-C34;
A6-B4-C35;
A6-B4-C36;
A6-B4-C37;
A6-B4-C38;
A6-B4-C39;
A6-B4-C40;
A6-B4-C41;
A6-B4-C42;
A6-B4-C43;

-continued

A6-B4-C44;
A6-B4-C45;
A6-B4-C46;
A6-B4-C47;
A6-B4-C48;
A6-B4-C49;
A6-B4-C50;
A6-B4-C51;
A6-B4-C52;
A6-B4-C53;
A6-B4-C54;
A6-B4-C55;
A6-B4-C56;
A6-B4-C57;
A6-B4-C58;
A6-B4-C59;
A6-B4-C60;
A6-B4-C61;
A6-B4-C62;
A6-B4-C63;
A6-B4-C64;
A6-B4-C65;
A6-B4-C66;
A6-B4-C67;
A6-B4-C68;
A7-B4-C1;
A7-B4-C2;
A7-B4-C3;
A7-B4-C4;
A7-B4-C5;
A7-B4-C6;
A7-B4-C7;
A7-B4-C8;
A7-B4-C9;
A7-B4-C10;
A7-B4-C11;
A7-B4-C12;
A7-B4-C13;
A7-B4-C14;
A7-B4-C15;
A7-B4-C16;
A7-B4-C17;
A7-B4-C18;
A7-B4-C19;
A7-B4-C20;
A7-B4-C21;
A7-B4-C22;
A7-B4-C23;
A7-B4-C24;
A7-B4-C25;
A7-B4-C26;
A7-B4-C27;
A7-B4-C28;
A7-B4-C29;
A7-B4-C30;
A7-B4-C31;
A7-B4-C32;
A7-B4-C33;
A7-B4-C34;
A7-B4-C35;
A7-B4-C36;
A7-B4-C37;
A7-B4-C38;
A7-B4-C39;
A7-B4-C40;
A7-B4-C41;
A7-B4-C42;
A7-B4-C43;
A7-B4-C44;
A7-B4-C45;
A7-B4-C46;
A7-B4-C47;
A7-B4-C48;
A7-B4-C49;
A7-B4-C50;
A7-B4-C51;
A7-B4-C52;
A7-B4-C53;
A7-B4-C54;

-continued

A7-B4-C55;
A7-B4-C56;
A7-B4-C57;
A7-B4-C58;
A7-B4-C59;
A7-B4-C60;
A7-B4-C61;
A7-B4-C62;
A7-B4-C63;
A7-B4-C64;
A7-B4-C65;
A7-B4-C66;
A7-B4-C67;
A7-B4-C68;
A8-B4-C1;
A8-B4-C2;
A8-B4-C3;
A8-B4-C4;
A8-B4-C5;
A8-B4-C6;
A8-B4-C7;
A8-B4-C8;
A8-B4-C9;
A8-B4-C10;
A8-B4-C11;
A8-B4-C12;
A8-B4-C13;
A8-B4-C14;
A8-B4-C15;
A8-B4-C16;
A8-B4-C17;
A8-B4-C18;
A8-B4-C19;
A8-B4-C20;
A8-B4-C21;
A8-B4-C22;
A8-B4-C23;
A8-B4-C24;
A8-B4-C25;
A8-B4-C26;
A8-B4-C27;
A8-B4-C28;
A8-B4-C29;
A8-B4-C30;
A8-B4-C31;
A8-B4-C32;
A8-B4-C33;
A8-B4-C34;
A8-B4-C35;
A8-B4-C36;
A8-B4-C37;
A8-B4-C38;
A8-B4-C39;
A8-B4-C40;
A8-B4-C41;
A8-B4-C42;
A8-B4-C43;
A8-B4-C44;
A8-B4-C45;
A8-B4-C46;
A8-B4-C47;
A8-B4-C48;
A8-B4-C49;
A8-B4-C50;
A8-B4-C51;
A8-B4-C52;
A8-B4-C53;
A8-B4-C54;
A8-B4-C55;
A8-B4-C56;
A8-B4-C57;
A8-B4-C58;
A8-B4-C59;
A8-B4-C60;
A8-B4-C61;
A8-B4-C62;
A8-B4-C63;
A8-B4-C64;
A8-B4-C65;

-continued

A8-B4-C66;
A8-B4-C67;
A8-B4-C68;
A9-B4-C1;
A9-B4-C2;
A9-B4-C3;
A9-B4-C4;
A9-B4-C5;
A9-B4-C6;
A9-B4-C7;
A9-B4-C8;
A9-B4-C9;
A9-B4-C10;
A9-B4-C11;
A9-B4-C12;
A9-B4-C13;
A9-B4-C14;
A9-B4-C15;
A9-B4-C16;
A9-B4-C17;
A9-B4-C18;
A9-B4-C19;
A9-B4-C20;
A9-B4-C21;
A9-B4-C22;
A9-B4-C23;
A9-B4-C24;
A9-B4-C25;
A9-B4-C26;
A9-B4-C27;
A9-B4-C28;
A9-B4-C29;
A9-B4-C30;
A9-B4-C31;
A9-B4-C32;
A9-B4-C33;
A9-B4-C34;
A9-B4-C35;
A9-B4-C36;
A9-B4-C37;
A9-B4-C38;
A9-B4-C39;
A9-B4-C40;
A9-B4-C41;
A9-B4-C42;
A9-B4-C43;
A9-B4-C44;
A9-B4-C45;
A9-B4-C46;
A9-B4-C47;
A9-B4-C48;
A9-B4-C49;
A9-B4-C50;
A9-B4-C51;
A9-B4-C52;
A9-B4-C53;
A9-B4-C54;
A9-B4-C55;
A9-B4-C56;
A9-B4-C57;
A9-B4-C58;
A9-B4-C59;
A9-B4-C60;
A9-B4-C61;
A9-B4-C62;
A9-B4-C63;
A9-B4-C64;
A9-B4-C65;
A9-B4-C66;
A9-B4-C67;
A9-B4-C68;
A10-B4-C1;
A10-B4-C2;
A10-B4-C3;
A10-B4-C4;
A10-B4-C5;
A10-B4-C6;
A10-B4-C7;
A10-B4-C8;

-continued

A10-B4-C9;
A10-B4-C10;
A10-B4-C11;
A10-B4-C12;
A10-B4-C13;
A10-B4-C14;
A10-B4-C15;
A10-B4-C16;
A10-B4-C17;
A10-B4-C18;
A10-B4-C19;
A10-B4-C20;
A10-B4-C21;
A10-B4-C22;
A10-B4-C23;
A10-B4-C24;
A10-B4-C25;
A10-B4-C26;
A10-B4-C27;
A10-B4-C28;
A10-B4-C29;
A10-B4-C30;
A10-B4-C31;
A10-B4-C32;
A10-B4-C33;
A10-B4-C34;
A10-B4-C35;
A10-B4-C36;
A10-B4-C37;
A10-B4-C38;
A10-B4-C39;
A10-B4-C40;
A10-B4-C41;
A10-B4-C42;
A10-B4-C43;
A10-B4-C44;
A10-B4-C45;
A10-B4-C46;
A10-B4-C47;
A10-B4-C48;
A10-B4-C49;
A10-B4-C50;
A10-B4-C51;
A10-B4-C52;
A10-B4-C53;
A10-B4-C54;
A10-B4-C55;
A10-B4-C56;
A10-B4-C57;
A10-B4-C58;
A10-B4-C59;
A10-B4-C60;
A10-B4-C61;
A10-B4-C62;
A10-B4-C63;
A10-B4-C64;
A10-B4-C65;
A10-B4-C66;
A10-B4-C67;
A10-B4-C68;
A11-B4-C1;
A11-B4-C2;
A11-B4-C3;
A11-B4-C4;
A11-B4-C5;
A11-B4-C6;
A11-B4-C7;
A11-B4-C8;
A11-B4-C9;
A11-B4-C10;
A11-B4-C11;
A11-B4-C12;
A11-B4-C13;
A11-B4-C14;
A11-B4-C15;
A11-B4-C16;
A11-B4-C17;
A11-B4-C18;
A11-B4-C19;

-continued

A11-B4-C20;
A11-B4-C21;
A11-B4-C22;
A11-B4-C23;
A11-B4-C24;
A11-B4-C25;
A11-B4-C26;
A11-B4-C27;
A11-B4-C28;
A11-B4-C29;
A11-B4-C30;
A11-B4-C31;
A11-B4-C32;
A11-B4-C33;
A11-B4-C34;
A11-B4-C35;
A11-B4-C36;
A11-B4-C37;
A11-B4-C38;
A11-B4-C39;
A11-B4-C40;
A11-B4-C41;
A11-B4-C42;
A11-B4-C43;
A11-B4-C44;
A11-B4-C45;
A11-B4-C46;
A11-B4-C47;
A11-B4-C48;
A11-B4-C49;
A11-B4-C50;
A11-B4-C51;
A11-B4-C52;
A11-B4-C53;
A11-B4-C54;
A11-B4-C55;
A11-B4-C56;
A11-B4-C57;
A11-B4-C58;
A11-B4-C59;
A11-B4-C60;
A11-B4-C61;
A11-B4-C62;
A11-B4-C63;
A11-B4-C64;
A11-B4-C65;
A11-B4-C66;
A11-B4-C67;
A11-B4-C68;
A12-B4-C1;
A12-B4-C2;
A12-B4-C3;
A12-B4-C4;
A12-B4-C5;
A12-B4-C6;
A12-B4-C7;
A12-B4-C8;
A12-B4-C9;
A12-B4-C10;
A12-B4-C11;
A12-B4-C12;
A12-B4-C13;
A12-B4-C14;
A12-B4-C15;
A12-B4-C16;
A12-B4-C17;
A12-B4-C18;
A12-B4-C19;
A12-B4-C20;
A12-B4-C21;
A12-B4-C22;
A12-B4-C23;
A12-B4-C24;
A12-B4-C25;
A12-B4-C26;
A12-B4-C27;
A12-B4-C28;
A12-B4-C29;
A12-B4-C30;

-continued

A12-B4-C31;
A12-B4-C32;
A12-B4-C33;
A12-B4-C34;
A12-B4-C35;
A12-B4-C36;
A12-B4-C37;
A12-B4-C38;
A12-B4-C39;
A12-B4-C40;
A12-B4-C41;
A12-B4-C42;
A12-B4-C43;
A12-B4-C44;
A12-B4-C45;
A12-B4-C46;
A12-B4-C47;
A12-B4-C48;
A12-B4-C49;
A12-B4-C50;
A12-B4-C51;
A12-B4-C52;
A12-B4-C53;
A12-B4-C54;
A12-B4-C55;
A12-B4-C56;
A12-B4-C57;
A12-B4-C58;
A12-B4-C59;
A12-B4-C60;
A12-B4-C61;
A12-B4-C62;
A12-B4-C63;
A12-B4-C64;
A12-B4-C65;
A12-B4-C66;
A12-B4-C67;
A12-B4-C68;
A13-B4-C1;
A13-B4-C2;
A13-B4-C3;
A13-B4-C4;
A13-B4-C5;
A13-B4-C6;
A13-B4-C7;
A13-B4-C8;
A13-B4-C9;
A13-B4-C10;
A13-B4-C11;
A13-B4-C12;
A13-B4-C13;
A13-B4-C14;
A13-B4-C15;
A13-B4-C16;
A13-B4-C17;
A13-B4-C18;
A13-B4-C19;
A13-B4-C20;
A13-B4-C21;
A13-B4-C22;
A13-B4-C23;
A13-B4-C24;
A13-B4-C25;
A13-B4-C26;
A13-B4-C27;
A13-B4-C28;
A13-B4-C29;
A13-B4-C30;
A13-B4-C31;
A13-B4-C32;
A13-B4-C33;
A13-B4-C34;
A13-B4-C35;
A13-B4-C36;
A13-B4-C37;
A13-B4-C38;
A13-B4-C39;
A13-B4-C40;
A13-B4-C41;

-continued

A13-B4-C42;
A13-B4-C43;
A13-B4-C44;
A13-B4-C45;
A13-B4-C46;
A13-B4-C47;
A13-B4-C48;
A13-B4-C49;
A13-B4-C50;
A13-B4-C51;
A13-B4-C52;
A13-B4-C53;
A13-B4-C54;
A13-B4-C55;
A13-B4-C56;
A13-B4-C57;
A13-B4-C58;
A13-B4-C59;
A13-B4-C60;
A13-B4-C61;
A13-B4-C62;
A13-B4-C63;
A13-B4-C64;
A13-B4-C65;
A13-B4-C66;
A13-B4-C67;
A13-B4-C68;
A14-B4-C1;
A14-B4-C2;
A14-B4-C3;
A14-B4-C4;
A14-B4-C5;
A14-B4-C6;
A14-B4-C7;
A14-B4-C8;
A14-B4-C9;
A14-B4-C10;
A14-B4-C11;
A14-B4-C12;
A14-B4-C13;
A14-B4-C14;
A14-B4-C15;
A14-B4-C16;
A14-B4-C17;
A14-B4-C18;
A14-B4-C19;
A14-B4-C20;
A14-B4-C21;
A14-B4-C22;
A14-B4-C23;
A14-B4-C24;
A14-B4-C25;
A14-B4-C26;
A14-B4-C27;
A14-B4-C28;
A14-B4-C29;
A14-B4-C30;
A14-B4-C31;
A14-B4-C32;
A14-B4-C33;
A14-B4-C34;
A14-B4-C35;
A14-B4-C36;
A14-B4-C37;
A14-B4-C38;
A14-B4-C39;
A14-B4-C40;
A14-B4-C41;
A14-B4-C42;
A14-B4-C43;
A14-B4-C44;
A14-B4-C45;
A14-B4-C46;
A14-B4-C47;
A14-B4-C48;
A14-B4-C49;
A14-B4-C50;
A14-B4-C51;
A14-B4-C52;

-continued

A14-B4-C53;
A14-B4-C54;
A14-B4-C55;
A14-B4-C56;
A14-B4-C57;
A14-B4-C58;
A14-B4-C59;
A14-B4-C60;
A14-B4-C61;
A14-B4-C62;
A14-B4-C63;
A14-B4-C64;
A14-B4-C65;
A14-B4-C66;
A14-B4-C67;
A14-B4-C68;
A15-B4-C1;
A15-B4-C2;
A15-B4-C3;
A15-B4-C4;
A15-B4-C5;
A15-B4-C6;
A15-B4-C7;
A15-B4-C8;
A15-B4-C9;
A15-B4-C10;
A15-B4-C11;
A15-B4-C12;
A15-B4-C13;
A15-B4-C14;
A15-B4-C15;
A15-B4-C16;
A15-B4-C17;
A15-B4-C18;
A15-B4-C19;
A15-B4-C20;
A15-B4-C21;
A15-B4-C22;
A15-B4-C23;
A15-B4-C24;
A15-B4-C25;
A15-B4-C26;
A15-B4-C27;
A15-B4-C28;
A15-B4-C29;
A15-B4-C30;
A15-B4-C31;
A15-B4-C32;
A15-B4-C33;
A15-B4-C34;
A15-B4-C35;
A15-B4-C36;
A15-B4-C37;
A15-B4-C38;
A15-B4-C39;
A15-B4-C40;
A15-B4-C41;
A15-B4-C42;
A15-B4-C43;
A15-B4-C44;
A15-B4-C45;
A15-B4-C46;
A15-B4-C47;
A15-B4-C48;
A15-B4-C49;
A15-B4-C50;
A15-B4-C51;
A15-B4-C52;
A15-B4-C53;
A15-B4-C54;
A15-B4-C55;
A15-B4-C56;
A15-B4-C57;
A15-B4-C58;
A15-B4-C59;
A15-B4-C60;
A15-B4-C61;
A15-B4-C62;
A15-B4-C63;

-continued

A15-B4-C64;
A15-B4-C65;
A15-B4-C66;
A15-B4-C67;
A15-B4-C68;
A16-B4-C1;
A16-B4-C2;
A16-B4-C3;
A16-B4-C4;
A16-B4-C5;
A16-B4-C6;
A16-B4-C7;
A16-B4-C8;
A16-B4-C9;
A16-B4-C10;
A16-B4-C11;
A16-B4-C12;
A16-B4-C13;
A16-B4-C14;
A16-B4-C15;
A16-B4-C16;
A16-B4-C17;
A16-B4-C18;
A16-B4-C19;
A16-B4-C20;
A16-B4-C21;
A16-B4-C22;
A16-B4-C23;
A16-B4-C24;
A16-B4-C25;
A16-B4-C26;
A16-B4-C27;
A16-B4-C28;
A16-B4-C29;
A16-B4-C30;
A16-B4-C31;
A16-B4-C32;
A16-B4-C33;
A16-B4-C34;
A16-B4-C35;
A16-B4-C36;
A16-B4-C37;
A16-B4-C38;
A16-B4-C39;
A16-B4-C40;
A16-B4-C41;
A16-B4-C42;
A16-B4-C43;
A16-B4-C44;
A16-B4-C45;
A16-B4-C46;
A16-B4-C47;
A16-B4-C48;
A16-B4-C49;
A16-B4-C50;
A16-B4-C51;
A16-B4-C52;
A16-B4-C53;
A16-B4-C54;
A16-B4-C55;
A16-B4-C56;
A16-B4-C57;
A16-B4-C58;
A16-B4-C59;
A16-B4-C60;
A16-B4-C61;
A16-B4-C62;
A16-B4-C63;
A16-B4-C64;
A16-B4-C65;
A16-B4-C66;
A16-B4-C67;
A16-B4-C68;
A17-B4-C1;
A17-B4-C2;
A17-B4-C3;
A17-B4-C4;
A17-B4-C5;
A17-B4-C6;

A17-B4-C7;
A17-B4-C8;
A17-B4-C9;
A17-B4-C10;
A17-B4-C11;
A17-B4-C12;
A17-B4-C13;
A17-B4-C14;
A17-B4-C15;
A17-B4-C16;
A17-B4-C17;
A17-B4-C18;
A17-B4-C19;
A17-B4-C20;
A17-B4-C21;
A17-B4-C22;
A17-B4-C23;
A17-B4-C24;
A17-B4-C25;
A17-B4-C26;
A17-B4-C27;
A17-B4-C28;
A17-B4-C29;
A17-B4-C30;
A17-B4-C31;
A17-B4-C32;
A17-B4-C33;
A17-B4-C34;
A17-B4-C35;
A17-B4-C36;
A17-B4-C37;
A17-B4-C38;
A17-B4-C39;
A17-B4-C40;
A17-B4-C41;
A17-B4-C42;
A17-B4-C43;
A17-B4-C44;
A17-B4-C45;
A17-B4-C46;
A17-B4-C47;
A17-B4-C48;
A17-B4-C49;
A17-B4-C50;
A17-B4-C51;
A17-B4-C52;
A17-B4-C53;
A17-B4-C54;
A17-B4-C55;
A17-B4-C56;
A17-B4-C57;
A17-B4-C58;
A17-B4-C59;
A17-B4-C60;
A17-B4-C61;
A17-B4-C62;
A17-B4-C63;
A17-B4-C64;
A17-B4-C65;
A17-B4-C66;
A17-B4-C67;
A17-B4-C68;
A18-B4-C1;
A18-B4-C2;
A18-B4-C3;
A18-B4-C4;
A18-B4-C5;
A18-B4-C6;
A18-B4-C7;
A18-B4-C8;
A18-B4-C9;
A18-B4-C10;
A18-B4-C11;
A18-B4-C12;
A18-B4-C13;
A18-B4-C14;
A18-B4-C15;
A18-B4-C16;
A18-B4-C17;
A18-B4-C18;
A18-B4-C19;
A18-B4-C20;
A18-B4-C21;
A18-B4-C22;
A18-B4-C23;
A18-B4-C24;
A18-B4-C25;
A18-B4-C26;
A18-B4-C27;
A18-B4-C28;
A18-B4-C29;
A18-B4-C30;
A18-B4-C31;
A18-B4-C32;
A18-B4-C33;
A18-B4-C34;
A18-B4-C35;
A18-B4-C36;
A18-B4-C37;
A18-B4-C38;
A18-B4-C39;
A18-B4-C40;
A18-B4-C41;
A18-B4-C42;
A18-B4-C43;
A18-B4-C44;
A18-B4-C45;
A18-B4-C46;
A18-B4-C47;
A18-B4-C48;
A18-B4-C49;
A18-B4-C50;
A18-B4-C51;
A18-B4-C52;
A18-B4-C53;
A18-B4-C54;
A18-B4-C55;
A18-B4-C56;
A18-B4-C57;
A18-B4-C58;
A18-B4-C59;
A18-B4-C60;
A18-B4-C61;
A18-B4-C62;
A18-B4-C63;
A18-B4-C64;
A18-B4-C65;
A18-B4-C66;
A18-B4-C67;
A18-B4-C68;
A19-B4-C1;
A19-B4-C2;
A19-B4-C3;
A19-B4-C4;
A19-B4-C5;
A19-B4-C6;
A19-B4-C7;
A19-B4-C8;
A19-B4-C9;
A19-B4-C10;
A19-B4-C11;
A19-B4-C12;
A19-B4-C13;
A19-B4-C14;
A19-B4-C15;
A19-B4-C16;
A19-B4-C17;
A19-B4-C18;
A19-B4-C19;
A19-B4-C20;
A19-B4-C21;
A19-B4-C22;
A19-B4-C23;
A19-B4-C24;
A19-B4-C25;
A19-B4-C26;
A19-B4-C27;
A19-B4-C28;

-continued

A19-B4-C29;
A19-B4-C30;
A19-B4-C31;
A19-B4-C32;
A19-B4-C33;
A19-B4-C34;
A19-B4-C35;
A19-B4-C36;
A19-B4-C37;
A19-B4-C38;
A19-B4-C39;
A19-B4-C40;
A19-B4-C41;
A19-B4-C42;
A19-B4-C43;
A19-B4-C44;
A19-B4-C45;
A19-B4-C46;
A19-B4-C47;
A19-B4-C48;
A19-B4-C49;
A19-B4-C50;
A19-B4-C51;
A19-B4-C52;
A19-B4-C53;
A19-B4-C54;
A19-B4-C55;
A19-B4-C56;
A19-B4-C57;
A19-B4-C58;
A19-B4-C59;
A19-B4-C60;
A19-B4-C61;
A19-B4-C62;
A19-B4-C63;
A19-B4-C64;
A19-B4-C65;
A19-B4-C66;
A19-B4-C67;
A19-B4-C68;
A20-B4-C1;
A20-B4-C2;
A20-B4-C3;
A20-B4-C4;
A20-B4-C5;
A20-B4-C6;
A20-B4-C7;
A20-B4-C8;
A20-B4-C9;
A20-B4-C10;
A20-B4-C11;
A20-B4-C12;
A20-B4-C13;
A20-B4-C14;
A20-B4-C15;
A20-B4-C16;
A20-B4-C17;
A20-B4-C18;
A20-B4-C19;
A20-B4-C20;
A20-B4-C21;
A20-B4-C22;
A20-B4-C23;
A20-B4-C24;
A20-B4-C25;
A20-B4-C26;
A20-B4-C27;
A20-B4-C28;
A20-B4-C29;
A20-B4-C30;
A20-B4-C31;
A20-B4-C32;
A20-B4-C33;
A20-B4-C34;
A20-B4-C35;
A20-B4-C36;
A20-B4-C37;
A20-B4-C38;
A20-B4-C39;

-continued

A20-B4-C40;
A20-B4-C41;
A20-B4-C42;
A20-B4-C43;
A20-B4-C44;
A20-B4-C45;
A20-B4-C46;
A20-B4-C47;
A20-B4-C48;
A20-B4-C49;
A20-B4-C50;
A20-B4-C51;
A20-B4-C52;
A20-B4-C53;
A20-B4-C54;
A20-B4-C55;
A20-B4-C56;
A20-B4-C57;
A20-B4-C58;
A20-B4-C59;
A20-B4-C60;
A20-B4-C61;
A20-B4-C62;
A20-B4-C63;
A20-B4-C64;
A20-B4-C65;
A20-B4-C66;
A20-B4-C67;
A20-B4-C68;
A21-B4-C1;
A21-B4-C2;
A21-B4-C3;
A21-B4-C4;
A21-B4-C5;
A21-B4-C6;
A21-B4-C7;
A21-B4-C8;
A21-B4-C9;
A21-B4-C10;
A21-B4-C11;
A21-B4-C12;
A21-B4-C13;
A21-B4-C14;
A21-B4-C15;
A21-B4-C16;
A21-B4-C17;
A21-B4-C18;
A21-B4-C19;
A21-B4-C20;
A21-B4-C21;
A21-B4-C22;
A21-B4-C23;
A21-B4-C24;
A21-B4-C25;
A21-B4-C26;
A21-B4-C27;
A21-B4-C28;
A21-B4-C29;
A21-B4-C30;
A21-B4-C31;
A21-B4-C32;
A21-B4-C33;
A21-B4-C34;
A21-B4-C35;
A21-B4-C36;
A21-B4-C37;
A21-B4-C38;
A21-B4-C39;
A21-B4-C40;
A21-B4-C41;
A21-B4-C42;
A21-B4-C43;
A21-B4-C44;
A21-B4-C45;
A21-B4-C46;
A21-B4-C47;
A21-B4-C48;
A21-B4-C49;
A21-B4-C50;

-continued

A21-B4-C51;
A21-B4-C52;
A21-B4-C53;
A21-B4-C54;
A21-B4-C55;
A21-B4-C56;
A21-B4-C57;
A21-B4-C58;
A21-B4-C59;
A21-B4-C60;
A21-B4-C61;
A21-B4-C62;
A21-B4-C63;
A21-B4-C64;
A21-B4-C65;
A21-B4-C66;
A21-B4-C67;
A21-B4-C68;
A22-B4-C1;
A22-B4-C2;
A22-B4-C3;
A22-B4-C4;
A22-B4-C5;
A22-B4-C6;
A22-B4-C7;
A22-B4-C8;
A22-B4-C9;
A22-B4-C10;
A22-B4-C11;
A22-B4-C12;
A22-B4-C13;
A22-B4-C14;
A22-B4-C15;
A22-B4-C16;
A22-B4-C17;
A22-B4-C18;
A22-B4-C19;
A22-B4-C20;
A22-B4-C21;
A22-B4-C22;
A22-B4-C23;
A22-B4-C24;
A22-B4-C25;
A22-B4-C26;
A22-B4-C27;
A22-B4-C28;
A22-B4-C29;
A22-B4-C30;
A22-B4-C31;
A22-B4-C32;
A22-B4-C33;
A22-B4-C34;
A22-B4-C35;
A22-B4-C36;
A22-B4-C37;
A22-B4-C38;
A22-B4-C39;
A22-B4-C40;
A22-B4-C41;
A22-B4-C42;
A22-B4-C43;
A22-B4-C44;
A22-B4-C45;
A22-B4-C46;
A22-B4-C47;
A22-B4-C48;
A22-B4-C49;
A22-B4-C50;
A22-B4-C51;
A22-B4-C52;
A22-B4-C53;
A22-B4-C54;
A22-B4-C55;
A22-B4-C56;
A22-B4-C57;
A22-B4-C58;
A22-B4-C59;
A22-B4-C60;
A22-B4-C61;

-continued

A22-B4-C62;
A22-B4-C63;
A22-B4-C64;
A22-B4-C65;
A22-B4-C66;
A22-B4-C67;
A22-B4-C68;
A23-B4-C1;
A23-B4-C2;
A23-B4-C3;
A23-B4-C4;
A23-B4-C5;
A23-B4-C6;
A23-B4-C7;
A23-B4-C8;
A23-B4-C9;
A23-B4-C10;
A23-B4-C11;
A23-B4-C12;
A23-B4-C13;
A23-B4-C14;
A23-B4-C15;
A23-B4-C16;
A23-B4-C17;
A23-B4-C18;
A23-B4-C19;
A23-B4-C20;
A23-B4-C21;
A23-B4-C22;
A23-B4-C23;
A23-B4-C24;
A23-B4-C25;
A23-B4-C26;
A23-B4-C27;
A23-B4-C28;
A23-B4-C29;
A23-B4-C30;
A23-B4-C31;
A23-B4-C32;
A23-B4-C33;
A23-B4-C34;
A23-B4-C35;
A23-B4-C36;
A23-B4-C37;
A23-B4-C38;
A23-B4-C39;
A23-B4-C40;
A23-B4-C41;
A23-B4-C42;
A23-B4-C43;
A23-B4-C44;
A23-B4-C45;
A23-B4-C46;
A23-B4-C47;
A23-B4-C48;
A23-B4-C49;
A23-B4-C50;
A23-B4-C51;
A23-B4-C52;
A23-B4-C53;
A23-B4-C54;
A23-B4-C55;
A23-B4-C56;
A23-B4-C57;
A23-B4-C58;
A23-B4-C59;
A23-B4-C60;
A23-B4-C61;
A23-B4-C62;
A23-B4-C63;
A23-B4-C64;
A23-B4-C65;
A23-B4-C66;
A23-B4-C67;
A23-B4-C68;
A24-B4-C1;
A24-B4-C2;
A24-B4-C3;
A24-B4-C4;

-continued

A24-B4-C5;
A24-B4-C6;
A24-B4-C7;
A24-B4-C8;
A24-B4-C9;
A24-B4-C10;
A24-B4-C11;
A24-B4-C12;
A24-B4-C13;
A24-B4-C14;
A24-B4-C15;
A24-B4-C16;
A24-B4-C17;
A24-B4-C18;
A24-B4-C19;
A24-B4-C20;
A24-B4-C21;
A24-B4-C22;
A24-B4-C23;
A24-B4-C24;
A24-B4-C25;
A24-B4-C26;
A24-B4-C27;
A24-B4-C28;
A24-B4-C29;
A24-B4-C30;
A24-B4-C31;
A24-B4-C32;
A24-B4-C33;
A24-B4-C34;
A24-B4-C35;
A24-B4-C36;
A24-B4-C37;
A24-B4-C38;
A24-B4-C39;
A24-B4-C40;
A24-B4-C41;
A24-B4-C42;
A24-B4-C43;
A24-B4-C44;
A24-B4-C45;
A24-B4-C46;
A24-B4-C47;
A24-B4-C48;
A24-B4-C49;
A24-B4-C50;
A24-B4-C51;
A24-B4-C52;
A24-B4-C53;
A24-B4-C54;
A24-B4-C55;
A24-B4-C56;
A24-B4-C57;
A24-B4-C58;
A24-B4-C59;
A24-B4-C60;
A24-B4-C61;
A24-B4-C62;
A24-B4-C63;
A24-B4-C64;
A24-B4-C65;
A24-B4-C66;
A24-B4-C67;
A24-B4-C68;
A25-B4-C1;
A25-B4-C2;
A25-B4-C3;
A25-B4-C4;
A25-B4-C5;
A25-B4-C6;
A25-B4-C7;
A25-B4-C8;
A25-B4-C9;
A25-B4-C10;
A25-B4-C11;
A25-B4-C12;
A25-B4-C13;
A25-B4-C14;
A25-B4-C15;

-continued

A25-B4-C16;
A25-B4-C17;
A25-B4-C18;
A25-B4-C19;
A25-B4-C20;
A25-B4-C21;
A25-B4-C22;
A25-B4-C23;
A25-B4-C24;
A25-B4-C25;
A25-B4-C26;
A25-B4-C27;
A25-B4-C28;
A25-B4-C29;
A25-B4-C30;
A25-B4-C31;
A25-B4-C32;
A25-B4-C33;
A25-B4-C34;
A25-B4-C35;
A25-B4-C36;
A25-B4-C37;
A25-B4-C38;
A25-B4-C39;
A25-B4-C40;
A25-B4-C41;
A25-B4-C42;
A25-B4-C43;
A25-B4-C44;
A25-B4-C45;
A25-B4-C46;
A25-B4-C47;
A25-B4-C48;
A25-B4-C49;
A25-B4-C50;
A25-B4-C51;
A25-B4-C52;
A25-B4-C53;
A25-B4-C54;
A25-B4-C55;
A25-B4-C56;
A25-B4-C57;
A25-B4-C58;
A25-B4-C59;
A25-B4-C60;
A25-B4-C61;
A25-B4-C62;
A25-B4-C63;
A25-B4-C64;
A25-B4-C65;
A25-B4-C66;
A25-B4-C67;
A25-B4-C68;
A26-B4-C1;
A26-B4-C2;
A26-B4-C3;
A26-B4-C4;
A26-B4-C5;
A26-B4-C6;
A26-B4-C7;
A26-B4-C8;
A26-B4-C9;
A26-B4-C10;
A26-B4-C11;
A26-B4-C12;
A26-B4-C13;
A26-B4-C14;
A26-B4-C15;
A26-B4-C16;
A26-B4-C17;
A26-B4-C18;
A26-B4-C19;
A26-B4-C20;
A26-B4-C21;
A26-B4-C22;
A26-B4-C23;
A26-B4-C24;
A26-B4-C25;
A26-B4-C26;

-continued

A26-B4-C27;
A26-B4-C28;
A26-B4-C29;
A26-B4-C30;
A26-B4-C31;
A26-B4-C32;
A26-B4-C33;
A26-B4-C34;
A26-B4-C35;
A26-B4-C36;
A26-B4-C37;
A26-B4-C38;
A26-B4-C39;
A26-B4-C40;
A26-B4-C41;
A26-B4-C42;
A26-B4-C43;
A26-B4-C44;
A26-B4-C45;
A26-B4-C46;
A26-B4-C47;
A26-B4-C48;
A26-B4-C49;
A26-B4-C50;
A26-B4-C51;
A26-B4-C52;
A26-B4-C53;
A26-B4-C54;
A26-B4-C55;
A26-B4-C56;
A26-B4-C57;
A26-B4-C58;
A26-B4-C59;
A26-B4-C60;
A26-B4-C61;
A26-B4-C62;
A26-B4-C63;
A26-B4-C64;
A26-B4-C65;
A26-B4-C66;
A26-B4-C67;
A26-B4-C68;
A27-B4-C1;
A27-B4-C2;
A27-B4-C3;
A27-B4-C4;
A27-B4-C5;
A27-B4-C6;
A27-B4-C7;
A27-B4-C8;
A27-B4-C9;
A27-B4-C10;
A27-B4-C11;
A27-B4-C12;
A27-B4-C13;
A27-B4-C14;
A27-B4-C15;
A27-B4-C16;
A27-B4-C17;
A27-B4-C18;
A27-B4-C19;
A27-B4-C20;
A27-B4-C21;
A27-B4-C22;
A27-B4-C23;
A27-B4-C24;
A27-B4-C25;
A27-B4-C26;
A27-B4-C27;
A27-B4-C28;
A27-B4-C29;
A27-B4-C30;
A27-B4-C31;
A27-B4-C32;
A27-B4-C33;
A27-B4-C34;
A27-B4-C35;
A27-B4-C36;
A27-B4-C37;

-continued

A27-B4-C38;
A27-B4-C39;
A27-B4-C40;
A27-B4-C41;
A27-B4-C42;
A27-B4-C43;
A27-B4-C44;
A27-B4-C45;
A27-B4-C46;
A27-B4-C47;
A27-B4-C48;
A27-B4-C49;
A27-B4-C50;
A27-B4-C51;
A27-B4-C52;
A27-B4-C53;
A27-B4-C54;
A27-B4-C55;
A27-B4-C56;
A27-B4-C57;
A27-B4-C58;
A27-B4-C59;
A27-B4-C60;
A27-B4-C61;
A27-B4-C62;
A27-B4-C63;
A27-B4-C64;
A27-B4-C65;
A27-B4-C66;
A27-B4-C67;
A27-B4-C68;
A28-B4-C1;
A28-B4-C2;
A28-B4-C3;
A28-B4-C4;
A28-B4-C5;
A28-B4-C6;
A28-B4-C7;
A28-B4-C8;
A28-B4-C9;
A28-B4-C10;
A28-B4-C11;
A28-B4-C12;
A28-B4-C13;
A28-B4-C14;
A28-B4-C15;
A28-B4-C16;
A28-B4-C17;
A28-B4-C18;
A28-B4-C19;
A28-B4-C20;
A28-B4-C21;
A28-B4-C22;
A28-B4-C23;
A28-B4-C24;
A28-B4-C25;
A28-B4-C26;
A28-B4-C27;
A28-B4-C28;
A28-B4-C29;
A28-B4-C30;
A28-B4-C31;
A28-B4-C32;
A28-B4-C33;
A28-B4-C34;
A28-B4-C35;
A28-B4-C36;
A28-B4-C37;
A28-B4-C38;
A28-B4-C39;
A28-B4-C40;
A28-B4-C41;
A28-B4-C42;
A28-B4-C43;
A28-B4-C44;
A28-B4-C45;
A28-B4-C46;
A28-B4-C47;
A28-B4-C48;

-continued

A28-B4-C49;
A28-B4-C50;
A28-B4-C51;
A28-B4-C52;
A28-B4-C53;
A28-B4-C54;
A28-B4-C55;
A28-B4-C56;
A28-B4-C57;
A28-B4-C58;
A28-B4-C59;
A28-B4-C60;
A28-B4-C61;
A28-B4-C62;
A28-B4-C63;
A28-B4-C64;
A28-B4-C65;
A28-B4-C66;
A28-B4-C67;
A28-B4-C68;
A29-B4-C1;
A29-B4-C2;
A29-B4-C3;
A29-B4-C4;
A29-B4-C5;
A29-B4-C6;
A29-B4-C7;
A29-B4-C8;
A29-B4-C9;
A29-B4-C10;
A29-B4-C11;
A29-B4-C12;
A29-B4-C13;
A29-B4-C14;
A29-B4-C15;
A29-B4-C16;
A29-B4-C17;
A29-B4-C18;
A29-B4-C19;
A29-B4-C20;
A29-B4-C21;
A29-B4-C22;
A29-B4-C23;
A29-B4-C24;
A29-B4-C25;
A29-B4-C26;
A29-B4-C27;
A29-B4-C28;
A29-B4-C29;
A29-B4-C30;
A29-B4-C31;
A29-B4-C32;
A29-B4-C33;
A29-B4-C34;
A29-B4-C35;
A29-B4-C36;
A29-B4-C37;
A29-B4-C38;
A29-B4-C39;
A29-B4-C40;
A29-B4-C41;
A29-B4-C42;
A29-B4-C43;
A29-B4-C44;
A29-B4-C45;
A29-B4-C46;
A29-B4-C47;
A29-B4-C48;
A29-B4-C49;
A29-B4-C50;
A29-B4-C51;
A29-B4-C52;
A29-B4-C53;
A29-B4-C54;
A29-B4-C55;
A29-B4-C56;
A29-B4-C57;
A29-B4-C58;
A29-B4-C59;

-continued

A29-B4-C60;
A29-B4-C61;
A29-B4-C62;
A29-B4-C63;
A29-B4-C64;
A29-B4-C65;
A29-B4-C66;
A29-B4-C67;
A29-B4-C68;
A30-B4-C1;
A30-B4-C2;
A30-B4-C3;
A30-B4-C4;
A30-B4-C5;
A30-B4-C6;
A30-B4-C7;
A30-B4-C8;
A30-B4-C9;
A30-B4-C10;
A30-B4-C11;
A30-B4-C12;
A30-B4-C13;
A30-B4-C14;
A30-B4-C15;
A30-B4-C16;
A30-B4-C17;
A30-B4-C18;
A30-B4-C19;
A30-B4-C20;
A30-B4-C21;
A30-B4-C22;
A30-B4-C23;
A30-B4-C24;
A30-B4-C25;
A30-B4-C26;
A30-B4-C27;
A30-B4-C28;
A30-B4-C29;
A30-B4-C30;
A30-B4-C31;
A30-B4-C32;
A30-B4-C33;
A30-B4-C34;
A30-B4-C35;
A30-B4-C36;
A30-B4-C37;
A30-B4-C38;
A30-B4-C39;
A30-B4-C40;
A30-B4-C41;
A30-B4-C42;
A30-B4-C43;
A30-B4-C44;
A30-B4-C45;
A30-B4-C46;
A30-B4-C47;
A30-B4-C48;
A30-B4-C49;
A30-B4-C50;
A30-B4-C51;
A30-B4-C52;
A30-B4-C53;
A30-B4-C54;
A30-B4-C55;
A30-B4-C56;
A30-B4-C57;
A30-B4-C58;
A30-B4-C59;
A30-B4-C60;
A30-B4-C61;
A30-B4-C62;
A30-B4-C63;
A30-B4-C64;
A30-B4-C65;
A30-B4-C66;
A30-B4-C67;
A30-B4-C68;
A31-B4-C1;
A31-B4-C2;

-continued

A31-B4-C3;
A31-B4-C4;
A31-B4-C5;
A31-B4-C6;
A31-B4-C7;
A31-B4-C8;
A31-B4-C9;
A31-B4-C10;
A31-B4-C11;
A31-B4-C12;
A31-B4-C13;
A31-B4-C14;
A31-B4-C15;
A31-B4-C16;
A31-B4-C17;
A31-B4-C18;
A31-B4-C19;
A31-B4-C20;
A31-B4-C21;
A31-B4-C22;
A31-B4-C23;
A31-B4-C24;
A31-B4-C25;
A31-B4-C26;
A31-B4-C27;
A31-B4-C28;
A31-B4-C29;
A31-B4-C30;
A31-B4-C31;
A31-B4-C32;
A31-B4-C33;
A31-B4-C34;
A31-B4-C35;
A31-B4-C36;
A31-B4-C37;
A31-B4-C38;
A31-B4-C39;
A31-B4-C40;
A31-B4-C41;
A31-B4-C42;
A31-B4-C43;
A31-B4-C44;
A31-B4-C45;
A31-B4-C46;
A31-B4-C47;
A31-B4-C48;
A31-B4-C49;
A31-B4-C50;
A31-B4-C51;
A31-B4-C52;
A31-B4-C53;
A31-B4-C54;
A31-B4-C55;
A31-B4-C56;
A31-B4-C57;
A31-B4-C58;
A31-B4-C59;
A31-B4-C60;
A31-B4-C61;
A31-B4-C62;
A31-B4-C63;
A31-B4-C64;
A31-B4-C65;
A31-B4-C66;
A31-B4-C67;
A31-B4-C68;
A32-B4-C1;
A32-B4-C2;
A32-B4-C3;
A32-B4-C4;
A32-B4-C5;
A32-B4-C6;
A32-B4-C7;
A32-B4-C8;
A32-B4-C9;
A32-B4-C10;
A32-B4-C11;
A32-B4-C12;
A32-B4-C13;

-continued

A32-B4-C14;
A32-B4-C15;
A32-B4-C16;
A32-B4-C17;
A32-B4-C18;
A32-B4-C19;
A32-B4-C20;
A32-B4-C21;
A32-B4-C22;
A32-B4-C23;
A32-B4-C24;
A32-B4-C25;
A32-B4-C26;
A32-B4-C27;
A32-B4-C28;
A32-B4-C29;
A32-B4-C30;
A32-B4-C31;
A32-B4-C32;
A32-B4-C33;
A32-B4-C34;
A32-B4-C35;
A32-B4-C36;
A32-B4-C37;
A32-B4-C38;
A32-B4-C39;
A32-B4-C40;
A32-B4-C41;
A32-B4-C42;
A32-B4-C43;
A32-B4-C44;
A32-B4-C45;
A32-B4-C46;
A32-B4-C47;
A32-B4-C48;
A32-B4-C49;
A32-B4-C50;
A32-B4-C51;
A32-B4-C52;
A32-B4-C53;
A32-B4-C54;
A32-B4-C55;
A32-B4-C56;
A32-B4-C57;
A32-B4-C58;
A32-B4-C59;
A32-B4-C60;
A32-B4-C61;
A32-B4-C62;
A32-B4-C63;
A32-B4-C64;
A32-B4-C65;
A32-B4-C66;
A32-B4-C67;
A32-B4-C68;
A33-B4-C1;
A33-B4-C2;
A33-B4-C3;
A33-B4-C4;
A33-B4-C5;
A33-B4-C6;
A33-B4-C7;
A33-B4-C8;
A33-B4-C9;
A33-B4-C10;
A33-B4-C11;
A33-B4-C12;
A33-B4-C13;
A33-B4-C14;
A33-B4-C15;
A33-B4-C16;
A33-B4-C17;
A33-B4-C18;
A33-B4-C19;
A33-B4-C20;
A33-B4-C21;
A33-B4-C22;
A33-B4-C23;
A33-B4-C24;

-continued

A33-B4-C25;
A33-B4-C26;
A33-B4-C27;
A33-B4-C28;
A33-B4-C29;
A33-B4-C30;
A33-B4-C31;
A33-B4-C32;
A33-B4-C33;
A33-B4-C34;
A33-B4-C35;
A33-B4-C36;
A33-B4-C37;
A33-B4-C38;
A33-B4-C39;
A33-B4-C40;
A33-B4-C41;
A33-B4-C42;
A33-B4-C43;
A33-B4-C44;
A33-B4-C45;
A33-B4-C46;
A33-B4-C47;
A33-B4-C48;
A33-B4-C49;
A33-B4-C50;
A33-B4-C51;
A33-B4-C52;
A33-B4-C53;
A33-B4-C54;
A33-B4-C55;
A33-B4-C56;
A33-B4-C57;
A33-B4-C58;
A33-B4-C59;
A33-B4-C60;
A33-B4-C61;
A33-B4-C62;
A33-B4-C63;
A33-B4-C64;
A33-B4-C65;
A33-B4-C66;
A33-B4-C67;
A33-B4-C68;
A34-B4-C1;
A34-B4-C2;
A34-B4-C3;
A34-B4-C4;
A34-B4-C5;
A34-B4-C6;
A34-B4-C7;
A34-B4-C8;
A34-B4-C9;
A34-B4-C10;
A34-B4-C11;
A34-B4-C12;
A34-B4-C13;
A34-B4-C14;
A34-B4-C15;
A34-B4-C16;
A34-B4-C17;
A34-B4-C18;
A34-B4-C19;
A34-B4-C20;
A34-B4-C21;
A34-B4-C22;
A34-B4-C23;
A34-B4-C24;
A34-B4-C25;
A34-B4-C26;
A34-B4-C27;
A34-B4-C28;
A34-B4-C29;
A34-B4-C30;
A34-B4-C31;
A34-B4-C32;
A34-B4-C33;
A34-B4-C34;
A34-B4-C35;

-continued

A34-B4-C36;
A34-B4-C37;
A34-B4-C38;
A34-B4-C39;
A34-B4-C40;
A34-B4-C41;
A34-B4-C42;
A34-B4-C43;
A34-B4-C44;
A34-B4-C45;
A34-B4-C46;
A34-B4-C47;
A34-B4-C48;
A34-B4-C49;
A34-B4-C50;
A34-B4-C51;
A34-B4-C52;
A34-B4-C53;
A34-B4-C54;
A34-B4-C55;
A34-B4-C56;
A34-B4-C57;
A34-B4-C58;
A34-B4-C59;
A34-B4-C60;
A34-B4-C61;
A34-B4-C62;
A34-B4-C63;
A34-B4-C64;
A34-B4-C65;
A34-B4-C66;
A34-B4-C67;
A34-B4-C68;
A35-B4-C1;
A35-B4-C2;
A35-B4-C3;
A35-B4-C4;
A35-B4-C5;
A35-B4-C6;
A35-B4-C7;
A35-B4-C8;
A35-B4-C9;
A35-B4-C10;
A35-B4-C11;
A35-B4-C12;
A35-B4-C13;
A35-B4-C14;
A35-B4-C15;
A35-B4-C16;
A35-B4-C17;
A35-B4-C18;
A35-B4-C19;
A35-B4-C20;
A35-B4-C21;
A35-B4-C22;
A35-B4-C23;
A35-B4-C24;
A35-B4-C25;
A35-B4-C26;
A35-B4-C27;
A35-B4-C28;
A35-B4-C29;
A35-B4-C30;
A35-B4-C31;
A35-B4-C32;
A35-B4-C33;
A35-B4-C34;
A35-B4-C35;
A35-B4-C36;
A35-B4-C37;
A35-B4-C38;
A35-B4-C39;
A35-B4-C40;
A35-B4-C41;
A35-B4-C42;
A35-B4-C43;
A35-B4-C44;
A35-B4-C45;
A35-B4-C46;

-continued

A35-B4-C47;
A35-B4-C48;
A35-B4-C49;
A35-B4-C50;
A35-B4-C51;
A35-B4-C52;
A35-B4-C53;
A35-B4-C54;
A35-B4-C55;
A35-B4-C56;
A35-B4-C57;
A35-B4-C58;
A35-B4-C59;
A35-B4-C60;
A35-B4-C61;
A35-B4-C62;
A35-B4-C63;
A35-B4-C64;
A35-B4-C65;
A35-B4-C66;
A35-B4-C67;
A35-B4-C68;
A36-B4-C1;
A36-B4-C2;
A36-B4-C3;
A36-B4-C4;
A36-B4-C5;
A36-B4-C6;
A36-B4-C7;
A36-B4-C8;
A36-B4-C9;
A36-B4-C10;
A36-B4-C11;
A36-B4-C12;
A36-B4-C13;
A36-B4-C14;
A36-B4-C15;
A36-B4-C16;
A36-B4-C17;
A36-B4-C18;
A36-B4-C19;
A36-B4-C20;
A36-B4-C21;
A36-B4-C22;
A36-B4-C23;
A36-B4-C24;
A36-B4-C25;
A36-B4-C26;
A36-B4-C27;
A36-B4-C28;
A36-B4-C29;
A36-B4-C30;
A36-B4-C31;
A36-B4-C32;
A36-B4-C33;
A36-B4-C34;
A36-B4-C35;
A36-B4-C36;
A36-B4-C37;
A36-B4-C38;
A36-B4-C39;
A36-B4-C40;
A36-B4-C41;
A36-B4-C42;
A36-B4-C43;
A36-B4-C44;
A36-B4-C45;
A36-B4-C46;
A36-B4-C47;
A36-B4-C48;
A36-B4-C49;
A36-B4-C50;
A36-B4-C51;
A36-B4-C52;
A36-B4-C53;
A36-B4-C54;
A36-B4-C55;
A36-B4-C56;
A36-B4-C57;

-continued

A36-B4-C58;
A36-B4-C59;
A36-B4-C60;
A36-B4-C61;
A36-B4-C62;
A36-B4-C63;
A36-B4-C64;
A36-B4-C65;
A36-B4-C66;
A36-B4-C67;
A36-B4-C68;
A37-B4-C1;
A37-B4-C2;
A37-B4-C3;
A37-B4-C4;
A37-B4-C5;
A37-B4-C6;
A37-B4-C7;
A37-B4-C8;
A37-B4-C9;
A37-B4-C10;
A37-B4-C11;
A37-B4-C12;
A37-B4-C13;
A37-B4-C14;
A37-B4-C15;
A37-B4-C16;
A37-B4-C17;
A37-B4-C18;
A37-B4-C19;
A37-B4-C20;
A37-B4-C21;
A37-B4-C22;
A37-B4-C23;
A37-B4-C24;
A37-B4-C25;
A37-B4-C26;
A37-B4-C27;
A37-B4-C28;
A37-B4-C29;
A37-B4-C30;
A37-B4-C31;
A37-B4-C32;
A37-B4-C33;
A37-B4-C34;
A37-B4-C35;
A37-B4-C36;
A37-B4-C37;
A37-B4-C38;
A37-B4-C39;
A37-B4-C40;
A37-B4-C41;
A37-B4-C42;
A37-B4-C43;
A37-B4-C44;
A37-B4-C45;
A37-B4-C46;
A37-B4-C47;
A37-B4-C48;
A37-B4-C49;
A37-B4-C50;
A37-B4-C51;
A37-B4-C52;
A37-B4-C53;
A37-B4-C54;
A37-B4-C55;
A37-B4-C56;
A37-B4-C57;
A37-B4-C58;
A37-B4-C59;
A37-B4-C60;
A37-B4-C61;
A37-B4-C62;
A37-B4-C63;
A37-B4-C64;
A37-B4-C65;
A37-B4-C66;
A37-B4-C67;
A37-B4-C68;

-continued

A38-B4-C1;
A38-B4-C2;
A38-B4-C3;
A38-B4-C4;
A38-B4-C5;
A38-B4-C6;
A38-B4-C7;
A38-B4-C8;
A38-B4-C9;
A38-B4-C10;
A38-B4-C11;
A38-B4-C12;
A38-B4-C13;
A38-B4-C14;
A38-B4-C15;
A38-B4-C16;
A38-B4-C17;
A38-B4-C18;
A38-B4-C19;
A38-B4-C20;
A38-B4-C21;
A38-B4-C22;
A38-B4-C23;
A38-B4-C24;
A38-B4-C25;
A38-B4-C26;
A38-B4-C27;
A38-B4-C28;
A38-B4-C29;
A38-B4-C30;
A38-B4-C31;
A38-B4-C32;
A38-B4-C33;
A38-B4-C34;
A38-B4-C35;
A38-B4-C36;
A38-B4-C37;
A38-B4-C38;
A38-B4-C39;
A38-B4-C40;
A38-B4-C41;
A38-B4-C42;
A38-B4-C43;
A38-B4-C44;
A38-B4-C45;
A38-B4-C46;
A38-B4-C47;
A38-B4-C48;
A38-B4-C49;
A38-B4-C50;
A38-B4-C51;
A38-B4-C52;
A38-B4-C53;
A38-B4-C54;
A38-B4-C55;
A38-B4-C56;
A38-B4-C57;
A38-B4-C58;
A38-B4-C59;
A38-B4-C60;
A38-B4-C61;
A38-B4-C62;
A38-B4-C63;
A38-B4-C64;
A38-B4-C65;
A38-B4-C66;
A38-B4-C67;
A38-B4-C68;
A1-B5-C1;
A1-B5-C2;
A1-B5-C3;
A1-B5-C4;
A1-B5-C5;
A1-B5-C6;
A1-B5-C7;
A1-B5-C8;
A1-B5-C9;
A1-B5-C10;
A1-B5-C11;

-continued

A1-B5-C12;
A1-B5-C13;
A1-B5-C14;
A1-B5-C15;
A1-B5-C16;
A1-B5-C17;
A1-B5-C18;
A1-B5-C19;
A1-B5-C20;
A1-B5-C21;
A1-B5-C22;
A1-B5-C23;
A1-B5-C24;
A1-B5-C25;
A1-B5-C26;
A1-B5-C27;
A1-B5-C28;
A1-B5-C29;
A1-B5-C30;
A1-B5-C31;
A1-B5-C32;
A1-B5-C33;
A1-B5-C34;
A1-B5-C35;
A1-B5-C36;
A1-B5-C37;
A1-B5-C38;
A1-B5-C39;
A1-B5-C40;
A1-B5-C41;
A1-B5-C42;
A1-B5-C43;
A1-B5-C44;
A1-B5-C45;
A1-B5-C46;
A1-B5-C47;
A1-B5-C48;
A1-B5-C49;
A1-B5-C50;
A1-B5-C51;
A1-B5-C52;
A1-B5-C53;
A1-B5-C54;
A1-B5-C55;
A1-B5-C56;
A1-B5-C57;
A1-B5-C58;
A1-B5-C59;
A1-B5-C60;
A1-B5-C61;
A1-B5-C62;
A1-B5-C63;
A1-B5-C64;
A1-B5-C65;
A1-B5-C66;
A1-B5-C67;
A1-B5-C68;
A2-B5-C1;
A2-B5-C2;
A2-B5-C3;
A2-B5-C4;
A2-B5-C5;
A2-B5-C6;
A2-B5-C7;
A2-B5-C8;
A2-B5-C9;
A2-B5-C10;
A2-B5-C11;
A2-B5-C12;
A2-B5-C13;
A2-B5-C14;
A2-B5-C15;
A2-B5-C16;
A2-B5-C17;
A2-B5-C18;
A2-B5-C19;
A2-B5-C20;
A2-B5-C21;
A2-B5-C22;

-continued

A2-B5-C23;
A2-B5-C24;
A2-B5-C25;
A2-B5-C26;
A2-B5-C27;
A2-B5-C28;
A2-B5-C29;
A2-B5-C30;
A2-B5-C31;
A2-B5-C32;
A2-B5-C33;
A2-B5-C34;
A2-B5-C35;
A2-B5-C36;
A2-B5-C37;
A2-B5-C38;
A2-B5-C39;
A2-B5-C40;
A2-B5-C41;
A2-B5-C42;
A2-B5-C43;
A2-B5-C44;
A2-B5-C45;
A2-B5-C46;
A2-B5-C47;
A2-B5-C48;
A2-B5-C49;
A2-B5-C50;
A2-B5-C51;
A2-B5-C52;
A2-B5-C53;
A2-B5-C54;
A2-B5-C55;
A2-B5-C56;
A2-B5-C57;
A2-B5-C58;
A2-B5-C59;
A2-B5-C60;
A2-B5-C61;
A2-B5-C62;
A2-B5-C63;
A2-B5-C64;
A2-B5-C65;
A2-B5-C66;
A2-B5-C67;
A2-B5-C68;
A3-B5-C1;
A3-B5-C2;
A3-B5-C3;
A3-B5-C4;
A3-B5-C5;
A3-B5-C6;
A3-B5-C7;
A3-B5-C8;
A3-B5-C9;
A3-B5-C10;
A3-B5-C11;
A3-B5-C12;
A3-B5-C13;
A3-B5-C14;
A3-B5-C15;
A3-B5-C16;
A3-B5-C17;
A3-B5-C18;
A3-B5-C19;
A3-B5-C20;
A3-B5-C21;
A3-B5-C22;
A3-B5-C23;
A3-B5-C24;
A3-B5-C25;
A3-B5-C26;
A3-B5-C27;
A3-B5-C28;
A3-B5-C29;
A3-B5-C30;
A3-B5-C31;
A3-B5-C32;
A3-B5-C33;

-continued

A3-B5-C34;
A3-B5-C35;
A3-B5-C36;
A3-B5-C37;
A3-B5-C38;
A3-B5-C39;
A3-B5-C40;
A3-B5-C41;
A3-B5-C42;
A3-B5-C43;
A3-B5-C44;
A3-B5-C45;
A3-B5-C46;
A3-B5-C47;
A3-B5-C48;
A3-B5-C49;
A3-B5-C50;
A3-B5-C51;
A3-B5-C52;
A3-B5-C53;
A3-B5-C54;
A3-B5-C55;
A3-B5-C56;
A3-B5-C57;
A3-B5-C58;
A3-B5-C59;
A3-B5-C60;
A3-B5-C61;
A3-B5-C62;
A3-B5-C63;
A3-B5-C64;
A3-B5-C65;
A3-B5-C66;
A3-B5-C67;
A3-B5-C68;
A4-B5-C1;
A4-B5-C2;
A4-B5-C3;
A4-B5-C4;
A4-B5-C5;
A4-B5-C6;
A4-B5-C7;
A4-B5-C8;
A4-B5-C9;
A4-B5-C10;
A4-B5-C11;
A4-B5-C12;
A4-B5-C13;
A4-B5-C14;
A4-B5-C15;
A4-B5-C16;
A4-B5-C17;
A4-B5-C18;
A4-B5-C19;
A4-B5-C20;
A4-B5-C21;
A4-B5-C22;
A4-B5-C23;
A4-B5-C24;
A4-B5-C25;
A4-B5-C26;
A4-B5-C27;
A4-B5-C28;
A4-B5-C29;
A4-B5-C30;
A4-B5-C31;
A4-B5-C32;
A4-B5-C33;
A4-B5-C34;
A4-B5-C35;
A4-B5-C36;
A4-B5-C37;
A4-B5-C38;
A4-B5-C39;
A4-B5-C40;
A4-B5-C41;
A4-B5-C42;
A4-B5-C43;
A4-B5-C44;

A4-B5-C45;
A4-B5-C46;
A4-B5-C47;
A4-B5-C48;
A4-B5-C49;
A4-B5-C50;
A4-B5-C51;
A4-B5-C52;
A4-B5-C53;
A4-B5-C54;
A4-B5-C55;
A4-B5-C56;
A4-B5-C57;
A4-B5-C58;
A4-B5-C59;
A4-B5-C60;
A4-B5-C61;
A4-B5-C62;
A4-B5-C63;
A4-B5-C64;
A4-B5-C65;
A4-B5-C66;
A4-B5-C67;
A4-B5-C68;
A5-B5-C1;
A5-B5-C2;
A5-B5-C3;
A5-B5-C4;
A5-B5-C5;
A5-B5-C6;
A5-B5-C7;
A5-B5-C8;
A5-B5-C9;
A5-B5-C10;
A5-B5-C11;
A5-B5-C12;
A5-B5-C13;
A5-B5-C14;
A5-B5-C15;
A5-B5-C16;
A5-B5-C17;
A5-B5-C18;
A5-B5-C19;
A5-B5-C20;
A5-B5-C21;
A5-B5-C22;
A5-B5-C23;
A5-B5-C24;
A5-B5-C25;
A5-B5-C26;
A5-B5-C27;
A5-B5-C28;
A5-B5-C29;
A5-B5-C30;
A5-B5-C31;
A5-B5-C32;
A5-B5-C33;
A5-B5-C34;
A5-B5-C35;
A5-B5-C36;
A5-B5-C37;
A5-B5-C38;
A5-B5-C39;
A5-B5-C40;
A5-B5-C41;
A5-B5-C42;
A5-B5-C43;
A5-B5-C44;
A5-B5-C45;
A5-B5-C46;
A5-B5-C47;
A5-B5-C48;
A5-B5-C49;
A5-B5-C50;
A5-B5-C51;
A5-B5-C52;
A5-B5-C53;
A5-B5-C54;
A5-B5-C55;
A5-B5-C56;
A5-B5-C57;
A5-B5-C58;
A5-B5-C59;
A5-B5-C60;
A5-B5-C61;
A5-B5-C62;
A5-B5-C63;
A5-B5-C64;
A5-B5-C65;
A5-B5-C66;
A5-B5-C67;
A5-B5-C68;
A6-B5-C1;
A6-B5-C2;
A6-B5-C3;
A6-B5-C4;
A6-B5-C5;
A6-B5-C6;
A6-B5-C7;
A6-B5-C8;
A6-B5-C9;
A6-B5-C10;
A6-B5-C11;
A6-B5-C12;
A6-B5-C13;
A6-B5-C14;
A6-B5-C15;
A6-B5-C16;
A6-B5-C17;
A6-B5-C18;
A6-B5-C19;
A6-B5-C20;
A6-B5-C21;
A6-B5-C22;
A6-B5-C23;
A6-B5-C24;
A6-B5-C25;
A6-B5-C26;
A6-B5-C27;
A6-B5-C28;
A6-B5-C29;
A6-B5-C30;
A6-B5-C31;
A6-B5-C32;
A6-B5-C33;
A6-B5-C34;
A6-B5-C35;
A6-B5-C36;
A6-B5-C37;
A6-B5-C38;
A6-B5-C39;
A6-B5-C40;
A6-B5-C41;
A6-B5-C42;
A6-B5-C43;
A6-B5-C44;
A6-B5-C45;
A6-B5-C46;
A6-B5-C47;
A6-B5-C48;
A6-B5-C49;
A6-B5-C50;
A6-B5-C51;
A6-B5-C52;
A6-B5-C53;
A6-B5-C54;
A6-B5-C55;
A6-B5-C56;
A6-B5-C57;
A6-B5-C58;
A6-B5-C59;
A6-B5-C60;
A6-B5-C61;
A6-B5-C62;
A6-B5-C63;
A6-B5-C64;
A6-B5-C65;
A6-B5-C66;

-continued

A6-B5-C67;
A6-B5-C68;
A7-B5-C1;
A7-B5-C2;
A7-B5-C3;
A7-B5-C4;
A7-B5-C5;
A7-B5-C6;
A7-B5-C7;
A7-B5-C8;
A7-B5-C9;
A7-B5-C10;
A7-B5-C11;
A7-B5-C12;
A7-B5-C13;
A7-B5-C14;
A7-B5-C15;
A7-B5-C16;
A7-B5-C17;
A7-B5-C18;
A7-B5-C19;
A7-B5-C20;
A7-B5-C21;
A7-B5-C22;
A7-B5-C23;
A7-B5-C24;
A7-B5-C25;
A7-B5-C26;
A7-B5-C27;
A7-B5-C28;
A7-B5-C29;
A7-B5-C30;
A7-B5-C31;
A7-B5-C32;
A7-B5-C33;
A7-B5-C34;
A7-B5-C35;
A7-B5-C36;
A7-B5-C37;
A7-B5-C38;
A7-B5-C39;
A7-B5-C40;
A7-B5-C41;
A7-B5-C42;
A7-B5-C43;
A7-B5-C44;
A7-B5-C45;
A7-B5-C46;
A7-B5-C47;
A7-B5-C48;
A7-B5-C49;
A7-B5-C50;
A7-B5-C51;
A7-B5-C52;
A7-B5-C53;
A7-B5-C54;
A7-B5-C55;
A7-B5-C56;
A7-B5-C57;
A7-B5-C58;
A7-B5-C59;
A7-B5-C60;
A7-B5-C61;
A7-B5-C62;
A7-B5-C63;
A7-B5-C64;
A7-B5-C65;
A7-B5-C66;
A7-B5-C67;
A7-B5-C68;
A8-B5-C1;
A8-B5-C2;
A8-B5-C3;
A8-B5-C4;
A8-B5-C5;
A8-B5-C6;
A8-B5-C7;
A8-B5-C8;
A8-B5-C9;

-continued

A8-B5-C10;
A8-B5-C11;
A8-B5-C12;
A8-B5-C13;
A8-B5-C14;
A8-B5-C15;
A8-B5-C16;
A8-B5-C17;
A8-B5-C18;
A8-B5-C19;
A8-B5-C20;
A8-B5-C21;
A8-B5-C22;
A8-B5-C23;
A8-B5-C24;
A8-B5-C25;
A8-B5-C26;
A8-B5-C27;
A8-B5-C28;
A8-B5-C29;
A8-B5-C30;
A8-B5-C31;
A8-B5-C32;
A8-B5-C33;
A8-B5-C34;
A8-B5-C35;
A8-B5-C36;
A8-B5-C37;
A8-B5-C38;
A8-B5-C39;
A8-B5-C40;
A8-B5-C41;
A8-B5-C42;
A8-B5-C43;
A8-B5-C44;
A8-B5-C45;
A8-B5-C46;
A8-B5-C47;
A8-B5-C48;
A8-B5-C49;
A8-B5-C50;
A8-B5-C51;
A8-B5-C52;
A8-B5-C53;
A8-B5-C54;
A8-B5-C55;
A8-B5-C56;
A8-B5-C57;
A8-B5-C58;
A8-B5-C59;
A8-B5-C60;
A8-B5-C61;
A8-B5-C62;
A8-B5-C63;
A8-B5-C64;
A8-B5-C65;
A8-B5-C66;
A8-B5-C67;
A8-B5-C68;
A9-B5-C1;
A9-B5-C2;
A9-B5-C3;
A9-B5-C4;
A9-B5-C5;
A9-B5-C6;
A9-B5-C7;
A9-B5-C8;
A9-B5-C9;
A9-B5-C10;
A9-B5-C11;
A9-B5-C12;
A9-B5-C13;
A9-B5-C14;
A9-B5-C15;
A9-B5-C16;
A9-B5-C17;
A9-B5-C18;
A9-B5-C19;
A9-B5-C20;

-continued

A9-B5-C21;
A9-B5-C22;
A9-B5-C23;
A9-B5-C24;
A9-B5-C25;
A9-B5-C26;
A9-B5-C27;
A9-B5-C28;
A9-B5-C29;
A9-B5-C30;
A9-B5-C31;
A9-B5-C32;
A9-B5-C33;
A9-B5-C34;
A9-B5-C35;
A9-B5-C36;
A9-B5-C37;
A9-B5-C38;
A9-B5-C39;
A9-B5-C40;
A9-B5-C41;
A9-B5-C42;
A9-B5-C43;
A9-B5-C44;
A9-B5-C45;
A9-B5-C46;
A9-B5-C47;
A9-B5-C48;
A9-B5-C49;
A9-B5-C50;
A9-B5-C51;
A9-B5-C52;
A9-B5-C53;
A9-B5-C54;
A9-B5-C55;
A9-B5-C56;
A9-B5-C57;
A9-B5-C58;
A9-B5-C59;
A9-B5-C60;
A9-B5-C61;
A9-B5-C62;
A9-B5-C63;
A9-B5-C64;
A9-B5-C65;
A9-B5-C66;
A9-B5-C67;
A9-B5-C68;
A10-B5-C1;
A10-B5-C2;
A10-B5-C3;
A10-B5-C4;
A10-B5-C5;
A10-B5-C6;
A10-B5-C7;
A10-B5-C8;
A10-B5-C9;
A10-B5-C10;
A10-B5-C11;
A10-B5-C12;
A10-B5-C13;
A10-B5-C14;
A10-B5-C15;
A10-B5-C16;
A10-B5-C17;
A10-B5-C18;
A10-B5-C19;
A10-B5-C20;
A10-B5-C21;
A10-B5-C22;
A10-B5-C23;
A10-B5-C24;
A10-B5-C25;
A10-B5-C26;
A10-B5-C27;
A10-B5-C28;
A10-B5-C29;
A10-B5-C30;
A10-B5-C31;

-continued

A10-B5-C32;
A10-B5-C33;
A10-B5-C34;
A10-B5-C35;
A10-B5-C36;
A10-B5-C37;
A10-B5-C38;
A10-B5-C39;
A10-B5-C40;
A10-B5-C41;
A10-B5-C42;
A10-B5-C43;
A10-B5-C44;
A10-B5-C45;
A10-B5-C46;
A10-B5-C47;
A10-B5-C48;
A10-B5-C49;
A10-B5-C50;
A10-B5-C51;
A10-B5-C52;
A10-B5-C53;
A10-B5-C54;
A10-B5-C55;
A10-B5-C56;
A10-B5-C57;
A10-B5-C58;
A10-B5-C59;
A10-B5-C60;
A10-B5-C61;
A10-B5-C62;
A10-B5-C63;
A10-B5-C64;
A10-B5-C65;
A10-B5-C66;
A10-B5-C67;
A10-B5-C68;
A11-B5-C1;
A11-B5-C2;
A11-B5-C3;
A11-B5-C4;
A11-B5-C5;
A11-B5-C6;
A11-B5-C7;
A11-B5-C8;
A11-B5-C9;
A11-B5-C10;
A11-B5-C11;
A11-B5-C12;
A11-B5-C13;
A11-B5-C14;
A11-B5-C15;
A11-B5-C16;
A11-B5-C17;
A11-B5-C18;
A11-B5-C19;
A11-B5-C20;
A11-B5-C21;
A11-B5-C22;
A11-B5-C23;
A11-B5-C24;
A11-B5-C25;
A11-B5-C26;
A11-B5-C27;
A11-B5-C28;
A11-B5-C29;
A11-B5-C30;
A11-B5-C31;
A11-B5-C32;
A11-B5-C33;
A11-B5-C34;
A11-B5-C35;
A11-B5-C36;
A11-B5-C37;
A11-B5-C38;
A11-B5-C39;
A11-B5-C40;
A11-B5-C41;
A11-B5-C42;

-continued

A11-B5-C43;
A11-B5-C44;
A11-B5-C45;
A11-B5-C46;
A11-B5-C47;
A11-B5-C48;
A11-B5-C49;
A11-B5-C50;
A11-B5-C51;
A11-B5-C52;
A11-B5-C53;
A11-B5-C54;
A11-B5-C55;
A11-B5-C56;
A11-B5-C57;
A11-B5-C58;
A11-B5-C59;
A11-B5-C60;
A11-B5-C61;
A11-B5-C62;
A11-B5-C63;
A11-B5-C64;
A11-B5-C65;
A11-B5-C66;
A11-B5-C67;
A11-B5-C68;
A12-B5-C1;
A12-B5-C2;
A12-B5-C3;
A12-B5-C4;
A12-B5-C5;
A12-B5-C6;
A12-B5-C7;
A12-B5-C8;
A12-B5-C9;
A12-B5-C10;
A12-B5-C11;
A12-B5-C12;
A12-B5-C13;
A12-B5-C14;
A12-B5-C15;
A12-B5-C16;
A12-B5-C17;
A12-B5-C18;
A12-B5-C19;
A12-B5-C20;
A12-B5-C21;
A12-B5-C22;
A12-B5-C23;
A12-B5-C24;
A12-B5-C25;
A12-B5-C26;
A12-B5-C27;
A12-B5-C28;
A12-B5-C29;
A12-B5-C30;
A12-B5-C31;
A12-B5-C32;
A12-B5-C33;
A12-B5-C34;
A12-B5-C35;
A12-B5-C36;
A12-B5-C37;
A12-B5-C38;
A12-B5-C39;
A12-B5-C40;
A12-B5-C41;
A12-B5-C42;
A12-B5-C43;
A12-B5-C44;
A12-B5-C45;
A12-B5-C46;
A12-B5-C47;
A12-B5-C48;
A12-B5-C49;
A12-B5-C50;
A12-B5-C51;
A12-B5-C52;
A12-B5-C53;

-continued

A12-B5-C54;
A12-B5-C55;
A12-B5-C56;
A12-B5-C57;
A12-B5-C58;
A12-B5-C59;
A12-B5-C60;
A12-B5-C61;
A12-B5-C62;
A12-B5-C63;
A12-B5-C64;
A12-B5-C65;
A12-B5-C66;
A12-B5-C67;
A12-B5-C68;
A13-B5-C1;
A13-B5-C2;
A13-B5-C3;
A13-B5-C4;
A13-B5-C5;
A13-B5-C6;
A13-B5-C7;
A13-B5-C8;
A13-B5-C9;
A13-B5-C10;
A13-B5-C11;
A13-B5-C12;
A13-B5-C13;
A13-B5-C14;
A13-B5-C15;
A13-B5-C16;
A13-B5-C17;
A13-B5-C18;
A13-B5-C19;
A13-B5-C20;
A13-B5-C21;
A13-B5-C22;
A13-B5-C23;
A13-B5-C24;
A13-B5-C25;
A13-B5-C26;
A13-B5-C27;
A13-B5-C28;
A13-B5-C29;
A13-B5-C30;
A13-B5-C31;
A13-B5-C32;
A13-B5-C33;
A13-B5-C34;
A13-B5-C35;
A13-B5-C36;
A13-B5-C37;
A13-B5-C38;
A13-B5-C39;
A13-B5-C40;
A13-B5-C41;
A13-B5-C42;
A13-B5-C43;
A13-B5-C44;
A13-B5-C45;
A13-B5-C46;
A13-B5-C47;
A13-B5-C48;
A13-B5-C49;
A13-B5-C50;
A13-B5-C51;
A13-B5-C52;
A13-B5-C53;
A13-B5-C54;
A13-B5-C55;
A13-B5-C56;
A13-B5-C57;
A13-B5-C58;
A13-B5-C59;
A13-B5-C60;
A13-B5-C61;
A13-B5-C62;
A13-B5-C63;
A13-B5-C64;

A13-B5-C65;
A13-B5-C66;
A13-B5-C67;
A13-B5-C68;
A14-B5-C1;
A14-B5-C2;
A14-B5-C3;
A14-B5-C4;
A14-B5-C5;
A14-B5-C6;
A14-B5-C7;
A14-B5-C8;
A14-B5-C9;
A14-B5-C10;
A14-B5-C11;
A14-B5-C12;
A14-B5-C13;
A14-B5-C14;
A14-B5-C15;
A14-B5-C16;
A14-B5-C17;
A14-B5-C18;
A14-B5-C19;
A14-B5-C20;
A14-B5-C21;
A14-B5-C22;
A14-B5-C23;
A14-B5-C24;
A14-B5-C25;
A14-B5-C26;
A14-B5-C27;
A14-B5-C28;
A14-B5-C29;
A14-B5-C30;
A14-B5-C31;
A14-B5-C32;
A14-B5-C33;
A14-B5-C34;
A14-B5-C35;
A14-B5-C36;
A14-B5-C37;
A14-B5-C38;
A14-B5-C39;
A14-B5-C40;
A14-B5-C41;
A14-B5-C42;
A14-B5-C43;
A14-B5-C44;
A14-B5-C45;
A14-B5-C46;
A14-B5-C47;
A14-B5-C48;
A14-B5-C49;
A14-B5-C50;
A14-B5-C51;
A14-B5-C52;
A14-B5-C53;
A14-B5-C54;
A14-B5-C55;
A14-B5-C56;
A14-B5-C57;
A14-B5-C58;
A14-B5-C59;
A14-B5-C60;
A14-B5-C61;
A14-B5-C62;
A14-B5-C63;
A14-B5-C64;
A14-B5-C65;
A14-B5-C66;
A14-B5-C67;
A14-B5-C68;
A15-B5-C1;
A15-B5-C2;
A15-B5-C3;
A15-B5-C4;
A15-B5-C5;
A15-B5-C6;
A15-B5-C7;
A15-B5-C8;
A15-B5-C9;
A15-B5-C10;
A15-B5-C11;
A15-B5-C12;
A15-B5-C13;
A15-B5-C14;
A15-B5-C15;
A15-B5-C16;
A15-B5-C17;
A15-B5-C18;
A15-B5-C19;
A15-B5-C20;
A15-B5-C21;
A15-B5-C22;
A15-B5-C23;
A15-B5-C24;
A15-B5-C25;
A15-B5-C26;
A15-B5-C27;
A15-B5-C28;
A15-B5-C29;
A15-B5-C30;
A15-B5-C31;
A15-B5-C32;
A15-B5-C33;
A15-B5-C34;
A15-B5-C35;
A15-B5-C36;
A15-B5-C37;
A15-B5-C38;
A15-B5-C39;
A15-B5-C40;
A15-B5-C41;
A15-B5-C42;
A15-B5-C43;
A15-B5-C44;
A15-B5-C45;
A15-B5-C46;
A15-B5-C47;
A15-B5-C48;
A15-B5-C49;
A15-B5-C50;
A15-B5-C51;
A15-B5-C52;
A15-B5-C53;
A15-B5-C54;
A15-B5-C55;
A15-B5-C56;
A15-B5-C57;
A15-B5-C58;
A15-B5-C59;
A15-B5-C60;
A15-B5-C61;
A15-B5-C62;
A15-B5-C63;
A15-B5-C64;
A15-B5-C65;
A15-B5-C66;
A15-B5-C67;
A15-B5-C68;
A16-B5-C1;
A16-B5-C2;
A16-B5-C3;
A16-B5-C4;
A16-B5-C5;
A16-B5-C6;
A16-B5-C7;
A16-B5-C8;
A16-B5-C9;
A16-B5-C10;
A16-B5-C11;
A16-B5-C12;
A16-B5-C13;
A16-B5-C14;
A16-B5-C15;
A16-B5-C16;
A16-B5-C17;
A16-B5-C18;

-continued

A16-B5-C19;
A16-B5-C20;
A16-B5-C21;
A16-B5-C22;
A16-B5-C23;
A16-B5-C24;
A16-B5-C25;
A16-B5-C26;
A16-B5-C27;
A16-B5-C28;
A16-B5-C29;
A16-B5-C30;
A16-B5-C31;
A16-B5-C32;
A16-B5-C33;
A16-B5-C34;
A16-B5-C35;
A16-B5-C36;
A16-B5-C37;
A16-B5-C38;
A16-B5-C39;
A16-B5-C40;
A16-B5-C41;
A16-B5-C42;
A16-B5-C43;
A16-B5-C44;
A16-B5-C45;
A16-B5-C46;
A16-B5-C47;
A16-B5-C48;
A16-B5-C49;
A16-B5-C50;
A16-B5-C51;
A16-B5-C52;
A16-B5-C53;
A16-B5-C54;
A16-B5-C55;
A16-B5-C56;
A16-B5-C57;
A16-B5-C58;
A16-B5-C59;
A16-B5-C60;
A16-B5-C61;
A16-B5-C62;
A16-B5-C63;
A16-B5-C64;
A16-B5-C65;
A16-B5-C66;
A16-B5-C67;
A16-B5-C68;
A17-B5-C1;
A17-B5-C2;
A17-B5-C3;
A17-B5-C4;
A17-B5-C5;
A17-B5-C6;
A17-B5-C7;
A17-B5-C8;
A17-B5-C9;
A17-B5-C10;
A17-B5-C11;
A17-B5-C12;
A17-B5-C13;
A17-B5-C14;
A17-B5-C15;
A17-B5-C16;
A17-B5-C17;
A17-B5-C18;
A17-B5-C19;
A17-B5-C20;
A17-B5-C21;
A17-B5-C22;
A17-B5-C23;
A17-B5-C24;
A17-B5-C25;
A17-B5-C26;
A17-B5-C27;
A17-B5-C28;
A17-B5-C29;

-continued

A17-B5-C30;
A17-B5-C31;
A17-B5-C32;
A17-B5-C33;
A17-B5-C34;
A17-B5-C35;
A17-B5-C36;
A17-B5-C37;
A17-B5-C38;
A17-B5-C39;
A17-B5-C40;
A17-B5-C41;
A17-B5-C42;
A17-B5-C43;
A17-B5-C44;
A17-B5-C45;
A17-B5-C46;
A17-B5-C47;
A17-B5-C48;
A17-B5-C49;
A17-B5-C50;
A17-B5-C51;
A17-B5-C52;
A17-B5-C53;
A17-B5-C54;
A17-B5-C55;
A17-B5-C56;
A17-B5-C57;
A17-B5-C58;
A17-B5-C59;
A17-B5-C60;
A17-B5-C61;
A17-B5-C62;
A17-B5-C63;
A17-B5-C64;
A17-B5-C65;
A17-B5-C66;
A17-B5-C67;
A17-B5-C68;
A18-B5-C1;
A18-B5-C2;
A18-B5-C3;
A18-B5-C4;
A18-B5-C5;
A18-B5-C6;
A18-B5-C7;
A18-B5-C8;
A18-B5-C9;
A18-B5-C10;
A18-B5-C11;
A18-B5-C12;
A18-B5-C13;
A18-B5-C14;
A18-B5-C15;
A18-B5-C16;
A18-B5-C17;
A18-B5-C18;
A18-B5-C19;
A18-B5-C20;
A18-B5-C21;
A18-B5-C22;
A18-B5-C23;
A18-B5-C24;
A18-B5-C25;
A18-B5-C26;
A18-B5-C27;
A18-B5-C28;
A18-B5-C29;
A18-B5-C30;
A18-B5-C31;
A18-B5-C32;
A18-B5-C33;
A18-B5-C34;
A18-B5-C35;
A18-B5-C36;
A18-B5-C37;
A18-B5-C38;
A18-B5-C39;
A18-B5-C40;

-continued

A18-B5-C41;
A18-B5-C42;
A18-B5-C43;
A18-B5-C44;
A18-B5-C45;
A18-B5-C46;
A18-B5-C47;
A18-B5-C48;
A18-B5-C49;
A18-B5-C50;
A18-B5-C51;
A18-B5-C52;
A18-B5-C53;
A18-B5-C54;
A18-B5-C55;
A18-B5-C56;
A18-B5-C57;
A18-B5-C58;
A18-B5-C59;
A18-B5-C60;
A18-B5-C61;
A18-B5-C62;
A18-B5-C63;
A18-B5-C64;
A18-B5-C65;
A18-B5-C66;
A18-B5-C67;
A18-B5-C68;
A19-B5-C1;
A19-B5-C2;
A19-B5-C3;
A19-B5-C4;
A19-B5-C5;
A19-B5-C6;
A19-B5-C7;
A19-B5-C8;
A19-B5-C9;
A19-B5-C10;
A19-B5-C11;
A19-B5-C12;
A19-B5-C13;
A19-B5-C14;
A19-B5-C15;
A19-B5-C16;
A19-B5-C17;
A19-B5-C18;
A19-B5-C19;
A19-B5-C20;
A19-B5-C21;
A19-B5-C22;
A19-B5-C23;
A19-B5-C24;
A19-B5-C25;
A19-B5-C26;
A19-B5-C27;
A19-B5-C28;
A19-B5-C29;
A19-B5-C30;
A19-B5-C31;
A19-B5-C32;
A19-B5-C33;
A19-B5-C34;
A19-B5-C35;
A19-B5-C36;
A19-B5-C37;
A19-B5-C38;
A19-B5-C39;
A19-B5-C40;
A19-B5-C41;
A19-B5-C42;
A19-B5-C43;
A19-B5-C44;
A19-B5-C45;
A19-B5-C46;
A19-B5-C47;
A19-B5-C48;
A19-B5-C49;
A19-B5-C50;
A19-B5-C51;

-continued

A19-B5-C52;
A19-B5-C53;
A19-B5-C54;
A19-B5-C55;
A19-B5-C56;
A19-B5-C57;
A19-B5-C58;
A19-B5-C59;
A19-B5-C60;
A19-B5-C61;
A19-B5-C62;
A19-B5-C63;
A19-B5-C64;
A19-B5-C65;
A19-B5-C66;
A19-B5-C67;
A19-B5-C68;
A20-B5-C1;
A20-B5-C2;
A20-B5-C3;
A20-B5-C4;
A20-B5-C5;
A20-B5-C6;
A20-B5-C7;
A20-B5-C8;
A20-B5-C9;
A20-B5-C10;
A20-B5-C11;
A20-B5-C12;
A20-B5-C13;
A20-B5-C14;
A20-B5-C15;
A20-B5-C16;
A20-B5-C17;
A20-B5-C18;
A20-B5-C19;
A20-B5-C20;
A20-B5-C21;
A20-B5-C22;
A20-B5-C23;
A20-B5-C24;
A20-B5-C25;
A20-B5-C26;
A20-B5-C27;
A20-B5-C28;
A20-B5-C29;
A20-B5-C30;
A20-B5-C31;
A20-B5-C32;
A20-B5-C33;
A20-B5-C34;
A20-B5-C35;
A20-B5-C36;
A20-B5-C37;
A20-B5-C38;
A20-B5-C39;
A20-B5-C40;
A20-B5-C41;
A20-B5-C42;
A20-B5-C43;
A20-B5-C44;
A20-B5-C45;
A20-B5-C46;
A20-B5-C47;
A20-B5-C48;
A20-B5-C49;
A20-B5-C50;
A20-B5-C51;
A20-B5-C52;
A20-B5-C53;
A20-B5-C54;
A20-B5-C55;
A20-B5-C56;
A20-B5-C57;
A20-B5-C58;
A20-B5-C59;
A20-B5-C60;
A20-B5-C61;
A20-B5-C62;

-continued

A20-B5-C63;
A20-B5-C64;
A20-B5-C65;
A20-B5-C66;
A20-B5-C67;
A20-B5-C68;
A21-B5-C1;
A21-B5-C2;
A21-B5-C3;
A21-B5-C4;
A21-B5-C5;
A21-B5-C6;
A21-B5-C7;
A21-B5-C8;
A21-B5-C9;
A21-B5-C10;
A21-B5-C11;
A21-B5-C12;
A21-B5-C13;
A21-B5-C14;
A21-B5-C15;
A21-B5-C16;
A21-B5-C17;
A21-B5-C18;
A21-B5-C19;
A21-B5-C20;
A21-B5-C21;
A21-B5-C22;
A21-B5-C23;
A21-B5-C24;
A21-B5-C25;
A21-B5-C26;
A21-B5-C27;
A21-B5-C28;
A21-B5-C29;
A21-B5-C30;
A21-B5-C31;
A21-B5-C32;
A21-B5-C33;
A21-B5-C34;
A21-B5-C35;
A21-B5-C36;
A21-B5-C37;
A21-B5-C38;
A21-B5-C39;
A21-B5-C40;
A21-B5-C41;
A21-B5-C42;
A21-B5-C43;
A21-B5-C44;
A21-B5-C45;
A21-B5-C46;
A21-B5-C47;
A21-B5-C48;
A21-B5-C49;
A21-B5-C50;
A21-B5-C51;
A21-B5-C52;
A21-B5-C53;
A21-B5-C54;
A21-B5-C55;
A21-B5-C56;
A21-B5-C57;
A21-B5-C58;
A21-B5-C59;
A21-B5-C60;
A21-B5-C61;
A21-B5-C62;
A21-B5-C63;
A21-B5-C64;
A21-B5-C65;
A21-B5-C66;
A21-B5-C67;
A21-B5-C68;
A22-B5-C1;
A22-B5-C2;
A22-B5-C3;
A22-B5-C4;
A22-B5-C5;

-continued

A22-B5-C6;
A22-B5-C7;
A22-B5-C8;
A22-B5-C9;
A22-B5-C10;
A22-B5-C11;
A22-B5-C12;
A22-B5-C13;
A22-B5-C14;
A22-B5-C15;
A22-B5-C16;
A22-B5-C17;
A22-B5-C18;
A22-B5-C19;
A22-B5-C20;
A22-B5-C21;
A22-B5-C22;
A22-B5-C23;
A22-B5-C24;
A22-B5-C25;
A22-B5-C26;
A22-B5-C27;
A22-B5-C28;
A22-B5-C29;
A22-B5-C30;
A22-B5-C31;
A22-B5-C32;
A22-B5-C33;
A22-B5-C34;
A22-B5-C35;
A22-B5-C36;
A22-B5-C37;
A22-B5-C38;
A22-B5-C39;
A22-B5-C40;
A22-B5-C41;
A22-B5-C42;
A22-B5-C43;
A22-B5-C44;
A22-B5-C45;
A22-B5-C46;
A22-B5-C47;
A22-B5-C48;
A22-B5-C49;
A22-B5-C50;
A22-B5-C51;
A22-B5-C52;
A22-B5-C53;
A22-B5-C54;
A22-B5-C55;
A22-B5-C56;
A22-B5-C57;
A22-B5-C58;
A22-B5-C59;
A22-B5-C60;
A22-B5-C61;
A22-B5-C62;
A22-B5-C63;
A22-B5-C64;
A22-B5-C65;
A22-B5-C66;
A22-B5-C67;
A22-B5-C68;
A23-B5-C1;
A23-B5-C2;
A23-B5-C3;
A23-B5-C4;
A23-B5-C5;
A23-B5-C6;
A23-B5-C7;
A23-B5-C8;
A23-B5-C9;
A23-B5-C10;
A23-B5-C11;
A23-B5-C12;
A23-B5-C13;
A23-B5-C14;
A23-B5-C15;
A23-B5-C16;

A23-B5-C17;
A23-B5-C18;
A23-B5-C19;
A23-B5-C20;
A23-B5-C21;
A23-B5-C22;
A23-B5-C23;
A23-B5-C24;
A23-B5-C25;
A23-B5-C26;
A23-B5-C27;
A23-B5-C28;
A23-B5-C29;
A23-B5-C30;
A23-B5-C31;
A23-B5-C32;
A23-B5-C33;
A23-B5-C34;
A23-B5-C35;
A23-B5-C36;
A23-B5-C37;
A23-B5-C38;
A23-B5-C39;
A23-B5-C40;
A23-B5-C41;
A23-B5-C42;
A23-B5-C43;
A23-B5-C44;
A23-B5-C45;
A23-B5-C46;
A23-B5-C47;
A23-B5-C48;
A23-B5-C49;
A23-B5-C50;
A23-B5-C51;
A23-B5-C52;
A23-B5-C53;
A23-B5-C54;
A23-B5-C55;
A23-B5-C56;
A23-B5-C57;
A23-B5-C58;
A23-B5-C59;
A23-B5-C60;
A23-B5-C61;
A23-B5-C62;
A23-B5-C63;
A23-B5-C64;
A23-B5-C65;
A23-B5-C66;
A23-B5-C67;
A23-B5-C68;
A24-B5-C1;
A24-B5-C2;
A24-B5-C3;
A24-B5-C4;
A24-B5-C5;
A24-B5-C6;
A24-B5-C7;
A24-B5-C8;
A24-B5-C9;
A24-B5-C10;
A24-B5-C11;
A24-B5-C12;
A24-B5-C13;
A24-B5-C14;
A24-B5-C15;
A24-B5-C16;
A24-B5-C17;
A24-B5-C18;
A24-B5-C19;
A24-B5-C20;
A24-B5-C21;
A24-B5-C22;
A24-B5-C23;
A24-B5-C24;
A24-B5-C25;
A24-B5-C26;
A24-B5-C27;
A24-B5-C28;
A24-B5-C29;
A24-B5-C30;
A24-B5-C31;
A24-B5-C32;
A24-B5-C33;
A24-B5-C34;
A24-B5-C35;
A24-B5-C36;
A24-B5-C37;
A24-B5-C38;
A24-B5-C39;
A24-B5-C40;
A24-B5-C41;
A24-B5-C42;
A24-B5-C43;
A24-B5-C44;
A24-B5-C45;
A24-B5-C46;
A24-B5-C47;
A24-B5-C48;
A24-B5-C49;
A24-B5-C50;
A24-B5-C51;
A24-B5-C52;
A24-B5-C53;
A24-B5-C54;
A24-B5-C55;
A24-B5-C56;
A24-B5-C57;
A24-B5-C58;
A24-B5-C59;
A24-B5-C60;
A24-B5-C61;
A24-B5-C62;
A24-B5-C63;
A24-B5-C64;
A24-B5-C65;
A24-B5-C66;
A24-B5-C67;
A24-B5-C68;
A25-B5-C1;
A25-B5-C2;
A25-B5-C3;
A25-B5-C4;
A25-B5-C5;
A25-B5-C6;
A25-B5-C7;
A25-B5-C8;
A25-B5-C9;
A25-B5-C10;
A25-B5-C11;
A25-B5-C12;
A25-B5-C13;
A25-B5-C14;
A25-B5-C15;
A25-B5-C16;
A25-B5-C17;
A25-B5-C18;
A25-B5-C19;
A25-B5-C20;
A25-B5-C21;
A25-B5-C22;
A25-B5-C23;
A25-B5-C24;
A25-B5-C25;
A25-B5-C26;
A25-B5-C27;
A25-B5-C28;
A25-B5-C29;
A25-B5-C30;
A25-B5-C31;
A25-B5-C32;
A25-B5-C33;
A25-B5-C34;
A25-B5-C35;
A25-B5-C36;
A25-B5-C37;
A25-B5-C38;

-continued

A25-B5-C39;
A25-B5-C40;
A25-B5-C41;
A25-B5-C42;
A25-B5-C43;
A25-B5-C44;
A25-B5-C45;
A25-B5-C46;
A25-B5-C47;
A25-B5-C48;
A25-B5-C49;
A25-B5-C50;
A25-B5-C51;
A25-B5-C52;
A25-B5-C53;
A25-B5-C54;
A25-B5-C55;
A25-B5-C56;
A25-B5-C57;
A25-B5-C58;
A25-B5-C59;
A25-B5-C60;
A25-B5-C61;
A25-B5-C62;
A25-B5-C63;
A25-B5-C64;
A25-B5-C65;
A25-B5-C66;
A25-B5-C67;
A25-B5-C68;
A26-B5-C1;
A26-B5-C2;
A26-B5-C3;
A26-B5-C4;
A26-B5-C5;
A26-B5-C6;
A26-B5-C7;
A26-B5-C8;
A26-B5-C9;
A26-B5-C10;
A26-B5-C11;
A26-B5-C12;
A26-B5-C13;
A26-B5-C14;
A26-B5-C15;
A26-B5-C16;
A26-B5-C17;
A26-B5-C18;
A26-B5-C19;
A26-B5-C20;
A26-B5-C21;
A26-B5-C22;
A26-B5-C23;
A26-B5-C24;
A26-B5-C25;
A26-B5-C26;
A26-B5-C27;
A26-B5-C28;
A26-B5-C29;
A26-B5-C30;
A26-B5-C31;
A26-B5-C32;
A26-B5-C33;
A26-B5-C34;
A26-B5-C35;
A26-B5-C36;
A26-B5-C37;
A26-B5-C38;
A26-B5-C39;
A26-B5-C40;
A26-B5-C41;
A26-B5-C42;
A26-B5-C43;
A26-B5-C44;
A26-B5-C45;
A26-B5-C46;
A26-B5-C47;
A26-B5-C48;
A26-B5-C49;

-continued

A26-B5-C50;
A26-B5-C51;
A26-B5-C52;
A26-B5-C53;
A26-B5-C54;
A26-B5-C55;
A26-B5-C56;
A26-B5-C57;
A26-B5-C58;
A26-B5-C59;
A26-B5-C60;
A26-B5-C61;
A26-B5-C62;
A26-B5-C63;
A26-B5-C64;
A26-B5-C65;
A26-B5-C66;
A26-B5-C67;
A26-B5-C68;
A27-B5-C1;
A27-B5-C2;
A27-B5-C3;
A27-B5-C4;
A27-B5-C5;
A27-B5-C6;
A27-B5-C7;
A27-B5-C8;
A27-B5-C9;
A27-B5-C10;
A27-B5-C11;
A27-B5-C12;
A27-B5-C13;
A27-B5-C14;
A27-B5-C15;
A27-B5-C16;
A27-B5-C17;
A27-B5-C18;
A27-B5-C19;
A27-B5-C20;
A27-B5-C21;
A27-B5-C22;
A27-B5-C23;
A27-B5-C24;
A27-B5-C25;
A27-B5-C26;
A27-B5-C27;
A27-B5-C28;
A27-B5-C29;
A27-B5-C30;
A27-B5-C31;
A27-B5-C32;
A27-B5-C33;
A27-B5-C34;
A27-B5-C35;
A27-B5-C36;
A27-B5-C37;
A27-B5-C38;
A27-B5-C39;
A27-B5-C40;
A27-B5-C41;
A27-B5-C42;
A27-B5-C43;
A27-B5-C44;
A27-B5-C45;
A27-B5-C46;
A27-B5-C47;
A27-B5-C48;
A27-B5-C49;
A27-B5-C50;
A27-B5-C51;
A27-B5-C52;
A27-B5-C53;
A27-B5-C54;
A27-B5-C55;
A27-B5-C56;
A27-B5-C57;
A27-B5-C58;
A27-B5-C59;
A27-B5-C60;

A27-B5-C61;
A27-B5-C62;
A27-B5-C63;
A27-B5-C64;
A27-B5-C65;
A27-B5-C66;
A27-B5-C67;
A27-B5-C68;
A28-B5-C1;
A28-B5-C2;
A28-B5-C3;
A28-B5-C4;
A28-B5-C5;
A28-B5-C6;
A28-B5-C7;
A28-B5-C8;
A28-B5-C9;
A28-B5-C10;
A28-B5-C11;
A28-B5-C12;
A28-B5-C13;
A28-B5-C14;
A28-B5-C15;
A28-B5-C16;
A28-B5-C17;
A28-B5-C18;
A28-B5-C19;
A28-B5-C20;
A28-B5-C21;
A28-B5-C22;
A28-B5-C23;
A28-B5-C24;
A28-B5-C25;
A28-B5-C26;
A28-B5-C27;
A28-B5-C28;
A28-B5-C29;
A28-B5-C30;
A28-B5-C31;
A28-B5-C32;
A28-B5-C33;
A28-B5-C34;
A28-B5-C35;
A28-B5-C36;
A28-B5-C37;
A28-B5-C38;
A28-B5-C39;
A28-B5-C40;
A28-B5-C41;
A28-B5-C42;
A28-B5-C43;
A28-B5-C44;
A28-B5-C45;
A28-B5-C46;
A28-B5-C47;
A28-B5-C48;
A28-B5-C49;
A28-B5-C50;
A28-B5-C51;
A28-B5-C52;
A28-B5-C53;
A28-B5-C54;
A28-B5-C55;
A28-B5-C56;
A28-B5-C57;
A28-B5-C58;
A28-B5-C59;
A28-B5-C60;
A28-B5-C61;
A28-B5-C62;
A28-B5-C63;
A28-B5-C64;
A28-B5-C65;
A28-B5-C66;
A28-B5-C67;
A28-B5-C68;
A29-B5-C1;
A29-B5-C2;
A29-B5-C3;
A29-B5-C4;
A29-B5-C5;
A29-B5-C6;
A29-B5-C7;
A29-B5-C8;
A29-B5-C9;
A29-B5-C10;
A29-B5-C11;
A29-B5-C12;
A29-B5-C13;
A29-B5-C14;
A29-B5-C15;
A29-B5-C16;
A29-B5-C17;
A29-B5-C18;
A29-B5-C19;
A29-B5-C20;
A29-B5-C21;
A29-B5-C22;
A29-B5-C23;
A29-B5-C24;
A29-B5-C25;
A29-B5-C26;
A29-B5-C27;
A29-B5-C28;
A29-B5-C29;
A29-B5-C30;
A29-B5-C31;
A29-B5-C32;
A29-B5-C33;
A29-B5-C34;
A29-B5-C35;
A29-B5-C36;
A29-B5-C37;
A29-B5-C38;
A29-B5-C39;
A29-B5-C40;
A29-B5-C41;
A29-B5-C42;
A29-B5-C43;
A29-B5-C44;
A29-B5-C45;
A29-B5-C46;
A29-B5-C47;
A29-B5-C48;
A29-B5-C49;
A29-B5-C50;
A29-B5-C51;
A29-B5-C52;
A29-B5-C53;
A29-B5-C54;
A29-B5-C55;
A29-B5-C56;
A29-B5-C57;
A29-B5-C58;
A29-B5-C59;
A29-B5-C60;
A29-B5-C61;
A29-B5-C62;
A29-B5-C63;
A29-B5-C64;
A29-B5-C65;
A29-B5-C66;
A29-B5-C67;
A29-B5-C68;
A30-B5-C1;
A30-B5-C2;
A30-B5-C3;
A30-B5-C4;
A30-B5-C5;
A30-B5-C6;
A30-B5-C7;
A30-B5-C8;
A30-B5-C9;
A30-B5-C10;
A30-B5-C11;
A30-B5-C12;
A30-B5-C13;
A30-B5-C14;

-continued

A30-B5-C15;
A30-B5-C16;
A30-B5-C17;
A30-B5-C18;
A30-B5-C19;
A30-B5-C20;
A30-B5-C21;
A30-B5-C22;
A30-B5-C23;
A30-B5-C24;
A30-B5-C25;
A30-B5-C26;
A30-B5-C27;
A30-B5-C28;
A30-B5-C29;
A30-B5-C30;
A30-B5-C31;
A30-B5-C32;
A30-B5-C33;
A30-B5-C34;
A30-B5-C35;
A30-B5-C36;
A30-B5-C37;
A30-B5-C38;
A30-B5-C39;
A30-B5-C40;
A30-B5-C41;
A30-B5-C42;
A30-B5-C43;
A30-B5-C44;
A30-B5-C45;
A30-B5-C46;
A30-B5-C47;
A30-B5-C48;
A30-B5-C49;
A30-B5-C50;
A30-B5-C51;
A30-B5-C52;
A30-B5-C53;
A30-B5-C54;
A30-B5-C55;
A30-B5-C56;
A30-B5-C57;
A30-B5-C58;
A30-B5-C59;
A30-B5-C60;
A30-B5-C61;
A30-B5-C62;
A30-B5-C63;
A30-B5-C64;
A30-B5-C65;
A30-B5-C66;
A30-B5-C67;
A30-B5-C68;
A31-B5-C1;
A31-B5-C2;
A31-B5-C3;
A31-B5-C4;
A31-B5-C5;
A31-B5-C6;
A31-B5-C7;
A31-B5-C8;
A31-B5-C9;
A31-B5-C10;
A31-B5-C11;
A31-B5-C12;
A31-B5-C13;
A31-B5-C14;
A31-B5-C15;
A31-B5-C16;
A31-B5-C17;
A31-B5-C18;
A31-B5-C19;
A31-B5-C20;
A31-B5-C21;
A31-B5-C22;
A31-B5-C23;
A31-B5-C24;
A31-B5-C25;

-continued

A31-B5-C26;
A31-B5-C27;
A31-B5-C28;
A31-B5-C29;
A31-B5-C30;
A31-B5-C31;
A31-B5-C32;
A31-B5-C33;
A31-B5-C34;
A31-B5-C35;
A31-B5-C36;
A31-B5-C37;
A31-B5-C38;
A31-B5-C39;
A31-B5-C40;
A31-B5-C41;
A31-B5-C42;
A31-B5-C43;
A31-B5-C44;
A31-B5-C45;
A31-B5-C46;
A31-B5-C47;
A31-B5-C48;
A31-B5-C49;
A31-B5-C50;
A31-B5-C51;
A31-B5-C52;
A31-B5-C53;
A31-B5-C54;
A31-B5-C55;
A31-B5-C56;
A31-B5-C57;
A31-B5-C58;
A31-B5-C59;
A31-B5-C60;
A31-B5-C61;
A31-B5-C62;
A31-B5-C63;
A31-B5-C64;
A31-B5-C65;
A31-B5-C66;
A31-B5-C67;
A31-B5-C68;
A32-B5-C1;
A32-B5-C2;
A32-B5-C3;
A32-B5-C4;
A32-B5-C5;
A32-B5-C6;
A32-B5-C7;
A32-B5-C8;
A32-B5-C9;
A32-B5-C10;
A32-B5-C11;
A32-B5-C12;
A32-B5-C13;
A32-B5-C14;
A32-B5-C15;
A32-B5-C16;
A32-B5-C17;
A32-B5-C18;
A32-B5-C19;
A32-B5-C20;
A32-B5-C21;
A32-B5-C22;
A32-B5-C23;
A32-B5-C24;
A32-B5-C25;
A32-B5-C26;
A32-B5-C27;
A32-B5-C28;
A32-B5-C29;
A32-B5-C30;
A32-B5-C31;
A32-B5-C32;
A32-B5-C33;
A32-B5-C34;
A32-B5-C35;
A32-B5-C36;

-continued

A32-B5-C37;
A32-B5-C38;
A32-B5-C39;
A32-B5-C40;
A32-B5-C41;
A32-B5-C42;
A32-B5-C43;
A32-B5-C44;
A32-B5-C45;
A32-B5-C46;
A32-B5-C47;
A32-B5-C48;
A32-B5-C49;
A32-B5-C50;
A32-B5-C51;
A32-B5-C52;
A32-B5-C53;
A32-B5-C54;
A32-B5-C55;
A32-B5-C56;
A32-B5-C57;
A32-B5-C58;
A32-B5-C59;
A32-B5-C60;
A32-B5-C61;
A32-B5-C62;
A32-B5-C63;
A32-B5-C64;
A32-B5-C65;
A32-B5-C66;
A32-B5-C67;
A32-B5-C68;
A33-B5-C1;
A33-B5-C2;
A33-B5-C3;
A33-B5-C4;
A33-B5-C5;
A33-B5-C6;
A33-B5-C7;
A33-B5-C8;
A33-B5-C9;
A33-B5-C10;
A33-B5-C11;
A33-B5-C12;
A33-B5-C13;
A33-B5-C14;
A33-B5-C15;
A33-B5-C16;
A33-B5-C17;
A33-B5-C18;
A33-B5-C19;
A33-B5-C20;
A33-B5-C21;
A33-B5-C22;
A33-B5-C23;
A33-B5-C24;
A33-B5-C25;
A33-B5-C26;
A33-B5-C27;
A33-B5-C28;
A33-B5-C29;
A33-B5-C30;
A33-B5-C31;
A33-B5-C32;
A33-B5-C33;
A33-B5-C34;
A33-B5-C35;
A33-B5-C36;
A33-B5-C37;
A33-B5-C38;
A33-B5-C39;
A33-B5-C40;
A33-B5-C41;
A33-B5-C42;
A33-B5-C43;
A33-B5-C44;
A33-B5-C45;
A33-B5-C46;
A33-B5-C47;

-continued

A33-B5-C48;
A33-B5-C49;
A33-B5-C50;
A33-B5-C51;
A33-B5-C52;
A33-B5-C53;
A33-B5-C54;
A33-B5-C55;
A33-B5-C56;
A33-B5-C57;
A33-B5-C58;
A33-B5-C59;
A33-B5-C60;
A33-B5-C61;
A33-B5-C62;
A33-B5-C63;
A33-B5-C64;
A33-B5-C65;
A33-B5-C66;
A33-B5-C67;
A33-B5-C68;
A34-B5-C1;
A34-B5-C2;
A34-B5-C3;
A34-B5-C4;
A34-B5-C5;
A34-B5-C6;
A34-B5-C7;
A34-B5-C8;
A34-B5-C9;
A34-B5-C10;
A34-B5-C11;
A34-B5-C12;
A34-B5-C13;
A34-B5-C14;
A34-B5-C15;
A34-B5-C16;
A34-B5-C17;
A34-B5-C18;
A34-B5-C19;
A34-B5-C20;
A34-B5-C21;
A34-B5-C22;
A34-B5-C23;
A34-B5-C24;
A34-B5-C25;
A34-B5-C26;
A34-B5-C27;
A34-B5-C28;
A34-B5-C29;
A34-B5-C30;
A34-B5-C31;
A34-B5-C32;
A34-B5-C33;
A34-B5-C34;
A34-B5-C35;
A34-B5-C36;
A34-B5-C37;
A34-B5-C38;
A34-B5-C39;
A34-B5-C40;
A34-B5-C41;
A34-B5-C42;
A34-B5-C43;
A34-B5-C44;
A34-B5-C45;
A34-B5-C46;
A34-B5-C47;
A34-B5-C48;
A34-B5-C49;
A34-B5-C50;
A34-B5-C51;
A34-B5-C52;
A34-B5-C53;
A34-B5-C54;
A34-B5-C55;
A34-B5-C56;
A34-B5-C57;
A34-B5-C58;

A34-B5-C59;
A34-B5-C60;
A34-B5-C61;
A34-B5-C62;
A34-B5-C63;
A34-B5-C64;
A34-B5-C65;
A34-B5-C66;
A34-B5-C67;
A34-B5-C68;
A35-B5-C1;
A35-B5-C2;
A35-B5-C3;
A35-B5-C4;
A35-B5-C5;
A35-B5-C6;
A35-B5-C7;
A35-B5-C8;
A35-B5-C9;
A35-B5-C10;
A35-B5-C11;
A35-B5-C12;
A35-B5-C13;
A35-B5-C14;
A35-B5-C15;
A35-B5-C16;
A35-B5-C17;
A35-B5-C18;
A35-B5-C19;
A35-B5-C20;
A35-B5-C21;
A35-B5-C22;
A35-B5-C23;
A35-B5-C24;
A35-B5-C25;
A35-B5-C26;
A35-B5-C27;
A35-B5-C28;
A35-B5-C29;
A35-B5-C30;
A35-B5-C31;
A35-B5-C32;
A35-B5-C33;
A35-B5-C34;
A35-B5-C35;
A35-B5-C36;
A35-B5-C37;
A35-B5-C38;
A35-B5-C39;
A35-B5-C40;
A35-B5-C41;
A35-B5-C42;
A35-B5-C43;
A35-B5-C44;
A35-B5-C45;
A35-B5-C46;
A35-B5-C47;
A35-B5-C48;
A35-B5-C49;
A35-B5-C50;
A35-B5-C51;
A35-B5-C52;
A35-B5-C53;
A35-B5-C54;
A35-B5-C55;
A35-B5-C56;
A35-B5-C57;
A35-B5-C58;
A35-B5-C59;
A35-B5-C60;
A35-B5-C61;
A35-B5-C62;
A35-B5-C63;
A35-B5-C64;
A35-B5-C65;
A35-B5-C66;
A35-B5-C67;
A35-B5-C68;
A36-B5-C1;
A36-B5-C2;
A36-B5-C3;
A36-B5-C4;
A36-B5-C5;
A36-B5-C6;
A36-B5-C7;
A36-B5-C8;
A36-B5-C9;
A36-B5-C10;
A36-B5-C11;
A36-B5-C12;
A36-B5-C13;
A36-B5-C14;
A36-B5-C15;
A36-B5-C16;
A36-B5-C17;
A36-B5-C18;
A36-B5-C19;
A36-B5-C20;
A36-B5-C21;
A36-B5-C22;
A36-B5-C23;
A36-B5-C24;
A36-B5-C25;
A36-B5-C26;
A36-B5-C27;
A36-B5-C28;
A36-B5-C29;
A36-B5-C30;
A36-B5-C31;
A36-B5-C32;
A36-B5-C33;
A36-B5-C34;
A36-B5-C35;
A36-B5-C36;
A36-B5-C37;
A36-B5-C38;
A36-B5-C39;
A36-B5-C40;
A36-B5-C41;
A36-B5-C42;
A36-B5-C43;
A36-B5-C44;
A36-B5-C45;
A36-B5-C46;
A36-B5-C47;
A36-B5-C48;
A36-B5-C49;
A36-B5-C50;
A36-B5-C51;
A36-B5-C52;
A36-B5-C53;
A36-B5-C54;
A36-B5-C55;
A36-B5-C56;
A36-B5-C57;
A36-B5-C58;
A36-B5-C59;
A36-B5-C60;
A36-B5-C61;
A36-B5-C62;
A36-B5-C63;
A36-B5-C64;
A36-B5-C65;
A36-B5-C66;
A36-B5-C67;
A36-B5-C68;
A37-B5-C1;
A37-B5-C2;
A37-B5-C3;
A37-B5-C4;
A37-B5-C5;
A37-B5-C6;
A37-B5-C7;
A37-B5-C8;
A37-B5-C9;
A37-B5-C10;
A37-B5-C11;
A37-B5-C12;

A37-B5-C13;
A37-B5-C14;
A37-B5-C15;
A37-B5-C16;
A37-B5-C17;
A37-B5-C18;
A37-B5-C19;
A37-B5-C20;
A37-B5-C21;
A37-B5-C22;
A37-B5-C23;
A37-B5-C24;
A37-B5-C25;
A37-B5-C26;
A37-B5-C27;
A37-B5-C28;
A37-B5-C29;
A37-B5-C30;
A37-B5-C31;
A37-B5-C32;
A37-B5-C33;
A37-B5-C34;
A37-B5-C35;
A37-B5-C36;
A37-B5-C37;
A37-B5-C38;
A37-B5-C39;
A37-B5-C40;
A37-B5-C41;
A37-B5-C42;
A37-B5-C43;
A37-B5-C44;
A37-B5-C45;
A37-B5-C46;
A37-B5-C47;
A37-B5-C48;
A37-B5-C49;
A37-B5-C50;
A37-B5-C51;
A37-B5-C52;
A37-B5-C53;
A37-B5-C54;
A37-B5-C55;
A37-B5-C56;
A37-B5-C57;
A37-B5-C58;
A37-B5-C59;
A37-B5-C60;
A37-B5-C61;
A37-B5-C62;
A37-B5-C63;
A37-B5-C64;
A37-B5-C65;
A37-B5-C66;
A37-B5-C67;
A37-B5-C68;
A38-B5-C1;
A38-B5-C2;
A38-B5-C3;
A38-B5-C4;
A38-B5-C5;
A38-B5-C6;
A38-B5-C7;
A38-B5-C8;
A38-B5-C9;
A38-B5-C10;
A38-B5-C11;
A38-B5-C12;
A38-B5-C13;
A38-B5-C14;
A38-B5-C15;
A38-B5-C16;
A38-B5-C17;
A38-B5-C18;
A38-B5-C19;
A38-B5-C20;
A38-B5-C21;
A38-B5-C22;
A38-B5-C23;
A38-B5-C24;
A38-B5-C25;
A38-B5-C26;
A38-B5-C27;
A38-B5-C28;
A38-B5-C29;
A38-B5-C30;
A38-B5-C31;
A38-B5-C32;
A38-B5-C33;
A38-B5-C34;
A38-B5-C35;
A38-B5-C36;
A38-B5-C37;
A38-B5-C38;
A38-B5-C39;
A38-B5-C40;
A38-B5-C41;
A38-B5-C42;
A38-B5-C43;
A38-B5-C44;
A38-B5-C45;
A38-B5-C46;
A38-B5-C47;
A38-B5-C48;
A38-B5-C49;
A38-B5-C50;
A38-B5-C51;
A38-B5-C52;
A38-B5-C53;
A38-B5-C54;
A38-B5-C55;
A38-B5-C56;
A38-B5-C57;
A38-B5-C58;
A38-B5-C59;
A38-B5-C60;
A38-B5-C61;
A38-B5-C62;
A38-B5-C63;
A38-B5-C64;
A38-B5-C65;
A38-B5-C66;
A38-B5-C67;
A38-B5-C68;
A1-B6-C1;
A1-B6-C2;
A1-B6-C3;
A1-B6-C4;
A1-B6-C5;
A1-B6-C6;
A1-B6-C7;
A1-B6-C8;
A1-B6-C9;
A1-B6-C10;
A1-B6-C11;
A1-B6-C12;
A1-B6-C13;
A1-B6-C14;
A1-B6-C15;
A1-B6-C16;
A1-B6-C17;
A1-B6-C18;
A1-B6-C19;
A1-B6-C20;
A1-B6-C21;
A1-B6-C22;
A1-B6-C23;
A1-B6-C24;
A1-B6-C25;
A1-B6-C26;
A1-B6-C27;
A1-B6-C28;
A1-B6-C29;
A1-B6-C30;
A1-B6-C31;
A1-B6-C32;
A1-B6-C33;
A1-B6-C34;

-continued

A1-B6-C35;
A1-B6-C36;
A1-B6-C37;
A1-B6-C38;
A1-B6-C39;
A1-B6-C40;
A1-B6-C41;
A1-B6-C42;
A1-B6-C43;
A1-B6-C44;
A1-B6-C45;
A1-B6-C46;
A1-B6-C47;
A1-B6-C48;
A1-B6-C49;
A1-B6-C50;
A1-B6-C51;
A1-B6-C52;
A1-B6-C53;
A1-B6-C54;
A1-B6-C55;
A1-B6-C56;
A1-B6-C57;
A1-B6-C58;
A1-B6-C59;
A1-B6-C60;
A1-B6-C61;
A1-B6-C62;
A1-B6-C63;
A1-B6-C64;
A1-B6-C65;
A1-B6-C66;
A1-B6-C67;
A1-B6-C68;
A2-B6-C1;
A2-B6-C2;
A2-B6-C3;
A2-B6-C4;
A2-B6-C5;
A2-B6-C6;
A2-B6-C7;
A2-B6-C8;
A2-B6-C9;
A2-B6-C10;
A2-B6-C11;
A2-B6-C12;
A2-B6-C13;
A2-B6-C14;
A2-B6-C15;
A2-B6-C16;
A2-B6-C17;
A2-B6-C18;
A2-B6-C19;
A2-B6-C20;
A2-B6-C21;
A2-B6-C22;
A2-B6-C23;
A2-B6-C24;
A2-B6-C25;
A2-B6-C26;
A2-B6-C27;
A2-B6-C28;
A2-B6-C29;
A2-B6-C30;
A2-B6-C31;
A2-B6-C32;
A2-B6-C33;
A2-B6-C34;
A2-B6-C35;
A2-B6-C36;
A2-B6-C37;
A2-B6-C38;
A2-B6-C39;
A2-B6-C40;
A2-B6-C41;
A2-B6-C42;
A2-B6-C43;
A2-B6-C44;
A2-B6-C45;

-continued

A2-B6-C46;
A2-B6-C47;
A2-B6-C48;
A2-B6-C49;
A2-B6-C50;
A2-B6-C51;
A2-B6-C52;
A2-B6-C53;
A2-B6-C54;
A2-B6-C55;
A2-B6-C56;
A2-B6-C57;
A2-B6-C58;
A2-B6-C59;
A2-B6-C60;
A2-B6-C61;
A2-B6-C62;
A2-B6-C63;
A2-B6-C64;
A2-B6-C65;
A2-B6-C66;
A2-B6-C67;
A2-B6-C68;
A3-B6-C1;
A3-B6-C2;
A3-B6-C3;
A3-B6-C4;
A3-B6-C5;
A3-B6-C6;
A3-B6-C7;
A3-B6-C8;
A3-B6-C9;
A3-B6-C10;
A3-B6-C11;
A3-B6-C12;
A3-B6-C13;
A3-B6-C14;
A3-B6-C15;
A3-B6-C16;
A3-B6-C17;
A3-B6-C18;
A3-B6-C19;
A3-B6-C20;
A3-B6-C21;
A3-B6-C22;
A3-B6-C23;
A3-B6-C24;
A3-B6-C25;
A3-B6-C26;
A3-B6-C27;
A3-B6-C28;
A3-B6-C29;
A3-B6-C30;
A3-B6-C31;
A3-B6-C32;
A3-B6-C33;
A3-B6-C34;
A3-B6-C35;
A3-B6-C36;
A3-B6-C37;
A3-B6-C38;
A3-B6-C39;
A3-B6-C40;
A3-B6-C41;
A3-B6-C42;
A3-B6-C43;
A3-B6-C44;
A3-B6-C45;
A3-B6-C46;
A3-B6-C47;
A3-B6-C48;
A3-B6-C49;
A3-B6-C50;
A3-B6-C51;
A3-B6-C52;
A3-B6-C53;
A3-B6-C54;
A3-B6-C55;
A3-B6-C56;

A3-B6-C57;
A3-B6-C58;
A3-B6-C59;
A3-B6-C60;
A3-B6-C61;
A3-B6-C62;
A3-B6-C63;
A3-B6-C64;
A3-B6-C65;
A3-B6-C66;
A3-B6-C67;
A3-B6-C68;
A4-B6-C1;
A4-B6-C2;
A4-B6-C3;
A4-B6-C4;
A4-B6-C5;
A4-B6-C6;
A4-B6-C7;
A4-B6-C8;
A4-B6-C9;
A4-B6-C10;
A4-B6-C11;
A4-B6-C12;
A4-B6-C13;
A4-B6-C14;
A4-B6-C15;
A4-B6-C16;
A4-B6-C17;
A4-B6-C18;
A4-B6-C19;
A4-B6-C20;
A4-B6-C21;
A4-B6-C22;
A4-B6-C23;
A4-B6-C24;
A4-B6-C25;
A4-B6-C26;
A4-B6-C27;
A4-B6-C28;
A4-B6-C29;
A4-B6-C30;
A4-B6-C31;
A4-B6-C32;
A4-B6-C33;
A4-B6-C34;
A4-B6-C35;
A4-B6-C36;
A4-B6-C37;
A4-B6-C38;
A4-B6-C39;
A4-B6-C40;
A4-B6-C41;
A4-B6-C42;
A4-B6-C43;
A4-B6-C44;
A4-B6-C45;
A4-B6-C46;
A4-B6-C47;
A4-B6-C48;
A4-B6-C49;
A4-B6-C50;
A4-B6-C51;
A4-B6-C52;
A4-B6-C53;
A4-B6-C54;
A4-B6-C55;
A4-B6-C56;
A4-B6-C57;
A4-B6-C58;
A4-B6-C59;
A4-B6-C60;
A4-B6-C61;
A4-B6-C62;
A4-B6-C63;
A4-B6-C64;
A4-B6-C65;
A4-B6-C66;
A4-B6-C67;
A4-B6-C68;
A5-B6-C1;
A5-B6-C2;
A5-B6-C3;
A5-B6-C4;
A5-B6-C5;
A5-B6-C6;
A5-B6-C7;
A5-B6-C8;
A5-B6-C9;
A5-B6-C10;
A5-B6-C11;
A5-B6-C12;
A5-B6-C13;
A5-B6-C14;
A5-B6-C15;
A5-B6-C16;
A5-B6-C17;
A5-B6-C18;
A5-B6-C19;
A5-B6-C20;
A5-B6-C21;
A5-B6-C22;
A5-B6-C23;
A5-B6-C24;
A5-B6-C25;
A5-B6-C26;
A5-B6-C27;
A5-B6-C28;
A5-B6-C29;
A5-B6-C30;
A5-B6-C31;
A5-B6-C32;
A5-B6-C33;
A5-B6-C34;
A5-B6-C35;
A5-B6-C36;
A5-B6-C37;
A5-B6-C38;
A5-B6-C39;
A5-B6-C40;
A5-B6-C41;
A5-B6-C42;
A5-B6-C43;
A5-B6-C44;
A5-B6-C45;
A5-B6-C46;
A5-B6-C47;
A5-B6-C48;
A5-B6-C49;
A5-B6-C50;
A5-B6-C51;
A5-B6-C52;
A5-B6-C53;
A5-B6-C54;
A5-B6-C55;
A5-B6-C56;
A5-B6-C57;
A5-B6-C58;
A5-B6-C59;
A5-B6-C60;
A5-B6-C61;
A5-B6-C62;
A5-B6-C63;
A5-B6-C64;
A5-B6-C65;
A5-B6-C66;
A5-B6-C67;
A5-B6-C68;
A6-B6-C1;
A6-B6-C2;
A6-B6-C3;
A6-B6-C4;
A6-B6-C5;
A6-B6-C6;
A6-B6-C7;
A6-B6-C8;
A6-B6-C9;
A6-B6-C10;

-continued

A6-B6-C11;
A6-B6-C12;
A6-B6-C13;
A6-B6-C14;
A6-B6-C15;
A6-B6-C16;
A6-B6-C17;
A6-B6-C18;
A6-B6-C19;
A6-B6-C20;
A6-B6-C21;
A6-B6-C22;
A6-B6-C23;
A6-B6-C24;
A6-B6-C25;
A6-B6-C26;
A6-B6-C27;
A6-B6-C28;
A6-B6-C29;
A6-B6-C30;
A6-B6-C31;
A6-B6-C32;
A6-B6-C33;
A6-B6-C34;
A6-B6-C35;
A6-B6-C36;
A6-B6-C37;
A6-B6-C38;
A6-B6-C39;
A6-B6-C40;
A6-B6-C41;
A6-B6-C42;
A6-B6-C43;
A6-B6-C44;
A6-B6-C45;
A6-B6-C46;
A6-B6-C47;
A6-B6-C48;
A6-B6-C49;
A6-B6-C50;
A6-B6-C51;
A6-B6-C52;
A6-B6-C53;
A6-B6-C54;
A6-B6-C55;
A6-B6-C56;
A6-B6-C57;
A6-B6-C58;
A6-B6-C59;
A6-B6-C60;
A6-B6-C61;
A6-B6-C62;
A6-B6-C63;
A6-B6-C64;
A6-B6-C65;
A6-B6-C66;
A6-B6-C67;
A6-B6-C68;
A7-B6-C1;
A7-B6-C2;
A7-B6-C3;
A7-B6-C4;
A7-B6-C5;
A7-B6-C6;
A7-B6-C7;
A7-B6-C8;
A7-B6-C9;
A7-B6-C10;
A7-B6-C11;
A7-B6-C12;
A7-B6-C13;
A7-B6-C14;
A7-B6-C15;
A7-B6-C16;
A7-B6-C17;
A7-B6-C18;
A7-B6-C19;
A7-B6-C20;
A7-B6-C21;

-continued

A7-B6-C22;
A7-B6-C23;
A7-B6-C24;
A7-B6-C25;
A7-B6-C26;
A7-B6-C27;
A7-B6-C28;
A7-B6-C29;
A7-B6-C30;
A7-B6-C31;
A7-B6-C32;
A7-B6-C33;
A7-B6-C34;
A7-B6-C35;
A7-B6-C36;
A7-B6-C37;
A7-B6-C38;
A7-B6-C39;
A7-B6-C40;
A7-B6-C41;
A7-B6-C42;
A7-B6-C43;
A7-B6-C44;
A7-B6-C45;
A7-B6-C46;
A7-B6-C47;
A7-B6-C48;
A7-B6-C49;
A7-B6-C50;
A7-B6-C51;
A7-B6-C52;
A7-B6-C53;
A7-B6-C54;
A7-B6-C55;
A7-B6-C56;
A7-B6-C57;
A7-B6-C58;
A7-B6-C59;
A7-B6-C60;
A7-B6-C61;
A7-B6-C62;
A7-B6-C63;
A7-B6-C64;
A7-B6-C65;
A7-B6-C66;
A7-B6-C67;
A7-B6-C68;
A8-B6-C1;
A8-B6-C2;
A8-B6-C3;
A8-B6-C4;
A8-B6-C5;
A8-B6-C6;
A8-B6-C7;
A8-B6-C8;
A8-B6-C9;
A8-B6-C10;
A8-B6-C11;
A8-B6-C12;
A8-B6-C13;
A8-B6-C14;
A8-B6-C15;
A8-B6-C16;
A8-B6-C17;
A8-B6-C18;
A8-B6-C19;
A8-B6-C20;
A8-B6-C21;
A8-B6-C22;
A8-B6-C23;
A8-B6-C24;
A8-B6-C25;
A8-B6-C26;
A8-B6-C27;
A8-B6-C28;
A8-B6-C29;
A8-B6-C30;
A8-B6-C31;
A8-B6-C32;

-continued

A8-B6-C33;
A8-B6-C34;
A8-B6-C35;
A8-B6-C36;
A8-B6-C37;
A8-B6-C38;
A8-B6-C39;
A8-B6-C40;
A8-B6-C41;
A8-B6-C42;
A8-B6-C43;
A8-B6-C44;
A8-B6-C45;
A8-B6-C46;
A8-B6-C47;
A8-B6-C48;
A8-B6-C49;
A8-B6-C50;
A8-B6-C51;
A8-B6-C52;
A8-B6-C53;
A8-B6-C54;
A8-B6-C55;
A8-B6-C56;
A8-B6-C57;
A8-B6-C58;
A8-B6-C59;
A8-B6-C60;
A8-B6-C61;
A8-B6-C62;
A8-B6-C63;
A8-B6-C64;
A8-B6-C65;
A8-B6-C66;
A8-B6-C67;
A8-B6-C68;
A9-B6-C1;
A9-B6-C2;
A9-B6-C3;
A9-B6-C4;
A9-B6-C5;
A9-B6-C6;
A9-B6-C7;
A9-B6-C8;
A9-B6-C9;
A9-B6-C10;
A9-B6-C11;
A9-B6-C12;
A9-B6-C13;
A9-B6-C14;
A9-B6-C15;
A9-B6-C16;
A9-B6-C17;
A9-B6-C18;
A9-B6-C19;
A9-B6-C20;
A9-B6-C21;
A9-B6-C22;
A9-B6-C23;
A9-B6-C24;
A9-B6-C25;
A9-B6-C26;
A9-B6-C27;
A9-B6-C28;
A9-B6-C29;
A9-B6-C30;
A9-B6-C31;
A9-B6-C32;
A9-B6-C33;
A9-B6-C34;
A9-B6-C35;
A9-B6-C36;
A9-B6-C37;
A9-B6-C38;
A9-B6-C39;
A9-B6-C40;
A9-B6-C41;
A9-B6-C42;
A9-B6-C43;

-continued

A9-B6-C44;
A9-B6-C45;
A9-B6-C46;
A9-B6-C47;
A9-B6-C48;
A9-B6-C49;
A9-B6-C50;
A9-B6-C51;
A9-B6-C52;
A9-B6-C53;
A9-B6-C54;
A9-B6-C55;
A9-B6-C56;
A9-B6-C57;
A9-B6-C58;
A9-B6-C59;
A9-B6-C60;
A9-B6-C61;
A9-B6-C62;
A9-B6-C63;
A9-B6-C64;
A9-B6-C65;
A9-B6-C66;
A9-B6-C67;
A9-B6-C68;
A10-B6-C1;
A10-B6-C2;
A10-B6-C3;
A10-B6-C4;
A10-B6-C5;
A10-B6-C6;
A10-B6-C7;
A10-B6-C8;
A10-B6-C9;
A10-B6-C10;
A10-B6-C11;
A10-B6-C12;
A10-B6-C13;
A10-B6-C14;
A10-B6-C15;
A10-B6-C16;
A10-B6-C17;
A10-B6-C18;
A10-B6-C19;
A10-B6-C20;
A10-B6-C21;
A10-B6-C22;
A10-B6-C23;
A10-B6-C24;
A10-B6-C25;
A10-B6-C26;
A10-B6-C27;
A10-B6-C28;
A10-B6-C29;
A10-B6-C30;
A10-B6-C31;
A10-B6-C32;
A10-B6-C33;
A10-B6-C34;
A10-B6-C35;
A10-B6-C36;
A10-B6-C37;
A10-B6-C38;
A10-B6-C39;
A10-B6-C40;
A10-B6-C41;
A10-B6-C42;
A10-B6-C43;
A10-B6-C44;
A10-B6-C45;
A10-B6-C46;
A10-B6-C47;
A10-B6-C48;
A10-B6-C49;
A10-B6-C50;
A10-B6-C51;
A10-B6-C52;
A10-B6-C53;
A10-B6-C54;

A10-B6-C55;
A10-B6-C56;
A10-B6-C57;
A10-B6-C58;
A10-B6-C59;
A10-B6-C60;
A10-B6-C61;
A10-B6-C62;
A10-B6-C63;
A10-B6-C64;
A10-B6-C65;
A10-B6-C66;
A10-B6-C67;
A10-B6-C68;
A11-B6-C1;
A11-B6-C2;
A11-B6-C3;
A11-B6-C4;
A11-B6-C5;
A11-B6-C6;
A11-B6-C7;
A11-B6-C8;
A11-B6-C9;
A11-B6-C10;
A11-B6-C11;
A11-B6-C12;
A11-B6-C13;
A11-B6-C14;
A11-B6-C15;
A11-B6-C16;
A11-B6-C17;
A11-B6-C18;
A11-B6-C19;
A11-B6-C20;
A11-B6-C21;
A11-B6-C22;
A11-B6-C23;
A11-B6-C24;
A11-B6-C25;
A11-B6-C26;
A11-B6-C27;
A11-B6-C28;
A11-B6-C29;
A11-B6-C30;
A11-B6-C31;
A11-B6-C32;
A11-B6-C33;
A11-B6-C34;
A11-B6-C35;
A11-B6-C36;
A11-B6-C37;
A11-B6-C38;
A11-B6-C39;
A11-B6-C40;
A11-B6-C41;
A11-B6-C42;
A11-B6-C43;
A11-B6-C44;
A11-B6-C45;
A11-B6-C46;
A11-B6-C47;
A11-B6-C48;
A11-B6-C49;
A11-B6-C50;
A11-B6-C51;
A11-B6-C52;
A11-B6-C53;
A11-B6-C54;
A11-B6-C55;
A11-B6-C56;
A11-B6-C57;
A11-B6-C58;
A11-B6-C59;
A11-B6-C60;
A11-B6-C61;
A11-B6-C62;
A11-B6-C63;
A11-B6-C64;
A11-B6-C65;
A11-B6-C66;
A11-B6-C67;
A11-B6-C68;
A12-B6-C1;
A12-B6-C2;
A12-B6-C3;
A12-B6-C4;
A12-B6-C5;
A12-B6-C6;
A12-B6-C7;
A12-B6-C8;
A12-B6-C9;
A12-B6-C10;
A12-B6-C11;
A12-B6-C12;
A12-B6-C13;
A12-B6-C14;
A12-B6-C15;
A12-B6-C16;
A12-B6-C17;
A12-B6-C18;
A12-B6-C19;
A12-B6-C20;
A12-B6-C21;
A12-B6-C22;
A12-B6-C23;
A12-B6-C24;
A12-B6-C25;
A12-B6-C26;
A12-B6-C27;
A12-B6-C28;
A12-B6-C29;
A12-B6-C30;
A12-B6-C31;
A12-B6-C32;
A12-B6-C33;
A12-B6-C34;
A12-B6-C35;
A12-B6-C36;
A12-B6-C37;
A12-B6-C38;
A12-B6-C39;
A12-B6-C40;
A12-B6-C41;
A12-B6-C42;
A12-B6-C43;
A12-B6-C44;
A12-B6-C45;
A12-B6-C46;
A12-B6-C47;
A12-B6-C48;
A12-B6-C49;
A12-B6-C50;
A12-B6-C51;
A12-B6-C52;
A12-B6-C53;
A12-B6-C54;
A12-B6-C55;
A12-B6-C56;
A12-B6-C57;
A12-B6-C58;
A12-B6-C59;
A12-B6-C60;
A12-B6-C61;
A12-B6-C62;
A12-B6-C63;
A12-B6-C64;
A12-B6-C65;
A12-B6-C66;
A12-B6-C67;
A12-B6-C68;
A13-B6-C1;
A13-B6-C2;
A13-B6-C3;
A13-B6-C4;
A13-B6-C5;
A13-B6-C6;
A13-B6-C7;
A13-B6-C8;

A13-B6-C9;
A13-B6-C10;
A13-B6-C11;
A13-B6-C12;
A13-B6-C13;
A13-B6-C14;
A13-B6-C15;
A13-B6-C16;
A13-B6-C17;
A13-B6-C18;
A13-B6-C19;
A13-B6-C20;
A13-B6-C21;
A13-B6-C22;
A13-B6-C23;
A13-B6-C24;
A13-B6-C25;
A13-B6-C26;
A13-B6-C27;
A13-B6-C28;
A13-B6-C29;
A13-B6-C30;
A13-B6-C31;
A13-B6-C32;
A13-B6-C33;
A13-B6-C34;
A13-B6-C35;
A13-B6-C36;
A13-B6-C37;
A13-B6-C38;
A13-B6-C39;
A13-B6-C40;
A13-B6-C41;
A13-B6-C42;
A13-B6-C43;
A13-B6-C44;
A13-B6-C45;
A13-B6-C46;
A13-B6-C47;
A13-B6-C48;
A13-B6-C49;
A13-B6-C50;
A13-B6-C51;
A13-B6-C52;
A13-B6-C53;
A13-B6-C54;
A13-B6-C55;
A13-B6-C56;
A13-B6-C57;
A13-B6-C58;
A13-B6-C59;
A13-B6-C60;
A13-B6-C61;
A13-B6-C62;
A13-B6-C63;
A13-B6-C64;
A13-B6-C65;
A13-B6-C66;
A13-B6-C67;
A13-B6-C68;
A14-B6-C1;
A14-B6-C2;
A14-B6-C3;
A14-B6-C4;
A14-B6-C5;
A14-B6-C6;
A14-B6-C7;
A14-B6-C8;
A14-B6-C9;
A14-B6-C10;
A14-B6-C11;
A14-B6-C12;
A14-B6-C13;
A14-B6-C14;
A14-B6-C15;
A14-B6-C16;
A14-B6-C17;
A14-B6-C18;
A14-B6-C19;
A14-B6-C20;
A14-B6-C21;
A14-B6-C22;
A14-B6-C23;
A14-B6-C24;
A14-B6-C25;
A14-B6-C26;
A14-B6-C27;
A14-B6-C28;
A14-B6-C29;
A14-B6-C30;
A14-B6-C31;
A14-B6-C32;
A14-B6-C33;
A14-B6-C34;
A14-B6-C35;
A14-B6-C36;
A14-B6-C37;
A14-B6-C38;
A14-B6-C39;
A14-B6-C40;
A14-B6-C41;
A14-B6-C42;
A14-B6-C43;
A14-B6-C44;
A14-B6-C45;
A14-B6-C46;
A14-B6-C47;
A14-B6-C48;
A14-B6-C49;
A14-B6-C50;
A14-B6-C51;
A14-B6-C52;
A14-B6-C53;
A14-B6-C54;
A14-B6-C55;
A14-B6-C56;
A14-B6-C57;
A14-B6-C58;
A14-B6-C59;
A14-B6-C60;
A14-B6-C61;
A14-B6-C62;
A14-B6-C63;
A14-B6-C64;
A14-B6-C65;
A14-B6-C66;
A14-B6-C67;
A14-B6-C68;
A15-B6-C1;
A15-B6-C2;
A15-B6-C3;
A15-B6-C4;
A15-B6-C5;
A15-B6-C6;
A15-B6-C7;
A15-B6-C8;
A15-B6-C9;
A15-B6-C10;
A15-B6-C11;
A15-B6-C12;
A15-B6-C13;
A15-B6-C14;
A15-B6-C15;
A15-B6-C16;
A15-B6-C17;
A15-B6-C18;
A15-B6-C19;
A15-B6-C20;
A15-B6-C21;
A15-B6-C22;
A15-B6-C23;
A15-B6-C24;
A15-B6-C25;
A15-B6-C26;
A15-B6-C27;
A15-B6-C28;
A15-B6-C29;
A15-B6-C30;

-continued

A15-B6-C31;
A15-B6-C32;
A15-B6-C33;
A15-B6-C34;
A15-B6-C35;
A15-B6-C36;
A15-B6-C37;
A15-B6-C38;
A15-B6-C39;
A15-B6-C40;
A15-B6-C41;
A15-B6-C42;
A15-B6-C43;
A15-B6-C44;
A15-B6-C45;
A15-B6-C46;
A15-B6-C47;
A15-B6-C48;
A15-B6-C49;
A15-B6-C50;
A15-B6-C51;
A15-B6-C52;
A15-B6-C53;
A15-B6-C54;
A15-B6-C55;
A15-B6-C56;
A15-B6-C57;
A15-B6-C58;
A15-B6-C59;
A15-B6-C60;
A15-B6-C61;
A15-B6-C62;
A15-B6-C63;
A15-B6-C64;
A15-B6-C65;
A15-B6-C66;
A15-B6-C67;
A15-B6-C68;
A16-B6-C1;
A16-B6-C2;
A16-B6-C3;
A16-B6-C4;
A16-B6-C5;
A16-B6-C6;
A16-B6-C7;
A16-B6-C8;
A16-B6-C9;
A16-B6-C10;
A16-B6-C11;
A16-B6-C12;
A16-B6-C13;
A16-B6-C14;
A16-B6-C15;
A16-B6-C16;
A16-B6-C17;
A16-B6-C18;
A16-B6-C19;
A16-B6-C20;
A16-B6-C21;
A16-B6-C22;
A16-B6-C23;
A16-B6-C24;
A16-B6-C25;
A16-B6-C26;
A16-B6-C27;
A16-B6-C28;
A16-B6-C29;
A16-B6-C30;
A16-B6-C31;
A16-B6-C32;
A16-B6-C33;
A16-B6-C34;
A16-B6-C35;
A16-B6-C36;
A16-B6-C37;
A16-B6-C38;
A16-B6-C39;
A16-B6-C40;
A16-B6-C41;

-continued

A16-B6-C42;
A16-B6-C43;
A16-B6-C44;
A16-B6-C45;
A16-B6-C46;
A16-B6-C47;
A16-B6-C48;
A16-B6-C49;
A16-B6-C50;
A16-B6-C51;
A16-B6-C52;
A16-B6-C53;
A16-B6-C54;
A16-B6-C55;
A16-B6-C56;
A16-B6-C57;
A16-B6-C58;
A16-B6-C59;
A16-B6-C60;
A16-B6-C61;
A16-B6-C62;
A16-B6-C63;
A16-B6-C64;
A16-B6-C65;
A16-B6-C66;
A16-B6-C67;
A16-B6-C68;
A17-B6-C1;
A17-B6-C2;
A17-B6-C3;
A17-B6-C4;
A17-B6-C5;
A17-B6-C6;
A17-B6-C7;
A17-B6-C8;
A17-B6-C9;
A17-B6-C10;
A17-B6-C11;
A17-B6-C12;
A17-B6-C13;
A17-B6-C14;
A17-B6-C15;
A17-B6-C16;
A17-B6-C17;
A17-B6-C18;
A17-B6-C19;
A17-B6-C20;
A17-B6-C21;
A17-B6-C22;
A17-B6-C23;
A17-B6-C24;
A17-B6-C25;
A17-B6-C26;
A17-B6-C27;
A17-B6-C28;
A17-B6-C29;
A17-B6-C30;
A17-B6-C31;
A17-B6-C32;
A17-B6-C33;
A17-B6-C34;
A17-B6-C35;
A17-B6-C36;
A17-B6-C37;
A17-B6-C38;
A17-B6-C39;
A17-B6-C40;
A17-B6-C41;
A17-B6-C42;
A17-B6-C43;
A17-B6-C44;
A17-B6-C45;
A17-B6-C46;
A17-B6-C47;
A17-B6-C48;
A17-B6-C49;
A17-B6-C50;
A17-B6-C51;
A17-B6-C52;

-continued

A17-B6-C53;
A17-B6-C54;
A17-B6-C55;
A17-B6-C56;
A17-B6-C57;
A17-B6-C58;
A17-B6-C59;
A17-B6-C60;
A17-B6-C61;
A17-B6-C62;
A17-B6-C63;
A17-B6-C64;
A17-B6-C65;
A17-B6-C66;
A17-B6-C67;
A17-B6-C68;
A18-B6-C1;
A18-B6-C2;
A18-B6-C3;
A18-B6-C4;
A18-B6-C5;
A18-B6-C6;
A18-B6-C7;
A18-B6-C8;
A18-B6-C9;
A18-B6-C10;
A18-B6-C11;
A18-B6-C12;
A18-B6-C13;
A18-B6-C14;
A18-B6-C15;
A18-B6-C16;
A18-B6-C17;
A18-B6-C18;
A18-B6-C19;
A18-B6-C20;
A18-B6-C21;
A18-B6-C22;
A18-B6-C23;
A18-B6-C24;
A18-B6-C25;
A18-B6-C26;
A18-B6-C27;
A18-B6-C28;
A18-B6-C29;
A18-B6-C30;
A18-B6-C31;
A18-B6-C32;
A18-B6-C33;
A18-B6-C34;
A18-B6-C35;
A18-B6-C36;
A18-B6-C37;
A18-B6-C38;
A18-B6-C39;
A18-B6-C40;
A18-B6-C41;
A18-B6-C42;
A18-B6-C43;
A18-B6-C44;
A18-B6-C45;
A18-B6-C46;
A18-B6-C47;
A18-B6-C48;
A18-B6-C49;
A18-B6-C50;
A18-B6-C51;
A18-B6-C52;
A18-B6-C53;
A18-B6-C54;
A18-B6-C55;
A18-B6-C56;
A18-B6-C57;
A18-B6-C58;
A18-B6-C59;
A18-B6-C60;
A18-B6-C61;
A18-B6-C62;
A18-B6-C63;

-continued

A18-B6-C64;
A18-B6-C65;
A18-B6-C66;
A18-B6-C67;
A18-B6-C68;
A19-B6-C1;
A19-B6-C2;
A19-B6-C3;
A19-B6-C4;
A19-B6-C5;
A19-B6-C6;
A19-B6-C7;
A19-B6-C8;
A19-B6-C9;
A19-B6-C10;
A19-B6-C11;
A19-B6-C12;
A19-B6-C13;
A19-B6-C14;
A19-B6-C15;
A19-B6-C16;
A19-B6-C17;
A19-B6-C18;
A19-B6-C19;
A19-B6-C20;
A19-B6-C21;
A19-B6-C22;
A19-B6-C23;
A19-B6-C24;
A19-B6-C25;
A19-B6-C26;
A19-B6-C27;
A19-B6-C28;
A19-B6-C29;
A19-B6-C30;
A19-B6-C31;
A19-B6-C32;
A19-B6-C33;
A19-B6-C34;
A19-B6-C35;
A19-B6-C36;
A19-B6-C37;
A19-B6-C38;
A19-B6-C39;
A19-B6-C40;
A19-B6-C41;
A19-B6-C42;
A19-B6-C43;
A19-B6-C44;
A19-B6-C45;
A19-B6-C46;
A19-B6-C47;
A19-B6-C48;
A19-B6-C49;
A19-B6-C50;
A19-B6-C51;
A19-B6-C52;
A19-B6-C53;
A19-B6-C54;
A19-B6-C55;
A19-B6-C56;
A19-B6-C57;
A19-B6-C58;
A19-B6-C59;
A19-B6-C60;
A19-B6-C61;
A19-B6-C62;
A19-B6-C63;
A19-B6-C64;
A19-B6-C65;
A19-B6-C66;
A19-B6-C67;
A19-B6-C68;
A20-B6-C1;
A20-B6-C2;
A20-B6-C3;
A20-B6-C4;
A20-B6-C5;
A20-B6-C6;

-continued

A20-B6-C7;
A20-B6-C8;
A20-B6-C9;
A20-B6-C10;
A20-B6-C11;
A20-B6-C12;
A20-B6-C13;
A20-B6-C14;
A20-B6-C15;
A20-B6-C16;
A20-B6-C17;
A20-B6-C18;
A20-B6-C19;
A20-B6-C20;
A20-B6-C21;
A20-B6-C22;
A20-B6-C23;
A20-B6-C24;
A20-B6-C25;
A20-B6-C26;
A20-B6-C27;
A20-B6-C28;
A20-B6-C29;
A20-B6-C30;
A20-B6-C31;
A20-B6-C32;
A20-B6-C33;
A20-B6-C34;
A20-B6-C35;
A20-B6-C36;
A20-B6-C37;
A20-B6-C38;
A20-B6-C39;
A20-B6-C40;
A20-B6-C41;
A20-B6-C42;
A20-B6-C43;
A20-B6-C44;
A20-B6-C45;
A20-B6-C46;
A20-B6-C47;
A20-B6-C48;
A20-B6-C49;
A20-B6-C50;
A20-B6-C51;
A20-B6-C52;
A20-B6-C53;
A20-B6-C54;
A20-B6-C55;
A20-B6-C56;
A20-B6-C57;
A20-B6-C58;
A20-B6-C59;
A20-B6-C60;
A20-B6-C61;
A20-B6-C62;
A20-B6-C63;
A20-B6-C64;
A20-B6-C65;
A20-B6-C66;
A20-B6-C67;
A20-B6-C68;
A21-B6-C1;
A21-B6-C2;
A21-B6-C3;
A21-B6-C4;
A21-B6-C5;
A21-B6-C6;
A21-B6-C7;
A21-B6-C8;
A21-B6-C9;
A21-B6-C10;
A21-B6-C11;
A21-B6-C12;
A21-B6-C13;
A21-B6-C14;
A21-B6-C15;
A21-B6-C16;
A21-B6-C17;

-continued

A21-B6-C18;
A21-B6-C19;
A21-B6-C20;
A21-B6-C21;
A21-B6-C22;
A21-B6-C23;
A21-B6-C24;
A21-B6-C25;
A21-B6-C26;
A21-B6-C27;
A21-B6-C28;
A21-B6-C29;
A21-B6-C30;
A21-B6-C31;
A21-B6-C32;
A21-B6-C33;
A21-B6-C34;
A21-B6-C35;
A21-B6-C36;
A21-B6-C37;
A21-B6-C38;
A21-B6-C39;
A21-B6-C40;
A21-B6-C41;
A21-B6-C42;
A21-B6-C43;
A21-B6-C44;
A21-B6-C45;
A21-B6-C46;
A21-B6-C47;
A21-B6-C48;
A21-B6-C49;
A21-B6-C50;
A21-B6-C51;
A21-B6-C52;
A21-B6-C53;
A21-B6-C54;
A21-B6-C55;
A21-B6-C56;
A21-B6-C57;
A21-B6-C58;
A21-B6-C59;
A21-B6-C60;
A21-B6-C61;
A21-B6-C62;
A21-B6-C63;
A21-B6-C64;
A21-B6-C65;
A21-B6-C66;
A21-B6-C67;
A21-B6-C68;
A22-B6-C1;
A22-B6-C2;
A22-B6-C3;
A22-B6-C4;
A22-B6-C5;
A22-B6-C6;
A22-B6-C7;
A22-B6-C8;
A22-B6-C9;
A22-B6-C10;
A22-B6-C11;
A22-B6-C12;
A22-B6-C13;
A22-B6-C14;
A22-B6-C15;
A22-B6-C16;
A22-B6-C17;
A22-B6-C18;
A22-B6-C19;
A22-B6-C20;
A22-B6-C21;
A22-B6-C22;
A22-B6-C23;
A22-B6-C24;
A22-B6-C25;
A22-B6-C26;
A22-B6-C27;
A22-B6-C28;

A22-B6-C29;
A22-B6-C30;
A22-B6-C31;
A22-B6-C32;
A22-B6-C33;
A22-B6-C34;
A22-B6-C35;
A22-B6-C36;
A22-B6-C37;
A22-B6-C38;
A22-B6-C39;
A22-B6-C40;
A22-B6-C41;
A22-B6-C42;
A22-B6-C43;
A22-B6-C44;
A22-B6-C45;
A22-B6-C46;
A22-B6-C47;
A22-B6-C48;
A22-B6-C49;
A22-B6-C50;
A22-B6-C51;
A22-B6-C52;
A22-B6-C53;
A22-B6-C54;
A22-B6-C55;
A22-B6-C56;
A22-B6-C57;
A22-B6-C58;
A22-B6-C59;
A22-B6-C60;
A22-B6-C61;
A22-B6-C62;
A22-B6-C63;
A22-B6-C64;
A22-B6-C65;
A22-B6-C66;
A22-B6-C67;
A22-B6-C68;
A23-B6-C1;
A23-B6-C2;
A23-B6-C3;
A23-B6-C4;
A23-B6-C5;
A23-B6-C6;
A23-B6-C7;
A23-B6-C8;
A23-B6-C9;
A23-B6-C10;
A23-B6-C11;
A23-B6-C12;
A23-B6-C13;
A23-B6-C14;
A23-B6-C15;
A23-B6-C16;
A23-B6-C17;
A23-B6-C18;
A23-B6-C19;
A23-B6-C20;
A23-B6-C21;
A23-B6-C22;
A23-B6-C23;
A23-B6-C24;
A23-B6-C25;
A23-B6-C26;
A23-B6-C27;
A23-B6-C28;
A23-B6-C29;
A23-B6-C30;
A23-B6-C31;
A23-B6-C32;
A23-B6-C33;
A23-B6-C34;
A23-B6-C35;
A23-B6-C36;
A23-B6-C37;
A23-B6-C38;
A23-B6-C39;
A23-B6-C40;
A23-B6-C41;
A23-B6-C42;
A23-B6-C43;
A23-B6-C44;
A23-B6-C45;
A23-B6-C46;
A23-B6-C47;
A23-B6-C48;
A23-B6-C49;
A23-B6-C50;
A23-B6-C51;
A23-B6-C52;
A23-B6-C53;
A23-B6-C54;
A23-B6-C55;
A23-B6-C56;
A23-B6-C57;
A23-B6-C58;
A23-B6-C59;
A23-B6-C60;
A23-B6-C61;
A23-B6-C62;
A23-B6-C63;
A23-B6-C64;
A23-B6-C65;
A23-B6-C66;
A23-B6-C67;
A23-B6-C68;
A24-B6-C1;
A24-B6-C2;
A24-B6-C3;
A24-B6-C4;
A24-B6-C5;
A24-B6-C6;
A24-B6-C7;
A24-B6-C8;
A24-B6-C9;
A24-B6-C10;
A24-B6-C11;
A24-B6-C12;
A24-B6-C13;
A24-B6-C14;
A24-B6-C15;
A24-B6-C16;
A24-B6-C17;
A24-B6-C18;
A24-B6-C19;
A24-B6-C20;
A24-B6-C21;
A24-B6-C22;
A24-B6-C23;
A24-B6-C24;
A24-B6-C25;
A24-B6-C26;
A24-B6-C27;
A24-B6-C28;
A24-B6-C29;
A24-B6-C30;
A24-B6-C31;
A24-B6-C32;
A24-B6-C33;
A24-B6-C34;
A24-B6-C35;
A24-B6-C36;
A24-B6-C37;
A24-B6-C38;
A24-B6-C39;
A24-B6-C40;
A24-B6-C41;
A24-B6-C42;
A24-B6-C43;
A24-B6-C44;
A24-B6-C45;
A24-B6-C46;
A24-B6-C47;
A24-B6-C48;
A24-B6-C49;
A24-B6-C50;

-continued

A24-B6-C51;
A24-B6-C52;
A24-B6-C53;
A24-B6-C54;
A24-B6-C55;
A24-B6-C56;
A24-B6-C57;
A24-B6-C58;
A24-B6-C59;
A24-B6-C60;
A24-B6-C61;
A24-B6-C62;
A24-B6-C63;
A24-B6-C64;
A24-B6-C65;
A24-B6-C66;
A24-B6-C67;
A24-B6-C68;
A25-B6-C1;
A25-B6-C2;
A25-B6-C3;
A25-B6-C4;
A25-B6-C5;
A25-B6-C6;
A25-B6-C7;
A25-B6-C8;
A25-B6-C9;
A25-B6-C10;
A25-B6-C11;
A25-B6-C12;
A25-B6-C13;
A25-B6-C14;
A25-B6-C15;
A25-B6-C16;
A25-B6-C17;
A25-B6-C18;
A25-B6-C19;
A25-B6-C20;
A25-B6-C21;
A25-B6-C22;
A25-B6-C23;
A25-B6-C24;
A25-B6-C25;
A25-B6-C26;
A25-B6-C27;
A25-B6-C28;
A25-B6-C29;
A25-B6-C30;
A25-B6-C31;
A25-B6-C32;
A25-B6-C33;
A25-B6-C34;
A25-B6-C35;
A25-B6-C36;
A25-B6-C37;
A25-B6-C38;
A25-B6-C39;
A25-B6-C40;
A25-B6-C41;
A25-B6-C42;
A25-B6-C43;
A25-B6-C44;
A25-B6-C45;
A25-B6-C46;
A25-B6-C47;
A25-B6-C48;
A25-B6-C49;
A25-B6-C50;
A25-B6-C51;
A25-B6-C52;
A25-B6-C53;
A25-B6-C54;
A25-B6-C55;
A25-B6-C56;
A25-B6-C57;
A25-B6-C58;
A25-B6-C59;
A25-B6-C60;
A25-B6-C61;

-continued

A25-B6-C62;
A25-B6-C63;
A25-B6-C64;
A25-B6-C65;
A25-B6-C66;
A25-B6-C67;
A25-B6-C68;
A26-B6-C1;
A26-B6-C2;
A26-B6-C3;
A26-B6-C4;
A26-B6-C5;
A26-B6-C6;
A26-B6-C7;
A26-B6-C8;
A26-B6-C9;
A26-B6-C10;
A26-B6-C11;
A26-B6-C12;
A26-B6-C13;
A26-B6-C14;
A26-B6-C15;
A26-B6-C16;
A26-B6-C17;
A26-B6-C18;
A26-B6-C19;
A26-B6-C20;
A26-B6-C21;
A26-B6-C22;
A26-B6-C23;
A26-B6-C24;
A26-B6-C25;
A26-B6-C26;
A26-B6-C27;
A26-B6-C28;
A26-B6-C29;
A26-B6-C30;
A26-B6-C31;
A26-B6-C32;
A26-B6-C33;
A26-B6-C34;
A26-B6-C35;
A26-B6-C36;
A26-B6-C37;
A26-B6-C38;
A26-B6-C39;
A26-B6-C40;
A26-B6-C41;
A26-B6-C42;
A26-B6-C43;
A26-B6-C44;
A26-B6-C45;
A26-B6-C46;
A26-B6-C47;
A26-B6-C48;
A26-B6-C49;
A26-B6-C50;
A26-B6-C51;
A26-B6-C52;
A26-B6-C53;
A26-B6-C54;
A26-B6-C55;
A26-B6-C56;
A26-B6-C57;
A26-B6-C58;
A26-B6-C59;
A26-B6-C60;
A26-B6-C61;
A26-B6-C62;
A26-B6-C63;
A26-B6-C64;
A26-B6-C65;
A26-B6-C66;
A26-B6-C67;
A26-B6-C68;
A27-B6-C1;
A27-B6-C2;
A27-B6-C3;
A27-B6-C4;

-continued

A27-B6-C5;
A27-B6-C6;
A27-B6-C7;
A27-B6-C8;
A27-B6-C9;
A27-B6-C10;
A27-B6-C11;
A27-B6-C12;
A27-B6-C13;
A27-B6-C14;
A27-B6-C15;
A27-B6-C16;
A27-B6-C17;
A27-B6-C18;
A27-B6-C19;
A27-B6-C20;
A27-B6-C21;
A27-B6-C22;
A27-B6-C23;
A27-B6-C24;
A27-B6-C25;
A27-B6-C26;
A27-B6-C27;
A27-B6-C28;
A27-B6-C29;
A27-B6-C30;
A27-B6-C31;
A27-B6-C32;
A27-B6-C33;
A27-B6-C34;
A27-B6-C35;
A27-B6-C36;
A27-B6-C37;
A27-B6-C38;
A27-B6-C39;
A27-B6-C40;
A27-B6-C41;
A27-B6-C42;
A27-B6-C43;
A27-B6-C44;
A27-B6-C45;
A27-B6-C46;
A27-B6-C47;
A27-B6-C48;
A27-B6-C49;
A27-B6-C50;
A27-B6-C51;
A27-B6-C52;
A27-B6-C53;
A27-B6-C54;
A27-B6-C55;
A27-B6-C56;
A27-B6-C57;
A27-B6-C58;
A27-B6-C59;
A27-B6-C60;
A27-B6-C61;
A27-B6-C62;
A27-B6-C63;
A27-B6-C64;
A27-B6-C65;
A27-B6-C66;
A27-B6-C67;
A27-B6-C68;
A28-B6-C1;
A28-B6-C2;
A28-B6-C3;
A28-B6-C4;
A28-B6-C5;
A28-B6-C6;
A28-B6-C7;
A28-B6-C8;
A28-B6-C9;
A28-B6-C10;
A28-B6-C11;
A28-B6-C12;
A28-B6-C13;
A28-B6-C14;
A28-B6-C15;

-continued

A28-B6-C16;
A28-B6-C17;
A28-B6-C18;
A28-B6-C19;
A28-B6-C20;
A28-B6-C21;
A28-B6-C22;
A28-B6-C23;
A28-B6-C24;
A28-B6-C25;
A28-B6-C26;
A28-B6-C27;
A28-B6-C28;
A28-B6-C29;
A28-B6-C30;
A28-B6-C31;
A28-B6-C32;
A28-B6-C33;
A28-B6-C34;
A28-B6-C35;
A28-B6-C36;
A28-B6-C37;
A28-B6-C38;
A28-B6-C39;
A28-B6-C40;
A28-B6-C41;
A28-B6-C42;
A28-B6-C43;
A28-B6-C44;
A28-B6-C45;
A28-B6-C46;
A28-B6-C47;
A28-B6-C48;
A28-B6-C49;
A28-B6-C50;
A28-B6-C51;
A28-B6-C52;
A28-B6-C53;
A28-B6-C54;
A28-B6-C55;
A28-B6-C56;
A28-B6-C57;
A28-B6-C58;
A28-B6-C59;
A28-B6-C60;
A28-B6-C61;
A28-B6-C62;
A28-B6-C63;
A28-B6-C64;
A28-B6-C65;
A28-B6-C66;
A28-B6-C67;
A28-B6-C68;
A29-B6-C1;
A29-B6-C2;
A29-B6-C3;
A29-B6-C4;
A29-B6-C5;
A29-B6-C6;
A29-B6-C7;
A29-B6-C8;
A29-B6-C9;
A29-B6-C10;
A29-B6-C11;
A29-B6-C12;
A29-B6-C13;
A29-B6-C14;
A29-B6-C15;
A29-B6-C16;
A29-B6-C17;
A29-B6-C18;
A29-B6-C19;
A29-B6-C20;
A29-B6-C21;
A29-B6-C22;
A29-B6-C23;
A29-B6-C24;
A29-B6-C25;
A29-B6-C26;

-continued

A29-B6-C27;
A29-B6-C28;
A29-B6-C29;
A29-B6-C30;
A29-B6-C31;
A29-B6-C32;
A29-B6-C33;
A29-B6-C34;
A29-B6-C35;
A29-B6-C36;
A29-B6-C37;
A29-B6-C38;
A29-B6-C39;
A29-B6-C40;
A29-B6-C41;
A29-B6-C42;
A29-B6-C43;
A29-B6-C44;
A29-B6-C45;
A29-B6-C46;
A29-B6-C47;
A29-B6-C48;
A29-B6-C49;
A29-B6-C50;
A29-B6-C51;
A29-B6-C52;
A29-B6-C53;
A29-B6-C54;
A29-B6-C55;
A29-B6-C56;
A29-B6-C57;
A29-B6-C58;
A29-B6-C59;
A29-B6-C60;
A29-B6-C61;
A29-B6-C62;
A29-B6-C63;
A29-B6-C64;
A29-B6-C65;
A29-B6-C66;
A29-B6-C67;
A29-B6-C68;
A30-B6-C1;
A30-B6-C2;
A30-B6-C3;
A30-B6-C4;
A30-B6-C5;
A30-B6-C6;
A30-B6-C7;
A30-B6-C8;
A30-B6-C9;
A30-B6-C10;
A30-B6-C11;
A30-B6-C12;
A30-B6-C13;
A30-B6-C14;
A30-B6-C15;
A30-B6-C16;
A30-B6-C17;
A30-B6-C18;
A30-B6-C19;
A30-B6-C20;
A30-B6-C21;
A30-B6-C22;
A30-B6-C23;
A30-B6-C24;
A30-B6-C25;
A30-B6-C26;
A30-B6-C27;
A30-B6-C28;
A30-B6-C29;
A30-B6-C30;
A30-B6-C31;
A30-B6-C32;
A30-B6-C33;
A30-B6-C34;
A30-B6-C35;
A30-B6-C36;
A30-B6-C37;

-continued

A30-B6-C38;
A30-B6-C39;
A30-B6-C40;
A30-B6-C41;
A30-B6-C42;
A30-B6-C43;
A30-B6-C44;
A30-B6-C45;
A30-B6-C46;
A30-B6-C47;
A30-B6-C48;
A30-B6-C49;
A30-B6-C50;
A30-B6-C51;
A30-B6-C52;
A30-B6-C53;
A30-B6-C54;
A30-B6-C55;
A30-B6-C56;
A30-B6-C57;
A30-B6-C58;
A30-B6-C59;
A30-B6-C60;
A30-B6-C61;
A30-B6-C62;
A30-B6-C63;
A30-B6-C64;
A30-B6-C65;
A30-B6-C66;
A30-B6-C67;
A30-B6-C68;
A31-B6-C1;
A31-B6-C2;
A31-B6-C3;
A31-B6-C4;
A31-B6-C5;
A31-B6-C6;
A31-B6-C7;
A31-B6-C8;
A31-B6-C9;
A31-B6-C10;
A31-B6-C11;
A31-B6-C12;
A31-B6-C13;
A31-B6-C14;
A31-B6-C15;
A31-B6-C16;
A31-B6-C17;
A31-B6-C18;
A31-B6-C19;
A31-B6-C20;
A31-B6-C21;
A31-B6-C22;
A31-B6-C23;
A31-B6-C24;
A31-B6-C25;
A31-B6-C26;
A31-B6-C27;
A31-B6-C28;
A31-B6-C29;
A31-B6-C30;
A31-B6-C31;
A31-B6-C32;
A31-B6-C33;
A31-B6-C34;
A31-B6-C35;
A31-B6-C36;
A31-B6-C37;
A31-B6-C38;
A31-B6-C39;
A31-B6-C40;
A31-B6-C41;
A31-B6-C42;
A31-B6-C43;
A31-B6-C44;
A31-B6-C45;
A31-B6-C46;
A31-B6-C47;
A31-B6-C48;

A31-B6-C49;
A31-B6-C50;
A31-B6-C51;
A31-B6-C52;
A31-B6-C53;
A31-B6-C54;
A31-B6-C55;
A31-B6-C56;
A31-B6-C57;
A31-B6-C58;
A31-B6-C59;
A31-B6-C60;
A31-B6-C61;
A31-B6-C62;
A31-B6-C63;
A31-B6-C64;
A31-B6-C65;
A31-B6-C66;
A31-B6-C67;
A31-B6-C68;
A32-B6-C1;
A32-B6-C2;
A32-B6-C3;
A32-B6-C4;
A32-B6-C5;
A32-B6-C6;
A32-B6-C7;
A32-B6-C8;
A32-B6-C9;
A32-B6-C10;
A32-B6-C11;
A32-B6-C12;
A32-B6-C13;
A32-B6-C14;
A32-B6-C15;
A32-B6-C16;
A32-B6-C17;
A32-B6-C18;
A32-B6-C19;
A32-B6-C20;
A32-B6-C21;
A32-B6-C22;
A32-B6-C23;
A32-B6-C24;
A32-B6-C25;
A32-B6-C26;
A32-B6-C27;
A32-B6-C28;
A32-B6-C29;
A32-B6-C30;
A32-B6-C31;
A32-B6-C32;
A32-B6-C33;
A32-B6-C34;
A32-B6-C35;
A32-B6-C36;
A32-B6-C37;
A32-B6-C38;
A32-B6-C39;
A32-B6-C40;
A32-B6-C41;
A32-B6-C42;
A32-B6-C43;
A32-B6-C44;
A32-B6-C45;
A32-B6-C46;
A32-B6-C47;
A32-B6-C48;
A32-B6-C49;
A32-B6-C50;
A32-B6-C51;
A32-B6-C52;
A32-B6-C53;
A32-B6-C54;
A32-B6-C55;
A32-B6-C56;
A32-B6-C57;
A32-B6-C58;
A32-B6-C59;
A32-B6-C60;
A32-B6-C61;
A32-B6-C62;
A32-B6-C63;
A32-B6-C64;
A32-B6-C65;
A32-B6-C66;
A32-B6-C67;
A32-B6-C68;
A33-B6-C1;
A33-B6-C2;
A33-B6-C3;
A33-B6-C4;
A33-B6-C5;
A33-B6-C6;
A33-B6-C7;
A33-B6-C8;
A33-B6-C9;
A33-B6-C10;
A33-B6-C11;
A33-B6-C12;
A33-B6-C13;
A33-B6-C14;
A33-B6-C15;
A33-B6-C16;
A33-B6-C17;
A33-B6-C18;
A33-B6-C19;
A33-B6-C20;
A33-B6-C21;
A33-B6-C22;
A33-B6-C23;
A33-B6-C24;
A33-B6-C25;
A33-B6-C26;
A33-B6-C27;
A33-B6-C28;
A33-B6-C29;
A33-B6-C30;
A33-B6-C31;
A33-B6-C32;
A33-B6-C33;
A33-B6-C34;
A33-B6-C35;
A33-B6-C36;
A33-B6-C37;
A33-B6-C38;
A33-B6-C39;
A33-B6-C40;
A33-B6-C41;
A33-B6-C42;
A33-B6-C43;
A33-B6-C44;
A33-B6-C45;
A33-B6-C46;
A33-B6-C47;
A33-B6-C48;
A33-B6-C49;
A33-B6-C50;
A33-B6-C51;
A33-B6-C52;
A33-B6-C53;
A33-B6-C54;
A33-B6-C55;
A33-B6-C56;
A33-B6-C57;
A33-B6-C58;
A33-B6-C59;
A33-B6-C60;
A33-B6-C61;
A33-B6-C62;
A33-B6-C63;
A33-B6-C64;
A33-B6-C65;
A33-B6-C66;
A33-B6-C67;
A33-B6-C68;
A34-B6-C1;
A34-B6-C2;

-continued

A34-B6-C3;
A34-B6-C4;
A34-B6-C5;
A34-B6-C6;
A34-B6-C7;
A34-B6-C8;
A34-B6-C9;
A34-B6-C10;
A34-B6-C11;
A34-B6-C12;
A34-B6-C13;
A34-B6-C14;
A34-B6-C15;
A34-B6-C16;
A34-B6-C17;
A34-B6-C18;
A34-B6-C19;
A34-B6-C20;
A34-B6-C21;
A34-B6-C22;
A34-B6-C23;
A34-B6-C24;
A34-B6-C25;
A34-B6-C26;
A34-B6-C27;
A34-B6-C28;
A34-B6-C29;
A34-B6-C30;
A34-B6-C31;
A34-B6-C32;
A34-B6-C33;
A34-B6-C34;
A34-B6-C35;
A34-B6-C36;
A34-B6-C37;
A34-B6-C38;
A34-B6-C39;
A34-B6-C40;
A34-B6-C41;
A34-B6-C42;
A34-B6-C43;
A34-B6-C44;
A34-B6-C45;
A34-B6-C46;
A34-B6-C47;
A34-B6-C48;
A34-B6-C49;
A34-B6-C50;
A34-B6-C51;
A34-B6-C52;
A34-B6-C53;
A34-B6-C54;
A34-B6-C55;
A34-B6-C56;
A34-B6-C57;
A34-B6-C58;
A34-B6-C59;
A34-B6-C60;
A34-B6-C61;
A34-B6-C62;
A34-B6-C63;
A34-B6-C64;
A34-B6-C65;
A34-B6-C66;
A34-B6-C67;
A34-B6-C68;
A35-B6-C1;
A35-B6-C2;
A35-B6-C3;
A35-B6-C4;
A35-B6-C5;
A35-B6-C6;
A35-B6-C7;
A35-B6-C8;
A35-B6-C9;
A35-B6-C10;
A35-B6-C11;
A35-B6-C12;
A35-B6-C13;

-continued

A35-B6-C14;
A35-B6-C15;
A35-B6-C16;
A35-B6-C17;
A35-B6-C18;
A35-B6-C19;
A35-B6-C20;
A35-B6-C21;
A35-B6-C22;
A35-B6-C23;
A35-B6-C24;
A35-B6-C25;
A35-B6-C26;
A35-B6-C27;
A35-B6-C28;
A35-B6-C29;
A35-B6-C30;
A35-B6-C31;
A35-B6-C32;
A35-B6-C33;
A35-B6-C34;
A35-B6-C35;
A35-B6-C36;
A35-B6-C37;
A35-B6-C38;
A35-B6-C39;
A35-B6-C40;
A35-B6-C41;
A35-B6-C42;
A35-B6-C43;
A35-B6-C44;
A35-B6-C45;
A35-B6-C46;
A35-B6-C47;
A35-B6-C48;
A35-B6-C49;
A35-B6-C50;
A35-B6-C51;
A35-B6-C52;
A35-B6-C53;
A35-B6-C54;
A35-B6-C55;
A35-B6-C56;
A35-B6-C57;
A35-B6-C58;
A35-B6-C59;
A35-B6-C60;
A35-B6-C61;
A35-B6-C62;
A35-B6-C63;
A35-B6-C64;
A35-B6-C65;
A35-B6-C66;
A35-B6-C67;
A35-B6-C68;
A36-B6-C1;
A36-B6-C2;
A36-B6-C3;
A36-B6-C4;
A36-B6-C5;
A36-B6-C6;
A36-B6-C7;
A36-B6-C8;
A36-B6-C9;
A36-B6-C10;
A36-B6-C11;
A36-B6-C12;
A36-B6-C13;
A36-B6-C14;
A36-B6-C15;
A36-B6-C16;
A36-B6-C17;
A36-B6-C18;
A36-B6-C19;
A36-B6-C20;
A36-B6-C21;
A36-B6-C22;
A36-B6-C23;
A36-B6-C24;

-continued

A36-B6-C25;
A36-B6-C26;
A36-B6-C27;
A36-B6-C28;
A36-B6-C29;
A36-B6-C30;
A36-B6-C31;
A36-B6-C32;
A36-B6-C33;
A36-B6-C34;
A36-B6-C35;
A36-B6-C36;
A36-B6-C37;
A36-B6-C38;
A36-B6-C39;
A36-B6-C40;
A36-B6-C41;
A36-B6-C42;
A36-B6-C43;
A36-B6-C44;
A36-B6-C45;
A36-B6-C46;
A36-B6-C47;
A36-B6-C48;
A36-B6-C49;
A36-B6-C50;
A36-B6-C51;
A36-B6-C52;
A36-B6-C53;
A36-B6-C54;
A36-B6-C55;
A36-B6-C56;
A36-B6-C57;
A36-B6-C58;
A36-B6-C59;
A36-B6-C60;
A36-B6-C61;
A36-B6-C62;
A36-B6-C63;
A36-B6-C64;
A36-B6-C65;
A36-B6-C66;
A36-B6-C67;
A36-B6-C68;
A37-B6-C1;
A37-B6-C2;
A37-B6-C3;
A37-B6-C4;
A37-B6-C5;
A37-B6-C6;
A37-B6-C7;
A37-B6-C8;
A37-B6-C9;
A37-B6-C10;
A37-B6-C11;
A37-B6-C12;
A37-B6-C13;
A37-B6-C14;
A37-B6-C15;
A37-B6-C16;
A37-B6-C17;
A37-B6-C18;
A37-B6-C19;
A37-B6-C20;
A37-B6-C21;
A37-B6-C22;
A37-B6-C23;
A37-B6-C24;
A37-B6-C25;
A37-B6-C26;
A37-B6-C27;
A37-B6-C28;
A37-B6-C29;
A37-B6-C30;
A37-B6-C31;
A37-B6-C32;
A37-B6-C33;
A37-B6-C34;
A37-B6-C35;

-continued

A37-B6-C36;
A37-B6-C37;
A37-B6-C38;
A37-B6-C39;
A37-B6-C40;
A37-B6-C41;
A37-B6-C42;
A37-B6-C43;
A37-B6-C44;
A37-B6-C45;
A37-B6-C46;
A37-B6-C47;
A37-B6-C48;
A37-B6-C49;
A37-B6-C50;
A37-B6-C51;
A37-B6-C52;
A37-B6-C53;
A37-B6-C54;
A37-B6-C55;
A37-B6-C56;
A37-B6-C57;
A37-B6-C58;
A37-B6-C59;
A37-B6-C60;
A37-B6-C61;
A37-B6-C62;
A37-B6-C63;
A37-B6-C64;
A37-B6-C65;
A37-B6-C66;
A37-B6-C67;
A37-B6-C68;
A38-B6-C1;
A38-B6-C2;
A38-B6-C3;
A38-B6-C4;
A38-B6-C5;
A38-B6-C6;
A38-B6-C7;
A38-B6-C8;
A38-B6-C9;
A38-B6-C10;
A38-B6-C11;
A38-B6-C12;
A38-B6-C13;
A38-B6-C14;
A38-B6-C15;
A38-B6-C16;
A38-B6-C17;
A38-B6-C18;
A38-B6-C19;
A38-B6-C20;
A38-B6-C21;
A38-B6-C22;
A38-B6-C23;
A38-B6-C24;
A38-B6-C25;
A38-B6-C26;
A38-B6-C27;
A38-B6-C28;
A38-B6-C29;
A38-B6-C30;
A38-B6-C31;
A38-B6-C32;
A38-B6-C33;
A38-B6-C34;
A38-B6-C35;
A38-B6-C36;
A38-B6-C37;
A38-B6-C38;
A38-B6-C39;
A38-B6-C40;
A38-B6-C41;
A38-B6-C42;
A38-B6-C43;
A38-B6-C44;
A38-B6-C45;
A38-B6-C46;

-continued

A38-B6-C47;
A38-B6-C48;
A38-B6-C49;
A38-B6-C50;
A38-B6-C51;
A38-B6-C52;
A38-B6-C53;
A38-B6-C54;
A38-B6-C55;
A38-B6-C56;
A38-B6-C57;
A38-B6-C58;
A38-B6-C59;
A38-B6-C60;
A38-B6-C61;
A38-B6-C62;
A38-B6-C63;
A38-B6-C64;
A38-B6-C65;
A38-B6-C66;
A38-B6-C67;
A38-B6-C68;
A1-B7-C1;
A1-B7-C2;
A1-B7-C3;
A1-B7-C4;
A1-B7-C5;
A1-B7-C6;
A1-B7-C7;
A1-B7-C8;
A1-B7-C9;
A1-B7-C10;
A1-B7-C11;
A1-B7-C12;
A1-B7-C13;
A1-B7-C14;
A1-B7-C15;
A1-B7-C16;
A1-B7-C17;
A1-B7-C18;
A1-B7-C19;
A1-B7-C20;
A1-B7-C21;
A1-B7-C22;
A1-B7-C23;
A1-B7-C24;
A1-B7-C25;
A1-B7-C26;
A1-B7-C27;
A1-B7-C28;
A1-B7-C29;
A1-B7-C30;
A1-B7-C31;
A1-B7-C32;
A1-B7-C33;
A1-B7-C34;
A1-B7-C35;
A1-B7-C36;
A1-B7-C37;
A1-B7-C38;
A1-B7-C39;
A1-B7-C40;
A1-B7-C41;
A1-B7-C42;
A1-B7-C43;
A1-B7-C44;
A1-B7-C45;
A1-B7-C46;
A1-B7-C47;
A1-B7-C48;
A1-B7-C49;
A1-B7-C50;
A1-B7-C51;
A1-B7-C52;
A1-B7-C53;
A1-B7-C54;
A1-B7-C55;
A1-B7-C56;
A1-B7-C57;

-continued

A1-B7-C58;
A1-B7-C59;
A1-B7-C60;
A1-B7-C61;
A1-B7-C62;
A1-B7-C63;
A1-B7-C64;
A1-B7-C65;
A1-B7-C66;
A1-B7-C67;
A1-B7-C68;
A2-B7-C1;
A2-B7-C2;
A2-B7-C3;
A2-B7-C4;
A2-B7-C5;
A2-B7-C6;
A2-B7-C7;
A2-B7-C8;
A2-B7-C9;
A2-B7-C10;
A2-B7-C11;
A2-B7-C12;
A2-B7-C13;
A2-B7-C14;
A2-B7-C15;
A2-B7-C16;
A2-B7-C17;
A2-B7-C18;
A2-B7-C19;
A2-B7-C20;
A2-B7-C21;
A2-B7-C22;
A2-B7-C23;
A2-B7-C24;
A2-B7-C25;
A2-B7-C26;
A2-B7-C27;
A2-B7-C28;
A2-B7-C29;
A2-B7-C30;
A2-B7-C31;
A2-B7-C32;
A2-B7-C33;
A2-B7-C34;
A2-B7-C35;
A2-B7-C36;
A2-B7-C37;
A2-B7-C38;
A2-B7-C39;
A2-B7-C40;
A2-B7-C41;
A2-B7-C42;
A2-B7-C43;
A2-B7-C44;
A2-B7-C45;
A2-B7-C46;
A2-B7-C47;
A2-B7-C48;
A2-B7-C49;
A2-B7-C50;
A2-B7-C51;
A2-B7-C52;
A2-B7-C53;
A2-B7-C54;
A2-B7-C55;
A2-B7-C56;
A2-B7-C57;
A2-B7-C58;
A2-B7-C59;
A2-B7-C60;
A2-B7-C61;
A2-B7-C62;
A2-B7-C63;
A2-B7-C64;
A2-B7-C65;
A2-B7-C66;
A2-B7-C67;
A2-B7-C68;

A3-B7-C1;
A3-B7-C2;
A3-B7-C3;
A3-B7-C4;
A3-B7-C5;
A3-B7-C6;
A3-B7-C7;
A3-B7-C8;
A3-B7-C9;
A3-B7-C10;
A3-B7-C11;
A3-B7-C12;
A3-B7-C13;
A3-B7-C14;
A3-B7-C15;
A3-B7-C16;
A3-B7-C17;
A3-B7-C18;
A3-B7-C19;
A3-B7-C20;
A3-B7-C21;
A3-B7-C22;
A3-B7-C23;
A3-B7-C24;
A3-B7-C25;
A3-B7-C26;
A3-B7-C27;
A3-B7-C28;
A3-B7-C29;
A3-B7-C30;
A3-B7-C31;
A3-B7-C32;
A3-B7-C33;
A3-B7-C34;
A3-B7-C35;
A3-B7-C36;
A3-B7-C37;
A3-B7-C38;
A3-B7-C39;
A3-B7-C40;
A3-B7-C41;
A3-B7-C42;
A3-B7-C43;
A3-B7-C44;
A3-B7-C45;
A3-B7-C46;
A3-B7-C47;
A3-B7-C48;
A3-B7-C49;
A3-B7-C50;
A3-B7-C51;
A3-B7-C52;
A3-B7-C53;
A3-B7-C54;
A3-B7-C55;
A3-B7-C56;
A3-B7-C57;
A3-B7-C58;
A3-B7-C59;
A3-B7-C60;
A3-B7-C61;
A3-B7-C62;
A3-B7-C63;
A3-B7-C64;
A3-B7-C65;
A3-B7-C66;
A3-B7-C67;
A3-B7-C68;
A4-B7-C1;
A4-B7-C2;
A4-B7-C3;
A4-B7-C4;
A4-B7-C5;
A4-B7-C6;
A4-B7-C7;
A4-B7-C8;
A4-B7-C9;
A4-B7-C10;
A4-B7-C11;
A4-B7-C12;
A4-B7-C13;
A4-B7-C14;
A4-B7-C15;
A4-B7-C16;
A4-B7-C17;
A4-B7-C18;
A4-B7-C19;
A4-B7-C20;
A4-B7-C21;
A4-B7-C22;
A4-B7-C23;
A4-B7-C24;
A4-B7-C25;
A4-B7-C26;
A4-B7-C27;
A4-B7-C28;
A4-B7-C29;
A4-B7-C30;
A4-B7-C31;
A4-B7-C32;
A4-B7-C33;
A4-B7-C34;
A4-B7-C35;
A4-B7-C36;
A4-B7-C37;
A4-B7-C38;
A4-B7-C39;
A4-B7-C40;
A4-B7-C41;
A4-B7-C42;
A4-B7-C43;
A4-B7-C44;
A4-B7-C45;
A4-B7-C46;
A4-B7-C47;
A4-B7-C48;
A4-B7-C49;
A4-B7-C50;
A4-B7-C51;
A4-B7-C52;
A4-B7-C53;
A4-B7-C54;
A4-B7-C55;
A4-B7-C56;
A4-B7-C57;
A4-B7-C58;
A4-B7-C59;
A4-B7-C60;
A4-B7-C61;
A4-B7-C62;
A4-B7-C63;
A4-B7-C64;
A4-B7-C65;
A4-B7-C66;
A4-B7-C67;
A4-B7-C68;
A5-B7-C1;
A5-B7-C2;
A5-B7-C3;
A5-B7-C4;
A5-B7-C5;
A5-B7-C6;
A5-B7-C7;
A5-B7-C8;
A5-B7-C9;
A5-B7-C10;
A5-B7-C11;
A5-B7-C12;
A5-B7-C13;
A5-B7-C14;
A5-B7-C15;
A5-B7-C16;
A5-B7-C17;
A5-B7-C18;
A5-B7-C19;
A5-B7-C20;
A5-B7-C21;
A5-B7-C22;

-continued

A5-B7-C23;
A5-B7-C24;
A5-B7-C25;
A5-B7-C26;
A5-B7-C27;
A5-B7-C28;
A5-B7-C29;
A5-B7-C30;
A5-B7-C31;
A5-B7-C32;
A5-B7-C33;
A5-B7-C34;
A5-B7-C35;
A5-B7-C36;
A5-B7-C37;
A5-B7-C38;
A5-B7-C39;
A5-B7-C40;
A5-B7-C41;
A5-B7-C42;
A5-B7-C43;
A5-B7-C44;
A5-B7-C45;
A5-B7-C46;
A5-B7-C47;
A5-B7-C48;
A5-B7-C49;
A5-B7-C50;
A5-B7-C51;
A5-B7-C52;
A5-B7-C53;
A5-B7-C54;
A5-B7-C55;
A5-B7-C56;
A5-B7-C57;
A5-B7-C58;
A5-B7-C59;
A5-B7-C60;
A5-B7-C61;
A5-B7-C62;
A5-B7-C63;
A5-B7-C64;
A5-B7-C65;
A5-B7-C66;
A5-B7-C67;
A5-B7-C68;
A6-B7-C1;
A6-B7-C2;
A6-B7-C3;
A6-B7-C4;
A6-B7-C5;
A6-B7-C6;
A6-B7-C7;
A6-B7-C8;
A6-B7-C9;
A6-B7-C10;
A6-B7-C11;
A6-B7-C12;
A6-B7-C13;
A6-B7-C14;
A6-B7-C15;
A6-B7-C16;
A6-B7-C17;
A6-B7-C18;
A6-B7-C19;
A6-B7-C20;
A6-B7-C21;
A6-B7-C22;
A6-B7-C23;
A6-B7-C24;
A6-B7-C25;
A6-B7-C26;
A6-B7-C27;
A6-B7-C28;
A6-B7-C29;
A6-B7-C30;
A6-B7-C31;
A6-B7-C32;
A6-B7-C33;

-continued

A6-B7-C34;
A6-B7-C35;
A6-B7-C36;
A6-B7-C37;
A6-B7-C38;
A6-B7-C39;
A6-B7-C40;
A6-B7-C41;
A6-B7-C42;
A6-B7-C43;
A6-B7-C44;
A6-B7-C45;
A6-B7-C46;
A6-B7-C47;
A6-B7-C48;
A6-B7-C49;
A6-B7-C50;
A6-B7-C51;
A6-B7-C52;
A6-B7-C53;
A6-B7-C54;
A6-B7-C55;
A6-B7-C56;
A6-B7-C57;
A6-B7-C58;
A6-B7-C59;
A6-B7-C60;
A6-B7-C61;
A6-B7-C62;
A6-B7-C63;
A6-B7-C64;
A6-B7-C65;
A6-B7-C66;
A6-B7-C67;
A6-B7-C68;
A7-B7-C1;
A7-B7-C2;
A7-B7-C3;
A7-B7-C4;
A7-B7-C5;
A7-B7-C6;
A7-B7-C7;
A7-B7-C8;
A7-B7-C9;
A7-B7-C10;
A7-B7-C11;
A7-B7-C12;
A7-B7-C13;
A7-B7-C14;
A7-B7-C15;
A7-B7-C16;
A7-B7-C17;
A7-B7-C18;
A7-B7-C19;
A7-B7-C20;
A7-B7-C21;
A7-B7-C22;
A7-B7-C23;
A7-B7-C24;
A7-B7-C25;
A7-B7-C26;
A7-B7-C27;
A7-B7-C28;
A7-B7-C29;
A7-B7-C30;
A7-B7-C31;
A7-B7-C32;
A7-B7-C33;
A7-B7-C34;
A7-B7-C35;
A7-B7-C36;
A7-B7-C37;
A7-B7-C38;
A7-B7-C39;
A7-B7-C40;
A7-B7-C41;
A7-B7-C42;
A7-B7-C43;
A7-B7-C44;

A7-B7-C45;
A7-B7-C46;
A7-B7-C47;
A7-B7-C48;
A7-B7-C49;
A7-B7-C50;
A7-B7-C51;
A7-B7-C52;
A7-B7-C53;
A7-B7-C54;
A7-B7-C55;
A7-B7-C56;
A7-B7-C57;
A7-B7-C58;
A7-B7-C59;
A7-B7-C60;
A7-B7-C61;
A7-B7-C62;
A7-B7-C63;
A7-B7-C64;
A7-B7-C65;
A7-B7-C66;
A7-B7-C67;
A7-B7-C68;
A8-B7-C1;
A8-B7-C2;
A8-B7-C3;
A8-B7-C4;
A8-B7-C5;
A8-B7-C6;
A8-B7-C7;
A8-B7-C8;
A8-B7-C9;
A8-B7-C10;
A8-B7-C11;
A8-B7-C12;
A8-B7-C13;
A8-B7-C14;
A8-B7-C15;
A8-B7-C16;
A8-B7-C17;
A8-B7-C18;
A8-B7-C19;
A8-B7-C20;
A8-B7-C21;
A8-B7-C22;
A8-B7-C23;
A8-B7-C24;
A8-B7-C25;
A8-B7-C26;
A8-B7-C27;
A8-B7-C28;
A8-B7-C29;
A8-B7-C30;
A8-B7-C31;
A8-B7-C32;
A8-B7-C33;
A8-B7-C34;
A8-B7-C35;
A8-B7-C36;
A8-B7-C37;
A8-B7-C38;
A8-B7-C39;
A8-B7-C40;
A8-B7-C41;
A8-B7-C42;
A8-B7-C43;
A8-B7-C44;
A8-B7-C45;
A8-B7-C46;
A8-B7-C47;
A8-B7-C48;
A8-B7-C49;
A8-B7-C50;
A8-B7-C51;
A8-B7-C52;
A8-B7-C53;
A8-B7-C54;
A8-B7-C55;
A8-B7-C56;
A8-B7-C57;
A8-B7-C58;
A8-B7-C59;
A8-B7-C60;
A8-B7-C61;
A8-B7-C62;
A8-B7-C63;
A8-B7-C64;
A8-B7-C65;
A8-B7-C66;
A8-B7-C67;
A8-B7-C68;
A9-B7-C1;
A9-B7-C2;
A9-B7-C3;
A9-B7-C4;
A9-B7-C5;
A9-B7-C6;
A9-B7-C7;
A9-B7-C8;
A9-B7-C9;
A9-B7-C10;
A9-B7-C11;
A9-B7-C12;
A9-B7-C13;
A9-B7-C14;
A9-B7-C15;
A9-B7-C16;
A9-B7-C17;
A9-B7-C18;
A9-B7-C19;
A9-B7-C20;
A9-B7-C21;
A9-B7-C22;
A9-B7-C23;
A9-B7-C24;
A9-B7-C25;
A9-B7-C26;
A9-B7-C27;
A9-B7-C28;
A9-B7-C29;
A9-B7-C30;
A9-B7-C31;
A9-B7-C32;
A9-B7-C33;
A9-B7-C34;
A9-B7-C35;
A9-B7-C36;
A9-B7-C37;
A9-B7-C38;
A9-B7-C39;
A9-B7-C40;
A9-B7-C41;
A9-B7-C42;
A9-B7-C43;
A9-B7-C44;
A9-B7-C45;
A9-B7-C46;
A9-B7-C47;
A9-B7-C48;
A9-B7-C49;
A9-B7-C50;
A9-B7-C51;
A9-B7-C52;
A9-B7-C53;
A9-B7-C54;
A9-B7-C55;
A9-B7-C56;
A9-B7-C57;
A9-B7-C58;
A9-B7-C59;
A9-B7-C60;
A9-B7-C61;
A9-B7-C62;
A9-B7-C63;
A9-B7-C64;
A9-B7-C65;
A9-B7-C66;

-continued

A9-B7-C67;
A9-B7-C68;
A10-B7-C1;
A10-B7-C2;
A10-B7-C3;
A10-B7-C4;
A10-B7-C5;
A10-B7-C6;
A10-B7-C7;
A10-B7-C8;
A10-B7-C9;
A10-B7-C10;
A10-B7-C11;
A10-B7-C12;
A10-B7-C13;
A10-B7-C14;
A10-B7-C15;
A10-B7-C16;
A10-B7-C17;
A10-B7-C18;
A10-B7-C19;
A10-B7-C20;
A10-B7-C21;
A10-B7-C22;
A10-B7-C23;
A10-B7-C24;
A10-B7-C25;
A10-B7-C26;
A10-B7-C27;
A10-B7-C28;
A10-B7-C29;
A10-B7-C30;
A10-B7-C31;
A10-B7-C32;
A10-B7-C33;
A10-B7-C34;
A10-B7-C35;
A10-B7-C36;
A10-B7-C37;
A10-B7-C38;
A10-B7-C39;
A10-B7-C40;
A10-B7-C41;
A10-B7-C42;
A10-B7-C43;
A10-B7-C44;
A10-B7-C45;
A10-B7-C46;
A10-B7-C47;
A10-B7-C48;
A10-B7-C49;
A10-B7-C50;
A10-B7-C51;
A10-B7-C52;
A10-B7-C53;
A10-B7-C54;
A10-B7-C55;
A10-B7-C56;
A10-B7-C57;
A10-B7-C58;
A10-B7-C59;
A10-B7-C60;
A10-B7-C61;
A10-B7-C62;
A10-B7-C63;
A10-B7-C64;
A10-B7-C65;
A10-B7-C66;
A10-B7-C67;
A10-B7-C68;
A11-B7-C1;
A11-B7-C2;
A11-B7-C3;
A11-B7-C4;
A11-B7-C5;
A11-B7-C6;
A11-B7-C7;
A11-B7-C8;
A11-B7-C9;

-continued

A11-B7-C10;
A11-B7-C11;
A11-B7-C12;
A11-B7-C13;
A11-B7-C14;
A11-B7-C15;
A11-B7-C16;
A11-B7-C17;
A11-B7-C18;
A11-B7-C19;
A11-B7-C20;
A11-B7-C21;
A11-B7-C22;
A11-B7-C23;
A11-B7-C24;
A11-B7-C25;
A11-B7-C26;
A11-B7-C27;
A11-B7-C28;
A11-B7-C29;
A11-B7-C30;
A11-B7-C31;
A11-B7-C32;
A11-B7-C33;
A11-B7-C34;
A11-B7-C35;
A11-B7-C36;
A11-B7-C37;
A11-B7-C38;
A11-B7-C39;
A11-B7-C40;
A11-B7-C41;
A11-B7-C42;
A11-B7-C43;
A11-B7-C44;
A11-B7-C45;
A11-B7-C46;
A11-B7-C47;
A11-B7-C48;
A11-B7-C49;
A11-B7-C50;
A11-B7-C51;
A11-B7-C52;
A11-B7-C53;
A11-B7-C54;
A11-B7-C55;
A11-B7-C56;
A11-B7-C57;
A11-B7-C58;
A11-B7-C59;
A11-B7-C60;
A11-B7-C61;
A11-B7-C62;
A11-B7-C63;
A11-B7-C64;
A11-B7-C65;
A11-B7-C66;
A11-B7-C67;
A11-B7-C68;
A12-B7-C1;
A12-B7-C2;
A12-B7-C3;
A12-B7-C4;
A12-B7-C5;
A12-B7-C6;
A12-B7-C7;
A12-B7-C8;
A12-B7-C9;
A12-B7-C10;
A12-B7-C11;
A12-B7-C12;
A12-B7-C13;
A12-B7-C14;
A12-B7-C15;
A12-B7-C16;
A12-B7-C17;
A12-B7-C18;
A12-B7-C19;
A12-B7-C20;

A12-B7-C21;
A12-B7-C22;
A12-B7-C23;
A12-B7-C24;
A12-B7-C25;
A12-B7-C26;
A12-B7-C27;
A12-B7-C28;
A12-B7-C29;
A12-B7-C30;
A12-B7-C31;
A12-B7-C32;
A12-B7-C33;
A12-B7-C34;
A12-B7-C35;
A12-B7-C36;
A12-B7-C37;
A12-B7-C38;
A12-B7-C39;
A12-B7-C40;
A12-B7-C41;
A12-B7-C42;
A12-B7-C43;
A12-B7-C44;
A12-B7-C45;
A12-B7-C46;
A12-B7-C47;
A12-B7-C48;
A12-B7-C49;
A12-B7-C50;
A12-B7-C51;
A12-B7-C52;
A12-B7-C53;
A12-B7-C54;
A12-B7-C55;
A12-B7-C56;
A12-B7-C57;
A12-B7-C58;
A12-B7-C59;
A12-B7-C60;
A12-B7-C61;
A12-B7-C62;
A12-B7-C63;
A12-B7-C64;
A12-B7-C65;
A12-B7-C66;
A12-B7-C67;
A12-B7-C68;
A13-B7-C1;
A13-B7-C2;
A13-B7-C3;
A13-B7-C4;
A13-B7-C5;
A13-B7-C6;
A13-B7-C7;
A13-B7-C8;
A13-B7-C9;
A13-B7-C10;
A13-B7-C11;
A13-B7-C12;
A13-B7-C13;
A13-B7-C14;
A13-B7-C15;
A13-B7-C16;
A13-B7-C17;
A13-B7-C18;
A13-B7-C19;
A13-B7-C20;
A13-B7-C21;
A13-B7-C22;
A13-B7-C23;
A13-B7-C24;
A13-B7-C25;
A13-B7-C26;
A13-B7-C27;
A13-B7-C28;
A13-B7-C29;
A13-B7-C30;
A13-B7-C31;
A13-B7-C32;
A13-B7-C33;
A13-B7-C34;
A13-B7-C35;
A13-B7-C36;
A13-B7-C37;
A13-B7-C38;
A13-B7-C39;
A13-B7-C40;
A13-B7-C41;
A13-B7-C42;
A13-B7-C43;
A13-B7-C44;
A13-B7-C45;
A13-B7-C46;
A13-B7-C47;
A13-B7-C48;
A13-B7-C49;
A13-B7-C50;
A13-B7-C51;
A13-B7-C52;
A13-B7-C53;
A13-B7-C54;
A13-B7-C55;
A13-B7-C56;
A13-B7-C57;
A13-B7-C58;
A13-B7-C59;
A13-B7-C60;
A13-B7-C61;
A13-B7-C62;
A13-B7-C63;
A13-B7-C64;
A13-B7-C65;
A13-B7-C66;
A13-B7-C67;
A13-B7-C68;
A14-B7-C1;
A14-B7-C2;
A14-B7-C3;
A14-B7-C4;
A14-B7-C5;
A14-B7-C6;
A14-B7-C7;
A14-B7-C8;
A14-B7-C9;
A14-B7-C10;
A14-B7-C11;
A14-B7-C12;
A14-B7-C13;
A14-B7-C14;
A14-B7-C15;
A14-B7-C16;
A14-B7-C17;
A14-B7-C18;
A14-B7-C19;
A14-B7-C20;
A14-B7-C21;
A14-B7-C22;
A14-B7-C23;
A14-B7-C24;
A14-B7-C25;
A14-B7-C26;
A14-B7-C27;
A14-B7-C28;
A14-B7-C29;
A14-B7-C30;
A14-B7-C31;
A14-B7-C32;
A14-B7-C33;
A14-B7-C34;
A14-B7-C35;
A14-B7-C36;
A14-B7-C37;
A14-B7-C38;
A14-B7-C39;
A14-B7-C40;
A14-B7-C41;
A14-B7-C42;

-continued

A14-B7-C43;
A14-B7-C44;
A14-B7-C45;
A14-B7-C46;
A14-B7-C47;
A14-B7-C48;
A14-B7-C49;
A14-B7-C50;
A14-B7-C51;
A14-B7-C52;
A14-B7-C53;
A14-B7-C54;
A14-B7-C55;
A14-B7-C56;
A14-B7-C57;
A14-B7-C58;
A14-B7-C59;
A14-B7-C60;
A14-B7-C61;
A14-B7-C62;
A14-B7-C63;
A14-B7-C64;
A14-B7-C65;
A14-B7-C66;
A14-B7-C67;
A14-B7-C68;
A15-B7-C1;
A15-B7-C2;
A15-B7-C3;
A15-B7-C4;
A15-B7-C5;
A15-B7-C6;
A15-B7-C7;
A15-B7-C8;
A15-B7-C9;
A15-B7-C10;
A15-B7-C11;
A15-B7-C12;
A15-B7-C13;
A15-B7-C14;
A15-B7-C15;
A15-B7-C16;
A15-B7-C17;
A15-B7-C18;
A15-B7-C19;
A15-B7-C20;
A15-B7-C21;
A15-B7-C22;
A15-B7-C23;
A15-B7-C24;
A15-B7-C25;
A15-B7-C26;
A15-B7-C27;
A15-B7-C28;
A15-B7-C29;
A15-B7-C30;
A15-B7-C31;
A15-B7-C32;
A15-B7-C33;
A15-B7-C34;
A15-B7-C35;
A15-B7-C36;
A15-B7-C37;
A15-B7-C38;
A15-B7-C39;
A15-B7-C40;
A15-B7-C41;
A15-B7-C42;
A15-B7-C43;
A15-B7-C44;
A15-B7-C45;
A15-B7-C46;
A15-B7-C47;
A15-B7-C48;
A15-B7-C49;
A15-B7-C50;
A15-B7-C51;
A15-B7-C52;
A15-B7-C53;

-continued

A15-B7-C54;
A15-B7-C55;
A15-B7-C56;
A15-B7-C57;
A15-B7-C58;
A15-B7-C59;
A15-B7-C60;
A15-B7-C61;
A15-B7-C62;
A15-B7-C63;
A15-B7-C64;
A15-B7-C65;
A15-B7-C66;
A15-B7-C67;
A15-B7-C68;
A16-B7-C1;
A16-B7-C2;
A16-B7-C3;
A16-B7-C4;
A16-B7-C5;
A16-B7-C6;
A16-B7-C7;
A16-B7-C8;
A16-B7-C9;
A16-B7-C10;
A16-B7-C11;
A16-B7-C12;
A16-B7-C13;
A16-B7-C14;
A16-B7-C15;
A16-B7-C16;
A16-B7-C17;
A16-B7-C18;
A16-B7-C19;
A16-B7-C20;
A16-B7-C21;
A16-B7-C22;
A16-B7-C23;
A16-B7-C24;
A16-B7-C25;
A16-B7-C26;
A16-B7-C27;
A16-B7-C28;
A16-B7-C29;
A16-B7-C30;
A16-B7-C31;
A16-B7-C32;
A16-B7-C33;
A16-B7-C34;
A16-B7-C35;
A16-B7-C36;
A16-B7-C37;
A16-B7-C38;
A16-B7-C39;
A16-B7-C40;
A16-B7-C41;
A16-B7-C42;
A16-B7-C43;
A16-B7-C44;
A16-B7-C45;
A16-B7-C46;
A16-B7-C47;
A16-B7-C48;
A16-B7-C49;
A16-B7-C50;
A16-B7-C51;
A16-B7-C52;
A16-B7-C53;
A16-B7-C54;
A16-B7-C55;
A16-B7-C56;
A16-B7-C57;
A16-B7-C58;
A16-B7-C59;
A16-B7-C60;
A16-B7-C61;
A16-B7-C62;
A16-B7-C63;
A16-B7-C64;

-continued

A16-B7-C65;
A16-B7-C66;
A16-B7-C67;
A16-B7-C68;
A17-B7-C1;
A17-B7-C2;
A17-B7-C3;
A17-B7-C4;
A17-B7-C5;
A17-B7-C6;
A17-B7-C7;
A17-B7-C8;
A17-B7-C9;
A17-B7-C10;
A17-B7-C11;
A17-B7-C12;
A17-B7-C13;
A17-B7-C14;
A17-B7-C15;
A17-B7-C16;
A17-B7-C17;
A17-B7-C18;
A17-B7-C19;
A17-B7-C20;
A17-B7-C21;
A17-B7-C22;
A17-B7-C23;
A17-B7-C24;
A17-B7-C25;
A17-B7-C26;
A17-B7-C27;
A17-B7-C28;
A17-B7-C29;
A17-B7-C30;
A17-B7-C31;
A17-B7-C32;
A17-B7-C33;
A17-B7-C34;
A17-B7-C35;
A17-B7-C36;
A17-B7-C37;
A17-B7-C38;
A17-B7-C39;
A17-B7-C40;
A17-B7-C41;
A17-B7-C42;
A17-B7-C43;
A17-B7-C44;
A17-B7-C45;
A17-B7-C46;
A17-B7-C47;
A17-B7-C48;
A17-B7-C49;
A17-B7-C50;
A17-B7-C51;
A17-B7-C52;
A17-B7-C53;
A17-B7-C54;
A17-B7-C55;
A17-B7-C56;
A17-B7-C57;
A17-B7-C58;
A17-B7-C59;
A17-B7-C60;
A17-B7-C61;
A17-B7-C62;
A17-B7-C63;
A17-B7-C64;
A17-B7-C65;
A17-B7-C66;
A17-B7-C67;
A17-B7-C68;
A18-B7-C1;
A18-B7-C2;
A18-B7-C3;
A18-B7-C4;
A18-B7-C5;
A18-B7-C6;
A18-B7-C7;

-continued

A18-B7-C8;
A18-B7-C9;
A18-B7-C10;
A18-B7-C11;
A18-B7-C12;
A18-B7-C13;
A18-B7-C14;
A18-B7-C15;
A18-B7-C16;
A18-B7-C17;
A18-B7-C18;
A18-B7-C19;
A18-B7-C20;
A18-B7-C21;
A18-B7-C22;
A18-B7-C23;
A18-B7-C24;
A18-B7-C25;
A18-B7-C26;
A18-B7-C27;
A18-B7-C28;
A18-B7-C29;
A18-B7-C30;
A18-B7-C31;
A18-B7-C32;
A18-B7-C33;
A18-B7-C34;
A18-B7-C35;
A18-B7-C36;
A18-B7-C37;
A18-B7-C38;
A18-B7-C39;
A18-B7-C40;
A18-B7-C41;
A18-B7-C42;
A18-B7-C43;
A18-B7-C44;
A18-B7-C45;
A18-B7-C46;
A18-B7-C47;
A18-B7-C48;
A18-B7-C49;
A18-B7-C50;
A18-B7-C51;
A18-B7-C52;
A18-B7-C53;
A18-B7-C54;
A18-B7-C55;
A18-B7-C56;
A18-B7-C57;
A18-B7-C58;
A18-B7-C59;
A18-B7-C60;
A18-B7-C61;
A18-B7-C62;
A18-B7-C63;
A18-B7-C64;
A18-B7-C65;
A18-B7-C66;
A18-B7-C67;
A18-B7-C68;
A19-B7-C1;
A19-B7-C2;
A19-B7-C3;
A19-B7-C4;
A19-B7-C5;
A19-B7-C6;
A19-B7-C7;
A19-B7-C8;
A19-B7-C9;
A19-B7-C10;
A19-B7-C11;
A19-B7-C12;
A19-B7-C13;
A19-B7-C14;
A19-B7-C15;
A19-B7-C16;
A19-B7-C17;
A19-B7-C18;

-continued

A19-B7-C19;
A19-B7-C20;
A19-B7-C21;
A19-B7-C22;
A19-B7-C23;
A19-B7-C24;
A19-B7-C25;
A19-B7-C26;
A19-B7-C27;
A19-B7-C28;
A19-B7-C29;
A19-B7-C30;
A19-B7-C31;
A19-B7-C32;
A19-B7-C33;
A19-B7-C34;
A19-B7-C35;
A19-B7-C36;
A19-B7-C37;
A19-B7-C38;
A19-B7-C39;
A19-B7-C40;
A19-B7-C41;
A19-B7-C42;
A19-B7-C43;
A19-B7-C44;
A19-B7-C45;
A19-B7-C46;
A19-B7-C47;
A19-B7-C48;
A19-B7-C49;
A19-B7-C50;
A19-B7-C51;
A19-B7-C52;
A19-B7-C53;
A19-B7-C54;
A19-B7-C55;
A19-B7-C56;
A19-B7-C57;
A19-B7-C58;
A19-B7-C59;
A19-B7-C60;
A19-B7-C61;
A19-B7-C62;
A19-B7-C63;
A19-B7-C64;
A19-B7-C65;
A19-B7-C66;
A19-B7-C67;
A19-B7-C68;
A20-B7-C1;
A20-B7-C2;
A20-B7-C3;
A20-B7-C4;
A20-B7-C5;
A20-B7-C6;
A20-B7-C7;
A20-B7-C8;
A20-B7-C9;
A20-B7-C10;
A20-B7-C11;
A20-B7-C12;
A20-B7-C13;
A20-B7-C14;
A20-B7-C15;
A20-B7-C16;
A20-B7-C17;
A20-B7-C18;
A20-B7-C19;
A20-B7-C20;
A20-B7-C21;
A20-B7-C22;
A20-B7-C23;
A20-B7-C24;
A20-B7-C25;
A20-B7-C26;
A20-B7-C27;
A20-B7-C28;
A20-B7-C29;

-continued

A20-B7-C30;
A20-B7-C31;
A20-B7-C32;
A20-B7-C33;
A20-B7-C34;
A20-B7-C35;
A20-B7-C36;
A20-B7-C37;
A20-B7-C38;
A20-B7-C39;
A20-B7-C40;
A20-B7-C41;
A20-B7-C42;
A20-B7-C43;
A20-B7-C44;
A20-B7-C45;
A20-B7-C46;
A20-B7-C47;
A20-B7-C48;
A20-B7-C49;
A20-B7-C50;
A20-B7-C51;
A20-B7-C52;
A20-B7-C53;
A20-B7-C54;
A20-B7-C55;
A20-B7-C56;
A20-B7-C57;
A20-B7-C58;
A20-B7-C59;
A20-B7-C60;
A20-B7-C61;
A20-B7-C62;
A20-B7-C63;
A20-B7-C64;
A20-B7-C65;
A20-B7-C66;
A20-B7-C67;
A20-B7-C68;
A21-B7-C1;
A21-B7-C2;
A21-B7-C3;
A21-B7-C4;
A21-B7-C5;
A21-B7-C6;
A21-B7-C7;
A21-B7-C8;
A21-B7-C9;
A21-B7-C10;
A21-B7-C11;
A21-B7-C12;
A21-B7-C13;
A21-B7-C14;
A21-B7-C15;
A21-B7-C16;
A21-B7-C17;
A21-B7-C18;
A21-B7-C19;
A21-B7-C20;
A21-B7-C21;
A21-B7-C22;
A21-B7-C23;
A21-B7-C24;
A21-B7-C25;
A21-B7-C26;
A21-B7-C27;
A21-B7-C28;
A21-B7-C29;
A21-B7-C30;
A21-B7-C31;
A21-B7-C32;
A21-B7-C33;
A21-B7-C34;
A21-B7-C35;
A21-B7-C36;
A21-B7-C37;
A21-B7-C38;
A21-B7-C39;
A21-B7-C40;

A21-B7-C41;
A21-B7-C42;
A21-B7-C43;
A21-B7-C44;
A21-B7-C45;
A21-B7-C46;
A21-B7-C47;
A21-B7-C48;
A21-B7-C49;
A21-B7-C50;
A21-B7-C51;
A21-B7-C52;
A21-B7-C53;
A21-B7-C54;
A21-B7-C55;
A21-B7-C56;
A21-B7-C57;
A21-B7-C58;
A21-B7-C59;
A21-B7-C60;
A21-B7-C61;
A21-B7-C62;
A21-B7-C63;
A21-B7-C64;
A21-B7-C65;
A21-B7-C66;
A21-B7-C67;
A21-B7-C68;
A22-B7-C1;
A22-B7-C2;
A22-B7-C3;
A22-B7-C4;
A22-B7-C5;
A22-B7-C6;
A22-B7-C7;
A22-B7-C8;
A22-B7-C9;
A22-B7-C10;
A22-B7-C11;
A22-B7-C12;
A22-B7-C13;
A22-B7-C14;
A22-B7-C15;
A22-B7-C16;
A22-B7-C17;
A22-B7-C18;
A22-B7-C19;
A22-B7-C20;
A22-B7-C21;
A22-B7-C22;
A22-B7-C23;
A22-B7-C24;
A22-B7-C25;
A22-B7-C26;
A22-B7-C27;
A22-B7-C28;
A22-B7-C29;
A22-B7-C30;
A22-B7-C31;
A22-B7-C32;
A22-B7-C33;
A22-B7-C34;
A22-B7-C35;
A22-B7-C36;
A22-B7-C37;
A22-B7-C38;
A22-B7-C39;
A22-B7-C40;
A22-B7-C41;
A22-B7-C42;
A22-B7-C43;
A22-B7-C44;
A22-B7-C45;
A22-B7-C46;
A22-B7-C47;
A22-B7-C48;
A22-B7-C49;
A22-B7-C50;
A22-B7-C51;
A22-B7-C52;
A22-B7-C53;
A22-B7-C54;
A22-B7-C55;
A22-B7-C56;
A22-B7-C57;
A22-B7-C58;
A22-B7-C59;
A22-B7-C60;
A22-B7-C61;
A22-B7-C62;
A22-B7-C63;
A22-B7-C64;
A22-B7-C65;
A22-B7-C66;
A22-B7-C67;
A22-B7-C68;
A23-B7-C1;
A23-B7-C2;
A23-B7-C3;
A23-B7-C4;
A23-B7-C5;
A23-B7-C6;
A23-B7-C7;
A23-B7-C8;
A23-B7-C9;
A23-B7-C10;
A23-B7-C11;
A23-B7-C12;
A23-B7-C13;
A23-B7-C14;
A23-B7-C15;
A23-B7-C16;
A23-B7-C17;
A23-B7-C18;
A23-B7-C19;
A23-B7-C20;
A23-B7-C21;
A23-B7-C22;
A23-B7-C23;
A23-B7-C24;
A23-B7-C25;
A23-B7-C26;
A23-B7-C27;
A23-B7-C28;
A23-B7-C29;
A23-B7-C30;
A23-B7-C31;
A23-B7-C32;
A23-B7-C33;
A23-B7-C34;
A23-B7-C35;
A23-B7-C36;
A23-B7-C37;
A23-B7-C38;
A23-B7-C39;
A23-B7-C40;
A23-B7-C41;
A23-B7-C42;
A23-B7-C43;
A23-B7-C44;
A23-B7-C45;
A23-B7-C46;
A23-B7-C47;
A23-B7-C48;
A23-B7-C49;
A23-B7-C50;
A23-B7-C51;
A23-B7-C52;
A23-B7-C53;
A23-B7-C54;
A23-B7-C55;
A23-B7-C56;
A23-B7-C57;
A23-B7-C58;
A23-B7-C59;
A23-B7-C60;
A23-B7-C61;
A23-B7-C62;

-continued

A23-B7-C63;
A23-B7-C64;
A23-B7-C65;
A23-B7-C66;
A23-B7-C67;
A23-B7-C68;
A24-B7-C1;
A24-B7-C2;
A24-B7-C3;
A24-B7-C4;
A24-B7-C5;
A24-B7-C6;
A24-B7-C7;
A24-B7-C8;
A24-B7-C9;
A24-B7-C10;
A24-B7-C11;
A24-B7-C12;
A24-B7-C13;
A24-B7-C14;
A24-B7-C15;
A24-B7-C16;
A24-B7-C17;
A24-B7-C18;
A24-B7-C19;
A24-B7-C20;
A24-B7-C21;
A24-B7-C22;
A24-B7-C23;
A24-B7-C24;
A24-B7-C25;
A24-B7-C26;
A24-B7-C27;
A24-B7-C28;
A24-B7-C29;
A24-B7-C30;
A24-B7-C31;
A24-B7-C32;
A24-B7-C33;
A24-B7-C34;
A24-B7-C35;
A24-B7-C36;
A24-B7-C37;
A24-B7-C38;
A24-B7-C39;
A24-B7-C40;
A24-B7-C41;
A24-B7-C42;
A24-B7-C43;
A24-B7-C44;
A24-B7-C45;
A24-B7-C46;
A24-B7-C47;
A24-B7-C48;
A24-B7-C49;
A24-B7-C50;
A24-B7-C51;
A24-B7-C52;
A24-B7-C53;
A24-B7-C54;
A24-B7-C55;
A24-B7-C56;
A24-B7-C57;
A24-B7-C58;
A24-B7-C59;
A24-B7-C60;
A24-B7-C61;
A24-B7-C62;
A24-B7-C63;
A24-B7-C64;
A24-B7-C65;
A24-B7-C66;
A24-B7-C67;
A24-B7-C68;
A25-B7-C1;
A25-B7-C2;
A25-B7-C3;
A25-B7-C4;
A25-B7-C5;

-continued

A25-B7-C6;
A25-B7-C7;
A25-B7-C8;
A25-B7-C9;
A25-B7-C10;
A25-B7-C11;
A25-B7-C12;
A25-B7-C13;
A25-B7-C14;
A25-B7-C15;
A25-B7-C16;
A25-B7-C17;
A25-B7-C18;
A25-B7-C19;
A25-B7-C20;
A25-B7-C21;
A25-B7-C22;
A25-B7-C23;
A25-B7-C24;
A25-B7-C25;
A25-B7-C26;
A25-B7-C27;
A25-B7-C28;
A25-B7-C29;
A25-B7-C30;
A25-B7-C31;
A25-B7-C32;
A25-B7-C33;
A25-B7-C34;
A25-B7-C35;
A25-B7-C36;
A25-B7-C37;
A25-B7-C38;
A25-B7-C39;
A25-B7-C40;
A25-B7-C41;
A25-B7-C42;
A25-B7-C43;
A25-B7-C44;
A25-B7-C45;
A25-B7-C46;
A25-B7-C47;
A25-B7-C48;
A25-B7-C49;
A25-B7-C50;
A25-B7-C51;
A25-B7-C52;
A25-B7-C53;
A25-B7-C54;
A25-B7-C55;
A25-B7-C56;
A25-B7-C57;
A25-B7-C58;
A25-B7-C59;
A25-B7-C60;
A25-B7-C61;
A25-B7-C62;
A25-B7-C63;
A25-B7-C64;
A25-B7-C65;
A25-B7-C66;
A25-B7-C67;
A25-B7-C68;
A26-B7-C1;
A26-B7-C2;
A26-B7-C3;
A26-B7-C4;
A26-B7-C5;
A26-B7-C6;
A26-B7-C7;
A26-B7-C8;
A26-B7-C9;
A26-B7-C10;
A26-B7-C11;
A26-B7-C12;
A26-B7-C13;
A26-B7-C14;
A26-B7-C15;
A26-B7-C16;

-continued

A26-B7-C17;
A26-B7-C18;
A26-B7-C19;
A26-B7-C20;
A26-B7-C21;
A26-B7-C22;
A26-B7-C23;
A26-B7-C24;
A26-B7-C25;
A26-B7-C26;
A26-B7-C27;
A26-B7-C28;
A26-B7-C29;
A26-B7-C30;
A26-B7-C31;
A26-B7-C32;
A26-B7-C33;
A26-B7-C34;
A26-B7-C35;
A26-B7-C36;
A26-B7-C37;
A26-B7-C38;
A26-B7-C39;
A26-B7-C40;
A26-B7-C41;
A26-B7-C42;
A26-B7-C43;
A26-B7-C44;
A26-B7-C45;
A26-B7-C46;
A26-B7-C47;
A26-B7-C48;
A26-B7-C49;
A26-B7-C50;
A26-B7-C51;
A26-B7-C52;
A26-B7-C53;
A26-B7-C54;
A26-B7-C55;
A26-B7-C56;
A26-B7-C57;
A26-B7-C58;
A26-B7-C59;
A26-B7-C60;
A26-B7-C61;
A26-B7-C62;
A26-B7-C63;
A26-B7-C64;
A26-B7-C65;
A26-B7-C66;
A26-B7-C67;
A26-B7-C68;
A27-B7-C1;
A27-B7-C2;
A27-B7-C3;
A27-B7-C4;
A27-B7-C5;
A27-B7-C6;
A27-B7-C7;
A27-B7-C8;
A27-B7-C9;
A27-B7-C10;
A27-B7-C11;
A27-B7-C12;
A27-B7-C13;
A27-B7-C14;
A27-B7-C15;
A27-B7-C16;
A27-B7-C17;
A27-B7-C18;
A27-B7-C19;
A27-B7-C20;
A27-B7-C21;
A27-B7-C22;
A27-B7-C23;
A27-B7-C24;
A27-B7-C25;
A27-B7-C26;
A27-B7-C27;

-continued

A27-B7-C28;
A27-B7-C29;
A27-B7-C30;
A27-B7-C31;
A27-B7-C32;
A27-B7-C33;
A27-B7-C34;
A27-B7-C35;
A27-B7-C36;
A27-B7-C37;
A27-B7-C38;
A27-B7-C39;
A27-B7-C40;
A27-B7-C41;
A27-B7-C42;
A27-B7-C43;
A27-B7-C44;
A27-B7-C45;
A27-B7-C46;
A27-B7-C47;
A27-B7-C48;
A27-B7-C49;
A27-B7-C50;
A27-B7-C51;
A27-B7-C52;
A27-B7-C53;
A27-B7-C54;
A27-B7-C55;
A27-B7-C56;
A27-B7-C57;
A27-B7-C58;
A27-B7-C59;
A27-B7-C60;
A27-B7-C61;
A27-B7-C62;
A27-B7-C63;
A27-B7-C64;
A27-B7-C65;
A27-B7-C66;
A27-B7-C67;
A27-B7-C68;
A28-B7-C1;
A28-B7-C2;
A28-B7-C3;
A28-B7-C4;
A28-B7-C5;
A28-B7-C6;
A28-B7-C7;
A28-B7-C8;
A28-B7-C9;
A28-B7-C10;
A28-B7-C11;
A28-B7-C12;
A28-B7-C13;
A28-B7-C14;
A28-B7-C15;
A28-B7-C16;
A28-B7-C17;
A28-B7-C18;
A28-B7-C19;
A28-B7-C20;
A28-B7-C21;
A28-B7-C22;
A28-B7-C23;
A28-B7-C24;
A28-B7-C25;
A28-B7-C26;
A28-B7-C27;
A28-B7-C28;
A28-B7-C29;
A28-B7-C30;
A28-B7-C31;
A28-B7-C32;
A28-B7-C33;
A28-B7-C34;
A28-B7-C35;
A28-B7-C36;
A28-B7-C37;
A28-B7-C38;

-continued

A28-B7-C39;
A28-B7-C40;
A28-B7-C41;
A28-B7-C42;
A28-B7-C43;
A28-B7-C44;
A28-B7-C45;
A28-B7-C46;
A28-B7-C47;
A28-B7-C48;
A28-B7-C49;
A28-B7-C50;
A28-B7-C51;
A28-B7-C52;
A28-B7-C53;
A28-B7-C54;
A28-B7-C55;
A28-B7-C56;
A28-B7-C57;
A28-B7-C58;
A28-B7-C59;
A28-B7-C60;
A28-B7-C61;
A28-B7-C62;
A28-B7-C63;
A28-B7-C64;
A28-B7-C65;
A28-B7-C66;
A28-B7-C67;
A28-B7-C68;
A29-B7-C1;
A29-B7-C2;
A29-B7-C3;
A29-B7-C4;
A29-B7-C5;
A29-B7-C6;
A29-B7-C7;
A29-B7-C8;
A29-B7-C9;
A29-B7-C10;
A29-B7-C11;
A29-B7-C12;
A29-B7-C13;
A29-B7-C14;
A29-B7-C15;
A29-B7-C16;
A29-B7-C17;
A29-B7-C18;
A29-B7-C19;
A29-B7-C20;
A29-B7-C21;
A29-B7-C22;
A29-B7-C23;
A29-B7-C24;
A29-B7-C25;
A29-B7-C26;
A29-B7-C27;
A29-B7-C28;
A29-B7-C29;
A29-B7-C30;
A29-B7-C31;
A29-B7-C32;
A29-B7-C33;
A29-B7-C34;
A29-B7-C35;
A29-B7-C36;
A29-B7-C37;
A29-B7-C38;
A29-B7-C39;
A29-B7-C40;
A29-B7-C41;
A29-B7-C42;
A29-B7-C43;
A29-B7-C44;
A29-B7-C45;
A29-B7-C46;
A29-B7-C47;
A29-B7-C48;
A29-B7-C49;

-continued

A29-B7-C50;
A29-B7-C51;
A29-B7-C52;
A29-B7-C53;
A29-B7-C54;
A29-B7-C55;
A29-B7-C56;
A29-B7-C57;
A29-B7-C58;
A29-B7-C59;
A29-B7-C60;
A29-B7-C61;
A29-B7-C62;
A29-B7-C63;
A29-B7-C64;
A29-B7-C65;
A29-B7-C66;
A29-B7-C67;
A29-B7-C68;
A30-B7-C1;
A30-B7-C2;
A30-B7-C3;
A30-B7-C4;
A30-B7-C5;
A30-B7-C6;
A30-B7-C7;
A30-B7-C8;
A30-B7-C9;
A30-B7-C10;
A30-B7-C11;
A30-B7-C12;
A30-B7-C13;
A30-B7-C14;
A30-B7-C15;
A30-B7-C16;
A30-B7-C17;
A30-B7-C18;
A30-B7-C19;
A30-B7-C20;
A30-B7-C21;
A30-B7-C22;
A30-B7-C23;
A30-B7-C24;
A30-B7-C25;
A30-B7-C26;
A30-B7-C27;
A30-B7-C28;
A30-B7-C29;
A30-B7-C30;
A30-B7-C31;
A30-B7-C32;
A30-B7-C33;
A30-B7-C34;
A30-B7-C35;
A30-B7-C36;
A30-B7-C37;
A30-B7-C38;
A30-B7-C39;
A30-B7-C40;
A30-B7-C41;
A30-B7-C42;
A30-B7-C43;
A30-B7-C44;
A30-B7-C45;
A30-B7-C46;
A30-B7-C47;
A30-B7-C48;
A30-B7-C49;
A30-B7-C50;
A30-B7-C51;
A30-B7-C52;
A30-B7-C53;
A30-B7-C54;
A30-B7-C55;
A30-B7-C56;
A30-B7-C57;
A30-B7-C58;
A30-B7-C59;
A30-B7-C60;

-continued

A30-B7-C61;
A30-B7-C62;
A30-B7-C63;
A30-B7-C64;
A30-B7-C65;
A30-B7-C66;
A30-B7-C67;
A30-B7-C68;
A31-B7-C1;
A31-B7-C2;
A31-B7-C3;
A31-B7-C4;
A31-B7-C5;
A31-B7-C6;
A31-B7-C7;
A31-B7-C8;
A31-B7-C9;
A31-B7-C10;
A31-B7-C11;
A31-B7-C12;
A31-B7-C13;
A31-B7-C14;
A31-B7-C15;
A31-B7-C16;
A31-B7-C17;
A31-B7-C18;
A31-B7-C19;
A31-B7-C20;
A31-B7-C21;
A31-B7-C22;
A31-B7-C23;
A31-B7-C24;
A31-B7-C25;
A31-B7-C26;
A31-B7-C27;
A31-B7-C28;
A31-B7-C29;
A31-B7-C30;
A31-B7-C31;
A31-B7-C32;
A31-B7-C33;
A31-B7-C34;
A31-B7-C35;
A31-B7-C36;
A31-B7-C37;
A31-B7-C38;
A31-B7-C39;
A31-B7-C40;
A31-B7-C41;
A31-B7-C42;
A31-B7-C43;
A31-B7-C44;
A31-B7-C45;
A31-B7-C46;
A31-B7-C47;
A31-B7-C48;
A31-B7-C49;
A31-B7-C50;
A31-B7-C51;
A31-B7-C52;
A31-B7-C53;
A31-B7-C54;
A31-B7-C55;
A31-B7-C56;
A31-B7-C57;
A31-B7-C58;
A31-B7-C59;
A31-B7-C60;
A31-B7-C61;
A31-B7-C62;
A31-B7-C63;
A31-B7-C64;
A31-B7-C65;
A31-B7-C66;
A31-B7-C67;
A31-B7-C68;
A32-B7-C1;
A32-B7-C2;
A32-B7-C3;

-continued

A32-B7-C4;
A32-B7-C5;
A32-B7-C6;
A32-B7-C7;
A32-B7-C8;
A32-B7-C9;
A32-B7-C10;
A32-B7-C11;
A32-B7-C12;
A32-B7-C13;
A32-B7-C14;
A32-B7-C15;
A32-B7-C16;
A32-B7-C17;
A32-B7-C18;
A32-B7-C19;
A32-B7-C20;
A32-B7-C21;
A32-B7-C22;
A32-B7-C23;
A32-B7-C24;
A32-B7-C25;
A32-B7-C26;
A32-B7-C27;
A32-B7-C28;
A32-B7-C29;
A32-B7-C30;
A32-B7-C31;
A32-B7-C32;
A32-B7-C33;
A32-B7-C34;
A32-B7-C35;
A32-B7-C36;
A32-B7-C37;
A32-B7-C38;
A32-B7-C39;
A32-B7-C40;
A32-B7-C41;
A32-B7-C42;
A32-B7-C43;
A32-B7-C44;
A32-B7-C45;
A32-B7-C46;
A32-B7-C47;
A32-B7-C48;
A32-B7-C49;
A32-B7-C50;
A32-B7-C51;
A32-B7-C52;
A32-B7-C53;
A32-B7-C54;
A32-B7-C55;
A32-B7-C56;
A32-B7-C57;
A32-B7-C58;
A32-B7-C59;
A32-B7-C60;
A32-B7-C61;
A32-B7-C62;
A32-B7-C63;
A32-B7-C64;
A32-B7-C65;
A32-B7-C66;
A32-B7-C67;
A32-B7-C68;
A33-B7-C1;
A33-B7-C2;
A33-B7-C3;
A33-B7-C4;
A33-B7-C5;
A33-B7-C6;
A33-B7-C7;
A33-B7-C8;
A33-B7-C9;
A33-B7-C10;
A33-B7-C11;
A33-B7-C12;
A33-B7-C13;
A33-B7-C14;

-continued

A33-B7-C15;
A33-B7-C16;
A33-B7-C17;
A33-B7-C18;
A33-B7-C19;
A33-B7-C20;
A33-B7-C21;
A33-B7-C22;
A33-B7-C23;
A33-B7-C24;
A33-B7-C25;
A33-B7-C26;
A33-B7-C27;
A33-B7-C28;
A33-B7-C29;
A33-B7-C30;
A33-B7-C31;
A33-B7-C32;
A33-B7-C33;
A33-B7-C34;
A33-B7-C35;
A33-B7-C36;
A33-B7-C37;
A33-B7-C38;
A33-B7-C39;
A33-B7-C40;
A33-B7-C41;
A33-B7-C42;
A33-B7-C43;
A33-B7-C44;
A33-B7-C45;
A33-B7-C46;
A33-B7-C47;
A33-B7-C48;
A33-B7-C49;
A33-B7-C50;
A33-B7-C51;
A33-B7-C52;
A33-B7-C53;
A33-B7-C54;
A33-B7-C55;
A33-B7-C56;
A33-B7-C57;
A33-B7-C58;
A33-B7-C59;
A33-B7-C60;
A33-B7-C61;
A33-B7-C62;
A33-B7-C63;
A33-B7-C64;
A33-B7-C65;
A33-B7-C66;
A33-B7-C67;
A33-B7-C68;
A34-B7-C1;
A34-B7-C2;
A34-B7-C3;
A34-B7-C4;
A34-B7-C5;
A34-B7-C6;
A34-B7-C7;
A34-B7-C8;
A34-B7-C9;
A34-B7-C10;
A34-B7-C11;
A34-B7-C12;
A34-B7-C13;
A34-B7-C14;
A34-B7-C15;
A34-B7-C16;
A34-B7-C17;
A34-B7-C18;
A34-B7-C19;
A34-B7-C20;
A34-B7-C21;
A34-B7-C22;
A34-B7-C23;
A34-B7-C24;
A34-B7-C25;
A34-B7-C26;
A34-B7-C27;
A34-B7-C28;
A34-B7-C29;
A34-B7-C30;
A34-B7-C31;
A34-B7-C32;
A34-B7-C33;
A34-B7-C34;
A34-B7-C35;
A34-B7-C36;
A34-B7-C37;
A34-B7-C38;
A34-B7-C39;
A34-B7-C40;
A34-B7-C41;
A34-B7-C42;
A34-B7-C43;
A34-B7-C44;
A34-B7-C45;
A34-B7-C46;
A34-B7-C47;
A34-B7-C48;
A34-B7-C49;
A34-B7-C50;
A34-B7-C51;
A34-B7-C52;
A34-B7-C53;
A34-B7-C54;
A34-B7-C55;
A34-B7-C56;
A34-B7-C57;
A34-B7-C58;
A34-B7-C59;
A34-B7-C60;
A34-B7-C61;
A34-B7-C62;
A34-B7-C63;
A34-B7-C64;
A34-B7-C65;
A34-B7-C66;
A34-B7-C67;
A34-B7-C68;
A35-B7-C1;
A35-B7-C2;
A35-B7-C3;
A35-B7-C4;
A35-B7-C5;
A35-B7-C6;
A35-B7-C7;
A35-B7-C8;
A35-B7-C9;
A35-B7-C10;
A35-B7-C11;
A35-B7-C12;
A35-B7-C13;
A35-B7-C14;
A35-B7-C15;
A35-B7-C16;
A35-B7-C17;
A35-B7-C18;
A35-B7-C19;
A35-B7-C20;
A35-B7-C21;
A35-B7-C22;
A35-B7-C23;
A35-B7-C24;
A35-B7-C25;
A35-B7-C26;
A35-B7-C27;
A35-B7-C28;
A35-B7-C29;
A35-B7-C30;
A35-B7-C31;
A35-B7-C32;
A35-B7-C33;
A35-B7-C34;
A35-B7-C35;
A35-B7-C36;

A35-B7-C37;
A35-B7-C38;
A35-B7-C39;
A35-B7-C40;
A35-B7-C41;
A35-B7-C42;
A35-B7-C43;
A35-B7-C44;
A35-B7-C45;
A35-B7-C46;
A35-B7-C47;
A35-B7-C48;
A35-B7-C49;
A35-B7-C50;
A35-B7-C51;
A35-B7-C52;
A35-B7-C53;
A35-B7-C54;
A35-B7-C55;
A35-B7-C56;
A35-B7-C57;
A35-B7-C58;
A35-B7-C59;
A35-B7-C60;
A35-B7-C61;
A35-B7-C62;
A35-B7-C63;
A35-B7-C64;
A35-B7-C65;
A35-B7-C66;
A35-B7-C67;
A35-B7-C68;
A36-B7-C1;
A36-B7-C2;
A36-B7-C3;
A36-B7-C4;
A36-B7-C5;
A36-B7-C6;
A36-B7-C7;
A36-B7-C8;
A36-B7-C9;
A36-B7-C10;
A36-B7-C11;
A36-B7-C12;
A36-B7-C13;
A36-B7-C14;
A36-B7-C15;
A36-B7-C16;
A36-B7-C17;
A36-B7-C18;
A36-B7-C19;
A36-B7-C20;
A36-B7-C21;
A36-B7-C22;
A36-B7-C23;
A36-B7-C24;
A36-B7-C25;
A36-B7-C26;
A36-B7-C27;
A36-B7-C28;
A36-B7-C29;
A36-B7-C30;
A36-B7-C31;
A36-B7-C32;
A36-B7-C33;
A36-B7-C34;
A36-B7-C35;
A36-B7-C36;
A36-B7-C37;
A36-B7-C38;
A36-B7-C39;
A36-B7-C40;
A36-B7-C41;
A36-B7-C42;
A36-B7-C43;
A36-B7-C44;
A36-B7-C45;
A36-B7-C46;
A36-B7-C47;
A36-B7-C48;
A36-B7-C49;
A36-B7-C50;
A36-B7-C51;
A36-B7-C52;
A36-B7-C53;
A36-B7-C54;
A36-B7-C55;
A36-B7-C56;
A36-B7-C57;
A36-B7-C58;
A36-B7-C59;
A36-B7-C60;
A36-B7-C61;
A36-B7-C62;
A36-B7-C63;
A36-B7-C64;
A36-B7-C65;
A36-B7-C66;
A36-B7-C67;
A36-B7-C68;
A37-B7-C1;
A37-B7-C2;
A37-B7-C3;
A37-B7-C4;
A37-B7-C5;
A37-B7-C6;
A37-B7-C7;
A37-B7-C8;
A37-B7-C9;
A37-B7-C10;
A37-B7-C11;
A37-B7-C12;
A37-B7-C13;
A37-B7-C14;
A37-B7-C15;
A37-B7-C16;
A37-B7-C17;
A37-B7-C18;
A37-B7-C19;
A37-B7-C20;
A37-B7-C21;
A37-B7-C22;
A37-B7-C23;
A37-B7-C24;
A37-B7-C25;
A37-B7-C26;
A37-B7-C27;
A37-B7-C28;
A37-B7-C29;
A37-B7-C30;
A37-B7-C31;
A37-B7-C32;
A37-B7-C33;
A37-B7-C34;
A37-B7-C35;
A37-B7-C36;
A37-B7-C37;
A37-B7-C38;
A37-B7-C39;
A37-B7-C40;
A37-B7-C41;
A37-B7-C42;
A37-B7-C43;
A37-B7-C44;
A37-B7-C45;
A37-B7-C46;
A37-B7-C47;
A37-B7-C48;
A37-B7-C49;
A37-B7-C50;
A37-B7-C51;
A37-B7-C52;
A37-B7-C53;
A37-B7-C54;
A37-B7-C55;
A37-B7-C56;
A37-B7-C57;
A37-B7-C58;

A37-B7-C59;
A37-B7-C60;
A37-B7-C61;
A37-B7-C62;
A37-B7-C63;
A37-B7-C64;
A37-B7-C65;
A37-B7-C66;
A37-B7-C67;
A37-B7-C68;
A38-B7-C1;
A38-B7-C2;
A38-B7-C3;
A38-B7-C4;
A38-B7-C5;
A38-B7-C6;
A38-B7-C7;
A38-B7-C8;
A38-B7-C9;
A38-B7-C10;
A38-B7-C11;
A38-B7-C12;
A38-B7-C13;
A38-B7-C14;
A38-B7-C15;
A38-B7-C16;
A38-B7-C17;
A38-B7-C18;
A38-B7-C19;
A38-B7-C20;
A38-B7-C21;
A38-B7-C22;
A38-B7-C23;
A38-B7-C24;
A38-B7-C25;
A38-B7-C26;
A38-B7-C27;
A38-B7-C28;
A38-B7-C29;
A38-B7-C30;
A38-B7-C31;
A38-B7-C32;
A38-B7-C33;
A38-B7-C34;
A38-B7-C35;
A38-B7-C36;
A38-B7-C37;
A38-B7-C38;
A38-B7-C39;
A38-B7-C40;
A38-B7-C41;
A38-B7-C42;
A38-B7-C43;
A38-B7-C44;
A38-B7-C45;
A38-B7-C46;
A38-B7-C47;
A38-B7-C48;
A38-B7-C49;
A38-B7-C50;
A38-B7-C51;
A38-B7-C52;
A38-B7-C53;
A38-B7-C54;
A38-B7-C55;
A38-B7-C56;
A38-B7-C57;
A38-B7-C58;
A38-B7-C59;
A38-B7-C60;
A38-B7-C61;
A38-B7-C62;
A38-B7-C63;
A38-B7-C64;
A38-B7-C65;
A38-B7-C66;
A38-B7-C67;
A38-B7-C68;
A1-B8-C1;
A1-B8-C2;
A1-B8-C3;
A1-B8-C4;
A1-B8-C5;
A1-B8-C6;
A1-B8-C7;
A1-B8-C8;
A1-B8-C9;
A1-B8-C10;
A1-B8-C11;
A1-B8-C12;
A1-B8-C13;
A1-B8-C14;
A1-B8-C15;
A1-B8-C16;
A1-B8-C17;
A1-B8-C18;
A1-B8-C19;
A1-B8-C20;
A1-B8-C21;
A1-B8-C22;
A1-B8-C23;
A1-B8-C24;
A1-B8-C25;
A1-B8-C26;
A1-B8-C27;
A1-B8-C28;
A1-B8-C29;
A1-B8-C30;
A1-B8-C31;
A1-B8-C32;
A1-B8-C33;
A1-B8-C34;
A1-B8-C35;
A1-B8-C36;
A1-B8-C37;
A1-B8-C38;
A1-B8-C39;
A1-B8-C40;
A1-B8-C41;
A1-B8-C42;
A1-B8-C43;
A1-B8-C44;
A1-B8-C45;
A1-B8-C46;
A1-B8-C47;
A1-B8-C48;
A1-B8-C49;
A1-B8-C50;
A1-B8-C51;
A1-B8-C52;
A1-B8-C53;
A1-B8-C54;
A1-B8-C55;
A1-B8-C56;
A1-B8-C57;
A1-B8-C58;
A1-B8-C59;
A1-B8-C60;
A1-B8-C61;
A1-B8-C62;
A1-B8-C63;
A1-B8-C64;
A1-B8-C65;
A1-B8-C66;
A1-B8-C67;
A1-B8-C68;
A2-B8-C1;
A2-B8-C2;
A2-B8-C3;
A2-B8-C4;
A2-B8-C5;
A2-B8-C6;
A2-B8-C7;
A2-B8-C8;
A2-B8-C9;
A2-B8-C10;
A2-B8-C11;
A2-B8-C12;

-continued

A2-B8-C13;
A2-B8-C14;
A2-B8-C15;
A2-B8-C16;
A2-B8-C17;
A2-B8-C18;
A2-B8-C19;
A2-B8-C20;
A2-B8-C21;
A2-B8-C22;
A2-B8-C23;
A2-B8-C24;
A2-B8-C25;
A2-B8-C26;
A2-B8-C27;
A2-B8-C28;
A2-B8-C29;
A2-B8-C30;
A2-B8-C31;
A2-B8-C32;
A2-B8-C33;
A2-B8-C34;
A2-B8-C35;
A2-B8-C36;
A2-B8-C37;
A2-B8-C38;
A2-B8-C39;
A2-B8-C40;
A2-B8-C41;
A2-B8-C42;
A2-B8-C43;
A2-B8-C44;
A2-B8-C45;
A2-B8-C46;
A2-B8-C47;
A2-B8-C48;
A2-B8-C49;
A2-B8-C50;
A2-B8-C51;
A2-B8-C52;
A2-B8-C53;
A2-B8-C54;
A2-B8-C55;
A2-B8-C56;
A2-B8-C57;
A2-B8-C58;
A2-B8-C59;
A2-B8-C60;
A2-B8-C61;
A2-B8-C62;
A2-B8-C63;
A2-B8-C64;
A2-B8-C65;
A2-B8-C66;
A2-B8-C67;
A2-B8-C68;
A3-B8-C1;
A3-B8-C2;
A3-B8-C3;
A3-B8-C4;
A3-B8-C5;
A3-B8-C6;
A3-B8-C7;
A3-B8-C8;
A3-B8-C9;
A3-B8-C10;
A3-B8-C11;
A3-B8-C12;
A3-B8-C13;
A3-B8-C14;
A3-B8-C15;
A3-B8-C16;
A3-B8-C17;
A3-B8-C18;
A3-B8-C19;
A3-B8-C20;
A3-B8-C21;
A3-B8-C22;
A3-B8-C23;
A3-B8-C24;
A3-B8-C25;
A3-B8-C26;
A3-B8-C27;
A3-B8-C28;
A3-B8-C29;
A3-B8-C30;
A3-B8-C31;
A3-B8-C32;
A3-B8-C33;
A3-B8-C34;
A3-B8-C35;
A3-B8-C36;
A3-B8-C37;
A3-B8-C38;
A3-B8-C39;
A3-B8-C40;
A3-B8-C41;
A3-B8-C42;
A3-B8-C43;
A3-B8-C44;
A3-B8-C45;
A3-B8-C46;
A3-B8-C47;
A3-B8-C48;
A3-B8-C49;
A3-B8-C50;
A3-B8-C51;
A3-B8-C52;
A3-B8-C53;
A3-B8-C54;
A3-B8-C55;
A3-B8-C56;
A3-B8-C57;
A3-B8-C58;
A3-B8-C59;
A3-B8-C60;
A3-B8-C61;
A3-B8-C62;
A3-B8-C63;
A3-B8-C64;
A3-B8-C65;
A3-B8-C66;
A3-B8-C67;
A3-B8-C68;
A4-B8-C1;
A4-B8-C2;
A4-B8-C3;
A4-B8-C4;
A4-B8-C5;
A4-B8-C6;
A4-B8-C7;
A4-B8-C8;
A4-B8-C9;
A4-B8-C10;
A4-B8-C11;
A4-B8-C12;
A4-B8-C13;
A4-B8-C14;
A4-B8-C15;
A4-B8-C16;
A4-B8-C17;
A4-B8-C18;
A4-B8-C19;
A4-B8-C20;
A4-B8-C21;
A4-B8-C22;
A4-B8-C23;
A4-B8-C24;
A4-B8-C25;
A4-B8-C26;
A4-B8-C27;
A4-B8-C28;
A4-B8-C29;
A4-B8-C30;
A4-B8-C31;
A4-B8-C32;
A4-B8-C33;
A4-B8-C34;

A4-B8-C35;
A4-B8-C36;
A4-B8-C37;
A4-B8-C38;
A4-B8-C39;
A4-B8-C40;
A4-B8-C41;
A4-B8-C42;
A4-B8-C43;
A4-B8-C44;
A4-B8-C45;
A4-B8-C46;
A4-B8-C47;
A4-B8-C48;
A4-B8-C49;
A4-B8-C50;
A4-B8-C51;
A4-B8-C52;
A4-B8-C53;
A4-B8-C54;
A4-B8-C55;
A4-B8-C56;
A4-B8-C57;
A4-B8-C58;
A4-B8-C59;
A4-B8-C60;
A4-B8-C61;
A4-B8-C62;
A4-B8-C63;
A4-B8-C64;
A4-B8-C65;
A4-B8-C66;
A4-B8-C67;
A4-B8-C68;
A5-B8-C1;
A5-B8-C2;
A5-B8-C3;
A5-B8-C4;
A5-B8-C5;
A5-B8-C6;
A5-B8-C7;
A5-B8-C8;
A5-B8-C9;
A5-B8-C10;
A5-B8-C11;
A5-B8-C12;
A5-B8-C13;
A5-B8-C14;
A5-B8-C15;
A5-B8-C16;
A5-B8-C17;
A5-B8-C18;
A5-B8-C19;
A5-B8-C20;
A5-B8-C21;
A5-B8-C22;
A5-B8-C23;
A5-B8-C24;
A5-B8-C25;
A5-B8-C26;
A5-B8-C27;
A5-B8-C28;
A5-B8-C29;
A5-B8-C30;
A5-B8-C31;
A5-B8-C32;
A5-B8-C33;
A5-B8-C34;
A5-B8-C35;
A5-B8-C36;
A5-B8-C37;
A5-B8-C38;
A5-B8-C39;
A5-B8-C40;
A5-B8-C41;
A5-B8-C42;
A5-B8-C43;
A5-B8-C44;
A5-B8-C45;
A5-B8-C46;
A5-B8-C47;
A5-B8-C48;
A5-B8-C49;
A5-B8-C50;
A5-B8-C51;
A5-B8-C52;
A5-B8-C53;
A5-B8-C54;
A5-B8-C55;
A5-B8-C56;
A5-B8-C57;
A5-B8-C58;
A5-B8-C59;
A5-B8-C60;
A5-B8-C61;
A5-B8-C62;
A5-B8-C63;
A5-B8-C64;
A5-B8-C65;
A5-B8-C66;
A5-B8-C67;
A5-B8-C68;
A6-B8-C1;
A6-B8-C2;
A6-B8-C3;
A6-B8-C4;
A6-B8-C5;
A6-B8-C6;
A6-B8-C7;
A6-B8-C8;
A6-B8-C9;
A6-B8-C10;
A6-B8-C11;
A6-B8-C12;
A6-B8-C13;
A6-B8-C14;
A6-B8-C15;
A6-B8-C16;
A6-B8-C17;
A6-B8-C18;
A6-B8-C19;
A6-B8-C20;
A6-B8-C21;
A6-B8-C22;
A6-B8-C23;
A6-B8-C24;
A6-B8-C25;
A6-B8-C26;
A6-B8-C27;
A6-B8-C28;
A6-B8-C29;
A6-B8-C30;
A6-B8-C31;
A6-B8-C32;
A6-B8-C33;
A6-B8-C34;
A6-B8-C35;
A6-B8-C36;
A6-B8-C37;
A6-B8-C38;
A6-B8-C39;
A6-B8-C40;
A6-B8-C41;
A6-B8-C42;
A6-B8-C43;
A6-B8-C44;
A6-B8-C45;
A6-B8-C46;
A6-B8-C47;
A6-B8-C48;
A6-B8-C49;
A6-B8-C50;
A6-B8-C51;
A6-B8-C52;
A6-B8-C53;
A6-B8-C54;
A6-B8-C55;
A6-B8-C56;

A6-B8-C57;
A6-B8-C58;
A6-B8-C59;
A6-B8-C60;
A6-B8-C61;
A6-B8-C62;
A6-B8-C63;
A6-B8-C64;
A6-B8-C65;
A6-B8-C66;
A6-B8-C67;
A6-B8-C68;
A7-B8-C1;
A7-B8-C2;
A7-B8-C3;
A7-B8-C4;
A7-B8-C5;
A7-B8-C6;
A7-B8-C7;
A7-B8-C8;
A7-B8-C9;
A7-B8-C10;
A7-B8-C11;
A7-B8-C12;
A7-B8-C13;
A7-B8-C14;
A7-B8-C15;
A7-B8-C16;
A7-B8-C17;
A7-B8-C18;
A7-B8-C19;
A7-B8-C20;
A7-B8-C21;
A7-B8-C22;
A7-B8-C23;
A7-B8-C24;
A7-B8-C25;
A7-B8-C26;
A7-B8-C27;
A7-B8-C28;
A7-B8-C29;
A7-B8-C30;
A7-B8-C31;
A7-B8-C32;
A7-B8-C33;
A7-B8-C34;
A7-B8-C35;
A7-B8-C36;
A7-B8-C37;
A7-B8-C38;
A7-B8-C39;
A7-B8-C40;
A7-B8-C41;
A7-B8-C42;
A7-B8-C43;
A7-B8-C44;
A7-B8-C45;
A7-B8-C46;
A7-B8-C47;
A7-B8-C48;
A7-B8-C49;
A7-B8-C50;
A7-B8-C51;
A7-B8-C52;
A7-B8-C53;
A7-B8-C54;
A7-B8-C55;
A7-B8-C56;
A7-B8-C57;
A7-B8-C58;
A7-B8-C59;
A7-B8-C60;
A7-B8-C61;
A7-B8-C62;
A7-B8-C63;
A7-B8-C64;
A7-B8-C65;
A7-B8-C66;
A7-B8-C67;
A7-B8-C68;
A8-B8-C1;
A8-B8-C2;
A8-B8-C3;
A8-B8-C4;
A8-B8-C5;
A8-B8-C6;
A8-B8-C7;
A8-B8-C8;
A8-B8-C9;
A8-B8-C10;
A8-B8-C11;
A8-B8-C12;
A8-B8-C13;
A8-B8-C14;
A8-B8-C15;
A8-B8-C16;
A8-B8-C17;
A8-B8-C18;
A8-B8-C19;
A8-B8-C20;
A8-B8-C21;
A8-B8-C22;
A8-B8-C23;
A8-B8-C24;
A8-B8-C25;
A8-B8-C26;
A8-B8-C27;
A8-B8-C28;
A8-B8-C29;
A8-B8-C30;
A8-B8-C31;
A8-B8-C32;
A8-B8-C33;
A8-B8-C34;
A8-B8-C35;
A8-B8-C36;
A8-B8-C37;
A8-B8-C38;
A8-B8-C39;
A8-B8-C40;
A8-B8-C41;
A8-B8-C42;
A8-B8-C43;
A8-B8-C44;
A8-B8-C45;
A8-B8-C46;
A8-B8-C47;
A8-B8-C48;
A8-B8-C49;
A8-B8-C50;
A8-B8-C51;
A8-B8-C52;
A8-B8-C53;
A8-B8-C54;
A8-B8-C55;
A8-B8-C56;
A8-B8-C57;
A8-B8-C58;
A8-B8-C59;
A8-B8-C60;
A8-B8-C61;
A8-B8-C62;
A8-B8-C63;
A8-B8-C64;
A8-B8-C65;
A8-B8-C66;
A8-B8-C67;
A8-B8-C68;
A9-B8-C1;
A9-B8-C2;
A9-B8-C3;
A9-B8-C4;
A9-B8-C5;
A9-B8-C6;
A9-B8-C7;
A9-B8-C8;
A9-B8-C9;
A9-B8-C10;

A9-B8-C11;
A9-B8-C12;
A9-B8-C13;
A9-B8-C14;
A9-B8-C15;
A9-B8-C16;
A9-B8-C17;
A9-B8-C18;
A9-B8-C19;
A9-B8-C20;
A9-B8-C21;
A9-B8-C22;
A9-B8-C23;
A9-B8-C24;
A9-B8-C25;
A9-B8-C26;
A9-B8-C27;
A9-B8-C28;
A9-B8-C29;
A9-B8-C30;
A9-B8-C31;
A9-B8-C32;
A9-B8-C33;
A9-B8-C34;
A9-B8-C35;
A9-B8-C36;
A9-B8-C37;
A9-B8-C38;
A9-B8-C39;
A9-B8-C40;
A9-B8-C41;
A9-B8-C42;
A9-B8-C43;
A9-B8-C44;
A9-B8-C45;
A9-B8-C46;
A9-B8-C47;
A9-B8-C48;
A9-B8-C49;
A9-B8-C50;
A9-B8-C51;
A9-B8-C52;
A9-B8-C53;
A9-B8-C54;
A9-B8-C55;
A9-B8-C56;
A9-B8-C57;
A9-B8-C58;
A9-B8-C59;
A9-B8-C60;
A9-B8-C61;
A9-B8-C62;
A9-B8-C63;
A9-B8-C64;
A9-B8-C65;
A9-B8-C66;
A9-B8-C67;
A9-B8-C68;
A10-B8-C1;
A10-B8-C2;
A10-B8-C3;
A10-B8-C4;
A10-B8-C5;
A10-B8-C6;
A10-B8-C7;
A10-B8-C8;
A10-B8-C9;
A10-B8-C10;
A10-B8-C11;
A10-B8-C12;
A10-B8-C13;
A10-B8-C14;
A10-B8-C15;
A10-B8-C16;
A10-B8-C17;
A10-B8-C18;
A10-B8-C19;
A10-B8-C20;
A10-B8-C21;
A10-B8-C22;
A10-B8-C23;
A10-B8-C24;
A10-B8-C25;
A10-B8-C26;
A10-B8-C27;
A10-B8-C28;
A10-B8-C29;
A10-B8-C30;
A10-B8-C31;
A10-B8-C32;
A10-B8-C33;
A10-B8-C34;
A10-B8-C35;
A10-B8-C36;
A10-B8-C37;
A10-B8-C38;
A10-B8-C39;
A10-B8-C40;
A10-B8-C41;
A10-B8-C42;
A10-B8-C43;
A10-B8-C44;
A10-B8-C45;
A10-B8-C46;
A10-B8-C47;
A10-B8-C48;
A10-B8-C49;
A10-B8-C50;
A10-B8-C51;
A10-B8-C52;
A10-B8-C53;
A10-B8-C54;
A10-B8-C55;
A10-B8-C56;
A10-B8-C57;
A10-B8-C58;
A10-B8-C59;
A10-B8-C60;
A10-B8-C61;
A10-B8-C62;
A10-B8-C63;
A10-B8-C64;
A10-B8-C65;
A10-B8-C66;
A10-B8-C67;
A10-B8-C68;
A11-B8-C1;
A11-B8-C2;
A11-B8-C3;
A11-B8-C4;
A11-B8-C5;
A11-B8-C6;
A11-B8-C7;
A11-B8-C8;
A11-B8-C9;
A11-B8-C10;
A11-B8-C11;
A11-B8-C12;
A11-B8-C13;
A11-B8-C14;
A11-B8-C15;
A11-B8-C16;
A11-B8-C17;
A11-B8-C18;
A11-B8-C19;
A11-B8-C20;
A11-B8-C21;
A11-B8-C22;
A11-B8-C23;
A11-B8-C24;
A11-B8-C25;
A11-B8-C26;
A11-B8-C27;
A11-B8-C28;
A11-B8-C29;
A11-B8-C30;
A11-B8-C31;
A11-B8-C32;

A11-B8-C33;
A11-B8-C34;
A11-B8-C35;
A11-B8-C36;
A11-B8-C37;
A11-B8-C38;
A11-B8-C39;
A11-B8-C40;
A11-B8-C41;
A11-B8-C42;
A11-B8-C43;
A11-B8-C44;
A11-B8-C45;
A11-B8-C46;
A11-B8-C47;
A11-B8-C48;
A11-B8-C49;
A11-B8-C50;
A11-B8-C51;
A11-B8-C52;
A11-B8-C53;
A11-B8-C54;
A11-B8-C55;
A11-B8-C56;
A11-B8-C57;
A11-B8-C58;
A11-B8-C59;
A11-B8-C60;
A11-B8-C61;
A11-B8-C62;
A11-B8-C63;
A11-B8-C64;
A11-B8-C65;
A11-B8-C66;
A11-B8-C67;
A11-B8-C68;
A12-B8-C1;
A12-B8-C2;
A12-B8-C3;
A12-B8-C4;
A12-B8-C5;
A12-B8-C6;
A12-B8-C7;
A12-B8-C8;
A12-B8-C9;
A12-B8-C10;
A12-B8-C11;
A12-B8-C12;
A12-B8-C13;
A12-B8-C14;
A12-B8-C15;
A12-B8-C16;
A12-B8-C17;
A12-B8-C18;
A12-B8-C19;
A12-B8-C20;
A12-B8-C21;
A12-B8-C22;
A12-B8-C23;
A12-B8-C24;
A12-B8-C25;
A12-B8-C26;
A12-B8-C27;
A12-B8-C28;
A12-B8-C29;
A12-B8-C30;
A12-B8-C31;
A12-B8-C32;
A12-B8-C33;
A12-B8-C34;
A12-B8-C35;
A12-B8-C36;
A12-B8-C37;
A12-B8-C38;
A12-B8-C39;
A12-B8-C40;
A12-B8-C41;
A12-B8-C42;
A12-B8-C43;
A12-B8-C44;
A12-B8-C45;
A12-B8-C46;
A12-B8-C47;
A12-B8-C48;
A12-B8-C49;
A12-B8-C50;
A12-B8-C51;
A12-B8-C52;
A12-B8-C53;
A12-B8-C54;
A12-B8-C55;
A12-B8-C56;
A12-B8-C57;
A12-B8-C58;
A12-B8-C59;
A12-B8-C60;
A12-B8-C61;
A12-B8-C62;
A12-B8-C63;
A12-B8-C64;
A12-B8-C65;
A12-B8-C66;
A12-B8-C67;
A12-B8-C68;
A13-B8-C1;
A13-B8-C2;
A13-B8-C3;
A13-B8-C4;
A13-B8-C5;
A13-B8-C6;
A13-B8-C7;
A13-B8-C8;
A13-B8-C9;
A13-B8-C10;
A13-B8-C11;
A13-B8-C12;
A13-B8-C13;
A13-B8-C14;
A13-B8-C15;
A13-B8-C16;
A13-B8-C17;
A13-B8-C18;
A13-B8-C19;
A13-B8-C20;
A13-B8-C21;
A13-B8-C22;
A13-B8-C23;
A13-B8-C24;
A13-B8-C25;
A13-B8-C26;
A13-B8-C27;
A13-B8-C28;
A13-B8-C29;
A13-B8-C30;
A13-B8-C31;
A13-B8-C32;
A13-B8-C33;
A13-B8-C34;
A13-B8-C35;
A13-B8-C36;
A13-B8-C37;
A13-B8-C38;
A13-B8-C39;
A13-B8-C40;
A13-B8-C41;
A13-B8-C42;
A13-B8-C43;
A13-B8-C44;
A13-B8-C45;
A13-B8-C46;
A13-B8-C47;
A13-B8-C48;
A13-B8-C49;
A13-B8-C50;
A13-B8-C51;
A13-B8-C52;
A13-B8-C53;
A13-B8-C54;

A13-B8-C55;
A13-B8-C56;
A13-B8-C57;
A13-B8-C58;
A13-B8-C59;
A13-B8-C60;
A13-B8-C61;
A13-B8-C62;
A13-B8-C63;
A13-B8-C64;
A13-B8-C65;
A13-B8-C66;
A13-B8-C67;
A13-B8-C68;
A14-B8-C1;
A14-B8-C2;
A14-B8-C3;
A14-B8-C4;
A14-B8-C5;
A14-B8-C6;
A14-B8-C7;
A14-B8-C8;
A14-B8-C9;
A14-B8-C10;
A14-B8-C11;
A14-B8-C12;
A14-B8-C13;
A14-B8-C14;
A14-B8-C15;
A14-B8-C16;
A14-B8-C17;
A14-B8-C18;
A14-B8-C19;
A14-B8-C20;
A14-B8-C21;
A14-B8-C22;
A14-B8-C23;
A14-B8-C24;
A14-B8-C25;
A14-B8-C26;
A14-B8-C27;
A14-B8-C28;
A14-B8-C29;
A14-B8-C30;
A14-B8-C31;
A14-B8-C32;
A14-B8-C33;
A14-B8-C34;
A14-B8-C35;
A14-B8-C36;
A14-B8-C37;
A14-B8-C38;
A14-B8-C39;
A14-B8-C40;
A14-B8-C41;
A14-B8-C42;
A14-B8-C43;
A14-B8-C44;
A14-B8-C45;
A14-B8-C46;
A14-B8-C47;
A14-B8-C48;
A14-B8-C49;
A14-B8-C50;
A14-B8-C51;
A14-B8-C52;
A14-B8-C53;
A14-B8-C54;
A14-B8-C55;
A14-B8-C56;
A14-B8-C57;
A14-B8-C58;
A14-B8-C59;
A14-B8-C60;
A14-B8-C61;
A14-B8-C62;
A14-B8-C63;
A14-B8-C64;
A14-B8-C65;
A14-B8-C66;
A14-B8-C67;
A14-B8-C68;
A15-B8-C1;
A15-B8-C2;
A15-B8-C3;
A15-B8-C4;
A15-B8-C5;
A15-B8-C6;
A15-B8-C7;
A15-B8-C8;
A15-B8-C9;
A15-B8-C10;
A15-B8-C11;
A15-B8-C12;
A15-B8-C13;
A15-B8-C14;
A15-B8-C15;
A15-B8-C16;
A15-B8-C17;
A15-B8-C18;
A15-B8-C19;
A15-B8-C20;
A15-B8-C21;
A15-B8-C22;
A15-B8-C23;
A15-B8-C24;
A15-B8-C25;
A15-B8-C26;
A15-B8-C27;
A15-B8-C28;
A15-B8-C29;
A15-B8-C30;
A15-B8-C31;
A15-B8-C32;
A15-B8-C33;
A15-B8-C34;
A15-B8-C35;
A15-B8-C36;
A15-B8-C37;
A15-B8-C38;
A15-B8-C39;
A15-B8-C40;
A15-B8-C41;
A15-B8-C42;
A15-B8-C43;
A15-B8-C44;
A15-B8-C45;
A15-B8-C46;
A15-B8-C47;
A15-B8-C48;
A15-B8-C49;
A15-B8-C50;
A15-B8-C51;
A15-B8-C52;
A15-B8-C53;
A15-B8-C54;
A15-B8-C55;
A15-B8-C56;
A15-B8-C57;
A15-B8-C58;
A15-B8-C59;
A15-B8-C60;
A15-B8-C61;
A15-B8-C62;
A15-B8-C63;
A15-B8-C64;
A15-B8-C65;
A15-B8-C66;
A15-B8-C67;
A15-B8-C68;
A16-B8-C1;
A16-B8-C2;
A16-B8-C3;
A16-B8-C4;
A16-B8-C5;
A16-B8-C6;
A16-B8-C7;
A16-B8-C8;

A16-B8-C9;
A16-B8-C10;
A16-B8-C11;
A16-B8-C12;
A16-B8-C13;
A16-B8-C14;
A16-B8-C15;
A16-B8-C16;
A16-B8-C17;
A16-B8-C18;
A16-B8-C19;
A16-B8-C20;
A16-B8-C21;
A16-B8-C22;
A16-B8-C23;
A16-B8-C24;
A16-B8-C25;
A16-B8-C26;
A16-B8-C27;
A16-B8-C28;
A16-B8-C29;
A16-B8-C30;
A16-B8-C31;
A16-B8-C32;
A16-B8-C33;
A16-B8-C34;
A16-B8-C35;
A16-B8-C36;
A16-B8-C37;
A16-B8-C38;
A16-B8-C39;
A16-B8-C40;
A16-B8-C41;
A16-B8-C42;
A16-B8-C43;
A16-B8-C44;
A16-B8-C45;
A16-B8-C46;
A16-B8-C47;
A16-B8-C48;
A16-B8-C49;
A16-B8-C50;
A16-B8-C51;
A16-B8-C52;
A16-B8-C53;
A16-B8-C54;
A16-B8-C55;
A16-B8-C56;
A16-B8-C57;
A16-B8-C58;
A16-B8-C59;
A16-B8-C60;
A16-B8-C61;
A16-B8-C62;
A16-B8-C63;
A16-B8-C64;
A16-B8-C65;
A16-B8-C66;
A16-B8-C67;
A16-B8-C68;
A17-B8-C1;
A17-B8-C2;
A17-B8-C3;
A17-B8-C4;
A17-B8-C5;
A17-B8-C6;
A17-B8-C7;
A17-B8-C8;
A17-B8-C9;
A17-B8-C10;
A17-B8-C11;
A17-B8-C12;
A17-B8-C13;
A17-B8-C14;
A17-B8-C15;
A17-B8-C16;
A17-B8-C17;
A17-B8-C18;
A17-B8-C19;
A17-B8-C20;
A17-B8-C21;
A17-B8-C22;
A17-B8-C23;
A17-B8-C24;
A17-B8-C25;
A17-B8-C26;
A17-B8-C27;
A17-B8-C28;
A17-B8-C29;
A17-B8-C30;
A17-B8-C31;
A17-B8-C32;
A17-B8-C33;
A17-B8-C34;
A17-B8-C35;
A17-B8-C36;
A17-B8-C37;
A17-B8-C38;
A17-B8-C39;
A17-B8-C40;
A17-B8-C41;
A17-B8-C42;
A17-B8-C43;
A17-B8-C44;
A17-B8-C45;
A17-B8-C46;
A17-B8-C47;
A17-B8-C48;
A17-B8-C49;
A17-B8-C50;
A17-B8-C51;
A17-B8-C52;
A17-B8-C53;
A17-B8-C54;
A17-B8-C55;
A17-B8-C56;
A17-B8-C57;
A17-B8-C58;
A17-B8-C59;
A17-B8-C60;
A17-B8-C61;
A17-B8-C62;
A17-B8-C63;
A17-B8-C64;
A17-B8-C65;
A17-B8-C66;
A17-B8-C67;
A17-B8-C68;
A18-B8-C1;
A18-B8-C2;
A18-B8-C3;
A18-B8-C4;
A18-B8-C5;
A18-B8-C6;
A18-B8-C7;
A18-B8-C8;
A18-B8-C9;
A18-B8-C10;
A18-B8-C11;
A18-B8-C12;
A18-B8-C13;
A18-B8-C14;
A18-B8-C15;
A18-B8-C16;
A18-B8-C17;
A18-B8-C18;
A18-B8-C19;
A18-B8-C20;
A18-B8-C21;
A18-B8-C22;
A18-B8-C23;
A18-B8-C24;
A18-B8-C25;
A18-B8-C26;
A18-B8-C27;
A18-B8-C28;
A18-B8-C29;
A18-B8-C30;

A18-B8-C31;
A18-B8-C32;
A18-B8-C33;
A18-B8-C34;
A18-B8-C35;
A18-B8-C36;
A18-B8-C37;
A18-B8-C38;
A18-B8-C39;
A18-B8-C40;
A18-B8-C41;
A18-B8-C42;
A18-B8-C43;
A18-B8-C44;
A18-B8-C45;
A18-B8-C46;
A18-B8-C47;
A18-B8-C48;
A18-B8-C49;
A18-B8-C50;
A18-B8-C51;
A18-B8-C52;
A18-B8-C53;
A18-B8-C54;
A18-B8-C55;
A18-B8-C56;
A18-B8-C57;
A18-B8-C58;
A18-B8-C59;
A18-B8-C60;
A18-B8-C61;
A18-B8-C62;
A18-B8-C63;
A18-B8-C64;
A18-B8-C65;
A18-B8-C66;
A18-B8-C67;
A18-B8-C68;
A19-B8-C1;
A19-B8-C2;
A19-B8-C3;
A19-B8-C4;
A19-B8-C5;
A19-B8-C6;
A19-B8-C7;
A19-B8-C8;
A19-B8-C9;
A19-B8-C10;
A19-B8-C11;
A19-B8-C12;
A19-B8-C13;
A19-B8-C14;
A19-B8-C15;
A19-B8-C16;
A19-B8-C17;
A19-B8-C18;
A19-B8-C19;
A19-B8-C20;
A19-B8-C21;
A19-B8-C22;
A19-B8-C23;
A19-B8-C24;
A19-B8-C25;
A19-B8-C26;
A19-B8-C27;
A19-B8-C28;
A19-B8-C29;
A19-B8-C30;
A19-B8-C31;
A19-B8-C32;
A19-B8-C33;
A19-B8-C34;
A19-B8-C35;
A19-B8-C36;
A19-B8-C37;
A19-B8-C38;
A19-B8-C39;
A19-B8-C40;
A19-B8-C41;
A19-B8-C42;
A19-B8-C43;
A19-B8-C44;
A19-B8-C45;
A19-B8-C46;
A19-B8-C47;
A19-B8-C48;
A19-B8-C49;
A19-B8-C50;
A19-B8-C51;
A19-B8-C52;
A19-B8-C53;
A19-B8-C54;
A19-B8-C55;
A19-B8-C56;
A19-B8-C57;
A19-B8-C58;
A19-B8-C59;
A19-B8-C60;
A19-B8-C61;
A19-B8-C62;
A19-B8-C63;
A19-B8-C64;
A19-B8-C65;
A19-B8-C66;
A19-B8-C67;
A19-B8-C68;
A20-B8-C1;
A20-B8-C2;
A20-B8-C3;
A20-B8-C4;
A20-B8-C5;
A20-B8-C6;
A20-B8-C7;
A20-B8-C8;
A20-B8-C9;
A20-B8-C10;
A20-B8-C11;
A20-B8-C12;
A20-B8-C13;
A20-B8-C14;
A20-B8-C15;
A20-B8-C16;
A20-B8-C17;
A20-B8-C18;
A20-B8-C19;
A20-B8-C20;
A20-B8-C21;
A20-B8-C22;
A20-B8-C23;
A20-B8-C24;
A20-B8-C25;
A20-B8-C26;
A20-B8-C27;
A20-B8-C28;
A20-B8-C29;
A20-B8-C30;
A20-B8-C31;
A20-B8-C32;
A20-B8-C33;
A20-B8-C34;
A20-B8-C35;
A20-B8-C36;
A20-B8-C37;
A20-B8-C38;
A20-B8-C39;
A20-B8-C40;
A20-B8-C41;
A20-B8-C42;
A20-B8-C43;
A20-B8-C44;
A20-B8-C45;
A20-B8-C46;
A20-B8-C47;
A20-B8-C48;
A20-B8-C49;
A20-B8-C50;
A20-B8-C51;
A20-B8-C52;

A20-B8-C53;
A20-B8-C54;
A20-B8-C55;
A20-B8-C56;
A20-B8-C57;
A20-B8-C58;
A20-B8-C59;
A20-B8-C60;
A20-B8-C61;
A20-B8-C62;
A20-B8-C63;
A20-B8-C64;
A20-B8-C65;
A20-B8-C66;
A20-B8-C67;
A20-B8-C68;
A21-B8-C1;
A21-B8-C2;
A21-B8-C3;
A21-B8-C4;
A21-B8-C5;
A21-B8-C6;
A21-B8-C7;
A21-B8-C8;
A21-B8-C9;
A21-B8-C10;
A21-B8-C11;
A21-B8-C12;
A21-B8-C13;
A21-B8-C14;
A21-B8-C15;
A21-B8-C16;
A21-B8-C17;
A21-B8-C18;
A21-B8-C19;
A21-B8-C20;
A21-B8-C21;
A21-B8-C22;
A21-B8-C23;
A21-B8-C24;
A21-B8-C25;
A21-B8-C26;
A21-B8-C27;
A21-B8-C28;
A21-B8-C29;
A21-B8-C30;
A21-B8-C31;
A21-B8-C32;
A21-B8-C33;
A21-B8-C34;
A21-B8-C35;
A21-B8-C36;
A21-B8-C37;
A21-B8-C38;
A21-B8-C39;
A21-B8-C40;
A21-B8-C41;
A21-B8-C42;
A21-B8-C43;
A21-B8-C44;
A21-B8-C45;
A21-B8-C46;
A21-B8-C47;
A21-B8-C48;
A21-B8-C49;
A21-B8-C50;
A21-B8-C51;
A21-B8-C52;
A21-B8-C53;
A21-B8-C54;
A21-B8-C55;
A21-B8-C56;
A21-B8-C57;
A21-B8-C58;
A21-B8-C59;
A21-B8-C60;
A21-B8-C61;
A21-B8-C62;
A21-B8-C63;
A21-B8-C64;
A21-B8-C65;
A21-B8-C66;
A21-B8-C67;
A21-B8-C68;
A22-B8-C1;
A22-B8-C2;
A22-B8-C3;
A22-B8-C4;
A22-B8-C5;
A22-B8-C6;
A22-B8-C7;
A22-B8-C8;
A22-B8-C9;
A22-B8-C10;
A22-B8-C11;
A22-B8-C12;
A22-B8-C13;
A22-B8-C14;
A22-B8-C15;
A22-B8-C16;
A22-B8-C17;
A22-B8-C18;
A22-B8-C19;
A22-B8-C20;
A22-B8-C21;
A22-B8-C22;
A22-B8-C23;
A22-B8-C24;
A22-B8-C25;
A22-B8-C26;
A22-B8-C27;
A22-B8-C28;
A22-B8-C29;
A22-B8-C30;
A22-B8-C31;
A22-B8-C32;
A22-B8-C33;
A22-B8-C34;
A22-B8-C35;
A22-B8-C36;
A22-B8-C37;
A22-B8-C38;
A22-B8-C39;
A22-B8-C40;
A22-B8-C41;
A22-B8-C42;
A22-B8-C43;
A22-B8-C44;
A22-B8-C45;
A22-B8-C46;
A22-B8-C47;
A22-B8-C48;
A22-B8-C49;
A22-B8-C50;
A22-B8-C51;
A22-B8-C52;
A22-B8-C53;
A22-B8-C54;
A22-B8-C55;
A22-B8-C56;
A22-B8-C57;
A22-B8-C58;
A22-B8-C59;
A22-B8-C60;
A22-B8-C61;
A22-B8-C62;
A22-B8-C63;
A22-B8-C64;
A22-B8-C65;
A22-B8-C66;
A22-B8-C67;
A22-B8-C68;
A23-B8-C1;
A23-B8-C2;
A23-B8-C3;
A23-B8-C4;
A23-B8-C5;
A23-B8-C6;

A23-B8-C7;
A23-B8-C8;
A23-B8-C9;
A23-B8-C10;
A23-B8-C11;
A23-B8-C12;
A23-B8-C13;
A23-B8-C14;
A23-B8-C15;
A23-B8-C16;
A23-B8-C17;
A23-B8-C18;
A23-B8-C19;
A23-B8-C20;
A23-B8-C21;
A23-B8-C22;
A23-B8-C23;
A23-B8-C24;
A23-B8-C25;
A23-B8-C26;
A23-B8-C27;
A23-B8-C28;
A23-B8-C29;
A23-B8-C30;
A23-B8-C31;
A23-B8-C32;
A23-B8-C33;
A23-B8-C34;
A23-B8-C35;
A23-B8-C36;
A23-B8-C37;
A23-B8-C38;
A23-B8-C39;
A23-B8-C40;
A23-B8-C41;
A23-B8-C42;
A23-B8-C43;
A23-B8-C44;
A23-B8-C45;
A23-B8-C46;
A23-B8-C47;
A23-B8-C48;
A23-B8-C49;
A23-B8-C50;
A23-B8-C51;
A23-B8-C52;
A23-B8-C53;
A23-B8-C54;
A23-B8-C55;
A23-B8-C56;
A23-B8-C57;
A23-B8-C58;
A23-B8-C59;
A23-B8-C60;
A23-B8-C61;
A23-B8-C62;
A23-B8-C63;
A23-B8-C64;
A23-B8-C65;
A23-B8-C66;
A23-B8-C67;
A23-B8-C68;
A24-B8-C1;
A24-B8-C2;
A24-B8-C3;
A24-B8-C4;
A24-B8-C5;
A24-B8-C6;
A24-B8-C7;
A24-B8-C8;
A24-B8-C9;
A24-B8-C10;
A24-B8-C11;
A24-B8-C12;
A24-B8-C13;
A24-B8-C14;
A24-B8-C15;
A24-B8-C16;
A24-B8-C17;
A24-B8-C18;
A24-B8-C19;
A24-B8-C20;
A24-B8-C21;
A24-B8-C22;
A24-B8-C23;
A24-B8-C24;
A24-B8-C25;
A24-B8-C26;
A24-B8-C27;
A24-B8-C28;
A24-B8-C29;
A24-B8-C30;
A24-B8-C31;
A24-B8-C32;
A24-B8-C33;
A24-B8-C34;
A24-B8-C35;
A24-B8-C36;
A24-B8-C37;
A24-B8-C38;
A24-B8-C39;
A24-B8-C40;
A24-B8-C41;
A24-B8-C42;
A24-B8-C43;
A24-B8-C44;
A24-B8-C45;
A24-B8-C46;
A24-B8-C47;
A24-B8-C48;
A24-B8-C49;
A24-B8-C50;
A24-B8-C51;
A24-B8-C52;
A24-B8-C53;
A24-B8-C54;
A24-B8-C55;
A24-B8-C56;
A24-B8-C57;
A24-B8-C58;
A24-B8-C59;
A24-B8-C60;
A24-B8-C61;
A24-B8-C62;
A24-B8-C63;
A24-B8-C64;
A24-B8-C65;
A24-B8-C66;
A24-B8-C67;
A24-B8-C68;
A25-B8-C1;
A25-B8-C2;
A25-B8-C3;
A25-B8-C4;
A25-B8-C5;
A25-B8-C6;
A25-B8-C7;
A25-B8-C8;
A25-B8-C9;
A25-B8-C10;
A25-B8-C11;
A25-B8-C12;
A25-B8-C13;
A25-B8-C14;
A25-B8-C15;
A25-B8-C16;
A25-B8-C17;
A25-B8-C18;
A25-B8-C19;
A25-B8-C20;
A25-B8-C21;
A25-B8-C22;
A25-B8-C23;
A25-B8-C24;
A25-B8-C25;
A25-B8-C26;
A25-B8-C27;
A25-B8-C28;

A25-B8-C29;
A25-B8-C30;
A25-B8-C31;
A25-B8-C32;
A25-B8-C33;
A25-B8-C34;
A25-B8-C35;
A25-B8-C36;
A25-B8-C37;
A25-B8-C38;
A25-B8-C39;
A25-B8-C40;
A25-B8-C41;
A25-B8-C42;
A25-B8-C43;
A25-B8-C44;
A25-B8-C45;
A25-B8-C46;
A25-B8-C47;
A25-B8-C48;
A25-B8-C49;
A25-B8-C50;
A25-B8-C51;
A25-B8-C52;
A25-B8-C53;
A25-B8-C54;
A25-B8-C55;
A25-B8-C56;
A25-B8-C57;
A25-B8-C58;
A25-B8-C59;
A25-B8-C60;
A25-B8-C61;
A25-B8-C62;
A25-B8-C63;
A25-B8-C64;
A25-B8-C65;
A25-B8-C66;
A25-B8-C67;
A25-B8-C68;
A26-B8-C1;
A26-B8-C2;
A26-B8-C3;
A26-B8-C4;
A26-B8-C5;
A26-B8-C6;
A26-B8-C7;
A26-B8-C8;
A26-B8-C9;
A26-B8-C10;
A26-B8-C11;
A26-B8-C12;
A26-B8-C13;
A26-B8-C14;
A26-B8-C15;
A26-B8-C16;
A26-B8-C17;
A26-B8-C18;
A26-B8-C19;
A26-B8-C20;
A26-B8-C21;
A26-B8-C22;
A26-B8-C23;
A26-B8-C24;
A26-B8-C25;
A26-B8-C26;
A26-B8-C27;
A26-B8-C28;
A26-B8-C29;
A26-B8-C30;
A26-B8-C31;
A26-B8-C32;
A26-B8-C33;
A26-B8-C34;
A26-B8-C35;
A26-B8-C36;
A26-B8-C37;
A26-B8-C38;
A26-B8-C39;
A26-B8-C40;
A26-B8-C41;
A26-B8-C42;
A26-B8-C43;
A26-B8-C44;
A26-B8-C45;
A26-B8-C46;
A26-B8-C47;
A26-B8-C48;
A26-B8-C49;
A26-B8-C50;
A26-B8-C51;
A26-B8-C52;
A26-B8-C53;
A26-B8-C54;
A26-B8-C55;
A26-B8-C56;
A26-B8-C57;
A26-B8-C58;
A26-B8-C59;
A26-B8-C60;
A26-B8-C61;
A26-B8-C62;
A26-B8-C63;
A26-B8-C64;
A26-B8-C65;
A26-B8-C66;
A26-B8-C67;
A26-B8-C68;
A27-B8-C1;
A27-B8-C2;
A27-B8-C3;
A27-B8-C4;
A27-B8-C5;
A27-B8-C6;
A27-B8-C7;
A27-B8-C8;
A27-B8-C9;
A27-B8-C10;
A27-B8-C11;
A27-B8-C12;
A27-B8-C13;
A27-B8-C14;
A27-B8-C15;
A27-B8-C16;
A27-B8-C17;
A27-B8-C18;
A27-B8-C19;
A27-B8-C20;
A27-B8-C21;
A27-B8-C22;
A27-B8-C23;
A27-B8-C24;
A27-B8-C25;
A27-B8-C26;
A27-B8-C27;
A27-B8-C28;
A27-B8-C29;
A27-B8-C30;
A27-B8-C31;
A27-B8-C32;
A27-B8-C33;
A27-B8-C34;
A27-B8-C35;
A27-B8-C36;
A27-B8-C37;
A27-B8-C38;
A27-B8-C39;
A27-B8-C40;
A27-B8-C41;
A27-B8-C42;
A27-B8-C43;
A27-B8-C44;
A27-B8-C45;
A27-B8-C46;
A27-B8-C47;
A27-B8-C48;
A27-B8-C49;
A27-B8-C50;

-continued

A27-B8-C51;
A27-B8-C52;
A27-B8-C53;
A27-B8-C54;
A27-B8-C55;
A27-B8-C56;
A27-B8-C57;
A27-B8-C58;
A27-B8-C59;
A27-B8-C60;
A27-B8-C61;
A27-B8-C62;
A27-B8-C63;
A27-B8-C64;
A27-B8-C65;
A27-B8-C66;
A27-B8-C67;
A27-B8-C68;
A28-B8-C1;
A28-B8-C2;
A28-B8-C3;
A28-B8-C4;
A28-B8-C5;
A28-B8-C6;
A28-B8-C7;
A28-B8-C8;
A28-B8-C9;
A28-B8-C10;
A28-B8-C11;
A28-B8-C12;
A28-B8-C13;
A28-B8-C14;
A28-B8-C15;
A28-B8-C16;
A28-B8-C17;
A28-B8-C18;
A28-B8-C19;
A28-B8-C20;
A28-B8-C21;
A28-B8-C22;
A28-B8-C23;
A28-B8-C24;
A28-B8-C25;
A28-B8-C26;
A28-B8-C27;
A28-B8-C28;
A28-B8-C29;
A28-B8-C30;
A28-B8-C31;
A28-B8-C32;
A28-B8-C33;
A28-B8-C34;
A28-B8-C35;
A28-B8-C36;
A28-B8-C37;
A28-B8-C38;
A28-B8-C39;
A28-B8-C40;
A28-B8-C41;
A28-B8-C42;
A28-B8-C43;
A28-B8-C44;
A28-B8-C45;
A28-B8-C46;
A28-B8-C47;
A28-B8-C48;
A28-B8-C49;
A28-B8-C50;
A28-B8-C51;
A28-B8-C52;
A28-B8-C53;
A28-B8-C54;
A28-B8-C55;
A28-B8-C56;
A28-B8-C57;
A28-B8-C58;
A28-B8-C59;
A28-B8-C60;
A28-B8-C61;

-continued

A28-B8-C62;
A28-B8-C63;
A28-B8-C64;
A28-B8-C65;
A28-B8-C66;
A28-B8-C67;
A28-B8-C68;
A29-B8-C1;
A29-B8-C2;
A29-B8-C3;
A29-B8-C4;
A29-B8-C5;
A29-B8-C6;
A29-B8-C7;
A29-B8-C8;
A29-B8-C9;
A29-B8-C10;
A29-B8-C11;
A29-B8-C12;
A29-B8-C13;
A29-B8-C14;
A29-B8-C15;
A29-B8-C16;
A29-B8-C17;
A29-B8-C18;
A29-B8-C19;
A29-B8-C20;
A29-B8-C21;
A29-B8-C22;
A29-B8-C23;
A29-B8-C24;
A29-B8-C25;
A29-B8-C26;
A29-B8-C27;
A29-B8-C28;
A29-B8-C29;
A29-B8-C30;
A29-B8-C31;
A29-B8-C32;
A29-B8-C33;
A29-B8-C34;
A29-B8-C35;
A29-B8-C36;
A29-B8-C37;
A29-B8-C38;
A29-B8-C39;
A29-B8-C40;
A29-B8-C41;
A29-B8-C42;
A29-B8-C43;
A29-B8-C44;
A29-B8-C45;
A29-B8-C46;
A29-B8-C47;
A29-B8-C48;
A29-B8-C49;
A29-B8-C50;
A29-B8-C51;
A29-B8-C52;
A29-B8-C53;
A29-B8-C54;
A29-B8-C55;
A29-B8-C56;
A29-B8-C57;
A29-B8-C58;
A29-B8-C59;
A29-B8-C60;
A29-B8-C61;
A29-B8-C62;
A29-B8-C63;
A29-B8-C64;
A29-B8-C65;
A29-B8-C66;
A29-B8-C67;
A29-B8-C68;
A30-B8-C1;
A30-B8-C2;
A30-B8-C3;
A30-B8-C4;

-continued

A30-B8-C5;
A30-B8-C6;
A30-B8-C7;
A30-B8-C8;
A30-B8-C9;
A30-B8-C10;
A30-B8-C11;
A30-B8-C12;
A30-B8-C13;
A30-B8-C14;
A30-B8-C15;
A30-B8-C16;
A30-B8-C17;
A30-B8-C18;
A30-B8-C19;
A30-B8-C20;
A30-B8-C21;
A30-B8-C22;
A30-B8-C23;
A30-B8-C24;
A30-B8-C25;
A30-B8-C26;
A30-B8-C27;
A30-B8-C28;
A30-B8-C29;
A30-B8-C30;
A30-B8-C31;
A30-B8-C32;
A30-B8-C33;
A30-B8-C34;
A30-B8-C35;
A30-B8-C36;
A30-B8-C37;
A30-B8-C38;
A30-B8-C39;
A30-B8-C40;
A30-B8-C41;
A30-B8-C42;
A30-B8-C43;
A30-B8-C44;
A30-B8-C45;
A30-B8-C46;
A30-B8-C47;
A30-B8-C48;
A30-B8-C49;
A30-B8-C50;
A30-B8-C51;
A30-B8-C52;
A30-B8-C53;
A30-B8-C54;
A30-B8-C55;
A30-B8-C56;
A30-B8-C57;
A30-B8-C58;
A30-B8-C59;
A30-B8-C60;
A30-B8-C61;
A30-B8-C62;
A30-B8-C63;
A30-B8-C64;
A30-B8-C65;
A30-B8-C66;
A30-B8-C67;
A30-B8-C68;
A31-B8-C1;
A31-B8-C2;
A31-B8-C3;
A31-B8-C4;
A31-B8-C5;
A31-B8-C6;
A31-B8-C7;
A31-B8-C8;
A31-B8-C9;
A31-B8-C10;
A31-B8-C11;
A31-B8-C12;
A31-B8-C13;
A31-B8-C14;
A31-B8-C15;

-continued

A31-B8-C16;
A31-B8-C17;
A31-B8-C18;
A31-B8-C19;
A31-B8-C20;
A31-B8-C21;
A31-B8-C22;
A31-B8-C23;
A31-B8-C24;
A31-B8-C25;
A31-B8-C26;
A31-B8-C27;
A31-B8-C28;
A31-B8-C29;
A31-B8-C30;
A31-B8-C31;
A31-B8-C32;
A31-B8-C33;
A31-B8-C34;
A31-B8-C35;
A31-B8-C36;
A31-B8-C37;
A31-B8-C38;
A31-B8-C39;
A31-B8-C40;
A31-B8-C41;
A31-B8-C42;
A31-B8-C43;
A31-B8-C44;
A31-B8-C45;
A31-B8-C46;
A31-B8-C47;
A31-B8-C48;
A31-B8-C49;
A31-B8-C50;
A31-B8-C51;
A31-B8-C52;
A31-B8-C53;
A31-B8-C54;
A31-B8-C55;
A31-B8-C56;
A31-B8-C57;
A31-B8-C58;
A31-B8-C59;
A31-B8-C60;
A31-B8-C61;
A31-B8-C62;
A31-B8-C63;
A31-B8-C64;
A31-B8-C65;
A31-B8-C66;
A31-B8-C67;
A31-B8-C68;
A32-B8-C1;
A32-B8-C2;
A32-B8-C3;
A32-B8-C4;
A32-B8-C5;
A32-B8-C6;
A32-B8-C7;
A32-B8-C8;
A32-B8-C9;
A32-B8-C10;
A32-B8-C11;
A32-B8-C12;
A32-B8-C13;
A32-B8-C14;
A32-B8-C15;
A32-B8-C16;
A32-B8-C17;
A32-B8-C18;
A32-B8-C19;
A32-B8-C20;
A32-B8-C21;
A32-B8-C22;
A32-B8-C23;
A32-B8-C24;
A32-B8-C25;
A32-B8-C26;

-continued

A32-B8-C27;
A32-B8-C28;
A32-B8-C29;
A32-B8-C30;
A32-B8-C31;
A32-B8-C32;
A32-B8-C33;
A32-B8-C34;
A32-B8-C35;
A32-B8-C36;
A32-B8-C37;
A32-B8-C38;
A32-B8-C39;
A32-B8-C40;
A32-B8-C41;
A32-B8-C42;
A32-B8-C43;
A32-B8-C44;
A32-B8-C45;
A32-B8-C46;
A32-B8-C47;
A32-B8-C48;
A32-B8-C49;
A32-B8-C50;
A32-B8-C51;
A32-B8-C52;
A32-B8-C53;
A32-B8-C54;
A32-B8-C55;
A32-B8-C56;
A32-B8-C57;
A32-B8-C58;
A32-B8-C59;
A32-B8-C60;
A32-B8-C61;
A32-B8-C62;
A32-B8-C63;
A32-B8-C64;
A32-B8-C65;
A32-B8-C66;
A32-B8-C67;
A32-B8-C68;
A33-B8-C1;
A33-B8-C2;
A33-B8-C3;
A33-B8-C4;
A33-B8-C5;
A33-B8-C6;
A33-B8-C7;
A33-B8-C8;
A33-B8-C9;
A33-B8-C10;
A33-B8-C11;
A33-B8-C12;
A33-B8-C13;
A33-B8-C14;
A33-B8-C15;
A33-B8-C16;
A33-B8-C17;
A33-B8-C18;
A33-B8-C19;
A33-B8-C20;
A33-B8-C21;
A33-B8-C22;
A33-B8-C23;
A33-B8-C24;
A33-B8-C25;
A33-B8-C26;
A33-B8-C27;
A33-B8-C28;
A33-B8-C29;
A33-B8-C30;
A33-B8-C31;
A33-B8-C32;
A33-B8-C33;
A33-B8-C34;
A33-B8-C35;
A33-B8-C36;
A33-B8-C37;

-continued

A33-B8-C38;
A33-B8-C39;
A33-B8-C40;
A33-B8-C41;
A33-B8-C42;
A33-B8-C43;
A33-B8-C44;
A33-B8-C45;
A33-B8-C46;
A33-B8-C47;
A33-B8-C48;
A33-B8-C49;
A33-B8-C50;
A33-B8-C51;
A33-B8-C52;
A33-B8-C53;
A33-B8-C54;
A33-B8-C55;
A33-B8-C56;
A33-B8-C57;
A33-B8-C58;
A33-B8-C59;
A33-B8-C60;
A33-B8-C61;
A33-B8-C62;
A33-B8-C63;
A33-B8-C64;
A33-B8-C65;
A33-B8-C66;
A33-B8-C67;
A33-B8-C68;
A34-B8-C1;
A34-B8-C2;
A34-B8-C3;
A34-B8-C4;
A34-B8-C5;
A34-B8-C6;
A34-B8-C7;
A34-B8-C8;
A34-B8-C9;
A34-B8-C10;
A34-B8-C11;
A34-B8-C12;
A34-B8-C13;
A34-B8-C14;
A34-B8-C15;
A34-B8-C16;
A34-B8-C17;
A34-B8-C18;
A34-B8-C19;
A34-B8-C20;
A34-B8-C21;
A34-B8-C22;
A34-B8-C23;
A34-B8-C24;
A34-B8-C25;
A34-B8-C26;
A34-B8-C27;
A34-B8-C28;
A34-B8-C29;
A34-B8-C30;
A34-B8-C31;
A34-B8-C32;
A34-B8-C33;
A34-B8-C34;
A34-B8-C35;
A34-B8-C36;
A34-B8-C37;
A34-B8-C38;
A34-B8-C39;
A34-B8-C40;
A34-B8-C41;
A34-B8-C42;
A34-B8-C43;
A34-B8-C44;
A34-B8-C45;
A34-B8-C46;
A34-B8-C47;
A34-B8-C48;

-continued

A34-B8-C49;
A34-B8-C50;
A34-B8-C51;
A34-B8-C52;
A34-B8-C53;
A34-B8-C54;
A34-B8-C55;
A34-B8-C56;
A34-B8-C57;
A34-B8-C58;
A34-B8-C59;
A34-B8-C60;
A34-B8-C61;
A34-B8-C62;
A34-B8-C63;
A34-B8-C64;
A34-B8-C65;
A34-B8-C66;
A34-B8-C67;
A34-B8-C68;
A35-B8-C1;
A35-B8-C2;
A35-B8-C3;
A35-B8-C4;
A35-B8-C5;
A35-B8-C6;
A35-B8-C7;
A35-B8-C8;
A35-B8-C9;
A35-B8-C10;
A35-B8-C11;
A35-B8-C12;
A35-B8-C13;
A35-B8-C14;
A35-B8-C15;
A35-B8-C16;
A35-B8-C17;
A35-B8-C18;
A35-B8-C19;
A35-B8-C20;
A35-B8-C21;
A35-B8-C22;
A35-B8-C23;
A35-B8-C24;
A35-B8-C25;
A35-B8-C26;
A35-B8-C27;
A35-B8-C28;
A35-B8-C29;
A35-B8-C30;
A35-B8-C31;
A35-B8-C32;
A35-B8-C33;
A35-B8-C34;
A35-B8-C35;
A35-B8-C36;
A35-B8-C37;
A35-B8-C38;
A35-B8-C39;
A35-B8-C40;
A35-B8-C41;
A35-B8-C42;
A35-B8-C43;
A35-B8-C44;
A35-B8-C45;
A35-B8-C46;
A35-B8-C47;
A35-B8-C48;
A35-B8-C49;
A35-B8-C50;
A35-B8-C51;
A35-B8-C52;
A35-B8-C53;
A35-B8-C54;
A35-B8-C55;
A35-B8-C56;
A35-B8-C57;
A35-B8-C58;
A35-B8-C59;

-continued

A35-B8-C60;
A35-B8-C61;
A35-B8-C62;
A35-B8-C63;
A35-B8-C64;
A35-B8-C65;
A35-B8-C66;
A35-B8-C67;
A35-B8-C68;
A36-B8-C1;
A36-B8-C2;
A36-B8-C3;
A36-B8-C4;
A36-B8-C5;
A36-B8-C6;
A36-B8-C7;
A36-B8-C8;
A36-B8-C9;
A36-B8-C10;
A36-B8-C11;
A36-B8-C12;
A36-B8-C13;
A36-B8-C14;
A36-B8-C15;
A36-B8-C16;
A36-B8-C17;
A36-B8-C18;
A36-B8-C19;
A36-B8-C20;
A36-B8-C21;
A36-B8-C22;
A36-B8-C23;
A36-B8-C24;
A36-B8-C25;
A36-B8-C26;
A36-B8-C27;
A36-B8-C28;
A36-B8-C29;
A36-B8-C30;
A36-B8-C31;
A36-B8-C32;
A36-B8-C33;
A36-B8-C34;
A36-B8-C35;
A36-B8-C36;
A36-B8-C37;
A36-B8-C38;
A36-B8-C39;
A36-B8-C40;
A36-B8-C41;
A36-B8-C42;
A36-B8-C43;
A36-B8-C44;
A36-B8-C45;
A36-B8-C46;
A36-B8-C47;
A36-B8-C48;
A36-B8-C49;
A36-B8-C50;
A36-B8-C51;
A36-B8-C52;
A36-B8-C53;
A36-B8-C54;
A36-B8-C55;
A36-B8-C56;
A36-B8-C57;
A36-B8-C58;
A36-B8-C59;
A36-B8-C60;
A36-B8-C61;
A36-B8-C62;
A36-B8-C63;
A36-B8-C64;
A36-B8-C65;
A36-B8-C66;
A36-B8-C67;
A36-B8-C68;
A37-B8-C1;
A37-B8-C2;

-continued

A37-B8-C3;
A37-B8-C4;
A37-B8-C5;
A37-B8-C6;
A37-B8-C7;
A37-B8-C8;
A37-B8-C9;
A37-B8-C10;
A37-B8-C11;
A37-B8-C12;
A37-B8-C13;
A37-B8-C14;
A37-B8-C15;
A37-B8-C16;
A37-B8-C17;
A37-B8-C18;
A37-B8-C19;
A37-B8-C20;
A37-B8-C21;
A37-B8-C22;
A37-B8-C23;
A37-B8-C24;
A37-B8-C25;
A37-B8-C26;
A37-B8-C27;
A37-B8-C28;
A37-B8-C29;
A37-B8-C30;
A37-B8-C31;
A37-B8-C32;
A37-B8-C33;
A37-B8-C34;
A37-B8-C35;
A37-B8-C36;
A37-B8-C37;
A37-B8-C38;
A37-B8-C39;
A37-B8-C40;
A37-B8-C41;
A37-B8-C42;
A37-B8-C43;
A37-B8-C44;
A37-B8-C45;
A37-B8-C46;
A37-B8-C47;
A37-B8-C48;
A37-B8-C49;
A37-B8-C50;
A37-B8-C51;
A37-B8-C52;
A37-B8-C53;
A37-B8-C54;
A37-B8-C55;
A37-B8-C56;
A37-B8-C57;
A37-B8-C58;
A37-B8-C59;
A37-B8-C60;
A37-B8-C61;
A37-B8-C62;
A37-B8-C63;
A37-B8-C64;
A37-B8-C65;
A37-B8-C66;
A37-B8-C67;
A37-B8-C68;
A38-B8-C1;
A38-B8-C2;
A38-B8-C3;
A38-B8-C4;
A38-B8-C5;
A38-B8-C6;
A38-B8-C7;
A38-B8-C8;
A38-B8-C9;
A38-B8-C10;
A38-B8-C11;
A38-B8-C12;
A38-B8-C13;
A38-B8-C14;
A38-B8-C15;
A38-B8-C16;
A38-B8-C17;
A38-B8-C18;
A38-B8-C19;
A38-B8-C20;
A38-B8-C21;
A38-B8-C22;
A38-B8-C23;
A38-B8-C24;
A38-B8-C25;
A38-B8-C26;
A38-B8-C27;
A38-B8-C28;
A38-B8-C29;
A38-B8-C30;
A38-B8-C31;
A38-B8-C32;
A38-B8-C33;
A38-B8-C34;
A38-B8-C35;
A38-B8-C36;
A38-B8-C37;
A38-B8-C38;
A38-B8-C39;
A38-B8-C40;
A38-B8-C41;
A38-B8-C42;
A38-B8-C43;
A38-B8-C44;
A38-B8-C45;
A38-B8-C46;
A38-B8-C47;
A38-B8-C48;
A38-B8-C49;
A38-B8-C50;
A38-B8-C51;
A38-B8-C52;
A38-B8-C53;
A38-B8-C54;
A38-B8-C55;
A38-B8-C56;
A38-B8-C57;
A38-B8-C58;
A38-B8-C59;
A38-B8-C60;
A38-B8-C61;
A38-B8-C62;
A38-B8-C63;
A38-B8-C64;
A38-B8-C65;
A38-B8-C66;
A38-B8-C67;
A38-B8-C68.

Thus, for example, in the above list the compound denoted as A1-B1-C1 is the product of the combination of group A1 in Table 1 and B1 in Table 2 and C1 in Table 3, namely

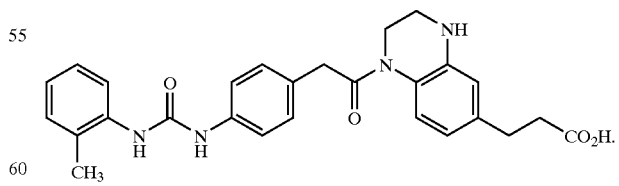

Preferred compounds of the invention are:
3-(1-{[3-methoxy-4-(3-o-tolyl-ureido)-phenyl]-acetyl}-1,2,3,4-tetrahydro-quinoxalin-6-yl)-propionic acid;
3-(1-{[3-methoxy-4-(3-o-tolyl-ureido)-phenyl]-acetyl}-1,2,3,4-tetrahydro-quinoxalin-6-yl)-butyric acid;

3-(4-acetyl-1-{[3-methoxy-4-(3-o-tolyl-ureido)-phenyl]-acetyl}-1,2,3,4tetrahydro-quinoxalin-6-yl)-propionic acid;

3-(4-benzoyl-1-{[3-methoxy-4-(3-o-tolyl-ureido)-phenyl]-acetyl}-1,2,3,4-tetrahydro-quinoxalin-6-yl)-propionic acid;

4-(7-(2-carboxyethyl)-4-{[3-methoxy-4-(3-o-tolyl-ureido)-phenyl]-acetyl}-3,4-dihydro-2H-quinoxalin-1-yl)-4-oxo-butyric acid;

3-(4-(3-dimethylamino-propionyl)-1-{[3-methoxy-4-(3-o-tolyl-ureido)-phenyl]-acetyl}-1,2,3,4-tetrahydro-quinoxalin-6-yl)-propionic acid;

7-(2-carboxy-ethyl)-4-{[3-methoxy-4-(3-o-tolyl-ureido)-phenyl]-acetyl}-3,4-dihydro-2H-quinoxaline-1-carboxylic acid tert-butyl ester;

3-(4-{[3-methoxy-4-(3-o-tolyl-ureido)-phenyl]-acetyl}-3,4-dihydro-2H-benzo[1,4]oxazin-7-yl)-5-methyl-hexanoic acid;

3-(4-{[3-methoxy-4-(3-o-tolyl-ureido)-phenyl]-acetyl}-3,4-dihydro-2H-benzo[1,4]oxazin-7-yl)-3-phenylpropanoic acid;

3-(4-{[3-methoxy-4-(3-o-tolyl-ureido)-phenyl]-acetyl}-3,4-dihydro-2H-benzo[1,4]oxazin-7-yl)-3-o-tolylpropanoic acid;

3-(4-{[3-methoxy-4-(3-o-tolyl-ureido)-phenyl]-acetyl}-3,4-dihydro-2H-benzo[1,4]oxazin-7-yl)-butanoic acid;

3-(4-{[3-methoxy-4-(3-o-tolyl-ureido)-phenyl]-acetyl}-3,4-dihydro-2H-benzo[1,4]oxazin-7-yl)-4-methylpentanoic acid;

3-(4-benzoyl-1-{[3-methoxy-4-(3-o-tolyl-ureido)-phenyl]-acetyl-}1,2,3,4-tetrahydro-quinoxalin-6-yl)-butyric acid;

and the corresponding N-oxides, and their prodrugs; and pharmaceutically acceptable salts and solvates (e.g. hydrates) of such compounds and their N-oxides and prodrugs.

Especially preferred compounds of the invention are:

3-(1-{[3-methoxy-4-(3-[2-methylphenyl]-ureido)-phenyl]-acetyl}-1,2,3,4-tetrahydro-quinoxalin-6-yl)-propionic acid;

3-(1-{[3-methoxy-4-(3-o-tolyl-ureido)-phenyl]-acetyl}-1,2,3,4-tetrahydro-quinoxalin-6-yl)-butyric acid;

7-(2-carboxy-ethyl)-4-{[3-methoxy-4-(3-o-tolyl-ureido)-phenyl]-acetyl}-3,4-dihydro-2H-quinoxaline-1-carboxylic acid tert-butyl ester;

3-(4-{[3-methoxy-4-(3-o-tolyl-ureido)-phenyl]-acetyl}-3,4-dihydro-2H-benzo[1,4]oxazin-7-yl)-5-methyl-hexanoic acid;

3-(4-{[3-methoxy-4-(3-o-tolyl-ureido)-phenyl]-acetyl}-3,4-dihydro-2H-benzo[1,4]oxazin-7-yl)-3-phenylpropanoic acid;

3-(4-{[3-methoxy-4-(3-o-tolyl-ureido)-phenyl]-acetyl}-3,4-dihydro-2H-benzo[1,4]oxazin-7-yl)-3-o-tolylpropanoic acid;

3-(4-{[3-methoxy-4-(3-o-tolyl-ureido)-phenyl]-acetyl}-3,4-dihydro-2H-benzo[1,4]oxazin-7-yl)-butanoic acid;

3-(4-{[3-methoxy-4-(3-o-tolyl-ureido)-phenyl]-acetyl}-3,4-dihydro-2H-benzo[1,4]oxazin-7-yl)-4-methylpentanoic acid;

and the corresponding N-oxide, and its prodrugs; and pharmaceutically acceptable salts and solvates (e.g. hydrates) of such compounds and their N-oxides and prodrugs.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention block the interaction of the ligand VCAM-1 to its integrin receptor VLA-4 ($\alpha 4\beta 1$) according to tests described in the literature and described in vitro and in vivo procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of an inhibitor of $\alpha 4\beta 1$ mediated cell adhesion. For example, compounds of the present invention are useful in the treatment of inflammatory diseases, for example joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds may be useful in the treatment of acute synovitis, autoimmune diabetes, autoimmune encephalomyelitis, collitis, atherosclerosis, peripheral vascular disease, cardiovascular disease, multiple sclerosis, asthma, psoriasis restenosis, myocarditis, inflammatory bowel disease and melanoma cell division in metastasis.

A special embodiment of the therapeutic methods of the present invention is the treating of asthma.

Another special embodiment of the therapeutic methods of the present invention is the treating of joint inflammation.

Another special embodiment of the therapeutic methods of the present invention is the treating of inflammatory bowel disease.

According to a further feature of the invention there is provided a method for the treatment of a human or animal patient suffering from, or subject to, conditions which can be ameliorated by the administration of an inhibitor of the interaction of the ligand VCAM-1 to its integrin receptor VLA-4 ($\alpha 4\beta 1$), for example conditions as hereinbefore described, which comprises the administration to the patient of an effective amount of compound of the invention or a composition containing a compound of the invention. "Effective amount" is meant to describe an amount of compound of the present invention effective in inhibiting the interaction of the ligand VCAM-1 to its integrin receptor VLA-4 ($\alpha 4\beta 1$), and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of formula (I), wherein $R^1$, $R^2$, $A^1$, $L^1$ and $Z^1$ are as hereinbefore defined, and where Y is carboxy, may be prepared by hydrolysis of esters of formula (I), wherein $R^1$, $R^2$, $A^1$, $L^1$ and $Z^1$ are as hereinbefore defined and Y is a —$CO_2R^{16}$ group (in which $R^{16}$ is alkyl, alkenyl or arylalkyl). The hydrolysis may conveniently be carried out by alkaline hydrolysis using a base, such as an alkali metal hydroxide, e.g. lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (I), wherein $R^1$, $R^2$, $A^1$, $L^1$ and $Z^1$ are as hereinbefore defined, and where Y is carboxy, may be prepared by acid catalysed removal of the tert-butyl group of tert-butyl esters of formula (I), wherein $R^1$, $R^2$, $A^1$, $L^1$ and $Z^1$ are as hereinbefore defined and Y is a —$CO_2R^{16}$ group (in which $R^{16}$ is tert-butyl), using standard reaction conditions, for example reaction with trifluoroacetic acid at a temperature at about room temperature.

As another example compounds of formula (I), wherein $R^1$, $R^2$, $A^1$, $L^1$ and $Z^1$ are as hereinbefore defined, and where Y is carboxy, may be prepared by hydrogenation of compounds of formula (I) wherein $R^1$, $R^2$, $A^1$, $L^1$ and $Z^1$ are as hereinbefore defined and Y is a —$CO_2R^{16}$ group (in which $R^{16}$ is arylmethyl, e.g. benzyl). The reaction may be carried out in the presence of ammonium formate and a suitable metal catalyst, e.g. palladium, supported on an inert carrier such as carbon, preferably in a solvent such as methanol or ethanol and at a temperature at about reflux temperature. The reaction may alternatively be carried out in the presence of a suitable metal catalyst, e.g. platinum or palladium optionally supported on an inert carrier such as carbon, preferably in a solvent such as methanol or ethanol. This reaction is most suitable for compounds of formula (I) where $L^1$ does not contain carbon-carbon multiple bonds.

In a process A compounds of formula (I), containing an amide bond may be prepared by coupling of an acid [or an acid halide (or anhydride)] with an amine to give an amide bond using standard peptide coupling procedures as described hereinafter.

As an example of process A, esters of formula (I), wherein $R^2$, $A^1$, $L^1$ and $Z^1$ are as hereinbefore defined, $R^1$ is a group selected from $R^3$—$Z^3$—, $R^3$—$L^2$—$R^4$—$Z^3$—, $R^3$—$L^3$—$Ar^1$—$L^4$—$Z^3$— or $R^3$—$L^3$—$Ar^1$—$L^2$—$R^4$—$Z^3$— [in which $R^3$, $R^4$, $L^2$, $L^3$, $L^4$ and $Ar^1$ are as hereinbefore defined and $Z^3$ is C(=O)] and Y is a —$CO_2R^{16}$ group (in which $R^{16}$ is as hereinbefore defined), may be prepared by reacting a compound of formula (II):

$$R^{18}\text{—C(=O)—}X^1 \qquad (II)$$

wherein $R^{18}$ is $R^3$—, $R^3$—$L^2$—$R^4$—, $R^3$—$L^3$—$Ar^1$—$L^4$— or $R^3$—$L^3$—$Ar^1$—$L^2$—$R^4$— (in which $R^3$, $R^4$, $L^2$, $L^3$, $Ar^1$ and $L^4$ are as hereinbefore defined) and $X^1$ is a hydroxy group, a halogen, preferably chlorine, atom or —O—C(=O)—$R^{18}$ with an amine of formula (III):

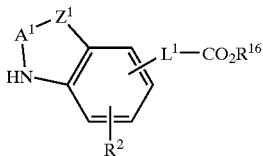

(III)

wherein $R^2$, $R^{16}$, $A^1$, $L^1$ and $Z^1$ are as hereinbefore defined. When $X^1$ is a hydroxy group the reaction may be carried out using standard peptide coupling procedures for example coupling in the presence of O—(7-azabenzotriazol-1-yl)-1,1,3,3-tetramethyluronium hexafluorophosphate and triethylamine (or diisopropylethylamine) in tetrahydrofuran (or dimethylformamide), at room temperature. When $X^1$ is a halogen atom the acylation reaction may be carried out with the aid of a base, such pyridine, preferably in a solvent such as tetrahydrofuran and at a temperature at about room temperature. When $X^1$ is —O—C(=O)—$R^{18}$ the reaction may be carried out in an inert solvent, such as dichloromethane, optionally in the presence of a base, such as triethylamine, and at a temperature at about room temperature.

Esters of formula (I), wherein $R^1$, $R^2$, $A^1$ and $Z^1$ are as hereinbefore defined, Y is a —$CO_2R^{16}$ group (in which $R^{16}$ is as hereinbefore defined) and $L^1$ contains a —$N(R^8)$—C(=O)—$R^9$ group (in which $R^8$ and $R^9$ are as hereinbefore defined) may be similarly prepared from the corresponding esters of formula (I) where $L^1$ contains a —$NHR^8$ group (in which $R^8$ is as hereinbefore defined) by reaction with a compound of formula $R^9$—C(=O)—$X^1$ wherein $R^9$ and $X^1$ are as hereinbefore defined.

Esters of formula (I), wherein $R^2$, $A^1$, $L^1$ and $Z^1$ are as hereinbefore defined, $R^1$ is a group selected from $R^3$—$Z^3$—, $R^3$—$L^2$—$R^4$—$Z^3$—, $R^3$—$L^3$—$Ar^1$—$L^4$—$Z^3$— or $R^3$—$L^3$—$Ar^1$—$L^2$—$R^4$—$Z^3$— (in which $R^3$, $R^4$, $L^2$, $L^3$, $L^4$ and $Ar^1$ are as hereinbefore defined and $Z^3$ is $SO_2$) and Y is —$CO_2R^{16}$ group (in which $R^{16}$ is as hereinbefore defined), may be prepared by sulphonylation of a compound of formula (III), wherein $R^2$, $R^{16}$, $A^1$, $L^1$ and $Z^1$ are as hereinbefore defined, using a sulphonyl chloride of formula (IV):

$$R^{18}\text{—}SO_2\text{—}Cl \qquad (IV)$$

wherein $R^{18}$ is as defined hereinabove. The reaction is preferably carried out with the aid of a base, such as a tertiary amine, for example triethylamine, preferably in a solvent such as tetrahydrofuran and at a temperature from about 0° C. to about room temperature.

Esters of formula (I), wherein $R^1$, $R^2$, $A^1$ and $Z^1$ are as hereinbefore defined, Y is a —$CO_2R^{16}$ group (in which $R^{16}$ is as hereinbefore defined) and $L^1$ contains a —$N(R^8)$—$SO_2$—$R^9$ group (in which $R^8$ and $R^9$ are as hereinbefore defined), may be similarly prepared from the corresponding esters of formula (I) where $L^1$ contains a —$NHR^8$ group (in which $R^8$ is as hereinbefore defined) by reaction with sulphonyl chlorides of formula $R^9$—$SO_2Cl$ wherein $R^9$ is as hereinbefore defined.

Esters of formula (I), wherein $R^2$, $A^1$, $L^1$ and $Z^1$ are as hereinbefore defined, $R^1$ is $R^3$—$L^3$—$Ar^1$—$L^4$—$Z^3$— (in which $R^3$, $L^3$, $L^4$ and $Ar^1$ are as hereinbefore defined, $Z^3$ is NHC(=O) and Y is a —$CO_2R^{16}$ group (in which $R^{16}$ is as hereinbefore defined), may be prepared by reacting a compound of formula (III), wherein $R^2$, $A^1$, $L^1$, $Z^1$ and $R^{16}$ are as hereinbefore defined, with an isocyanate of formula (V):

$$R^3\text{—}L^3\text{—}Ar^1\text{—}L^4\text{—}NCO \qquad (V)$$

wherein $R^3$, $L^3$, $L^4$ and $Ar^1$ are as hereinbefore defined. The reaction is preferably carried out with the aid of a base, such as a tertiary amine, for example triethylamine, preferably in a solvent such as dichloromethane, and at a temperature at about room temperature.

Esters of formula (I), wherein $R^2$, $A^1$, $L^1$ and $Z^1$ are as hereinbefore defined, $R^1$ is $R^3$—$Z^3$— [in which $R^3$ is as hereinbefore defined and $Z^3$ is NHC(=O)] may be similarly prepared by reacting a compound of formula (III), wherein $R^2$, $A^1$, $L^1$, $Z^1$ and $R^{16}$ are as hereinbefore defined, with an isocyanate of formula $R^3$—NCO wherein $R^3$ is as hereinbefore defined.

Esters of formula (I), wherein $R^2$, $A^1$, $L^1$ and $Z^1$ are as hereinbefore defined, $R^1$ is a group $R^3$—$Z^3$— (in which $R^3$ is as hereinbefore defined [except aryl and heteroaryl] and $Z^3$ is a direct bond), and Y is a —$CO_2R^{16}$ group (in which $R^{16}$ is as hereinbefore defined), may be prepared by alkylation of a compound of formula (III), wherein $R^2$, $A^1$, $L^1$, $Z^1$ and $R^{16}$ are as hereinbefore defined, with a compound of formula (VI):

$$R^3\text{—}X^2 \qquad (VI)$$

wherein $R^3$ is as immediately hereinbefore defined and $X^2$ is a halogen, preferably bromine, atom. The alkylation may for example be carried out in the presence of a base, such as an alkali metal hydride, e.g. sodium hydride, in dimethylformamide, or dimethyl sulphoxide, at a temperature from about 0° C. to about 100° C.

Esters of formula (I), wherein $R^2$, $A^1$, $L^1$ and $Z^1$ are as hereinbefore defined, $R^1$ is a group $R^3$—$L^2$—$R^4$—$Z^3$—, $R^3$—$L^4$—$Ar^1$—$L^4$—$Z^3$—, $R^3$—$L^4$—$Ar^1$—$L^2$—$R^4$—$Z^3$— or $R^3$—$L^3$—$Ar^1$—$L^4$—$Z^3$— (in which $R^3$, $L^3$ and $Ar^1$ are as hereinbefore defined, $L^4$ is an alkylene, alkenylene or alkynylene chain, and $Z^3$ is a direct bond) and Y is a —$CO_2R^{16}$ group (in which $R^{16}$ is as hereinbefore defined), may be similarly prepared by alkylation of a compound of formula (III), wherein $R^2$, $A^1$, $L^1$, $Z^1$ and $R^{16}$ are as hereinbefore defined, with a compound of formula (VIa):

$$R^{18}\text{—}X^2 \qquad (VIa)$$

wherein $R^{18}$ is $R^3$—$L^2$—$R^4$—, $R^3$—$L^3$—$Ar^1$—$L^4$— or $R^3$—$L^3$—$Ar^1$—$L^2$—$R^4$— (in which $R^3$, $R^4$, $L^2$, $L^3$, $AR^1$ and $L^4$ are as hereinbefore defined) and $X^2$ is a halogen, preferably bromine, atom.

Esters of formula (I), wherein $R^1$, $R^2$, $A^1$ and $Z^1$ are as hereinbefore defined, Y is a —$CO_2R^{16}$ group (in which $R^{16}$ is as hereinbefore defined) and $L^1$ contains a —$NHR^8$ group (in which $R^8$ is alkyl, arylalkyl, cycloalkylalkyl, heteroarylalkyl or heterocycloalkylalkyl), may be similarly prepared by alkylation of the corresponding derivatives of formula (I) where $L^1$ contains a —$NH_2$ group, with the appropriate alkyl (or arylalkyl, cycloalkylalkyl, heteroarylalkyl or heterocycloalkylalkyl) halide.

Esters of formula (I), wherein $R^2$, $A^1$, $L^1$ and $Z^1$ are as hereinbefore defined, $R^1$ is a group selected from $R^3$—$Z^3$— [in which $R^3$ is as hereinbefore defined and $Z^3$ is OC(=O)] may be prepared by reaction of a compound of formula (III), wherein $R^2$, $A^1$, $L^1$, $Z^1$ and $R^{16}$ are as hereinbefore defined, with a compound of formula (VII):

$$R^3\text{—O—C(=O)—}X^3 \qquad\qquad (VII)$$

wherein $R^3$ is as hereinbefore defined and $X^3$ is a halogen, preferably chlorine atom, or —O—C(=O)—$OR^9$ in the presence of a suitable base, such as triethylamine or pyridine, and at a temperature from about 0° C. to about room temperature.

Esters of formula (I), wherein $R^1$, $R^2$, $A^1$ and $Z^1$ are as hereinbefore defined, Y is a —$CO_2R^{16}$ group (in which $R^{16}$ is as hereinbefore defined) and $L^1$ contains a —$N(R^8)$—C (=O)—$OR^9$ group (in which $R^8$ and $R^9$ are as hereinbefore defined), may be similarly prepared from the corresponding derivatives of formula (I) where $L^1$ contains a —$NHR^8$ group (in which $R^8$ is as hereinbefore defined) by reaction with compounds of formula $R^9$O—C(=O)—$X^3$ wherein $R^9$ and $X^3$ are as hereinbefore defined.

Esters of formula (I), wherein $R^1$, $R^2$, $A^1$ and $Z^1$ are as hereinbefore defined, Y is a —$CO_2R^{16}$ group (in which $R^{16}$ is alkyl) and $L^1$ is

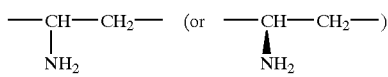

may be prepared by hydrogenation of the corresponding derivatives of formula (I), where $L^1$ is

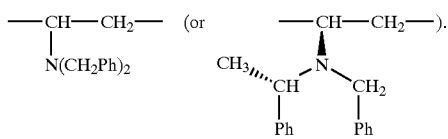

The reaction may be carried out in the presence of formic acid and a suitable metal catalyst, e.g. palladium, supported on an inert carrier such as carbon, at a temperature at about 60° C. The reaction may conveniently be carried out in the presence of a suitable metal catalyst, e.g. platinum or palladium optionally supported on an inert carrier such as carbon, preferably in a solvent such as methanol or ethanol.

Esters of formula (I), wherein $R^1$, $R^2$, $A^1$ and $Z^1$ are as hereinbefore defined, Y is a —$CO_2R^{16}$ group (in which $R^{16}$ is as hereinbefore defined) and $L^1$ is a

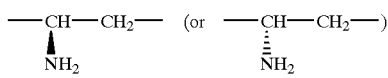

linkage, may also be obtained from the racemic mixture following standard recrystallisation of a suitable salt (for example recrystallisation of the tartrate salt), or by the application of standard enzymatic resolution procedures (for example those described by Soloshonok, V. A., et.al., Tetrahedron: Asymmetry 6 (1995) 7, 1601–1610).

Esters of formula (I), wherein $R^1$, $R^2$, $A^1$ and $Z^1$ are as hereinbefore defined, Y is a —$CO_2R^{16}$ group (in which $R^{16}$ is as hereinbefore defined) and $L^1$ is a

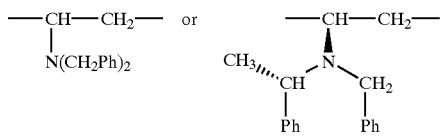

linkage, may be prepared by reacting an ester of formula (I), wherein $R^1$, $R^2$, $A^1$ and $Z^1$ are as hereinbefore defined, Y is a —$CO_2R^{16}$ group (in which $R^{16}$ is as hereinbefore defined) and $L^1$ is a —CH=CH— linkage, with an alkali metal hydride, such as sodium hydride, in an inert solvent, e.g. tetrahydrofuran, and at a temperature at about room temperature, and subsequent reaction with the anion derived from treating dibenzylamine, or (S)-N-benzyl-α-methylbenzylamine, with butyllithium, at a temperature at about −78° C.

Esters of formula (I), wherein $R^1$, $R^2$, $A^1$ and $L^1$ are as hereinbefore defined, Y is a —$CO_2R^{16}$ group (in which $R^{16}$ is as hereinbefore defined) and $Z^1$ is NH may be prepared by reductive cyclisation of a compound of formula (VIII):

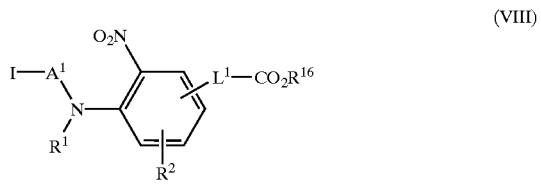

wherein $R^1$, $R^2$, $R^{16}$, $A^1$ and $L^1$ are as hereinbefore defined. The reaction may conveniently be carried out using tin (II) chloride in the presence of hydrochloric acid at a temperature up to about 80° C.

Esters of formula (I), wherein $R^1$, $R^2$, $A^1$ and $Z^1$ are as hereinbefore defined, Y is a —$CO_2R^{16}$ group (in which $R^{16}$ is as hereinbefore defined) and $L^1$ is alkenylene, alkynylene or cycloalkenylene in which the aliphatic carbon-carbon multiple bond is attached directly to the phenyl moiety in formula (I), may be prepared by coupling of compounds of formula (IX):

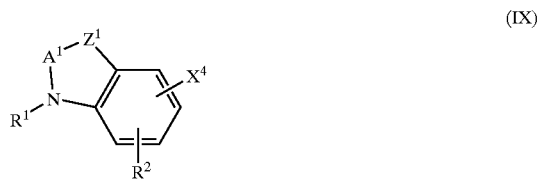

wherein $R^1$, $R^2$, $A^1$ and $Z^1$ are as hereinbefore defined and $X^4$ is a halogen, preferably bromine or iodine, atom with a compound of formula (X):

$$R^{19}\text{—}CO_2R^{16} \qquad\qquad (X)$$

wherein $R^{16}$ is as hereinbefore defined and $R^{19}$ is alkenyl, alkynyl or cycloalkenyl. When $X^4$ is a bromine or iodine atom the reaction may be conveniently carried out in the presence of palladium acetate, a triarylphosphine, such as tri-o-tolylphosphine, and a tertiary amine, such as tributylamine, at a temperature up to about 110° C. This reaction is particularly suitable for the preparation of esters of formula (I) in which $L^1$ is vinylene. When $X^4$ is a chlorine atom the reaction may be conveniently carried out in the presence of sodium iodide, nickel bromide, palladium(0) bis(dibenzylideneacetone), a triarylphosphine, such as tri-o-tolylphosphine, and a tertiary amine, such as tributylamine, at a temperature up to about 110° C.

According to a further feature of the present invention, compounds of the invention may be prepared by interconversion of other compounds of the invention.

For example compounds of formula (I), wherein $R^1$, $R^2$, $A^1$, $L^1$ and $Z^1$ are as hereinbefore defined and Y is a group —C(=O)—NHOH, may be prepared by reacting compounds of formula (I), wherein $R^1$, $R^2$, $A^1$, $L^1$ and $Z^1$ are as hereinbefore defined and Y is carboxy, with hydroxylamine using standard peptide coupling procedures such as treatment with a carbodiimide, for example dicyclohexylcarbodiimide, in the presence of triethylamine, in an inert solvent such as dichloromethane or tetrahydrofuran and at a temperature at about room temperature. The coupling may also be carried out using 1-hydroxybenzotriazole and 1-(3-dimethylaminopropyl)-3-ethylcarbodiimide in dichloromethane at room temperature. The preparation may also be carried out using an O-protected hydroxylamine such as O-(trimethylsilyl)hydroxylamine, O-(t-butyldimethylsilyl)-hydroxylamine, or O-(tetrahydropyranyl)hydroxylamine followed by treatment with acid.

As another example of the interconversion process, compounds of formula (I) containing sulphoxide linkages may be prepared by the oxidation of corresponding compounds containing —S— linkages. For example, the oxidation may conveniently be carried out by means of reaction with a peroxyacid, e.g. 3-chloroperbenzoic acid, preferably in an inert solvent, e.g. dichloromethane, preferably at or near room temperature, or alternatively by means of potassium hydrogen peroxomonosulphate in a medium such as aqueous methanol, buffered to about pH5, at temperatures between about 0° C. and room temperature. This latter method is preferred for compounds containing an acid-labile group.

As another example of the interconversion process, compounds of formula (I) containing sulphone linkages may be prepared by the oxidation of corresponding compounds containing —S— or sulphoxide linkages. For example, the oxidation may conveniently be carried out by means of reaction with a peroxyacid, e.g. 3-chloroperbenzoic acid, preferably in an inert solvent, e.g. dichloromethane, preferably at or near room temperature.

As another example of the interconversion process, compounds of formula (I), wherein $R^1$, $R^2$, $A^1$, $Z^1$ and Y are as hereinbefore defined, and $L^1$ is optionally substituted alkylene, may be prepared by hydrogenation of the corresponding compounds of formula (I) in which $L^1$ is the corresponding optionally substituted alkenylene. The hydrogenation may be carried out using hydrogen (optionally under pressure) in the presence of a suitable metal catalyst, e.g. platinum or palladium optionally supported on an inert carrier such as carbon, preferably in a solvent such as methanol or ethanol, and at a temperature at about room temperature.

As another example of the interconversion process, compounds of formula (I), wherein $R^1$, $R^2$, $A^1$, $L^1$ and $Z^1$ are as hereinbefore defined, $L^1$ is an alkylene linkage substituted by —CONY$^1$Y$^2$ and Y is carboxy, may be prepared by reacting compounds of formula (I), wherein $R^1$, $R^2$, $A^1$, $L^1$ and $Z^1$ are as hereinbefore defined, $L^1$ is an alkylene linkage substituted by —CO$_2$H and Y is carboxy, with an anhydride, such as trifluoroacetic anhydride, in an inert solvent e.g. tetrahydrofuran, followed by treatment with an amine HNY$^1$Y$^2$.

As another example of the interconversion process, compounds of formula (I) wherein $R^1$, $R^2$, $A^1$ and $Z^1$ are as hereinbefore defined, $L^1$ is a

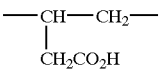

linkage and Y is carboxy, may be prepared by (i) reacting an ester of formula (I) wherein $R^1$, $R^2$, $A^1$ and $Z^1$ are as hereinbefore defined, $L^1$ is a —CH=CH— linkage and Y is —CO$_2$R$^{16}$ (in which $R^{16}$ is as hereinbefore defined) with dimethyl malonate, in the presence of an alkali metal alkoxide, such as sodium methoxide, in methanol and at a temperature at about reflux temperature and (ii) treatment of the resulting compounds of formula (I) wherein $R^1$, $R^2$, $A^1$ and $Z^1$ are as hereinbefore defined, $L^1$ is a

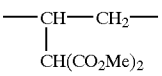

linkage and Y is —CO$_2$R$^{16}$ with hydrochloric acid at reflux temperature.

As another example of the interconversion process, compounds of the invention containing a heterocyclic group wherein the hetero atom is a nitrogen atom may be oxidised to their corresponding N-oxides. The oxidation may conveniently be carried out by means of reaction with a mixture of hydrogen peroxide and an organic acid, e.g. acetic acid, preferably at or above room temperature, for example at a temperature of about 60–90° C. Alternatively, the oxidation may be carried out by reaction with a peracid, for example peracetic acid or m-chloroperoxybenzoic acid, in an inert solvent such as chloroform or dichloromethane, at a temperature from about room temperature to reflux, preferably at elevated temperature. The oxidation may alternatively be carried out by reaction with hydrogen peroxide in the presence of sodium tungstate at temperatures between room temperature and about 60° C.

As another example of the interconversion process, esters of formula (I) in which $Z^1$ represents NR$^{17}$ in which $R^{17}$ is hydrogen may be prepared by acid catalysed removal of the tert-butyloxycarbonyl group in esters of formula (I), in which $Z^1$ represents NR$^{17}$ in which $R^{17}$ is —COO$^t$Bu. The reaction may conveniently be carried out using trifluoroacetic acid in an inert solvent, such as dichloromethane, and at a temperature at about 0° C.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation, of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

Compounds of formula (II) wherein $R^{18}$ is $R^3$—$L^3$—$Ar^1$—$L^4$— group (in which $R^3$, $R^4$, $L^2$, $L^3$, $L^4$ and $Ar^1$ are as hereinbefore defined) may be prepared by the application or adaptation of methods described in the specification of International Patent Application Publication No. WO 96/22966.

Acids of formula (II) wherein $R^{18}$ is $R^3$—$L^3$—$Ar^1$—$L^4$— (in which $R^3$ and $L^4$ are as defined above, $L^3$ is NH, $Ar^1$ is

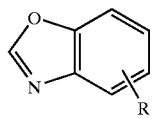

(in which R is as hereinbefore defined) and $X^1$ is a hydroxy group may be prepared by reaction of compounds of formula (I):

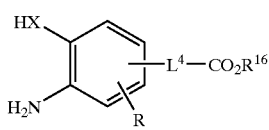

(1)

wherein R and $L^4$ are as hereinbefore defined, $R^{16}$ is lower alkyl and X is O, with isothiocyanates of formula $R^3$—N=S=O (in which $R^3$ is as hereinbefore defined) in ethanol and at room temperature, followed by reaction with a carbodiimide, such as dicyclohexylcarbodiimide or diisopropylcarbodiimide in ethanol and at a temperature from about room temperature to about reflux temperature, and subsequent hydrolysis using standard conditions, for example those described hereinbefore.

Acids of formula (II) wherein $R^{18}$ is $R^3$—$L^3$—$Ar^1$—$L^4$— (in which $R^3$ and $L^4$ are as hereinbefore defined, $Ar^1$ is

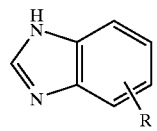

(in which R is as hereinbefore defined), $L^3$ is NH and $X^1$ is hydroxy may be similarly prepared from compounds of formula (1) wherein R, $L^4$ and $R^{16}$ are as hereinbefore defined and X is NH.

Acid chlorides of formula (II) wherein $R^{18}$ is as hereinbefore defined and $X^1$ is a chlorine atom may be prepared from the corresponding acids of formula (II) wherein $R^{18}$ is as hereinbefore defined and $X^1$ is hydroxy, by the application of standard procedures for the conversion of acids to acid chlorides for example by reaction with oxalyl chloride.

Compounds of formula (III) wherein $R^2$, $R^{16}$, $A^1$, $L^1$ and $Z^1$ are as defined hereinbefore, may be prepared by acid catalysed removal of the tert-butyloxycarbonyl group in compounds of formula (2):

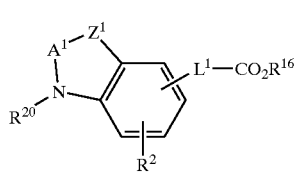

(2)

wherein $R^2$, $R^{16}$, $A^1$, $L^1$ and $Z^1$ are as defined hereinbefore and $R^{20}$ is —COO$^t$Bu. The reaction may conveniently be carried out using trifluoroacetic acid in an inert solvent, such as dichloromethane, and at a temperature at about 0° C. This reaction is particularly suitable for the preparation of compounds of formula (III) in which $Z^1$ is O and $A^1$ is ethylene.

Compounds of formula (III) wherein $R^2$, $A^1$ and $Z^1$ are as defined hereinbefore, $R^{16}$ is alkyl and $L^1$ is alkylene or cycloalkylene may be prepared by hydrogenation of compounds of formula (2) wherein $R^2$, $A^1$ and $Z^1$ are as defined hereinbefore, $R^{16}$ is alkyl, $R^{20}$ is H [or a protecting group (e.g. benzyl) that is conveniently removed during the hydrogenation] and $L^1$ is alkenylene, alkynylene or cycloalkenylene. The hydrogenation may be carried out using hydrogen (optionally under pressure) in the presence of a suitable catalyst, e.g. palladium hydroxide supported on an inert carrier such as carbon, in acetic acid and optionally in the presence of a co-solvent such as methanol or ethanol, and at a temperature at about room temperature. This reaction is particularly suitable for the preparation of compounds of formula (III) in which $Z^1$ is N—CO$_2^t$Bu and $A^1$ is ethylene.

Compounds of formula (2) wherein $R^2$, $A^1$ and $Z^1$ are as defined hereinbefore, $R^{16}$ is alkyl, $R^{20}$ is a suitable protecting group, such as tertiary-butyloxycarbonyl, and $L^1$ is alkylene or cycloalkylene may be prepared by reduction compounds of formula (2) wherein $R^2$, $A^1$ and $Z^1$ are as defined hereinbefore, $R^{16}$ is alkyl, $R^{20}$ is a suitable protecting group, such as tertiary-butyloxycarbonyl, and $L^1$ is alkenylene, alkynylene or cycloalkenylene. The reduction may be carried out in the presence of ammonium formate and a suitable metal catalyst, e.g. palladium, supported on an inert carrier such as carbon, preferably in a solvent such as methanol or ethanol and at a temperature at about reflux temperature. This reaction is particularly suitable for the preparation of compounds of formula (2) in which $Z^1$ is O and $A^1$ is ethylene.

Compounds of formula (2) wherein $R^2$, $A^1$ and $Z^1$ are as defined hereinbefore, $R^{16}$ is alkyl, $R^{20}$ is a protecting group (e.g. benzyl or tertiary-butyloxycarbonyl) and $L^1$ is alkenylene, alkynylene or cycloalkenylene in which the carbon-carbon multiple bond is attached directly to the phenyl moiety in formula (2), may be prepared by reaction compounds of formula (3):

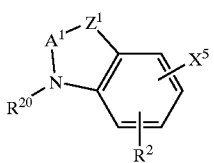

(3)

wherein $R^2$, $R^{20}$, $A^1$ and $Z^1$ are as just defined and $X^5$ is an iodine, or preferably a bromine, atom, with a compound of formula (X) wherein $R^{16}$ and $R^{19}$ are as hereinbefore defined using standard Heck reaction conditions, for example reaction in the presence of palladium acetate, triphenylphosphine and tributylamine at a temperature up to about 120° C.

Compounds of formula (3) wherein $R^2$ and $X^5$ are as just defined, $R^{20}$ is a protecting group (e.g. benzyl), $A^1$ represents an optionally substituted straight chain $C_{2-3}$alkylene linkage and $Z^1$ is NH may be prepared by reductive cyclisation of compounds of formula (4):

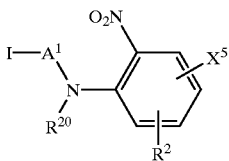

(4)

wherein $R^2$, $R^{20}$, $A^1$ and $X^5$ are as just defined. The reaction may conveniently be carried out using tin (II) chloride in the presence of hydrochloric acid at a temperature up to about 80° C. This reaction is particularly suitable for the preparation of compounds of formula (3) where $A^1$ is ethylene, $R^{20}$ is benzyl and $Z^1$ is NH.

Compounds of formula (4) wherein $R^2$ and $X^5$ are as hereinbefore defined, $A^1$ represents an optionally substituted straight chain $C_{2-3}$alkylene linkage and $R^{20}$ is a protecting group (e.g. benzyl) may be prepared by reaction of compounds of formula (5):

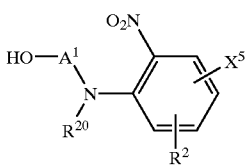

(5)

wherein $R^2$, $R^{20}$, $A^1$ and $X^5$ are as just defined, with an alkyl (or aryl)sulphonyl chloride in the presence of a tertiary base, such as triethylamine, followed by reaction with sodium iodide in acetone at reflux temperature.

Compounds of formula (VIII) wherein $R^1$, $R^2$, $R^{16}$ and $L^1$ are as hereinbefore defined and $A^1$ represents an optionally substituted straight chain $C_{2-3}$alkylene linkage may be similarly prepared from compounds of formula (6):

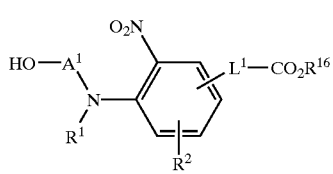

(6)

wherein $R^1$, $R^2$, $R^{16}$, $A^1$ and $L^1$ are as just defined.

Compounds of formula (5) wherein $R^2$ and $X^5$ are as hereinbefore defined, $R^{20}$ is a suitable protecting group, such as benzyl, and $A^1$ represents an optionally substituted straight chain $C_{2-3}$alkylene linkage may be prepared by compound of formula (7):

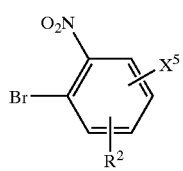

(7)

wherein $R^2$ and $X^5$ are as defined hereinbefore with compounds of formula (8):

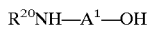

$R^{20}NH$—$A^1$—$OH$ (8)

wherein $R^{20}$ and $A^1$ are as just defined, in an inert solvent, such as n-butanol, and at a temperature up to reflux temperature.

Compounds of formula (6) $R^1$, $R^2$, $R^{16}$ and $L^1$ are as hereinbefore defined and $A^1$ represents an optionally substituted straight chain $C_{2-3}$alkylene linkage may be similarly prepared from compounds of formula (9):

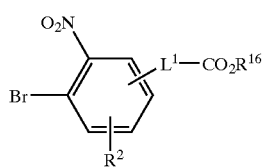

(9)

wherein $R^2$, $R^{16}$ and $L^1$ are as hereinbefore defined.

Compounds of formula (3) wherein $R^2$ and $X^5$ are as just defined, $R^{20}$ is a suitable protecting group (such as acetyl), $A^1$ represents an optionally substituted straight chain $C_{2-3}$alkylene linkage and $Z^1$ is O may be prepared by reaction of compounds of formula (10):

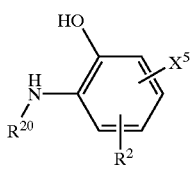

(10)

wherein $R^2$, $R^{20}$, $A^1$ and $X^5$ are as just defined with compounds of formula (11):

 (11)

wherein $A^1$ is as just defined, in the presence of a base, such as sodium hydroxide, and aliquat in an inert solvent, such as dichloromethane and at a temperature at about room temperature. This reaction is particularly suitable for the preparation of compounds of formula (3) where $A^1$ is an ethylene linkage.

Compounds of formula (2), wherein $R^2$, $A^1$ and $R^{16}$ are as defined hereinbefore and $L^1$ is an alkylene linkage substituted by —$CH_2OR^{14}$ (for example —$CH_2OCH_3$) may be prepared from compounds of formula (2), wherein $R^2$ and $R^{16}$ are as defined hereinbefore and $L^1$ is an alkenylene linkage where the carbon-carbon double bond is substituted by a methyl group, using the following standard reaction procedures: (i) allylic bromination with N-bromosuccinimide; (ii) displacement of the allylic bromo with $OR^{14}$ by reaction with an alkali metal salt of formula $R^{14}O^-M^+$ (for example sodium methoxide); (iii) hydrogenation.

Compounds of formula (III) wherein $R^2$, $R^{16}$, $A^1$ and $Z^1$ are as defined hereinbefore and $L^1$ is an optionally substituted arylene or an optionally substituted heteroaryldiyl linkage, maybe prepared by reacting a compound of formula (3) wherein $R^2$ $A^1$ and $Z^1$ are as hereinbefore defined and $X^5$ is iodo or bromo with a compound of formula (12):

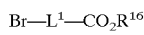 (12)

wherein $R^{16}$ are as defined hereinbefore and $L^1$ is an optionally substituted arylene or an optionally substituted heteroaryldiyl linkage, in the presence of a complex metal catalyst such as tetrakis(triphenylphosphine)palladium(0), using standard reaction conditions, for example those described by Trecourt et al, Tetrahedron, 51 (1995) 43, pages 11743–11750.

Compounds of formula (IX) wherein $R^1$, $R^2$, $A^1$ and $X^4$ are as hereinbefore defined and $Z^1$ is N—$R^9$, N—C(=O)—$R^9$, N—C(=O)—$OR^{14}$ or $NSO_2R^9$ may be prepared from compounds of formula (IX) wherein $R^1$, $R^2$, $A^1$ and $X^5$ are as hereinbefore defined and $Z^1$ is NH by standard alkylation, acylation (or peptide coupling) or sulphonylation procedures, for example those described hereinbefore.

Compounds of formula (3) wherein $R^2$, $A^1$ and $X^5$ are as defined hereinbefore, $R^{20}$ is a protecting group (e.g. benzyl) and $Z^1$ is N—$R^9$, N—C(=O)—$R^9$, N—C(=O)—$OR^{14}$ or $NSO_2R^9$ may be similarly prepared from compounds of formula wherein $R^2$, $A^1$ and $X^5$ are as defined hereinbefore, $R^{20}$ is a protecting group (e.g. benzyl) and $Z^1$ is NH.

Compounds of formula (III) or (2) wherein $R^2$ and $R^{16}$ are as defined hereinbefore and $L^1$ is

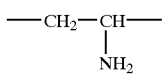

may be prepared by standard methodology for the preparation of α-amino-acids for example those described in Organic Syntheses Based On Name Reactions and Unnamed Reactions, A. Hassner and C. Stumer, Pergamon, pages 275 and 374.

Compounds of formula (2) wherein $R^2$, $R^{16}$, $A^1$ and $Z^1$ are as defined hereinbefore and $L^1$ is

may be prepared by reaction of compounds of formula (13):

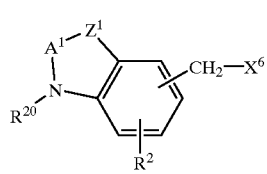 (13)

wherein $R^2$, $A^1$ and $Z^1$ are as defined hereinbefore and $X^6$ is a bromine or chlorine atom with the anion derived from reaction of (2R)-(−)-2,5-dihydro-3,6-dimethoxy-2-isopropylpyrazine with butyllithium according to the method described by D. L. Boger and D. Yohannes, J. Org. Chem. [JOCEAH], 1990, 55, for the preparation of compound 31 on page 6010.

Compounds of formula (2) wherein $R^2$, $R^{16}$ and $A^1$ are as hereinbefore defined and $L^1$ is a

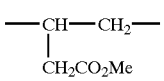

linkage, may be prepared by reacting compounds of formula (2) wherein $R^2$, $R^{16}$ and $A^1$ are as hereinbefore defined and $L^1$ is a —CH=CH— linkage, with dimethyl malonate, in the presence of an alkali metal alkoxide, such as sodium methoxide, in methanol and at a temperature at about reflux temperature.

Compounds of formula (I) wherein $R^1$, $R^2$ and $A^1$ are as hereinbefore defined and the moiety $L^1$—Y is 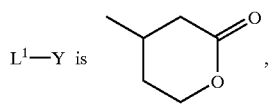, may be prepared coupling of compounds of formula (8) wherein $R^2$ and $A^1$ are as hereinbefore defined, and $X^6$ is a halogen, preferably bromine or iodine, atom with 5,6-dihydropyran-2-one in the presence of tetrakis(triphenylphosphine)palladium (0) and triethylamine in an inert solvent, such as dimethylformamide, at a temperature at about 95° C. and in a sealed vessel.

Intermediates of formulae (III), (VII), (IX), (5) and (8) are novel compounds and, as such, they and their processes described herein for their preparation constitute further features of the present invention.

The present invention is further Exemplified but not limited by the following illustrative Examples and Reference Examples.

400 HMz $^1$H nuclear magnetic resonance spectra (NMR) were recorded on a Bruker 400 DMX machine. 300 HMz $^1$H nuclear magnetic resonance spectra were recorded on a Bruker 300 AC or a Bruker 300 DPX machine. In the nuclear magnetic resonance spectra (NMR) the chemical shifts (δ) are expressed in ppm relative to tetramethylsilane. Abbreviations have the following significances: s=singlet; d=doublet; t=triplet; m=multiplet; q=quartet; dd=doublet of doublets; ddd=doublet of double doublets.

Electron Impact Mass Spectra, MS (EI), were recorded on a Finnigan SSQ 7000 spectrometer at 70 eV.

Desorption Chemical Ionization Mass Spectra, MS (CI), were recorded on a Finnigan SSQ 7000 spectrometer using ammonia as the reactant gas. Liquid Secondary Ion Mass Spectra, MS (LSIMS), were recorded on a VG AutoSpec spectrometer using a mixture of glycerol-thioglycerol 50/50 as the matrix. Electrospray Mass Spectra, MS (ES), were recorded on a Micromass Platform II spectrometer.

EXAMPLE 1

(a) 3-(1-{[3-Methoxy-4-(3-o-tolyl-ureido)-phenyl]-acetyl}-1,2,3,4-tetrahydro-quinoxalin-6-yl)-propionic acid A solution of ethyl 3-(1-{[3-methoxy-4-(3-o-tolyl-ureido)-phenyl]-acetyl}-1,2,3,4-tetrahydro -quinoxalin-6-yl)-propanoate (0.16 g, Reference Example 1) in anhydrous ethanol (3 ml), at 25° C., was treated dropwise with a solution of lithium hydroxide monohydrate (22 mg) in distilled water (1 ml). After stirring for 4 hours at 25° C. a further portion (10 mg) of lithium hydroxide monohydrate was added and stirring was continued for 16 hours at 25° C. The reaction mixture was evaporated under reduced pressure (2.7 kPa) at 40° C. and the residue was treated with distilled water (40 ml). The resulting solution was washed twice with diethyl ether (20 ml), then acidified to pH 3 by addition of hydrochloric acid (1.3 ml, 1N) and then extracted three times with ethyl acetate (25 ml). The combined organic extracts were washed twice with water (5 ml), then dried over magnesium sulphate and then evaporated under reduced pressure (2.7 kPa) at 40° C. to give the title compound (132 mg) as a foamy solid. $^1$H NMR [400 Hz, (CD$_3$)$_2$SO]: δ2.2 (s, 3H); 2.5 (bq, 2H); 2.7 (broad t, 2H); 3.2 (broad s, 2H); 3.65 (broad s, 2H); 3.8 (s, 5H); 6.1 (broad s, 1H); 6.4 (broad s, 1H); 6.45 (broad s, 1H); 6.7 (very broad s, 1H); 6.9 (t, J=8 Hz, 1H); 7.15 (m, 3H); 7.8 (d, J=8 Hz, 1H); 8 (broad s, 1H); 8.45(s, 1H); 8.6(s, 1H); 12.1 (broad s, 1H. MS (LSIMS: glycerol+thioglycerol): 503 (MH$^+$).

(b) By proceeding in a similar manner to Example 1(a) but using ethyl 3-(1-{[3-methoxy-4-(3-o-tolyl-ureido)-phenyl]-acetyl}-1,2,3,4-tetrahydro-quinoxalin-6-yl)-butanoate (Reference Example 17) and subjecting the crude product to preparative thick layer chromatography on silica (20×20 cm plates, 0.25 mm thickness) eluting with ethyl acetate there was prepared 3-(1-{[3-methoxy-4-(3-o-tolyl-ureido)-phenyl]-acetyl}-1,2,3,4-tetrahydro-quinoxalin-6-yl)-butyric acid as a white powder. $^1$H NMR [400 HMz, (CD$_3$)$_2$SO, at room temperature, a mixture of rotamers]: δ1.18 (d, J=7 Hz, 3H); 2.26 (s, 3H); 2.43 (m, 2H); 3.00 (broad band, 1H); 3.20 (broad band, 2H); 3.67 (m, 2H); 3.83 (broad band, 2H); 3.83 (s, 3H); from 6.00 to 7.60 (m, 9H); 7.80 (d, J=8 Hz, 1H); 8.01 (broad band, 1H); 8.48 (broad s, 1H); 8.58 (broad s, 1H). MS (EI): 516 (M$^+$).

(c) By proceeding in a similar manner to Example 1(a) but using ethyl 3-(4-acetyl-1-{[3-methoxy-4-(3-o-tolyl-ureido)-phenyl]acetyl}-1,2,3,4-tetrahydro-quinoxalin-6-yl)-propanoate [Reference Example 16(b)] and subjecting the reaction product to preparative thick layer chromatography on silica (20×20 cm plates, 0.25 mm thickness) eluting with a mixture of dichloromethane and methanol, 9:1, v/v there was prepared 3-(4-acetyl-1-{[3-methoxy-4-(3-o-tolyl-ureido)-phenyl]-acetyl}-1,2,3,4-tetrahydro-quinoxalin-6-yl)-propionic acid as a white foam following trituration with di-isopropyl ether. $^1$H NMR [300 MHz, (CD$_3$)$_2$SO, at room temperature, a mixture of rotamers]: δ2.01 (broad band, 3H); 2.26 (s, 3H); 2.56 (broad t, J=7.5 Hz, 2H); 2.83 (broad t, J=7.5 Hz, 2H); from 3.70 to 3.95 (m, 9H); from 6.45 to 6.85 (very broad band, 2H); 6.95 (broad t, J=7.5 Hz, 1H); from 7.05 to 7.25 (m, 3H); from 7.20 to 7.70 (very broad band, 2H); 7.80 (broad d, J=8 Hz, 1H); 7.96 (very broad d, J=8 Hz, 1H); 8.47 (broad s, 1H); 8.55 (broad s, 1H). MS (CI): 545 (MH$^+$).

(d) By proceeding in a similar manner to Example 1(a) but using ethyl 3-(4-benzoyl-1-{[3-methoxy-4-(3-o-tolyl-ureido)-phenyl]-acetyl}-1,2,3,4-tetrahydro-quinoxalin-6-yl)-propanoate [Reference Example 16(c)] followed by trituration of the reaction product with di-isopropyl ether there was prepared 3-(4-benzoyl-1-{[3-methoxy-4-(3-o-tolyl-ureido)-phenyl]-acetyl}-1,2,3,4-tetrahydro-quinoxalin-6-yl)-propionic acid as a white powder. $^1$H NMR (400 MHz, (CD$_3$)$_2$SO, at a temperature of 373° K.): δ2.19 (broad t, J=7.5 Hz, 2H); 2.27 (s, 3H); 2.58 (broad t, J=7.5 Hz, 2H); 3.83 (s, 3H); 3.92 (m, 2H); 3.95 (s, 2H); 4.00 (m, 2H); 6.65 (broad s, 1H); 6.76 (dd, J=8 and 1.5 Hz, 1H); 6.88 (d, J=1.5 Hz, 1H); from 6.95 to 7.05 (m, 2H); from 7.15 to 7.25 (m, 4H); 7.34 (broad t, J=7.5 Hz, 2H); 7.42 (broad t, J=7.5 Hz, 1H); 7.56 (d, J=8 Hz, 1H); 7.77 (broad d, J=8 Hz, 1H); 8.02 (d, J=8 Hz, 1H); 8.21 (broad s, 1H); 8.27 (broad s, 1H). MS, LSIMS 607 (MH$^+$).

(e) By proceeding in a similar manner to Example 1(a) but using ethyl 4-(7-(2-ethoxycarbonyl-ethyl)-4-{[3-methoxy-4-(3-o-tolyl-ureido)-phenyl]-acetyl}-3,4dihydro-2H-quinoxalin-1-yl)4-oxo-butanoate [Reference example 16(d)] and subjecting the reaction product to reverse phase HPLC [column RP-C18 Uptisphere 3 μ, Part#UP3ODB-10M Interchim, Montlucon, France; size 10×100 mm; Flow: 2 ml/minute, acetonitrile: Water, 80:20, v/v for 5 minutes then up to 50:50, v/v in 3 minutes and then steady for 30 minutes, wavelength 254 nm) there was prepared 4-(7-(2-carboxyethyl)-4-{[3-methoxy-4-(3-o-toly)-ureido)-phenyl]-acetyl}-3,4-dihydro-2H-quinoxalin-1-yl)-4-oxo-butyric acid as a white foam. HPLC: R$_T$=24.07 minutes.

(f) By proceeding in a similar manner to Example 1(a) but using ethyl 3-(4-(3-dimethylamino-propionyl)-1-{[3-methoxy-4-(3-o-tolyl-ureido)-phenyl]-acetyl}-1,2,3,4-tetrahydro -quinoxalin-6-yl)-propanoate (Reference Example 21) and subjecting the reaction product to preparative thick layer chromatography on silica (20×20 cm plates, 1 mm thickness) eluting with a mixture of dichloromethane and methanol, 9:1, v/v there was prepared 3-(4-(3-dimethylamino-propionyl)-1-{[3-methoxy-4-(3-o-tolyl-ureido)-phenyl]-acetyl}-1,2,3,4-tetrahydro-quinoxalin-6-yl)-propionic acid as a white foam. $^1$H NMR [400 MHz, (CD$_3$)$_2$SO, at a temperature of 373° K.): δ2.19(s, 6H); 2.28 (s, 3H); from 2.50 to 2.60 (m, 4H); 2.65 (broad t, J=6.5 Hz, 2H); 2.90 (t, J=7.5 Hz, 2H); from 3.80 to 3.90 (m, 7H); 3.91 (m, 2H); 6.69 (broad d, J=8 Hz, 1H); 6.81 (broad s, 1H); 6.98 (broad t, J=7.5 Hz, 1H); from 7.10 to 7.20 (m, 3H); 7.40 (broad s, 1H); 7.56 (d, J=8 Hz, 1H); 7.68 (broad d, J=8 Hz, 1H); 7.98 (d, J=8.5 Hz, 1H); 8.22 (broad band, 1H); 8.29 (broad s, 1H). MS: LSIMS 602 (MH$^+$).

(g) By proceeding in a similar manner to Example 1(a) but using 7-(2-ethoxycarbonyl-ethyl)-4-{[3-methoxy-4-(3-o-tolyl-ureido)-phenyl]-acetyl}-3,4-dihydro-2H-quinoxaline-1-carboxylic acid tert-butyl ester (Reference Example 2) there was prepared 7-(2-carboxy-ethyl)-4-{[3-methoxy-4-(3-o-tolyl-ureido)-phenyl]-acetyl}-3,4-dihydro-2H-quinoxaline-1-carboxylic acid tert-butyl ester as a white solid. $^1$H NMR [400 MHz, (CD$_3$)$_2$SO, at room temperature, a mixture of rotamers]: δ1.48 (s, 9H); 2.26 (s, 3H); 2.55 (m, 2H); 2.83 (broad t, J=7.5 Hz, 2H); 3.63 (m, 2H); from 3.75 to 3.90 (m, 7H); from 6.55 to 6.85 (very broad band, 2H); from 6.90 to 7.05 (m, 2H); from 7.10 to 7.25 (m, 2H); 7.45 (broad band, 1H); 7.63 (broad s, 1H); 7.78 (d, J=8 Hz, 1H); 8.03 (broad d, J=8 Hz, 1H); 8.50 (s, 1H); 8.56 (broad s, 1H); from 11.80 to 12.60 (very broad band, 1H). MS (DCI): 620 (MNH$_4^+$), 603 (MH$^+$).

EXAMPLE 2

(a) (R,S)-3-(4-{[3-Methoxy-4-(3-o-tolyl-ureido)-Phenyl]-acetyl}-3,4-dihydro-2H-benzo[1,4]oxazin-7-yl)-5-methyl-hexanoic acid A solution of (R,S) ethyl 3-(4-{[3-methoxy-4-(3-o-tolyl-ureido)-phenyl]-acetyl}-3,4-dihydro-2H benzo[1,4]oxazin-7-yl)-5-methylhexanoate [95 mg, Reference Example 10(a)] in methanol (20 ml) was treated with aqueous lithium hydroxide solution (2 ml, 2M). After stirring at room temperature for 16 hours the mixture was heated at 50° C. for 1 hour, then evaporated to low volume and then treated with water. The solution was acidified to pH=1 by addition of aqueous hydrochloric acid (1M). The precipitate was collected, sucked dry and then dried in a dessicator at 60° C. to afford the title compound (85 mg). LC-MS: $R_T$=3.74 minutes (89% by ELSD); MS (ES$^+$) 559(MH$^+$).

(b) By proceeding in a similar manner to Example 2 but using (R,S) ethyl 3-(4-{[3-methoxy-4-(3-o-tolyl-ureido)-phenyl]-acetyl}-3,4-dihydro-2H-benzo[1,4]oxazin-7-yl)-3-phenylpropanoate [Reference Example 10(c)] there was prepared (R,S)-3-(4-{[3-methoxy-4-(3-o-tolyl-ureido)-phenyl]-acetyl}-3,4-dihydro-2H-benzo[1,4]oxazin-7-yl)-3-phenylpropanoic acid as a near white solid. LC-MS: $R_T$=3.59 minutes (99% by ELSD); MS (ES$^+$) 580 (MH$^+$), 602 (MNa$^+$).

(c) By proceeding in a similar manner to Example 2 but using (R,S) ethyl 3-(4-{[3-methoxy-4-(3-o-tolyl-ureido)-phenyl]-acetyl}-3,4-dihydro-2H-benzo[1,4]oxazin-7-yl)-3-o-tolylpropanoate [Reference Example 10(d)] there was prepared (R,S)-3-(4-{[3-methoxy-4-(3-o-tolyl-ureido)-phenyl]-acetyl}-3,4-dihydro-2H-benzo[1,4]oxazin-7-yl)-3-o-tolylpropanoic acid as a white solid. LC-MS: $R_T$=3.67 minutes (100% by ELSD); MS (ES$^+$) 594 (MH$^+$), 616 (MNa$^+$).

(d) By proceeding in a similar manner to Example 2 but using (R,S) ethyl 3-(4-{[3-methoxy-4-(3-o-tolyl-ureido)-phenyl]-acetyl}-3,4-dihydro-2H-benzo[1,4]oxazin-7-yl)-butanoate [Reference Example 10(e)] there was prepared (R,S)-3-(4-{[3-methoxy-4-(3-o-tolyl-ureido)-phenyl]-acetyl}-3,4-dihydro-2H-benzo[1,4]oxazin-7-yl)-butanoic acid as an off-white solid. LC-MS: $R_T$=3.36 minutes (95% by ELSD); MS (ES$^+$) 518 (MH$^+$), 540 (MNa$^+$).

EXAMPLE 3

(a) (R,S)-3-(4-{[3-Methoxy-4-(3-o-tolyl-ureido)-phenyl]-acetyl}-3,4-dihydro-2H-benzo[1,4]oxazin-7-yl)-4-methylpentanoic acid A solution of (R,S) ethyl 3-(4-{[3-methoxy-4-(3-o-tolyl-ureido)-phenyl]-acetyl}-3,4-dihydro-2H-benzo[1,4]oxazin-7-yl)-4-methylpentanoate [100 mg, Reference Example 10(b)] in methanol (20 mL) was treated with aqueous sodium hydroxide (3 ml, 1M). The mixture was warmed to 50° C. for 1 hour, then stood at room temperature for 16 hours, then evaporated to low volume and then treated with water (20 ml). The solution was acidified to pH=1 by addition of aqueous hydrochloric acid (1M) and the resulting precipitate was collected, sucked dry and then dried in a dessicator at 60° C. to afford the title compound (80 mg) as a white solid. LC-MS: $R_T$=3.62 minutes (100% by ELSD); MS (ES$^+$) 546 (MH$^+$), 568 (MNa$^+$).

(b) By proceeding in a similar manner to Example 3(a) but using (R,S)-ethyl 3-{4-[3-(2-o-tolylamino-benzooxazol-6-yl)-propionyl]-3,4-dihydro2H-benzo[1,4]oxazin-7-yl}-butanoate [Reference Example 10(f)] there was prepared 3-{4-[3-(2-o-tolylamino-benzoxazol-6-yl)-propionyl]-3,4-dihydro-2H-benzo[1,4]oxazin-7-yl}-butanoic acid. LC-MS: $R_T$=3.43 minutes (100% by ELSD); MS (ES$^+$) 500 (MH$^+$).

EXAMPLE 4

3-(4-Benzoyl-1-{[3-methoxy-4-(3-o-tolyl-ureido)-phenyl]-acetyl}-1,2,3,4-tetrahydro-quinoxalin-6-yl)-butyric acid A stirred solution of ethyl 3-(4-benzoyl-1-{[3-methoxy-4-(3-o-tolyl-ureido)-phenyl]-acetyl}-1,2,3,4-tetrahydro-quinoxalin-6-yl)-butanoate [0.124 g, Reference Example 16(a)] in methanol (5 ml) was treated with sodium hydroxide solution (764 µl, 15%). The resulting mixture was heated to reflux for 30 minutes, then cooled to 40° C. and then evaporated (40 mbar, 40° C.). The residue was treated with distilled water (40 ml) and the aqueous solution was washed three times with ether (20 ml), then treated with hydrochloric acid (4 ml, 1M) and then extracted three times ethyl acetate (25 ml). The combined extracts were dried over magnesium sulfate then evaporated to dryness (40 mbar, 40° C.). The crude residue (91 mg) was subjected to preparative thin layer chromatography on silica(20×20 cm plates, 0.25 mm thickness) eluting with a mixture of dichloromethane and methanol (9:1, v/v) to give the title compound as a white powder (15 mg). $^1$H NMR (400 MHz, (CD$_3$)$_2$SO, at a temperature of 373° K.]: δ0.92 (d, J=7 Hz, 3H); 2.16 (d, J=7.5 Hz, 2H); 2.27(s, 3H); 2.80 to 3.05 (m, 1H); 3.84 (s, 3H); 3.94 (m, 2H); 3.96 (s, 2H); 4.01 (m, 2H); 6.60 (broad s, 1H); 6.76 (broad d, J=8 Hz, 1H); 6.88 (broad s, 1H); 6.95 to 7.05 (m, 2H); 7.10 to 7.20 (m, 4H); 7.33 (broad t, J=7.5 Hz, 2H); 7.40 (broad t, J=7.5 Hz, 1H); 7.56 (d, J=8 Hz, 1H); 7.68 (broad d, J=8 Hz, 1H); 8.04 (d, J=8.5 Hz, 1H); 8.23 (broad s, 1H); 8.29 (broad s, 1H). MS (ES): 621 (MH$^+$).

Reference Example 1

Ethyl 3-(1-{[3-methoxy-4-(3-o-tolyl-ureido)-phenyl]-acetyl}-1,2,3,4-tetrahydro-quinoxalin-6-yl)-propanoate A solution of 7-(-2-ethoxycarbonyl-ethyl)-4-{[3-methoxy-4-(3-o-tolyl-ureido)-phenyl]-acetyl}-3,4-dihydro-2H-quinoxaline-1-carboxylic acid tert-butyl ester (0.3 g, Reference Example 2) in dichloromethane (3 ml), at 0° C., was treated dropwise with trifluoroacetic acid (0.5 ml). After stirring for 2 hours at 0° C. a further portion of trifluoroacetic acid (0.5 ml) was added and stirring was continued for a further hour at 10° C. The reaction mixture was poured on crushed ice (50 ml), the pH of this mixture was adjusted to 8 by dropwise addition of sodium hydroxide (20 ml, 1N) and then the mixture was extracted twice with dichloromethane (25 ml). The combined organic extracts were washed twice with water (5 ml), then dried over magnesium sulphate and then evaporated under reduced pressure (2.7 kPa) at 40° C. The resulting white foamy solid (235 mg) was subjected to flash chromatography on silica (0.040–0.063 mm) eluting with a mixture of dichloromethane and methanol (99:1, v/v) to give the title compound (170 mg) as a white foamy solid. $^1$H NMR, 300 Hz, (CD$_3$)$_2$SO: δ1.2 (t, 3H); 2.3 (s, 3H); 2.6 (t, 2H); 2.8 (t, 2H); 3.25 (m, 2H); 3.7 (t, 2H); 3.85 (s, 2H); 3.9 (s, 3H); 4.1 (q, 2H); 5.8 (broad s, 1H); 6.4 (dd, J=8 Hz and 1.5 Hz, 1H); 6.5 (d, J=1.5 Hz, 1H); 6.7 (dd, J=8 Hz and 1.5 Hz, 1H); 6.85 (d, J=1.5 Hz, 1H); 7 (ddd, J=8, 8 and 1.5 Hz, 1H); 7.2 (m, 3H); 7.7 (broad d, J=8 Hz, 1H); 8 (d, J=8 Hz, 1H); 8.25 (s, 1H); 8.35 (s, 1H). MS (CI, NH$_3$): MNH$_4^+$ 548, MH$^+$ 531.

Reference Example 2

7-(-2-Ethoxycarbonyl-ethyl)-4-{[3-methoxy-4-(3-o-tolyl-ureido)-phenyl]-acetyl}-3,4-dihydro-2H-quinoxaline-1-carboxylic acid tert-butyl ester A stirred solution of 3-methoxy-4-[3-o-tolyl-ureido]phenylacetic acid (0.282 g, prepared as described in Example 52B of International Patent Application Publication No. WO 96/22966) in anhydrous tetrahydrofuran (5 ml), under an atmosphere of argon and at 25° C., was treated with powdered molecular sieves 4 Å (0.5 g), 7-(2-ethoxycarbonyl-ethyl)-1,2,3,4-tetrahydro-quinoxaline-1-carboxylic acid tert-butyl ester (0.2 g, Reference Example 3), triethylamine (0,336 ml), O-(7-azabenzotriazol-1-yl)-N, N,N',N'-tetramethyluronium hexafluorophosphate (0.273 g) and 4-dimethylaminopyridine (7 mg). After stirring at 25° C. for 3 hours the reaction mixture was filtered through a pad of celite and the filter pad was washed three times with ethyl acetate (10 ml). The combined filtrate and washings were washed twice with an aqueous saturated solution of ammonium chloride (20 ml), then with water (20 ml), then dried over magnesium sulphate and then evaporated under reduced pressure (2.7 kPa) at 40° C. The resulting white foamy solid (0.483 g) was subjected to flash chromatography on silica (0,040–0,063 mm) eluting with a mixture of cyclohexane and ethyl acetate (1:1, v/v) to give the title compound (0.3 g) as a white foamy solid. $^1$H NMR, 400 Hz, $(CD_3)_2SO$: δ1.2 (t, 3H); 1.5 (s, 9H); 2.3 (s, 3H); 2.65 (t, 2H); 2.9 (t, 2H); 3.65 (t, 2H); 3.85 (m, 7H); 4.1 (q, 2H); 6.7 (very broad s, 2H); 7.2 (m, 2H); 7.5 (very broad s, 1H); 7.65 (broad, 1H); 7.8 (d, J=8 Hz, 1H); 8.05 (broad d, J=8 Hz, 1H); 8.5 (s, 1H); 8.6 (broad s, 1H). MS (CI, $NH_3$): $MNH_4^+$ 648, $MH^+$ 631.

Reference Example 3

7-(2-Ethoxycarbonyl-ethyl)-1,2,3,4-tetrahydro-quinoxaline-1-carboxylic acid tert-butyl ester A stirred mixture of 4-benzyl-7-(2-ethoxycarbonyl-vinyl)-1,2,3,4-tetrahydro-quinoxaline-1-carboxylic acid tert-butyl ester (1.83 g, Reference Example 4), acetic acid (2 ml), methanol (40 ml) and 20% palladium dihydroxide on carbon powder (0.49 g) was hydrogenated in a 250 ml stainless steel pressure reactor at a pressure of 30 bars of hydrogen. After stirring for 20 hours at 25° C. the reaction mixture was filtered through a pad of celite and the filter pad was washed with dichloromethane (25 ml) then with methanol (25 ml). The combined filtrate and washings were evaporated under reduced pressure (2.7 kPa) at 40° C. The resulting brown oil (1.99 g) was subjected to flash chromatography on silica (0,040–0,063 mm) eluting initially with a mixture of cyclohexane and ethyl acetate (9:1, v/v) then with a mixture of cyclohexane and ethyl acetate (7:3, v/v) to give the title compound (0.856 g) as a yellow oil. 1H NMR, 300 MHz, $(CD_3)_2SO$: δ1.2 (t, 3H); 1.5 (s, 9H); 2.5 (t, 2H); 2.7 (t, 2H); 3.25 (m, 2H); 3.6 (broad t, 2H); 4.1 (q, 2H); 6 (broad s, 1H); 6.5 (d, J=8 Hz, 1H); 6.7 (dd, J=8 Hz and 1.5 Hz, 1H); 7.2 (broad s, 1H). MS (EI): $M^+$ 334 (40%), 278 (20%), 234 (100%), 189 (10%), 159 (10%), 147 (40%), 57 (40%).

Reference Example 4

(a) 4-Benzyl 7-(2-ethoxycarbonyl-vinyl)-1,2,3,4-tetrahydro-quinoxaline-1-carboxylic acid tert-butyl ester A mixture of 4-benzyl-7-bromo-1,2,3,4-tetrahydro-quinoxaline-1-carboxylic acid tert-butyl ester (2.4 g, Reference Example 5), tri-o-tolylphosphine (96 mg), palladium (II) acetate (24 mg) and ethyl acrylate (1.3 ml) in tributylamine (20 ml) was heated to 110° C. After stirring for 2 hours at 110° C. the mixture was treated with further portions of ethyl acrylate (1.3 ml), tri-o-tolylphosphine (96 mg) and palladium(II) acetate (24 mg) and stirring was continued for a further 16 hours at 110° C. The mixture was then treated with ethyl acrylate (2.6 ml) and stirring was continued for a further 5 hours at 110° C. The reaction mixture was cooled to room temperature then acidified to pH 2 by addition of hydrochloric acid (50 ml, 1N) and then extracted three times with ethyl acetate (50 ml). The combined organic extracts were washed with an aqueous saturated solution of sodium hydrogen carbonate (20 ml), then three times with water (20 ml), then dried over magnesium sulphate and then evaporated under reduced pressure (2.7 kPa) at 40° C. The resulting brown oil (5 g) was subjected to flash chromatography on silica (0,040–0,063 mm) eluting with a mixture of cyclohexane and ethyl acetate (9:1, v/v) to give the title compound (1.83 g) as a yellow oil. $^1$H NMR, 400 MHz, $(CD_3)_2SO$: δ1.3 (t, 3H); 1.5 (s, 9H); 3.5 (broad t, 2H); 3.8 (broad t, 2H); 4.15 (q, 2H); 4.65 (s, 2H); 6.25 (d, J=16 Hz, 1H); 6.65 (d, J=8 Hz, 1H); 7.3 (m, 4H); 7.4 (t, 2H); 7.5 (d, J=16 Hz, 1H); 7.7 (broad s, 1H). MS (EI): $M^+$ 422 (50%), 366 (60%), 322 (40%), 277 (20%), 231 (40%), 185 (10%), 157 (15%), 91 (100%), 57 (40%).

(b) By proceeding in a similar manner to Reference Example 4(a) but using 4tert-butyloxycarbonyl-7-bromo-3, 4-dihydro-2H-benzo[1,4]oxazine [Reference Example 5(b)] and ethyl (E)-5-methylhex-2-enoate and carrying out the reaction in dimethylformamide at 140° C. there was prepared (E)- and (Z)-3-(4-tert-butyloxycarbonyl-3,4-dihydro-2H-benzo[1,4]oxazin-7-yl)-5-methylhex-2-enoic acid ethyl ester (240 mg).

(c) By proceeding in a similar manner to Reference Example 4(a) but using 4-tert-butyloxycarbonyl-7-bromo-3, 4-dihydro-2H-benzo[1,4]oxazine [Reference Example 5(b)] and ethyl (E)-4-methylpent-2-enoate and carrying out the reaction in dimethylformamide at 140° C. there was prepared (E)- and (Z)-3-(4-tert-butyloxycarbonyl-3,4-dihydro-2H-benzo[1,4]oxazin-7-yl)-4-methylpent-2-enoic acid ethyl ester.

(d) By proceeding in a similar manner to Reference Example 4(a) but using 4-tert-butyloxycarbonyl-7-bromo-3, 4-dihydro-2H-benzo[1,4]oxazine [Reference Example 5(b)] and ethyl cinnamate and carrying out the reaction in dimethylformamide at 140° C. there was prepared (E)- and (Z)-3-(4-tert-butyloxycarbonyl-3,4-dihydro-2H-benzo[1.4]oxazin-7-yl)-3-phenyltrop-2-enoic acid ethyl ester.

(e) By proceeding in a similar manner to Reference Example 4(a) but using 4-tert-butyloxycarbonyl-7-bromo-3, 4-dihydro-2H-benzo[1,4]oxazine [Reference Example 5(b)] and (E)-ethyl 3-(2-methylphenyl)prop-2-enoate and carrying out the reaction in dimethylformamide at 140° C. there was prepared (E)- and (Z)-3-(4-tert-butyloxycarbonyl-3,4-dihydro-2H-benzo[1,4]oxazin-7-yl)-3-o-tolylprop-2-enoic acid ethyl ester.

(f) By proceeding in a similar manner to Reference Example 4(a) but using 4-tert-butyloxycarbonyl-7-bromo-3, 4-dihydro-2H-benzo[1,4]oxazine [Reference Example 5(b)] and ethyl crotonate and carrying out the reaction in dimethylformamide at 130° C. there was prepared (E)- and (Z)-3-(4tert-butyloxycarbonyl-3,4-dihydro-2H-benzo[1,4]oxazin-7-yl)-but-2-enoic acid ethyl ester.

Reference Example 5

(a) 4-Benzyl-7-bromo-1,2,3,4-tetrahydro-quinoxaline-1-carboxylic acid tert-butyl ester A mixture of 4-benzyl-7-bromo-1,2,3,4-tetrahydro-quinoxaline (3.28 g, Reference Example 6), di-tert-butyl dicarbonate (2.71 g) and sodium hydrogen carbonate (0.91 g) in anhydrous dichloromethane (20 ml) was stirred for 16 hours at 25° C., then further portions of di-tert-butyl dicarbonate (2.71 g) and sodium hydrogen carbonate (0.91 g) were added and the stirring was continued for 72 hours at 25° C. The reaction mixture was treated with distilled water (50 ml) and the organic phase was separated. The aqueous phase was extracted twice with dichloromethane (20 ml) and the combined organic phases were washed three times with water (20 ml), then dried over magnesium sulphate and then evaporated under reduced pressure (2.7 kPa) at 40° C. The residual solid (7.4 g) was recrystallised from diisopropyl ether to give the title compound (3.5 g) as a tan solid. $^1$H NMR, 400 MHz, $(CD_3)_2SO$: δ1.5 (s, 9H); 3.5 (broad t, 2H); 3.8 (broad t, 2H); 4.6 (s, 2H); 6.6 (d, J=8 Hz, 1H); 7.0 (dd, J=8 Hz and J=1.5 Hz, 1H); 7.2 (m, 3H); 7.4 (t, 2H); 7.6 (broad s, 1H). MS (EI): M$^+$ 404 and 402 (20%), 348 and 346 (90%), 303 and 301 (15%), 257 and 255 (20%), 213 and 211 (20%), 91 (100%), 57 (40%).

(b) By proceeding in a similar manner to Reference Example 5(a) but using 7-bromo-3,4-dihydro-2H-benzo[1,4]oxazine (Reference Example 12) and carrying out the reaction in the absence of sodium hydrogen carbonate in tetrahydrofuran at 50° C. there was prepared 4-tert-butyloxycarbonyl-7-bromo-3,4-dihydro-2H-benzo[1,4]oxazine as a crystalline white solid.

Reference Example 6
4-Benzyl-7-bromo-1,2,3,4-tetrahydro-quinoxaline

A stirred mixture of benzyl-(4-bromo-2-nitro-phenyl)-(2-iodo-ethyl)-amine (23.55 g, Reference Example 7), tin(II) chloride dihydrate (41.48 g), hydrochloric acid 12N (21.28 ml) and distilled water (45 ml) was heated to 80° C. for 1 hour then cooled to room temperature and then treated with distilled water (200 ml). The reaction mixture was neutralized to pH 7–8 by addition of an 32% aqueous ammonia solution (50 ml) and filtered through a pad of celite. The filter pad was washed three times with dichloromethane (250 ml). The filtrate and washings were combined. The organic phase was separated, then washed four times with distilled water (200 ml), then dried over magnesium sulphate and then evaporated under reduced pressure (2.7 kPa) at 40° C. The resulting brown oil (14.47 g) was subjected to flash chromatography on silica (0,040–0,063 mm) eluting initially with a mixture of cyclohexane and ethyl acetate (9:1, v/v) and then with a mixture of cyclohexane and ethyl acetate (7:3, v/v) to give the title compound (3.28 g) as a tan solid. $^1$H NMR, 300 MHz, $(CD_3)_2SO$: δ3.1 (broad s, 4H); 4.2 (s, 2H); 5.6 (broad s, 1H); 6.1 (d, J=8 Hz, 1H); 6.2 (dd, J=8 Hz and J=1.5 Hz, 1H); 6.3 (d, J=1.5 Hz, 1H); 7.25 (m, 5H). MS (EI): M$^+$ 304 and 302 (100%), 213 and 211 (100%), 132 (85%), 91 (60%).

Reference Example 7
Benzyl-(4-bromo-2-nitro-phenyl)-(2-iodo-ethyl)-amine

A mixture of methanesulphonic acid 2-[benzyl-(4-bromo-2-nitro-phenyl)-amino]-ethyl ester (25 g, Reference Example 8) and sodium iodide (16.23 g) in anhydrous acetone (100 ml) was heated at reflux for 4 hours when a further portion of sodium iodide (8.12 g) was added and refluxing was continued for a further 16 hours. The reaction mixture was evaporated under reduced pressure (2.7 kPa) at 40° C. and the residue was treated with distilled water (200 ml). The resulting mixture was extracted three times with dichloromethane (150 ml). The combined organic extracts were dried over magnesium sulphate and then evaporated under reduced pressure (2.7 kPa) at 40° C. The resulting brown oil (29,16 g) was subjected to flash chromatography on silica (0,040–0,063 mm) eluting with a mixture of cyclohexane and ethyl acetate (9:1, v/v) to give the title compound (23.55 g) as a yellow oil. $^1$H NMR, 300 HMz, $(CD_3)_2SO$: δ3.3 (m, 4H); 4.4 (s, 2H); 7.25(m, 5H); 7.4 (d, J=8 Hz, 1H); 7.6 (dd, J=8 Hz and J=1.5 Hz, 1H); 8 (d, J=1.5 Hz, 1H). MS (EI): M$^+$ 462 and 460 (5%), 445 and 443 (20%), 321 and 319 (10%), 91 (100%).

Reference Example 8
Methanesulphonic acid 2-[benzyl-(4-bromo-2-nitro-phenyl)-amino]-ethyl ester A solution of 2-[benzyl-(4-bromo-2-nitro-phenyl)-amino]-ethanol (19.52 g, Reference Example 9) and triethylamine (7.8 ml) in anhydrous tetrahydrofuran (95 ml), at 25° C., was treated dropwise with methanesulphonyl chloride (4.75 ml). After stirring for 4 hours at 25° C. a further portion of methanesulphonyl chloride (4.75 ml) was added and stirring was continued for a further 16 hours at 25° C. The reaction mixture was treated with water (100 ml), the organic phase was separated and the aqueous phase was extracted three times with ethyl acetate (150 ml). The combined organic phases were washed with saturated aqueous sodium hydrogen carbonate solution (50 ml), then three times with distilled water (50 ml), then dried over magnesium sulphate and then evaporated under reduced pressure (2.7 kPa) at 40° C. to give the title compound (25.41 g) as a brown oil. $^1$H NMR, 300 MHz, $(CD_3)_2SO$: δ3.1 (s, 3H); 3.4 (t, 2H); 4.2 (t, 2H); 4.4 (s, 2H); 7.2(m, 5H); 7.4 (d, J=8 Hz, 1H); 7.7 (dd, J=8 Hz and J=1.5 Hz, 1H); 8 (d, J=1.5 Hz, 1H). MS (EI): M$^+$ 430 and 428 (5%), 321 and 319 (20%), 91 (100%).

Reference Example 9
2-[Benzyl-(4-bromo-2-nitro-phenyl)-amino]-ethanol

A mixture of 2,5-dibromonitrobenzene (40 g) and N-benzylethanolamine (40.4 ml) in 1-butanol (160 ml) was heated at reflux for 18 hours then a further portion (20.2 ml) of N-benzylethanolamine was added and refluxing was continued for a further hour. The reaction mixture was evaporated under reduced pressure (2.7 kPa) at 40° C. and the residue was treated with water (500 ml) and the mixture was then extracted three times with diethyl ether (250 ml). The combined organic extracts were washed with hydrochloric acid (180 ml, 1N), then with an aqueous sodium hydrogen carbonate solution (20 ml, 5%), then twice with distilled water (50 ml), then dried over magnesium sulphate and then evaporated under reduced pressure (2.7 kPa) at 40° C. The resulting brown oil (47.1 g) was subjected to flash chromatography on silica (0,040–0,063 mm) eluting with dichloromethane to give the title compound (19.66 g) as a red oil. 1H NMR, 400 MHz, $(CD_3)_2SO$: δ3.1 (t, 2H); 3.5 (q, 2H); 4.5 (s, 2H); 4.6 (t, 1H); 7.3 (m, 6H); 7.6 (dd, J=8 Hz and J=1.5 Hz, 1H); 8 (d, J=1.5 Hz, 1H). MS (EI): M$^+$ 352 and 350 (5%), 321 and 319 (20%), 91 (100%).

Reference Example 10

(a) (R,S) Ethyl 3-(4-{[3-methoxy-4(3-o-tolyl-ureido)-phenyl]-acetyl}-3,4-dihydro-2H-benzo[1,4]oxazin-7-yl)-5-methylhexanoate A solution of (R,S)-3-(4-tert-butyloxycarbonyl-3,4-dihydro-2H-benzo[1,4]oxazin-7-yl)-5-methylhexanoic acid ethyl ester [90 mg, reference Example 11(a)] in dichloromethane (5 ml) was treated with trifluoroacetic acid (2 ml). After stirring for 30 minutes the mixture was evaporated to dryness. The residue was dissolved in dimethylformamide (10 ml) and the solution was treated with diisopropylethylamine (96 mg), then with [3-methoxy-4-(3-o-tolyl-ureido)-phenyl]-acetic acid (80 mg) and then with O-(7-azabenzotriazol-1-yl)-1,1,3,3-tetramethyluronium hexafluorophosphate (96 mg). The mixture was stirred at room temperature for 16 hours then partitioned between ethyl acetate (50 ml) and aqueous hydrochloric acid (50 ml, 1M). The organic phase was washed with 5% aqueous sodium bicarbonate (50 ml), then dried over magnesium sulphate and then evaporated. The residue was subjected to flash chromatography on silica eluting with a mixture of ethyl acetate and cyclohexane (1:1, v/v) to give the title compound (95 mg) as a colourless oil.

(b) By proceeding in a similar manner to Reference Example 10(a) but using (R,S)-3-(4-tert-butyloxycarbonyl-3,4-dihydro-2H-benzo[1,4]oxazin-7-yl)-4-methylpentanoic acid ethyl ester [Reference Example 11(b)] there was prepared (R,S) ethyl 3-(4-{[3-methoxy-4-(3-o-tolyl-ureido)-phenyl]-acetyl}-3,4-dihydro-2H-benzo[1,4]oxazin-7-yl)-4-methylpentanoate as a cream foam.

(c) By proceeding in a similar manner to Reference Example 10(a) but using (R,S)-3-(4-tert-butloxycarbonyl-3,4-dihydro-2H-benzo[1,4]oxazin-7-yl)-3-phenylpropanoic acid ethyl ester [Reference Example 11(c)] there was prepared (R,S) ethyl 3-(4-{[3-methoxy-4-(3-o-tolyl-ureido)-phenyl]-acetyl}-3,4-dihydro-2H-benzo[1,4]oxazin-7-yl)-3-phenylpropanoate as a white solid.

(d) By proceeding in a similar manner to Reference Example 10(a) but using (R,S)-3-(4-tert-butyloxycarbonyl-3,4-dihydro-2H-benzo[1,4]oxazin-7-yl)-3-o-tolylpropanoic acid ethyl ester [Reference Example 11(d)] there was prepared (R,S)-ethyl 3-(4-{[3-methoxy-4-(3-o-tolyl-ureido)-phenyl]-acetyl}-3,4-dihydro-2H-benzo[1,4]oxazin-7-yl)-3-o-tolylpropanoate as a white solid.

(e) By proceeding in a similar manner to Reference Example 10(a) but using (R,S)-3-(4-tert-butyloxycarbonyl-3,4-dihydro-2H-benzo[1,4]oxazin-7-yl)-butanoic acid ethyl ester [Reference Example 11(e)] there was prepared (R,S)-ethyl 3-(4-{[3-methoxy-4-(3-o-tolyl-ureido)-phenyl]-acetyl}-3,4-dihydro-2H-benzo[1,4]oxazin-7-yl)-butanoate as a colourless oil.

(f) By proceeding in a similar manner to Reference Example 10(a) but using (R,S)-3-(4-tert-butyloxycarbonyl-3,4-dihydro-2H-benzo[1,4]oxazin-7-yl)-butanoic acid ethyl ester [Reference Example 11(e)] and 3-(2-o-tolylamino-benzoxazol-6-yl)propanoic acid (Reference Example 14) there was prepared (R,S)-ethyl 3-{4-[3-(2-o-tolylamino-benzooxazol-6-yl)-propionyl]-3,4-dihydro-2H-benzo[1,4]oxazin-7-yl}-butanoate as a colourless gum.

Reference Example 11

(a) (R,S)-3-(4-tert-butyloxycarbonyl-3,4-dihydro-2H-benzo[1,4]oxazin-7-yl)-5-methylhexanoic acid ethyl ester A mixture of (E)- and (Z)-3-(4-tert-butyloxycarbonyl-3,4-dihydro-2H-benzo[1,4]oxazin-7-yl)-5-methylhex-2-enoic acid ethyl ester [240 mg, Reference Example 4(b)] and 10% palladium on charcoal (40 mg) in ethanol (30 ml) was treated with solid ammonium formate (2 g) and heated at 60° C. for 1 hour. Further aliquots of palladium on charcoal (40 mg) were added hourly during 5 hours. After cooling to room temperature, the mixture was filtered through diatomaceous earth and the filtrate evaporated to low volume then partitioned between ethyl acetate (50 ml) and water (50 ml). The organic phase was dried over magnesium sulphate and evaporated to afford the title compound (200 mg).

(b) By proceeding in a similar manner to Reference Example 11(a) but using (E)- and (Z)-3-(4-tert-butyloxycarbonyl-3,4-dihydro-2H-benzo[1,4]oxazin-7-yl)-4-methylpent-2-enoic acid ethyl ester [Reference Example 4(c)] there was prepared (R,S)-3-(4-tert-butyloxycarbonyl-3,4-dihydro-2H-benzo[1,4]oxazin-7-yl)-4-methylpentanoic acid ethyl ester.

(c) By proceeding in a similar manner to Reference Example 11(a) but using (E)- and (Z)-3-(4-tert-butyloxycarbonyl-3,4-dihydro-2H-benzo[1,4]oxazin-7-yl)-3-phenylprop-2-enoic acid ethyl ester [Reference Example 4(d)] there was prepared (R,S)-3-(4-tert-butyloxycarbonyl-3,4-dihydro-2H-benzo[1,4]oxazin-7-yl)-3-phenylpropanoic acid ethyl ester.

(d) By proceeding in a similar manner to Reference Example 11(a) but using (E)- and (Z)-3-(4-tert-butyloxycarbonyl-3,4-dihydro-2H-benzo[1,4]oxazin-7-yl)-3-o-tolylprop-2-enoic acid ethyl ester [Reference Example 4(e)] there was prepared (R,S)-3-(4-tert-butyloxycarbonyl-3,4-dihydro-2H-benzo[1,4]oxazin-7-yl)-3-o-tolylpropanoic acid ethyl ester.

(e) By proceeding in a similar manner to Reference Example 11(a) but using (E)- and (Z)-3-(4-tert-butyloxycarbonyl-3,4dihydro-2H-benzo[1,4]oxazin-7-yl)-but-2-enoic acid ethyl ester [Reference Example 4(f)] there was prepared (R,S)-3-(4-tert-butyloxycarbonyl-3,4-dihydro-2H-benzo[1,4]oxazin-7-yl)-butanoic acid ethyl ester as a colourless oil.

Reference Example 12
7-Bromo-3,4-dihydro-2H-benzo[1,4]oxazine

A solution of 4-acetyl-7-bromo-3,4-dihydro-2H-benzo[1,4]oxazine (9.5 g, Reference Example 13) in methanol (200 ml) was treated with aqueous sodium hydroxide (50 ml, 3M) was stirred at 50° C. for 2 hours. The mixture was evaporated to low bulk, then diluted with water (100 ml) and then extracted three times with dichloromethane (200 ml). The combined extracts were dried over magnesium sulphate then evaporated to give the title compound (6.0 g) as a brown oil.

Reference Example 13
4-Acetyl-7-bromo-3,4-dihydro-2H-benzo[1,4]oxazine

A mixture of 4-bromo-2-hydroxyacetanilide (9.4 g), powdered sodium hydroxide (6.56 g), aliquat 336 (2.0 g) and 1,2-dibromoethane (30.8 g) in a mixture of dichloromethane (100 mL) and acetonitrile (60 mL) was stirred at room temperature for 16 h, then allowed to stand for 24 h. The mixture was filtered through diatomaceous earth and the filter pad was washed with dichloromethane. The combined filtrate and washings were evaporated and the residue purified by flash chromatography (silica, using ethyl acetate/cyclohexane 1:1v/v as eluent) to give the title compound (9.5 g) as a light oil.

Reference Example 14
3-(2-o-Tolylamino-benzoxazol-6-yl)propanoic acid

A solution of ethyl 3-(2-o-tolylamino-benzoxazol-6-yl)propanoate (Reference Example 15) in methanol (50 ml) was treated with aqueous sodium hydroxide (5 ml, 1M). After stirring at 40° C. for 2 hours the mixture was evaporated to low volume and partitioned between ethyl acetate (50 ml) and water (50 ml). The aqueous phase was separated and acidified with aqueous hydrochloric acid (10 ml, 1M). The resulting precipitate was dried at 60° C. to give the title compound (1.1 g).

Reference Example 15
Ethyl 3-(2-o-tolylamino-benzoxazol-6-yl)propanoate

A solution of ethyl 3-(4-amino-3-hydroxyphenyl)-propionate (1.94 g) in ethanol (50 ml) was treated with o-tolyl isothiocyanate (1.66 g) and then heated at 40° C. for 2 hours. The mixture was evaporated then treated with ethanol (50 ml), then with diisopropylcarbodiimide (3 mL) and then stirred at 40° C. for 1 hour. The mixture was evaporated and the residue was treated with diethyl ether (50 ml) then filtered. The filtrate was evaporated to dryness and the residue subjected to flash chromatography on silica eluting with a mixture of ethyl acetate and cyclohexane (2:3, v/v) to give the title compound (1.6 g) as a colourless oil.

Reference Example 16

(a) 3-(4-Benzoyl-1-{[3-methoxy-4-(3-o-tolyl-ureido)-phenyl]-acetyl}-1,2,3,4-tetrahydro-quinoxalin-6-yl)-butyric acid ethyl ester Benzoyl chloride (22 μl) was added to a stirred mixture of 3-(1-{[3-methoxy-4-(3-o-tolyl-ureido)-phenyl]-acetyl}-1,2,3,4-tetrahydro-quinoxalin-6-yl)-butyric acid ethyl ester (0.110 g, Reference Example 17) and triethylamine (87.8 μl) in tetrahydrofuran (10 ml) cooled to 0° C. under an argon atmosphere. The mixture was stirred for 1 hour at 0° C., then allowed to warm to 20° C., then stirred at this temperature for 2 hours and then treated with a further aliquot of benzoyl chloride (11 μl). After stirring overnight the reaction mixture was treated with water (20 ml) then extracted three times with ethyl acetate (25 ml). The combined extracts were dried over magnesium sulfate then evaporated (40° C., 40 mbar). The crude residue (147 mg) was subjected to flash chromatography on silica (20 g, 0.040–0.063 mm particle size) eluting with a mixture of dichloromethane and methanol (99:1, v/v) to give the title compound as a white foam (132 mg). TLC: $R_F$ 13/56 (cyclohexane:ethyl acetate, 9:1, v/v). $^1$H NMR [400 HMz, $(CD_3)_2SO$, at a temperature of 383° K.]: δ0.96 (d, J=7 Hz, 3H); 1.16 (t, J=7 Hz, 3H); 2.24 (d, J=7.5 Hz, 2H); 2.28 (s, 3H); 2.93 (m, 1H); 3.83 (s, 3H); 3.94 (m, 2H); 3.96 (s, 21H); 4.02 (m, 2H); 4.04 (q, J=7 Hz, 2H); 6.63 (broad s ,1H); 6.76 (broad d, J=8 Hz, 1H); 6.90 (broad s, 1H); 6.99 (m, 2H); from 7.10 to 7.20 (m, 4H); 7.34 (broad t, J=7.5 Hz, 2H); 7.41 (broad t, J=7.5 Hz, 1H); 7.57 (d, J=8 Hz, 1H); 7.67 (broad d, J=8 Hz, 1H); 8.02 (d, J=8.5 Hz, 1H); 8.16 (broad s, 1H); 8.24 (broad s, 1H). MS (EI): 648 (M$^+$).

(b) By proceeding in a similar manner to Reference Example 16(a) but using acetyl chloride and ethyl 3-(1-{[3-methoxy-4-(3-o-tolyl-ureido)-phenyl]-acetyl}-1,2,3,4-tetrahydro-quinoxalin-6-yl)-propanoate (Reference Example 1) and subjecting the reaction product to flash chromatography on silica eluting with a mixture of cyclohexane and ethyl acetate (6:4 to 7:3, v/v) there was prepared 3-(4-acetyl-1-{[3-methoxy-4-(3-o-tolyl-ureido)-phenyl]-acetyl}-1,2,3,4-tetrahydro-quinoxalin-6-yl)-propionic acid ethyl ester as a white foam. 1H NMR [300 HMz, $(CD_3)_2SO$, at room temperature, a mixture of rotamers]: δ1.17 (d, J=7 Hz, 3H); from 1.85 to 2.15 (broad band, 3H); 2.26 (s, 3H); 2.65 (broad t, J=7.5 Hz, 2H); 2.86 (broad t, J=7.5 Hz, 2H); from 3.70 to 3.95 (m, 9H); 4.06 (m, 2H); from 6.40 to 7.70 (m, 8H); 7.81 (broad d, J=8 Hz, 1H); 7.95 (broad band, 1H); 8.48 (broad s, 1H); 8.56 (broad band, 1H). MS (ES): 572 (M$^+$).

(c) By proceeding in a similar manner to Reference Example 16(a) but using ethyl 3-(1-{[3-methoxy-4-(3-o-tolyl-ureido)-phenyl]-acetyl}-1,2,3,4-tetrahydro-quinoxalin-6-yl)-propanoate (Reference Example 1) there was prepared ethyl 3-(4-benzoyl-1-{[3-methoxy-4-(3-o-tolyl-ureido)-phenyl]-acetyl}-1,2,3,4-tetrahydro-quinoxalin-6-yl)-propanaote as a white powder following trituration with di-isopropyl ether. $^1$H NMR [400 HMz, $(CD_3)_2SO$, at room temperature, a mixture of rotamers]: δ1.17 (t, J=7 Hz, 3H); 2.14 (broad t, J=7.5 Hz, 2H); 2.24 (s, 3H); 2.51 (m, 2H); 3.80 (s, 3H); 3.89 (m, 2H); from 3.90 to 4.00 (m, 2H); 3.97 (s, 2H); 4.02 (m, 2H); 6.48 (broad band, 1H); 6.71 (broad band, 1H); 6.83 (broad band, 1H); from 6.90 to 7.25 (m, 6H); 7.31 (broad t, J=7.5 Hz, 2H); 7.40 (broad t, J=7.5 Hz, 1H); 7.60 (broad band, 1H); 7.77 (broad d, J=8 Hz, 1H); 8.06 (d, J=8.5 Hz, 1H); 8.47 (broad s, 1H); 8.54 (broad s, 1H). MS (EI): 634 (M$^+$).

(d) By proceeding in a similar manner to Reference Example 16(a) but using ethyl succinyl chloride and ethyl 3-(1-{[3-methoxy-4-(3-o-tolyl-ureido)-phenyl]-acetyl}-1,2,3,4-tetrahydro-quinoxalin-6-yl)-propanoate (Reference Example 1) and subjecting the reaction product to flash chromatography on silica eluting with a mixture of cyclohexane and ethyl acetate (9:1 to 1:1, v/v) there was prepared ethyl 4-(7-(2-ethoxycarbonyl-ethyl)-4-{[3-methoxy-4-(3-o-tolyl-ureido)-phenyl]-acetyl}-3,4-dihydro-2H-quinoxalin-1-yl)-4-oxo-butanoate as a white foam. $^1$H NMR [400 MHz, $(CD_3)_2SO$, at room temperature, a mixture of rotamers]: δ1.16 (m, 6H); 2.26 (s, 3H); 2.52 (m, 2H); 2.64 (broad t, J=7.5 Hz, 4H); 2.87 (broad t, J=7.5 Hz, 2H); from 3.75 to 3.90 (m, 9H); 4.05 (m, 4H); from 6.50 to 6.85 (very broad band, 2H); 6.95 (broad t, J=7.5 Hz, 1H); from 7.05 to 7.20 (m, 3H); from 7.30 to 7.75 (very broad band, 2H); 7.79 (d, J=8 Hz, 1H); 8.00 (broad d, J=8 Hz, 1H); 8.21 (broad s, 1H); 8.27 (broad band, 1H). MS (EI): 658 (M$^+$).

Reference Example 17
3-(1-{[3-Methoxy-4-(3-o-tolyl-ureido)-phenyl]-acetyl}-1,2,3,4-tetrahydro-quinoxalin-6-yl)-butyric acid ethyl ester.

Trifluoroacetic acid (574 μl) was added to a stirred solution of 7-(2-ethoxycarbonyl-1-methyl-ethyl)-4-{[3-methoxy-4-(3-o-tolyl-ureido)-phenyl]-acetyl}-3,4-dihydro-2H-quinoxaline-1-carboxylic acid tert-butyl ester (376 mg, Reference Example 18) in dichloromethane (4 ml) at 0° C. After stirring at 0° C. for 2 hours a further aliquot of trifluoroacetic acid (3.5 ml) was added and stirring was continued at 0° C. for a further 4 hours. The reaction mixture was poured onto a mixture of ice (75 ml) and sodium hydroxide solution (55 ml, 1M). The resulting mixture was extracted three times with dichloromethane (50 ml). The combined extracts were washed twice with water (20 ml), then dried over magnesium sulfate and then evaporated (40 mbar, 40° C.). The residue was subjected to flash chromatography (20 g silica, 0.040–0.063 mm particle size) eluting with a mixture of dichloromethane and methanol (99:1, v/v) to give the title compound as a white powder (279 mg). TLC: $R_F$=43/64 (dichloromethane:methanol, 9:1). 1H NMR (250 MHz, $(CD_3)_2SO$, at a temperature of 373° K.]: δ1.16 (t, J=7 Hz, 3H); 1.23 (d, J=7.5 Hz, 3H); 2.28 (s, 3H); from 2.45 to 2.55 (m, 2H); 3.06 (m, 1H); 3.25 (m, 2H); 3.69 (m, 2H); 3.82 (s, 2H); 3.85 (s, 3H); 4.05 (q, J=7 Hz, 2H); 5.73 (broad band :1H); 6.43 (dd, J=8 and 2 Hz, 1H); 6.50 (d, J=2 Hz, 1H); 6.70 (dd, J=9 and 1.5 Hz, 1H); 6.81 (d, J=1.5 Hz, 1H); 6.97 (broad t, J=7.5 Hz, 1H); from 7.10 to 7.30 (m, 3H); 7.71 (broad d, J=9 Hz, 1H); 7.98 (d, J=8.5 Hz, 1H); 8.25 (broad s, 1H); 8.29 (broad s, 1H). MS (EI): 544(M$^+$).

Reference Example 18
7-(2-Ethoxycarbonyl-1-methyl-ethyl)-4-{[3-methoxy-4-(3-o-tolyl-ureido)-phenyl]-acetyl}-3,4-dihydro-2H-quinoxaline-1-carboxylic acid tert-butyl ester A mixture of [3-methoxy-4-(3-o-tolyl-ureido)-phenyl]-acetic acid (0.536 g) and 7-(2-ethoxycarbonyl-1-methyl-ethyl)-3,4-dihydro-2H-quinoxaline-1-carboxylic acid tert-butyl ester (396 mg, Reference Example 19) in tetrahydrofuran (10 ml) containing 4 Angström molecular sieves (0.5 g) was treated with triethyl amine (638 μl), O-(7-azabenzotriazol-1-yl)-N,N,N',N'-tetramethyluronium hexafluorophosphate (518 mg) and $^4$-dimethyl-aminopyridin (14 mg). After stirring for 5 hours further aliquots of [3-methoxy-4-(3-o-tolyl-ureido)-phenyl]-acetic acid (0.178 g) and O-(7-azabenzotriazol-1-yl)-N,N,N',N'- tetramethyluronium hexafluorophosphate (172 mg) were added and stirring was continued for a further 18 hours. The reaction mixture was filtered through a celite and the filter pad was washed with ethyl acetate (50 ml). The combined filtrate and washings were washed three times with aqueous saturated ammonium chloride (20 ml), then dried over magnesium sulfate and then evaporated (40° C., 40 mbar). The residue (1.2 g) was submitted to chromatography (36 g silica, 0.040–0.063 mm particle size) eluting with a mixture of cyclohexane and ethyl acetate (70:30, v/v) to afford the title compound as a white powder (379 mg). TLC: $R_F$=15/65 (cyclohexane:ethyl acetate, 1:1). $^1$H NMR (400 HMz, (CD$_3$)2SO, at room temperature, we observe a mixture of rotamers): δ1.14 (t, J=7 Hz, 3l); 1.24 (d, J=7 Hz, 3H); 1.48 (s, 9 H); 2.26 (s, 3H); 2.58 (d, J=7.5 Hz, 2H); 3.17 (m, 1H); 3.64 (m, 2H); from 3.75 to 3.90 (m, 7H); 4.04 (q, J=7 Hz, 2H); from 6.55 to 6.85 (very broad band, 2H); 6.96 (t, J=7.5 Hz, 1H); 7.00 (broad d, J=8 Hz, 1H); from 7.10 to 7.20 (m, 2H); 7.46 (broad band, 1H); 7.64 (broad s, 1H); 7.78 (d, J=8 Hz, 1H); 8.01 (d, J=8 Hz, 1H); 8.48 (s, 1H); 8.54 (broad s, 1H). MS (EI): 644 (M$^+$).

Reference Example 19

7-(2-Ethoxycarbonyl-1-methyl-ethyl)-3,4-dihydro-2H-quinoxaline-1-carboxylic acid tert-butyl ester 4-Benzyl-7-(2-ethoxycarbonyl-1-methyl-vinyl)-3,4-dihydro-2H-quinoxaline-1-carboxylic acid tert-butyl ester. (0.905 g, Reference Example 20) was added to a stirred suspension of palladium dihydroxide on carbon (240 mg, 20%) in acetic acid and submitted to hydrogenation (30 bar) at 15° C. overnight. The resulting crude mixture was filtered through celite and the filter pad was washed with ethyl acetate. The combined filtrate and washings were evaporated (40 mbar, 40° C.). The residue was subjected to chromatography (30 g silica, 0.040–0.063 mm particle size) eluting with dichloromethane to afford the title compound as a colorless oil (485 mg). TLC: $R_F$=25/65 (cyclohexane:ethyl acetate, 7:3, v/v). $^1$H NMR (400 MHz, (CD$_3$)$_2$SO): δ1.14 (m, 6H); 1.48 (s, 9 H); 2.47 (d, J=7.5 Hz, 2H); 3.00 (m, 1H); 3.22 (m, 2H); 3.57 (m, 2H); 4.01 (q, J=7 Hz, 2H); 5.90 (broad band, 1H); 6.47 (d, J=8 Hz, 1H); 6.70 (dd, J=8 and 2 Hz, 1H); 7.20 (broad band, 1H). MS (EI): 348 (M$^+$).

Reference Example 20

4-Benzyl-7-(2-ethoxycarbonyl-1-methyl-vinyl)-3,4-dihydro-2H-quinoxaline-1-carboxylic acid tert-butyl ester A mixture of ethyl 3-(1-{[$^3$-methoxy-4-(3-o-tolyl-ureido)-phenyl]-acetyl}-1,2,3,4-tetrahydro-quinoxalin-6-yl)-propionate (4.4 g, Reference Example 1) tributylamine (50 ml), tri-ortho tolylphosphine (177 mg) and palladium acetate (444 mg) was heated 15 minutes at 80° C. then treated with ethyl crotonate (2.74 ml) and the resulting mixture was heated overnight at 120° C. After cooling to 20° C. the reaction mixture was treated with hydrochloric acid (350 ml, 1M) then extracted four times with ethyl acetate (200 ml). The combined extracts were washed with saturated aqueous sodium bicarbonate solution (200 ml), then with water (200 ml), then dried over magnesium sulfate and then evaporated. The residue was subjected to chromatography on silica (260 g, 0.040–0.063 mm particle size) eluting with a mixture of cyclohexane and ethyl acetate )95:5, v/v) to afford the title compound as a colorless oil (910 mg). $^1$H spectrum of NMR (400 MHz, (CD$_3$)$_2$SO): δ1.23 (t, J=7 Hz, 3H); 1.49 (s, 9 H); 2.47 (d, J=1.5 Hz, 3H); 3.49 (m, 2H); 3.78 (m, 2H); 4.11 (q, J=7 Hz, 2H); 4.62 (s, 2H); 6.04 (m, 1H); 6.64 (d, J=9 Hz, 1H); 7.19 (dd, J=9 and 2 Hz, 1H); 7.27 (m, 3H); 7.36 (broad t, J=7.5 Hz, 2H); 7.63 (broad s, 1H). MS (EI): 436 (M$^+$).

Reference Example 21

Ethyl 3-(4-(3-Dimethylamino-propionyl)-1-{[3-methoxy-4-(3-o-tolyl-ureido)-phenyl]-acetyl}-1,2,3,4-tetrahydro-quinoxalin-6-yl)-propanoate A stirred mixture of ethyl 3-(4-acryloyl-1-{[3-methoxy-4-(3-o-tolyl-ureido)-phenyl]-acetyl}-1,2,3,4-tetrahydro-quinoxalin-6-yl)-propanoate (283 mg, Reference Example 22) and methylamine (115 μl) in ethanol (5 ml) was heated at reflux for 8 hours, then treated with a further aliquot of methylamine (50 μl) and then heated at reflux for a further 2 hours. The reaction mixture was cooled to 20° C., then diluted with ethyl acetate, then treated with hydrochloric acid (50 ml, 0.1M) and separated. The ethyl acetate phase was washed with saturated aqueous sodium bicarbonate (10 ml), then washed three times with water (10 ml), then dried over magnesium sulfate and then evaporated under reduced pressure. The aqueous phase from above was extracted three times with dichloromethane (50 ml). The dichloromethane extracts were combined with the above ethyl acetate residue, dried over magnesium sulfate and then evaporated under reduced pressure. The crude residue (331 mg) was subjected to flash chromatography on silica (30 g, 0.040–0.063 mm particle size) eluting with a mixture of dichloromethane and methanol (99:1 to 96:4, v/v) to give the title compound as a white foam (275 mg). $^1$H NMR 400 MHz, (CD$_3$)$_2$SO, at a temperature of 383° K.]: δ1.20 (t, J=7 Hz, 3H); 2.19 (s, 6H); 2.28 (s, 3H); from 2.55 to 2.70 (m, 6H); from 2.75 to 3.00 (m, 2H); from 3.80 to 3.90 (m, 2H); 3.83 (s, 2H); 3.86 (s, 3H); 3.90 (m, 2H); 4.11(q, J=7 Hz, 2H); 6.67 (broad d, J=8 Hz, 1H); 6.81 (broad s, 1H); 6.99 (broad t, J=7.5 Hz, 1H); from 7.05 to 7.25 (m, 3H); 7.42 (broad s, 1H); 7.56 (d, J=8.5 Hz, 1H); 7.69 (broad d, J=8 Hz, 1H); 7.98 (d, J=8.5 Hz, 1H); 8.17 (broad s, 1H); 8.25 (broad s, 1H). MS (CI): 630 (MH$^+$).

Reference Example 22

Ethyl 3-(4-Acryloyl-1-{[3-methoxy-4-(3-o-tolyl-ureido)-phenyl]-acetyl}-1,2,3,4-tetrahydro-quinoxalin-6-yl)-propanoate 3-Bromo propionyl bromide (262 μl) was added to a stirred suspension of 3-(1-{[3-methoxy-4-(3-o-tolyl-ureido)-phenyl]-acetyl}-1,2,3,4-tetrahydro-quinoxalin-6-yl)-propionic acid ethyl ester (0.229 g, Reference Example 1) and triethylamine (680 μl) in tetrahydrofuran (10 ml) cooled to 0° C. under argon atmosphere. After stirring at 0° C. for 1 hour then at 20° C. overnight the mixture was treated with 3-bromo propionyl bromide (90 μl) and stirring was continued for 2 hours at 21° C. The reaction mixture was treated with water (25 ml) and after stirring for 15 minutes at 20° C. the mixture was extracted three times with ethyl acetate (25 ml). The combined extracts were washed with saturated aqueous sodium bicarbonate (10 ml), then washed four times with water (10 ml), then dried over magnesium sulfate and then evaporated to dryness under reduced pressure (40° C., 40 mbar). The residue (1.7 g) was subjected to flash chromatography on silica (50 g, 0.040–0.063 mm particle size) eluting with a mixture of cyclohexane and ethyl acetate (1:1, v/v) to give the title compound as a yellow foam (550 mg). TLC: $R_F$=30/72, silica, eluting with a mixture of dichloromethane and methanol (9:1, v/v). $^1$H NMR [400 MHz, (CD$_3$)$_2$SO, at a temperature of 373° K.]: δ1.20 (t, J=7 Hz, 3H); 2.28 (s,, 3H); 2.64 (t, J=7.5 Hz, 2H); 2.91 (t, J=7.5 Hz, 2H); 3.81 (s, 3H); 3.84 (s, 2H); 3.87 (m, 2H); 3.93 (m, 2H); 4.11 (q, J=7 Hz, 2H); 5.68 (dd, J=10.5 and 2 Hz, 1H); 6.21 (dd, J=17 and 2 Hz, 1H); 6.38 (dd, J=17 and 10.5 Hz, 1H); 6.58 (broad d, J=8 Hz, 1H); 6.75 (broad s, 1H); 6.99 (broad t, J=7.5 Hz, 1H); from 7.10 to 7.25 (m, 4H); 7.57 (d, J=8.5 Hz, 1H); 7.69 (broad d, J=8 Hz, 1H); 7.92 (d, J=8.5 Hz, 1H); 8.18 (broad s, 1H); 8.28 (broad s, 1H). MS (EI): 584 (M$^+$).

In Vitro and In Vivo Test Procedures

1. Inhibitory Effects of Compounds on VLA4 Dependent Cell Adhesion to Fibronectin and VCAM

1.1 Metabolic Labelling of RAMOS cells

RAMOS cells (a pre-B cell line from ECACC, Porton Down, UK) are cultured in RPMI culture medium (Gibco, UK) supplemented with 5% foetal calf serum (FCS, Gibco, UK). Prior to assay the cells are suspended at a concentration of $0.5 \times 10^6$ cells/ml RPMI and labelled with $400 \mu$Ci/100 mls of [$^3$H]-methionine (Amersham, UK) for 18 hours at 37° C.

1.2 96 Well Plate Preparation for Adhesion Assay

Cytostar plates (Amersham, UK) were coated with 50 $\mu$l/well of either 3 $\mu$g/ml human soluble VCAM-1 (R&D Systems Ltd, UK) or 28.8 $\mu$g/ml human tissue Fibronectin (Sigma, UK). In control non-specific binding wells 50 $\mu$l phosphate buffered saline was added. The plates were then left to dry in an incubator at 25° C., overnight. The next day the plates were blocked with 200 $\mu$l/well of Pucks buffer (Gibco, UK) supplemented with 1% BSA (Sigma, UK). The plates were left at room temperature in the dark for 2 hours. The blocking buffer was then disposed of and the plates dried by inverting the plate and gently tapping it on a paper tissue. 50 $\mu$l/well of 3.6% dimethyl sulphoxide in Pucks buffer supplemented with 5 mM manganese chloride (to activate the integrin receptor Sigma, UK) and 0.2% BSA (Sigma, UK), was added to the appropriate control test binding and non-specific binding assay wells in the plate. 50 $\mu$l/well of the test compounds at the appropriate concentrations diluted in 3.6% dimethyl sulphoxide in Pucks buffer supplemented with 5 mM manganese chloride and 0.2% BSA, was added to the test wells.

Metabolically labelled cells were suspended at $4 \times 10^6$ cells/ml in Pucks buffer that was supplemented with manganese chloride and BSA as above. 50 $\mu$l/well of cells in 3.6% dimethyl sulphoxide in Pucks buffer and supplements was added to all plate wells.

The same procedure exists for plates coated with either VCAM-1 or fibronectin and data is determined for compound inhibition of cell binding to both substrates.

1.3 Performance of Assay and Data Analysis

The plates containing cells in control or compound test wells are incubated in the dark at room temperature for 1 hour.

The plates are then counted on a Wallac Microbeta scintillation counter (Wallac, UK) and the captured data processed in Microsoft Excel (Microsoft, US). The data was expressed as an IC50, namely the concentration of inhibitor at which 50% of control binding occurs. The percentage binding is determined from the equation:

$$\{[(C_{TB}-C_{NS})-(C_I-C_{NS})]/(C_{TB}-C_{NS})\} \times 100 = \% \text{ binding}$$

where $C_{TB}$ are the counts bound to fibronectin (or VCAM-1) coated wells without inhibitor present, $C_{NS}$ are the counts present in wells without substrate, and $C_I$ are the counts present in wells containing a cell adhesion inhibitor.

"Compound data of this invention is expressed for $IC_{50}$s for inhibition of cell adhesion to both fibronectin and VCAM-1. Particular compounds of the invention inhibit cell adhesion to fibronectin and VCAM-1 with IC50s in the range 100 micromolar to 0.1 nanomolar. Preferred compounds of the invention inhibit cell adhesion to fibronectin and VCAM-1 with IC50s in the range 10 nanomolar to 0.1 nanomolar."

2. Inhibition of Antigen-induced Airway Inflammation in the Mouse and Rat

2.1 Sensitization of the Animals

Rats (Brown Norway, Harland Olac, UK) are sensitized on days 0, 12 and 21 with ovalbumin (100 $\mu$g, intraperitoneally [i.p], Sigma, UK) administered with aluminium hydroxide adjuvant (100 mg, i.p., Sigma, UK) in saline (1 ml, i.p.).

In addition mice (C57) are sensitized on days 0 and 12 with ovalbumin (10 $\mu$g, i.p.) administered with aluminium hydroxide adjuvant (20 mg, i.p.) in saline (0.2 ml, i.p.).

2.2 Antigen Challenge

Rats are challenged on any one day between days 28–38, while mice are challenged on any one day between days 20–30.

The animals are challenged by exposure for 30 minutes (rats) or 1 hour (mice) to an aerosol of ovalbumin (10 g/l) generated by an ultrasonic nebulizer (deVilbiss Ultraneb, US) and passed into an exposure chamber.

2.3 Treatment Protocols

Animals are treated as required before or after antigen challenge. The aqueous-soluble compounds of this invention can be prepared in water (for oral, p.o. dosing) or saline (for intratracheal, i.t. dosing). Non-soluble compounds are prepared as suspensions by grinding and sonicating the solid in 0.5% methyl cellulose/0.2% polysorbate 80 in water (for p.o. dosing, both Merck UK Ltd., UK) or saline (for i.t. dosing). Dose volumes are: for rats 1 ml/kg, p.o. or 0.5 mg/kg, i.t.; for mice 10 ml/kg, p.o. or 1 ml/kg, i.t.

2.4 Assessment of Airway Inflammation

The cell accumulation in the lung is assessed 24 hours after challenge (rats) or 48–72 hours after challenge (mice). The animals are euthanized with sodium pentobarbitone (200 mg/kg, i.p., Pasteur Merieux, France) and the trachea is immediately cannulated. Cells are recovered from the airway lumen by bronchoalveolar lavage (BAL) and from the lung tissue by enzymatic (collagenase, Sigma, UK) disaggregation as follows.

BAL is performed by flushing the airways with 2 aliquots (each 10 ml/kg) RPMI 1640 medium (Gibco, UK) containing 10% fetal calf serum (FCS, Serotec Ltd., UK). The recovered BAL aliquots are pooled and cell counts made as described below.

Immediately after BAL, the lung vasculature is flushed with RPMI 1640/FCS to remove the blood pool of cells. The lung lobes are removed and cut into 0.5 mm pieces. Samples (rats: 400 mg; mice: 150 mg) of homogenous lung tissue are incubated in RPMI 1640/FCS with collagenase (20 U/ml for 2 hours, then 60 U/ml for 1 hour, 37° C.) to disaggregate cells from the tissue. Recovered cells are washed in RPMI 1640/FCS.

Counts of total leukocytes recovered from the airway lumen and the lung tissue are made with an automated cell counter (Cobas Argos, US). Differential counts of eosinophils, neutrophils and mononuclear cells are made by light microscopy of cytocentrifuge preparations stained with Wright-Giemza stain (Sigma, UK). T cells are counted by flow cytometry (EPICS XL, Coulter Electronics, US) using fluophore-labelled antibodies against CD2 (a pan-T cell marker used to quantify total T cells), CD4, CD8 and CD25 (a marker of activated T cells). All antibodies were supplied by Serotec Ltd., UK).

2.5 Data Analysis

The cell data was expressed as mean cell numbers in unchallenged, challenged and vehicle treated, and challenged and compound treated groups, including the standard error of the means. Statistical analysis of the difference

What is claimed is:

1. A compound of formula (Ia):

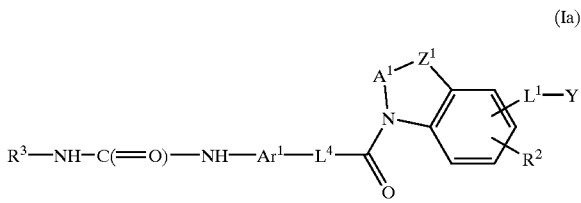

(Ia)

wherein:
$R^2$ represents hydrogen, halogen, $C_{1-4}$alkyl or $C_{1-4}$alkoxy;
$R^3$ is aryl optionally substituted by aryloxy, cyano, halo $C_{1-4}$alkoxy, $C_{1-4}$alkyl, nitro or $CF_3$;
$A^1$ represents ethylene;
$Ar^1$ is arylene optionally substituted by halo, $C_{1-4}$alkyl, $C_{1-4}$alkoxy, $C_{1-4}$alkylthio, $C_{1-4}$alkylsulphinyl or $C_{1-4}$alkylsulphonyl;
$L^1$ represents an ethylene linkage optionally substituted by alkyl or aryl optionally substituted by aryloxy, cyano, halo, $C_{1-4}$alkoxy, $C_{1-4}$alkyl, nitro or $CF_3$;
$L^4$ represents $C_{1-4}$alkylene;
Y is carboxy;
$Z^1$ represents O;
and the corresponding N-oxides, and their ester prodrugs; and pharmaceutically acceptable salts and solvates of such compounds and their N-oxides and ester prodrugs, wherein said ester prodrugs are alkyl ester prodrugs of the Y group.

2. A compound according to claim 1 in which $R^3$ is phenyl or phenyl substituted by one or two of aryloxy, cyano, halo, $C_{1-4}$alkoxy, $C_{1-4}$alkyl, nitro or $CF_3$.

3. A compound according to claim 1 in which $L^4$ is methylene, $Ar^1$ is optionally substituted p-phenylene and $R^3$ is optionally substituted phenyl.

4. A compound according to claim 3 in which $Ar^1$ is p-phenylene or p-phenylene substituted in the 3-position by halo, $C_{1-4}$alkyl, $C_{1-4}$alkoxy, $C_{1-4}$alkylthio, $C_{1-4}$alkylsulphinyl or $C_{1-4}$alkylsulphonyl and $R^3$ is phenyl substituted in the 2-position by $C_{1-4}$alkyl.

5. A compound according to claim 1 in which $R^2$ is hydrogen.

6. A compound according to claim 1 in which $L^1$ is a group

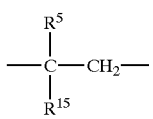

where $R^5$ is hydrogen or $C_{1-4}$alkyl and $R^{15}$ is hydrogen or $C_{1-4}$alkyl, or where $R^5$ is hydrogen and $R^{15}$ is optionally substituted aryl.

7. A compound according to claim 6 in which $L^1$ is a group

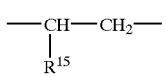

where $R^{15}$ represents hydrogen, $C_{1-4}$alkyl or optionally substituted aryl.

8. A compound according to claim 6 in which $L^1$ is a group

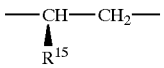

where $R^{15}$ represents hydrogen, $C_{1-4}$alkyl or optionally substituted aryl.

9. A compound according to claim 1 in which $L^1$ is a group

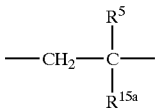

where $R^5$ is hydrogen or $C_{1-4}$alkyl and $R^{15a}$ represents hydrogen or $C_{1-4}$alkyl, or where $R^5$ is hydrogen and $R^{15a}$ represents optionally substituted aryl.

10. A compound according to claim 1 in which $R^3$ is phenyl substituted in the 2-position by $C_{1-4}$alkyl.

11. A compound according to claim 1 in which $Ar^1$ is p-phenylene or p-phenylene substituted in the 3-position by halo, $C_{1-4}$alkyl, $C_{1-4}$alkoxy, $C_{1-4}$alkylthio, $C_{1-4}$alkylsulphinyl or $C_{1-4}$alkylsulphonyl.

12. A compound according to claim 1 in which $L^4$ is methylene.

13. A compound according to claim 1 in which $R^2$ is hydrogen, $R^3$ is a 2-substituted phenyl, $Ar^1$ is optionally substituted m- or p-phenylene, and $L^1$ is a

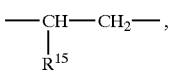

where $R^{15}$ represents hydrogen, $C_{1-4}$alkyl or optionally substituted aryl;
and the corresponding N-oxides, and their ester prodrugs; and pharmaceutically acceptable salts and solvates of such compounds and their N-oxides and ester prodrugs.

14. A compound according to claim 1 selected from:

3-(4-{[3-methoxy-4-(3-o-tolyl-ureido)-phenyl]-acetyl}-3,4-dihydro-2H-benzo[1,4]oxazin-7-yl)-5-methyl-hexanoic acid;

3-(4-{[3-methoxy-4-(3-o-tolyl-ureido)-phenyl]-acetyl}-3,4-dihydro-2H-benzo[1,4]oxazin-7-yl)-3-phenylpropanoic acid;

3-(4-{[3-methoxy-4-(3-o-tolyl-ureido)-phenyl]-acetyl}-3,4-dihydro-2H-benzo[1,4]oxazin-7-yl)-3-o-tolylpropanoic acid;

3-(4-{[3-methoxy-4-(3-o-tolyl-ureido)-phenyl]-acetyl}-3,4-dihydro-2H-benzo[1,4]oxazin-7-yl)-butanoic acid;

3-(4-{[3-methoxy-4-(3-o-tolyl-ureido)-phenyl]-acetyl}-3,4-dihydro-2H-benzo[1,4]oxazin-7-yl)-4-methylpentanoic acid;

and the corresponding N-oxides, and their ester prodrugs; and pharmaceutically acceptable salts and solvates of such compounds and their N-oxides and ester prodrugs.

15. A pharmaceutical composition comprising an effective amount of a compound according to claim 1 or a corresponding N-oxide, or an ester prodrug thereof; or a pharmaceutically acceptable salt or solvate of such a compound or its N-oxide or an ester prodrug thereof, in association with a pharmaceutically acceptable carrier or excipient.

16. A method for the treatment of a human or non-human animal patient suffering from, or subject to, a condition which can be ameliorated by the administration of an inhibitor of α4β1 mediated cell adhesion comprising administering to said patient an effective amount of a compound according to claim 1 or a corresponding N-oxide, or an ester prodrug thereof; or a pharmaceutically acceptable salt or solvate of such a compound or its N-oxide or an ester prodrug thereof, wherein said condition is selected from the group consisting of joint inflammation, acute synovitis, autoimmune diabetes, autoimmune encephalomyelitis, colitis, atherosclerosis, peripheral vascular disease, multiple sclerosis, asthma, psoriasis, restenosis, myocarditis, inflammatory bowel disease and melanoma cell division in metastasis.

17. A method according to claim 16 wherein said condition is asthma.

18. A method according to claim 16 wherein said condition is joint inflammation.

19. A method according to claim 16 wherein said condition is inflammatory bowel disease.

* * * * *